US012485132B2

(12) United States Patent
Hadd et al.

(10) Patent No.: US 12,485,132 B2
(45) Date of Patent: Dec. 2, 2025

(54) GPX4 INHIBITORS AND SENOLYTIC COMPOUNDS AND USES THEREOF

(71) Applicant: Rubedo Life Sciences, Inc., Sunnyvale, CA (US)

(72) Inventors: Michael Hadd, San Jose, CA (US); Paul Keitz, Redwood City, CA (US)

(73) Assignee: Rubedo Life Sciences, Inc., Sunnyvale, CA (US)

( * ) Notice: Subject to any disclaimer, the term of this patent is extended or adjusted under 35 U.S.C. 154(b) by 0 days.

(21) Appl. No.: 19/247,553

(22) Filed: Jun. 24, 2025

(65) Prior Publication Data

US 2025/0319109 A1 Oct. 16, 2025

Related U.S. Application Data

(63) Continuation of application No. 18/678,791, filed on May 30, 2024.

(60) Provisional application No. 63/572,605, filed on Apr. 1, 2024, provisional application No. 63/567,749, filed on Mar. 20, 2024, provisional application No. 63/505,128, filed on May 31, 2023.

(51) Int. Cl.

| | |
|---|---|
| ***C07J 41/00*** | (2006.01) |
| ***A61K 31/575*** | (2006.01) |
| ***A61K 31/704*** | (2006.01) |
| ***A61P 39/00*** | (2006.01) |
| ***C07H 15/18*** | (2006.01) |
| ***C07J 31/00*** | (2006.01) |
| ***C07J 43/00*** | (2006.01) |

(52) U.S. Cl.

CPC .......... *A61K 31/704* (2013.01); *A61K 31/575* (2013.01); *A61P 39/00* (2018.01); *C07H 15/18* (2013.01); *C07J 31/006* (2013.01); *C07J 41/0005* (2013.01); *C07J 41/0016* (2013.01); *C07J 43/003* (2013.01)

(58) Field of Classification Search

None

See application file for complete search history.

(56) References Cited

U.S. PATENT DOCUMENTS

| | | | |
|---|---|---|---|
| 4,550,100 | A | 10/1985 | Hofmeister et al. |
| 5,925,630 | A | 7/1999 | Upasani et al. |
| 6,664,443 | B1 | 12/2003 | Hutton et al. |
| 2012/0005765 | A1 | 1/2012 | Kumar et al. |
| 2013/0203718 | A1 | 8/2013 | Rafestin-Oblin et al. |

FOREIGN PATENT DOCUMENTS

| | | | | |
|---|---|---|---|---|
| WO | 2012/177927 | A1 | 12/2012 | |
| WO | 2013/090645 | A1 | 6/2013 | |
| WO | 2014/205244 | A1 | 12/2014 | |
| WO | WO-2020056349 | A2 * | 3/2020 | ................ A61P 1/16 |

OTHER PUBLICATIONS

Iyengar, Sudha K., et al. "Dissection of genomewide-scan data in extended families reveals a major locus and oligogenic susceptibility for age-related macular degeneration." Â The American Journal of Human Genetics Â 74.1 (2004): 20-39.

Kenealy, Shannon J., et al. "Linkage analysis for age-related macular degeneration supports a gene on chromosome 10q26." Â American Journal of Ophthalmology Â 137.4 (2004): 793-793.

Gorin, Michael B., et al. "The genetics of age-related macular degeneration." Â Mol Vis Â 5.2910562653 (1999).

Christen, William G., et al. "Dietary Ï‰-3 fatty acid and fish intake and incident age-related macular degeneration in women." Â Archives of ophthalmology Â 129.7 (2011): 921-929.

Kozlowski, Michael R. "RPE cell senescence: a key contributor to age-related macular degeneration." Â Medical hypotheses Â 78.4 (2012): 505-510.

Millen, Amy E., et al. "Vitamin D status and early age-related macular degeneration in postmenopausal women." Â Archives of ophthalmology Â 129.4 (2011): 481-489.

Iriyama, Aya, et al. "A2E, a pigment of the lipofuscin of retinal pigment epithelial cells, is an endogenous ligand for retinoic acid receptor." Â Journal of Biological Chemistry Â 283.18 (2008): 11947-11953.

Heys, Karl Robert, Sandra Leigh Cram, and Roger JW Truscott. "Massive increase in the stiffness of the human lens nucleus with age: the basis for presbyopia?." (2004): 956.

Petrash, J. Mark. "Aging and age-related diseases of the ocular lens and vitreous body." Â Investigative ophthalmology & visual science Â 54.14 (2013): ORSF54-ORSF59.

Krag, Susanne, and Troels T. Andreassen. "Mechanical properties of the human posterior lens capsule." Â Investigative ophthalmology & visual science Â 44.2 (2003): 691-696.

Krag, Susanne, Thomas Olsen, and Troels T. Andreassen. "Biomechanical characteristics of the human anterior lens capsule in relation to age." Â Investigative ophthalmology & visual science Â 38.2 (1997): 357-363.

(Continued)

*Primary Examiner* — Bahar Craigo

(74) *Attorney, Agent, or Firm* — Young Basile Hanlon & MacFarlane, P.C.

(57) ABSTRACT

The present invention relates to compounds that kill senescent cells i.e., senolytic compounds and compounds which inhibit GPX4. The present invention also provides compounds and methods for treating senescence-associated diseases or disorders, and compounds and methods for treating diseases or disorders impacted by GPX4.

10 Claims, 5 Drawing Sheets

(56) References Cited

OTHER PUBLICATIONS

Cummings, Christopher F., and Billy G. Hudson. “Lens capsule as a model to study type IV collagen.” Â Connective tissue research Â 55.1 (2014): 8-12.
Veis, Arthur, and David Schwartz. “The structure of acid-soluble basement membrane collagen from bovine anterior lens capsule: molecular parameters and thermal gelation properties.” Â Collagen and Related Research Â 1.3 (1981): 269-286.
Khoshnoodi, Jamshid, Vadim Pedchenko, and Billy G. Hudson. “Mammalian collagen IV.” Â Microscopy research and technique Â 71.5 (2008): 357-370.
Timpl, Rupert, Peter Bruckner, and Peter Fietzek. “Characterization of pepsin fragments of basement membrane collagen obtained from a mouse tumor.” Â European Journal of Biochemistry Â 95.2 (1979): 255-263.
Risteli, Juha, et al. “7â€S collagen: characterization of an unusual basement membrane structure.” Â European journal of biochemistry Â 108.1 (1980): 239-250.
Awasthi, Niranjan, Suqin Guo, and B. J. Wagner. “Posterior capsular opacification: a problem reduced but not yet eradicated.” Â Archives of ophthalmology Â 127.4 (2009): 555-562.
Raj, Shetal M., et al. “Post-operative capsular opacification: a review.” Â International journal of biomedical science: IJBS Â 3.4 (2007): 237.
Baker, Darren J., et al. “Opposing roles for p16Ink4a and p19Arf in senescence and ageing caused by BubR1 insufficiency.” Â Nature cell biology Â 10.7 (2008): 825-836.
Liton, Paloma B., et al. “Cellular senescence in the glaucomatous outflow pathway.” Â Experimental gerontology Â 40.8-9 (2005): 745-748.
Wesselink, Christiaan, Govert P. Heeg, and Nomdo M. Jansonius. “Glaucoma monitoring in a clinical setting: glaucoma progression analysis vs nonparametric progression analysis in the Groningen Longitudinal Glaucoma Study.” Â Archives of Ophthalmology Â 127.3 (2009): 270-274.
Tchkonia, Tamara, et al. “Fat tissue, aging, and cellular senescence.” Â Aging cell Â 9.5 (2010): 667-684.
Minamino, Tohru, et al. “A crucial role for adipose tissue p53 in the regulation of insulin resistance.” Â Nature medicine Â 15.9 (2009): 1082-1087.
Stanley, Andrew, and Turner Osler. “Senescence and the healing rates of venous ulcers.” Â Journal of vascular surgery Â 33.6 (2001): 1206-1211.
Guidry, Tera V., Robert L. Hunter Jr, and Jeffrey K. Actor. “Mycobacterial glycolipid trehalose 6, 6â€²-dimycolate-induced hypersensitive granulomas: contribution of CD4+ lymphocytes.” Â Microbiology Â 153.10 (2007): 3360-3369.
Holodiag, Pharmaparc II, Voie de l'Innovation, 27 100 Val de Reuil, France; accessed Jun. 29, 2023 http://www.holodiag.com.
Guillory, K., Chapter 5, pp. 202-205 in Polymorphism in Pharmaceutical Solids, (Brittain, H. ed.), Marcel Dekker, Inc., New York, NY, 1999.
Brittain, H., Chapter 6, pp. 205-208 in Polymorphism in Pharmaceutical Solids, (Brittain, H. ed.), Marcel Dekker, Inc. New York, 1999.
Niemer et al., Podocytes are the major source of IL-1α and IL-1β in human glomerulonephritides, Journal: Kidney International, : 1997, ISSN: 0085-2538.
Sis, B., et al. “Accelerated expression of senescence associated cell cycle inhibitor p16INK4A in kidneys with glomerular disease.” Â Kidney international Â 71.3 (2007): 218-226.
Hudson, Melissa M., et al. “Clinical ascertainment of health outcomes among adults treated for childhood cancer.” Â Jama Â 309.22 (2013): 2371-2381.
Espinoza, Sara E., and Linda P. Fried. “Risk factors for frailty in the older adult.” Â Clinical Geriatrics Â 15.6 (2007): 37.
Xue, Qian-Li. “The frailty syndrome: definition and natural history.” Â Clinics in geriatric medicine Â 27.1 (2011): 1-15.
Park, In-Kyung, Sean J. Morrison, and Michael F. Clarke. “Bmi1, stem cells, and senescence regulation.” Â The Journal of clinical investigation Â 113.2 (2004): 175-179.
Sousa-Victor, Pedro, et al. “Geriatric muscle stem cells switch reversible quiescence into senescence.” Â Nature Â 506.7488 (2014): 316-321.
Stockwell, Brent R., and Xuejun Jiang. “The chemistry and biology of ferroptosis.” Â Cell chemical biology Â 27.4 (2020): 365-375.
Skouta, Rachid, et al. “Ferrostatins inhibit oxidative lipid damage and cell death in diverse disease models.” Â Journal of the American Chemical Society Â 136.12 (2014): 4551-4556.
Miotto, Giovanni, et al. “Insight into the mechanism of ferroptosis inhibition by ferrostatin-1.” Â Redox biology Â 28 (2020): 101328.
Aoshiba K, Tsuji T, Nagai A. Bleomycin induces cellular senescence in alveolar epithelial cells. Eur Respir J. 2003;22(3):436â€43.
PubChem-SID-109450821, Modify Date: May 31, 2019 (May 31, 2019), p. 2, figure.
Kuilman T, Michaloglou C, Mooi WJ, Peeper DS. The essence of senescence. Genes Dev. Nov. 15, 2010;24(22):2463-79. doi: 10.1101/gad.1971610. PMID: 21078816; PMCID: PMC2975923.
Baker, Darren J., et al. “Naturally occurring p16Ink4a-positive cells shorten healthy lifespan.” Â Nature Â 530.7589 (2016): 184-189.
Baker, Darren J., et al. “Clearance of p16Ink4a-positive senescent cells delays ageing-associated disorders.” Â Nature Â 479.7372 (2011): 232-236.
Childs, Bennett G., et al. “Senescent intimal foam cells are deleterious at all stages of atherosclerosis.” Â Science Â 354.6311 (2016): 472-477.
Demaria, Marco, et al. “An essential role for senescent cells in optimal wound healing through secretion of PDGF-AA.” Â Developmental cell Â 31.6 (2014): 722-733.
Masaldan S, Clatworthy SAS, Gamell C, Meggyesy PM, Rigopoulos AT, Haupt S, Haupt Y, Denoyer D, Adlard PA, Bush AI, Cater MA. Iron accumulation in senescent cells is coupled with impaired ferritinophagy and inhibition of ferroptosis. Redox Biol. Apr. 2018;14:100-115. doi: 10.1016/j.redox.2017.08.015. Epub Sep. 1, 2017. PMID: 28888202; PMCID: PMC5596264.
Flor, Amy, et al. “Lipid-derived electrophiles mediate the effects of chemotherapeutic topoisomerase I poisons.” Â Cell chemical biology Â 28.6 (2021): 776-787.
Bae, Eun-Jin, et al. “TNF-Î± promotes Î±-synuclein propagation through stimulation of senescence-associated lysosomal exocytosis.” Â Experimental & Molecular Medicine Â 54.6 (2022): 788-800.
Stockwell, Brent R. “Ferroptosis turns 10: Emerging mechanisms, physiological functions, and therapeutic applications.” Â Cell Â 185.14 (2022): 2401-2421.
Bersuker, Kirill, et al. “The CoQ oxidoreductase FSP1 acts parallel to GPX4 to inhibit ferroptosis.” Â Nature Â 575.7784 (2019): 688-692.

(56) References Cited

OTHER PUBLICATIONS

Seibt, Tobias M., Bettina Proneth, and Marcus Conrad. "Role of GPX4 in ferroptosis and its pharmacological implication." Â Free Radical Biology and Medicine Â 133 (2019): 144-152.
Poltorack, Carson D., and Scott J. Dixon. "Understanding the role of cysteine in ferroptosis: progress & paradoxes." Â The FEBS journal Â 289.2 (2022): 374-385.
Cozza, Giorgio, et al. "Glutathione peroxidase 4-catalyzed reduction of lipid hydroperoxides in membranes: The polar head of membrane phospholipids binds the enzyme and addresses the fatty acid hydroperoxide group toward the redox center." Â Free Radical Biology and Medicine Â 112 (2017): 1-11.
Labrecque, Courtney L., and Brian Fuglestad. "Electrostatic drivers of GPx4 interactions with membrane, lipids, and DNA." Â Biochemistry Â 60.37 (2021): 2761-2772.
Viswanathan, Vasanthi S., et al. "Dependency of a therapy-resistant state of cancer cells on a lipid peroxidase pathway." Â Nature Â 547.7664 (2017): 453-457.
Liu, Hengrui, Stuart L. Schreiber, and Brent R. Stockwell. "Targeting dependency on the GPX4 lipid peroxide repair pathway for cancer therapy." Â Biochemistry Â 57.14 (2018): 2059-2060.
Pennesi, Mark E., Martha Neuringer, and Robert J. Courtney. "Animal models of age related macular degeneration." Â Molecular aspects of medicine Â 33.4 (2012): 487-509.
Zeiss, C. J. "Animals as models of age-related macular degeneration: an imperfect measure of the truth." Â Veterinary pathology Â 47.3 (2010): 396-413.
Chavala, Sai H., et al. "Retinal angiogenesis suppression through small molecule activation of p53." Â The Journal of clinical investigation Â 123.10 (2013): 4170-4181.
Peng, Ruoqi, et al. "Bleomycin induces molecular changes directly relevant to idiopathic pulmonary fibrosis: a model for â€œactiveâ€ disease." Â PloS one Â 8.4 (2013): e59348.
Mouratis, Marios A., and Vassilis Aidinis. "Modeling pulmonary fibrosis with bleomycin." Â Current opinion in pulmonary medicine Â 17.5 (2011): 355-361.
Campisi, Judith. "Aging, cellular senescence, and cancer." Â Annual review of physiology Â 75.1 (2013): 685-705.
Naylor, R. M., D. J. Baker, and J. M. Van Deursen. "Senescent cells: a novel therapeutic target for aging and age Â €related diseases." Â Clinical Pharmacology & Therapeutics â 93.1 (2013): 105-116.
Katzman, Wendy B., et al. "Age-related hyperkyphosis: its causes, consequences, and management." Â Journal of Orthopaedic & Sports Physical Therapy Â 40.6 (2010): 352-360.
De Boer, Jan, et al. "Premature aging in mice deficient in DNA repair and transcription." Â Science Â 296.5571 (2002): 1276-1279.
Shapiro, Steven D., and Edward P. Ingenito. "The pathogenesis of chronic obstructive pulmonary disease: advances in the past 100 years." Â American journal of respiratory cell and molecular biology Â 32.5 (2005): 367-372.
Minagawa, Shunsuke, et al. "Accelerated epithelial cell senescence in IPF and the inhibitory role of SIRT6 in TGF- Î²-induced senescence of human bronchial epithelial cells." Â American Journal of Physiology-Lung Cellular and Molecular Physiology Â 300.3 (2011): L391-L401.
Alder, Jonathan K., et al. "Short telomeres are a risk factor for idiopathic pulmonary fibrosis." Â Proceedings of the National Academy of Sciences Â 105.35 (2008): 13051-13056.
Fischer, Bernard M., et al. "Increased expression of senescence markers in cystic fibrosis airways." Â American Journal of Physiology-Lung Cellular and Molecular Physiology Â 304.6 (2013): L394-L400.
Hendel, A., et al. "Granzymes in age-related cardiovascular and pulmonary diseases." Â Cell Death & Differentiation Â 17.4 (2010): 596-606.
Chung, Hae Young, et al. "Molecular inflammation: underpinnings of aging and age-related diseases." Â Ageing research reviews Â 8.1 (2009): 18-30.
Demedts, Ingel K., et al. "Role of apoptosis in the pathogenesis of COPD and pulmonary emphysema." Â Respiratory research Â 7 (2006): 1-10.
Cohen, G. "The pathobiology of Parkinson's disease: biochemical aspects of dopamine neuron senescence." Â Journal of neural transmission. Supplementum Â 19 (1983): 89-103.
Hebert, Liesi E., et al. "Alzheimer disease in the US population: prevalence estimates using the 2000 census." Â Archives of neurology Â 60.8 (2003): 1119-1122.
Holcomb, Leigh, et al. "Accelerated Alzheimer-type phenotype in transgenic mice carrying both mutant amyloid precursor protein and presenilin 1 transgenes." Â Nature medicine Â 4.1 (1998): 97-100.
Borchelt, David R., et al. "Accelerated amyloid deposition in the brains of transgenic mice coexpressing mutant presenilin 1 and amyloid precursor proteins." Â Neuron Â 19.4 (1997): 939-945.
Dickson DW, Farlo J, Davies P, Crystal H, Fuld P, Yen SH. Alzheimer's disease. A double-labeling immunohistochemical study of senile plaques. Am J Pathol. Jul. 1988;132(1):86-101. PMID: 2456021; PMCID: PMC1880629.
Skovronsky, Daniel M., et al. "In vivo detection of amyloid plaques in a mouse model of Alzheimer's disease." Â Proceedings of the National Academy of Sciences Â 97.13 (2000): 7609-7614.
Klunk, William E., et al. "Imaging brain amyloid in Alzheimer's disease with Pittsburgh Compoundâ€B." Â Annals of Neurology: Official Journal of the American Neurological Association and the Child Neurology Society Â 55.3 (2004): 306-319.
Higuchi, Makoto, et al. "19F and 1H MRI detection of amyloid Î² plaques in vivo." Â Nature neuroscience Â 8.4 (2005): 527-533.
Wengenack, Thomas M., Geoffry L. Curran, and Joseph F. Poduslo. "Targeting Alzheimer amyloid plaques in vivo." Â Nature biotechnology Â 18.8 (2000): 868-872.
Nagele, Robert G., et al. "Contribution of glial cells to the development of amyloid plaques in Alzheimerâ€™s disease." Â Neurobiology of aging Â 25.5 (2004): 663-674.
Mandybur, T. I., and C. C. Chuirazzi. "Astrocytes and the plaques of Alzheimer's disease." Â Neurology Â 40.4 (1990): 635-635.
Liang, Bin, et al. "Calpain activation promotes BACE1 expression, amyloid precursor protein processing, and amyloid plaque formation in a transgenic mouse model of Alzheimer disease." Â Journal of Biological Chemistry Â 285.36 (2010): 27737-27744.
Go Ìˆtz, Ju Ìˆrgen, et al. "Tau filament formation in transgenic mice expressing P301L tau." Â Journal of Biological Chemistry Â 276.1 (2001): 529-534.

(56) References Cited

OTHER PUBLICATIONS

Ishihara, Takeshi, et al. "Age-dependent emergence and progression of a tauopathy in transgenic mice overexpressing the shortest human tau isoform." Â Neuron Â 24.3 (1999): 751-762.
Pepeu, Giancarlo. "Mild cognitive impairment: animal models." Â Dialogues in clinical neuroscience Â 6.4 (2004): 369-377.
Rich, Mark M., et al. "Reduced endplate currents underlie motor unit dysfunction in canine motor neuron disease." Â Journal of neurophysiology Â 88.6 (2002): 3293-3304.
Appel, Stanley H., et al. "Immunoglobulins from animal models of motor neuron disease and from human amyotrophic lateral sclerosis patients passively transfer physiological abnormalities to the neuromuscular junction." Â Proceedings of the National Academy of Sciences Â 88.2 (1991): 647-651.

* cited by examiner

GPX4 INHIBITORS AND SENOLYTIC COMPOUNDS AND USES THEREOF

CROSS REFERENCE TO RELATED APPLICATIONS

This application is a continuation of U.S. patent application Ser. No. 18/678,791, filed May 30, 2024, which claims priority to U.S. Provisional Application Ser. Nos. 63/505,128, 63/567,749 and 63/572,605, filed May 31, 2023, Mar. 20, 2024 and Apr. 1, 2024, respectively under 35 U.S.C. § 119 (e) which are herein incorporated by reference in their entirety for all purposes.

TECHNICAL FIELD

The present invention relates to compounds that kill senescent cells i.e., senolytic compounds and compounds which inhibit GPX4. The present invention also provides compounds and methods for treating senescence-associated diseases or disorders, and compounds and methods for treating diseases or disorders impacted by GPX4.

BACKGROUND

Senescence is a cellular program that imposes a stable arrest on damaged or old cells to prevent replication of these cells. As well as growth arrest, senescent cells undergo profound phenotypic changes that include chromatin reorganization, increase of beta-galactosidase activity (referred to as senescence-associated β-galactosidase or SA-β-Gal) and secretion of multiple factors, mainly pro-inflammatory, that are collectively referred to as the senescence-associated secretory phenotype (SASP).

Replicative senescence is activated upon serial passage of cells in culture (or as cells become older in an organism). Senescence is also induced by, for example, oncogene activation, irradiation and exposure to chemotherapeutic drugs. In addition, there are several drugs, the prototypic example being CDK4/CDK6 inhibitors such as Palbociclib, which induce senescence.

The stable growth arrest characteristic of senescence is implemented by the activation of the p16/Rb and p53/p21 pathways. The cyclin-dependent kinase inhibitors p16/NK4$^{a}$ and p21Cip1 inhibit CDK activity, resulting in Rb hypophosphorylation and G1 growth arrest (Kuilman et al., Genes Dev 2010 24, 2453-2479). Moreover, p16$^{INK4a}$ is specifically induced during senescence and used to identify senescent cells alone or in combination with other markers such as SA-β-Gal activity, formation of senescence-associated heterochromatin foci (SAHF) and others.

Senescent cells accumulate during age and are associated with many diseases, including cancer, fibrosis and many age-related pathologies. Recent evidence suggests that senescent cells are detrimental in multiple pathologies and their elimination confers many advantages, ameliorating multiple pathologies and increasing lifespan.

Senescent cells are present in many pre-neoplastic lesions, fibrotic tissues (e.g., in the liver, kidney, heart, pancreas) and old tissues. Senescent cells are also associated with a long list of other pathologies including neurological (e.g., brain aneurysm, Alzheimer's and Parkinson), pulmonary (e.g., idiopathic pulmonary fibrosis, chronic obstructive pulmonary disease and cystic fibrosis), ophthalmological (e.g., cataracts, glaucoma, macular degeneration), musculoskeletal (e.g., sarcopenia, disc degeneration, osteoarthritis), cardiovascular (e.g. atherosclerosis, cardiac fibrosis, aorta aneurysm), renal (e.g., kidney disease, transplant complications) and others such as diabetes, mucositis, hypertension and osteomyelofibrosis (OMF). While senescent cells have a protective role against cancer and limit most types of fibrosis, the accumulation of senescent cells during ageing and many other diseases is believed to be detrimental.

Evidence for the many detrimental effects of senescent cells (and the benefits caused by their selective elimination) was provided by a series of studies from the van Deursen lab (Baker et al., Nature 2016 530, 184-189; Baker et al., Nature 2011 479, 232-236; Childs et al., Science 2016 354, 472-477). These studies used transgenic mice (INK4-ATTAC mice) that express an inducible fusion protein specifically on senescent cells (taking advantage of the promoter of p16$^{Ink4a}$). Activation of this fusion protein, by addition of a drug that triggers its dimerization, results in the selective death of senescent cells.

The clearance of senescent cells increases lifespan by attenuating multiple age-related pathologies (Baker et al., Nature 2016 530, 184-189; Baker et al., Nature 2011 479, 232-236; Childs et al., 2016 Science 354, 472-477) by use of the above mice model. Clearance of senescent cells delayed tumorigenesis, and attenuated cataract formation, atherosclerosis and the age-related deterioration of kidney, fat and heart amongst other organs. The results obtained with INK4-ATTAC mice have been replicated in part in a different mouse model in which a tk transgene is expressed in senescent cells (3MR mice), allowing for their selective elimination upon ganciclovir treatment (Demaria et al., Dev Cell 2014 31, 722-733). Moreover, the elimination of senescent cells in chemotherapy reduced cancer recurrence and the side effects associated with chemotherapy. Importantly, the elimination of senescent cells has no side effects besides delaying wound healing if the senescent cells are eliminated during the healing process (Baker et al., Nature 2016 530, 184-189; Demaria et al., Dev Cell 2014 31, 722-733). However, the unifying prevalent hypothesis is that (pro-inflammatory) factors secreted by senescent cells hamper tissue homeostasis. This suggests that common mechanisms, mediated by senescent cells, could be responsible for the effects of many age-related pathologies.

Proof-of-concept studies have led to the identification of compounds that can selectively eliminate senescent cells (so-called "senolytics"). Several senolytic compounds have been identified to date, including dasatinib and quercetin, piperlongumine and Bcl2-family inhibitors such as ABT-263 and ABT-737. Currently Bc12 family inhibitors are the most promising senolytics, having been shown to kill a range of senescent cells in vivo, with reproducible effects in transgenic mice. Bcl2 inhibitors were initially developed as therapies for lymphoma. ABT-737 is a small molecule inhibitor of BCL-2, BCL-XL and BCL-w but has low solubility and oral bioavailability. ABT-263 inhibits the same molecules and is better suited for use in vivo but causes significant thrombocytopenia as a side-effect.

Iron accumulation is another indication which has been observed in a number of senescent cell conditions. For example, replicative and stress-induced senescent cell models generated in vitro displayed an up to thirty-fold increase in intracellular iron levels (Killea et al., Ann. N.Y. Acad. Sci. 2004, 1019:365-367; and Masaldan et al., Redox Biol. 2018 100-115). Senescent cells were shown to upregulate the expression of the transferrin receptor and ferritin subunits, which might contribute to the observed accumulation of high levels of ferritin-bound iron in lysosomes (Masaldan et al., Redox Biol. 2018, 100-115).

A main source of oxidative damage to cellular components are reactive oxygen species (ROS) and free radicals generated by the respiration chain as byproducts and ferrous iron that react via the Fenton reaction to produce oxidizing intermediates ($Fe_2^+ + H_2O_2 \rightarrow Fe_3^+ + \cdot OH + OH—$). In agreement with this, senescent cells are reported to accumulate highly oxidized and covalently cross-linked aggregates such as lipofuscin and neurofibrillary tangles (Flor et al., Cell Death Disc. 2017 3:17075; Bae et al., Exp Mol Med. 2022, 54 (6): 788-800; and Dekhrodi et al., Nat. Aging 2021 (1) 12:11107-1116). Furthermore, ferrous iron and a source of reducing equivalents can react with a bis-allylic hydrogen on a polyunsaturated lipid, generating a carbon-centered radical on the lipid chain, which can lead to a series of propagation and chain-branching reactions. Accumulation of lipid peroxides at cellular membranes can ultimately result in membrane permeabilization and cell death and has been described as a specific form of oxidative non-apoptotic cell death referred to as "ferroptosis" (Stockwell, Cell 2022 185 (14): 2401-2421).

Based on present evidence, biochemical events of lipid peroxidation represent a controlled biological process that involves oxygen, membrane phospholipids, ferrous iron, glutathione (GSH), GSH-dependent lipid hydroperoxidase glutathione peroxidase 4 (GPX4), α-tocopherol and coenzyme Q10 (CoQ10) (Bersuker et al., Nature 2019 575:688-692; Seibt et al., Free Radic Biol Med. 2019 133:133-144; and Polotrack et al., FEBS J. 2022 289*2): 374-385). In particular, glutathione peroxidase 4 (GPX4) has been established as a critical enzymatic regulator of iron-dependent lipid peroxidation and ferroptosis (Malorino et al., Antioxid Redox Signal. 2018 29 (1): 61-74). GPX4 contains a selenocysteine glutamine-tryptophan catalytic triad that reduces hydroperoxides to non-toxic alcohols. Different from other glutathione peroxidase family members, GPX4 is associated with membranes, where it reduces phospholipid hydroperoxides to phospholipid hydroxyls, thereby protecting cellular membranes from oxidative damage and negatively regulating ferroptosis (Cozza et al., Free Radic Biol Med. 2017 112:1-11; and Lebrecque et al., Biochemistry 2021 60 (37): 2761-2772).

Ferroptosis acts as a natural tumor suppressive and immune surveillance mechanism and can be induced by agents which bind to GPX4. Induction of ferroptosis by selectively inhibiting GPX4 can selectively target cancer cells including cancers with mesenchymal features and multiple therapy resistance (Viswananthan et al., Nature, 2017, 547:453-457; Hangauer et al., Nature, 2017, 561:247-250; and Lui et al., Biochemistry 2018, 57, 14, 2059-2060).

Accordingly, there is a need to identify more compounds, and classes of compounds with senolytic properties and/or compounds which inhibit GPX-4.

SUMMARY

In one aspect, a compound of Formula (I) which satisfies these and other needs is provided:

(I)

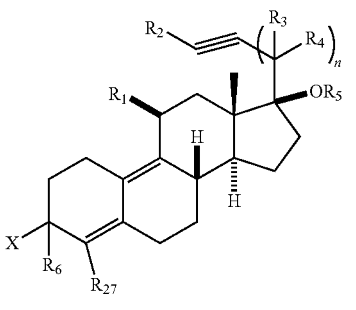

or pharmaceutically acceptable salts, hydrates or solvates thereof where $R_1$ is —$OR_{36}$, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl; $R_2$ is —H, —CN, —$CO_2R_7$, —$CONR_8R_9$, alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl; each $R_3$ and $R_4$ are independently, H, —F or alkyl; n is 1 or 2; Rs is —H, —$CO_2R_{10}$, —$C(O)R_{11}$, —$CONR_{12}R_{13}$, alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl; $R_6$ is —H, alkyl, substituted alkyl, alkenyl, substituted alkenyl, alkynyl, substituted alkynyl, aryl, substituted aryl, arylalkyl, substituted arylalkyl, arylalkenyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, substituted arylalkenyl, arylalkynyl, substituted arylalkynyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl or is absent when X is =O or =$NR_{14}$; $R_{27}$ is hydrogen, halo, alkyl, substituted alkyl, heteroalkyl, substituted heteroalkyl, —$NR_{28}R_{29}$, —$NCONR_{30}R_{31}$, —$CONR_{32}R_{33}$, —$CO_2R_{34}$, —$NCO_2R_{35}$; X is =O, =$NR_{14}$ or —$OR_{15}$; $R_{14}$ is —$OR_{16}$, —$NR_{17}R_{18}$ or —$N^+R^{40}R_{41}R_{42}$; $R_7$-$R_{10}$, $R_{12}$, $R_{13}$, $R_{15}$ and $R_{28}$-$R_{36}$ are independently —H, alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl or optionally $R_8$ and $R_9$, $R_{12}$ and $R_{13}$, $R_{28}$ and $R_{29}$, $R_{30}$ and $R_{31}$, $R_{32}$ and $R_{33}$ together with the atoms to which they are attached from a cycloheteroalkyl ring or a substituted cycloheteroalkyl ring; $R_{11}$ is alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl; $R_{16}$ is —H, alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl, substituted heteroarylalkynyl or is a carbohydrate derivative; $R_{17}$ and $R_{18}$ are independently —H, alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl, substituted heteroarylalkynyl or carbohydrate derivative, $R_{19}CO$—, $R_{20}R_{21}NCO$—, $R_{22}OCO$— or $R_{23}SO_2$—, provided that any substituted group is optionally substituted with a carbohydrate derivative and that both $R_{17}$ and $R_{18}$ are not $R_{19}CO$—, $R_{21}R_{20}NCO$—, $R_{22}OCO$— or $R_{23}SO_2$— or any combination thereof; $R_{19}$ is alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl, substituted heteroarylalkynyl or a carbohydrate derivative or optionally $R_{19}$ and $R_{17}$ together with the atoms to which they are attached form a cycloheteroalkyl ring or substituted cycloheteroalkyl ring provided that any substituted group is optionally substituted with a carbohydrate derivative; $R_{20}$ and $R_{21}$ are independently —H, alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl or a carbohydrate derivative or optionally $R_{20}$ and $R_{17}$ together with the atoms to which they are attached form a cycloheteroalkyl or substituted cycloheteroalkyl ring optionally substituted with ═O or optionally $R_{20}$ and $R_{21}$ together with the atoms to which they are attached form a cycloheteroalkyl or substituted cycloheteroalkyl ring provided that any substituted group is optionally substituted with a carbohydrate derivative; $R_{22}$ is alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl, substituted heteroarylalkynyl or a carbohydrate derivative or optionally $R_{22}$ and $R_{17}$ together with the atoms to which they are attached form a cycloheteroalkyl ring or substituted cycloheteroalkyl ring provided that any substituted group is optionally substituted with a carbohydrate derivative; and $R_{23}$ is alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl provided that any substituted group is optionally substituted with a carbohydrate derivative or optionally $R_{23}$ and $R_{17}$ together with the atoms to which they are attached form a cycloheteroalkyl ring or substituted cycloheteroalkyl ring provided that any substituted group is optionally substituted with a carbohydrate derivative; and $R^{40}$, $R_{41}$ and $R_{42}$ are alkyl.

In another aspect, a compound of Formula (II) which also satisfies these and other needs is provided:

(II)

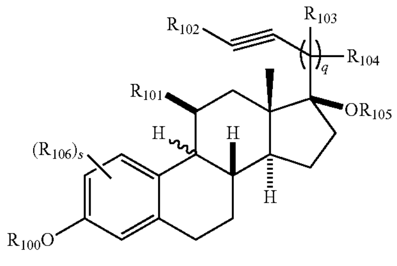

or pharmaceutically acceptable salts, N-oxides, hydrates or solvates thereof where $R_{100}$ is —H, —$CO_2R_{107}$, —C(O)$R_{108}$, —$CONR_{109}R_{110}$, alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl; $R_{101}$ is —$OR_{130}$, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl; $R_{102}$ is —H, —CN, —$CO_2R_{111}$, —$CONR_{112}R_{113}$, alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl; each $R_{103}$ and $R_{104}$ are independently, H, —F or alkyl provided that at least one of $R_{103}$ and $R_{104}$ is —F; q is 1 or 2; $R_{105}$ is —H, —$CO_2R_{114}$, —$C(O)R_{115}$, —$CONR_{116}R_{117}$, alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl; each $R_{106}$ is independently, —H, —$CO_2R_{118}$, —$C(O)R_{119}$, —$CONR_{120}R_{121}$, —$OR_{122}$, —$NR_{123}R_{124}$, —$NHR_{125}R_{126}C(O)R_{127}$, —$SO_2NR_{128}R_{129}$, alkyl, substituted alkyl, alkenyl, substituted alkenyl, alkynyl, substituted alkynyl, aryl, substituted aryl, arylalkyl, substituted arylalkyl, arylalkenyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, substituted arylalkenyl, arylalkynyl, substituted arylalkynyl, halo, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl; s is 0, 1 or 2; $R_{109}$-$R_{113}$, $R_{116}$-$R_{118}$, $R_{120}$-$R_{126}$, $R_{128}$-$R_{130}$ are independently, —H, alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl; $R_{107}$, $R_{108}$, $R_{114}$, $R_{115}$, $R_{116}$ and $R_{127}$ are independently alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl.

Also provided are derivatives, including salts, esters, enol ethers, enol esters, solvates, hydrates, metabolites and prodrugs of the compounds described herein. Further provided are pharmaceutical compositions which include the compounds provided herein and a pharmaceutically acceptable vehicle.

In still another aspect, methods of treating, preventing, or ameliorating symptoms of medical disorders such as, for example, senescence-associated diseases or disorders, and diseases or disorders impacted by GPX4 are provided.

DETAILED DESCRIPTION

Definitions

Figure 1:
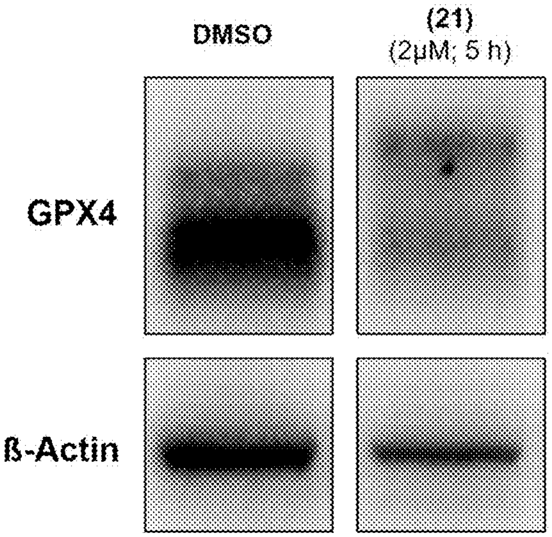
FIG. 1 illustrates electrophoretic gel mobility shift of GPX4 protein in response to treatment of cultured cell with compound 21.

Unless defined otherwise, all technical and scientific terms used herein have the same meaning as is commonly understood by one of ordinary skill in the art to which this invention belongs. If a plurality of definitions for a term exist herein, those in this section prevail unless stated otherwise.

As used herein, and unless otherwise specified, the terms "about" and "approximately," when used in connection with a property with a numeric value or range of values indicate that the value or range of values may deviate to an extent deemed reasonable to one of ordinary skill in the art while still describing the particular property. Specifically, the terms "about" and "approximately," when used in this context, indicate that the numeric value or range of values may vary by 5%, 4%, 3%, 2%, 1%, 0.9%, 0.8%, 0.7%, 0.6%, 0.5%, 0.4%, 0.3%, 0.2% or 0.1% of the recited value or range of values. Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

A dash ("-") that is not between two letters or symbols is used to indicate a point of attachment for a substituent. For example, $—C(O)NH_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms. It should be understood that u to v carbons includes u+1 to v, u+2 to v, u+3 to v, etc. carbons, u+1 to u+3 to v, u+1 to u+4 to v, u+2 to u+4 to v, etc. and cover all possible permutation of u and v.

"A feature of aging" as used herein, includes, but is not limited to, systemic decline of the immune system, muscle atrophy and decreased muscle strength, decreased skin elasticity, delayed wound healing, retinal atrophy, reduced lens transparency, reduced hearing, osteoporosis, sarcopenia, hair graying, skin wrinkling, poor vision, frailty, and cognitive impairment.

"Age-related disease or condition" as used herein includes, but is not limited to, a degenerative disease or a function-decreasing disorder such as Alzheimer's disease, Parkinson's disease, cataracts, macular degeneration, glaucoma, frailty, muscle weakness, cognitive impairment, atherosclerosis, acute coronary syndrome, myocardial infarction, stroke, hypertension, idiopathic pulmonary fibrosis (IPF), chronic obstructive pulmonary disease (COPD), osteoarthritis, type 2 diabetes, obesity, fat dysfunction, coronary artery disease, cerebrovascular disease, periodontal disease, cancer treatment-related disability such as atrophy and fibrosis in various tissues, brain and heart injury, and therapy-related myelodysplastic syndromes, and diseases associated with accelerated aging and/or defects in DNA damage repair and telomere maintenance such as progeroid syndromes (i.e. Hutchinson-Gilford progeria syndrome, Werner syndrome, Bloom syndrome, Rothmund-Thomson Syndrome, Cockayne syndrome, xeroderma pigmentosum, trichothiodystrophy, combined xeroderma pigmentosum-Cockayne syndrome, restrictive dermopathy), ataxia telangiectasia, Fanconi anemia, Friedreich's ataxia, dyskeratosis congenital, aplastic anemia, and others.

"Alkyl," by itself or as part of another substituent, refers to a saturated, branched, or straight-chain monovalent hydrocarbon radical derived by the removal of one hydrogen atom from a single carbon atom of a parent alkane. Typical alkyl groups include, but are not limited to, methyl; ethyl; propyls such as propan-1-yl, propan-2-yl, etc.; butyls such as butan-1-yl, butan-2-yl, 2-methyl-propan-1-yl, 2-methyl-propan-2-yl, etc.; and the like. In some aspects, an alkyl group comprises from 1 to 20 carbon atoms ($C_1$-$C_{20}$ alkyl). In other aspects, an alkyl group comprises from 1 to 10 carbon atoms ($C_1$-$C_{10}$ alkyl). In still other aspects, an alkyl group comprises from 1 to 6 carbon atoms ($C_1$-$C_6$ alkyl).

"Alkenyl," by itself or as part of another substituent, refers to an unsaturated branched, straight-chain having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, etc.; and the like. In some aspects, an alkenyl group comprises from 2 to 20 carbon atoms ($C_2$-$C_{20}$ alkenyl). In other aspects, an alkenyl group comprises from 2 to 10 carbon atoms ($C_2$-$C_{10}$ alkenyl). In still other aspects, an alkenyl group comprises from 2 to 6 carbon atoms ($C_2$-$C_6$ alkenyl).

"Alkynyl," by itself or as part of another substituent refers to an unsaturated branched, straight-chain having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In some aspects, an alkynyl group comprises from 2 to 20 carbon atoms ($C_2$-$C_{20}$ alkynyl). In other aspects, an alkynyl group comprises from 2 to 10 carbon atoms ($C_2$-$C_{10}$ alkynyl). In still other aspects, an alkynyl group comprises from 2 to 6 carbon atoms ($C_2$-$C_6$ alkynyl).

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, trinaphthalene and the like. In some aspects, an aryl group comprises from 6 to 30 carbon atoms ($C_6$-$C_{30}$ aryl). In other aspects, an aryl group comprises from 6 to 20 carbon atoms ($C_6$-$C_{20}$ aryl). In still other aspects, an aryl group comprises from 6 to 15 carbon atoms ($C_6$-$C_{15}$ aryl). In still other aspects, an aryl group comprises from 6 to 10 carbon atoms ($C_6$-$C_{10}$ aryl).

"Arylalkyl," by itself or as part of another substituent, refers to an acyclic alkyl group in which one of the hydrogen atoms bonded to a carbon atom, typically a terminal or $sp^3$ carbon atom, is replaced with an aryl group as, as defined herein. Typical arylalkyl groups include, but are not limited to, benzyl, 2-phenylethan-1-yl, 1-phenylethen-1-yl, naphthylmethyl, 2-naphthylethan-1-yl, 1-naphthylethen-1-yl, naphthobenzyl, 2-naphthophenylethan-1-yl and the like. In some aspects, an arylalkyl group is ($C_7$-$C_{40}$) arylalkyl, e.g., the alkyl moiety of the arylalkyl group is ($C_1$-$C_{10}$) alkyl and the aryl moiety is ($C_6$-$C_{30}$) aryl. In other aspects, an arylalkyl group is ($C_7$-$C_{30}$) arylalkyl, e.g., the alkyl moiety of the arylalkyl group is ($C_1$-$C_{10}$) alkyl and the aryl moiety is ($C_6$-$C_{20}$) aryl. In other aspects, an arylalkyl group is ($C_7$-$C_{20}$) arylalkyl, e.g., the alkyl moiety of the arylalkyl group is ($C_1$-$C_8$) alkyl and the aryl moiety is ($C_6$-$C_{12}$) aryl. In still other aspects, an arylalkyl group is ($C_7$-$C_{15}$) arylalkyl, e.g., the alkyl moiety of the arylalkyl group is ($C_1$-$C_5$) alkyl and the aryl moiety is ($C_6$-$C_{10}$) aryl.

"Arylalkenyl," by itself or as part of another substituent, refers to an acyclic alkenyl group in which one of the hydrogen atoms bonded to a carbon atom, is replaced with an aryl group as, as defined herein. In some aspects, an arylalkenyl group is ($C_8$-$C_{40}$) arylalkenyl, e.g., the alkenyl moiety of the arylalkenyl group is ($C_2$-$C_{10}$) alkenyl and the aryl moiety is ($C_6$-$C_{30}$) aryl. In other aspects, an arylalkenyl group is ($C_8$-$C_{30}$) arylalkenyl, e.g., the alkenyl moiety of the arylalkenyl group is ($C_2$-$C_{10}$) alkenyl and the aryl moiety is ($C_8$-$C_{20}$) aryl. In other aspects, an arylalkenyl group is ($C_8$-$C_{20}$) arylalkenyl, e.g., the alkenyl moiety of the arylalkenyl group is ($C_2$-$C_8$) alkenyl and the aryl moiety is ($C_6$-$C_{12}$) aryl. In still other aspects, an arylalkenyl group is ($C_8$-$C_{15}$) arylalkenyl, e.g., the alkenyl moiety of the arylalkenyl group is ($C_2$-$C_5$) alkenyl and the aryl moiety is ($C_6$-$C_{10}$) aryl.

"Arylalkynyl," by itself or as part of another substituent, refers to an acyclic alkynyl group in which one of the hydrogen atoms bonded to a carbon atom, is replaced with an aryl group as, as defined herein. In some aspects, an arylalkynyl group is ($C_8$-$C_{40}$) arylalkynyl, e.g., the alkynyl moiety of the arylalkynyl group is ($C_2$-$C_{10}$) alkynyl and the aryl moiety is ($C_6$-$C_{30}$) aryl. In other aspects, an arylalkynyl group is ($C_8$-$C_{30}$) arylalkynyl, e.g., the alkynyl moiety of the arylalkynyl group is ($C_2$-$C_{10}$) alkynyl and the aryl moiety is ($C_6$-$C_{20}$) aryl. In other aspects, an arylalkynyl group is ($C_8$-$C_{20}$) arylalkynyl, e.g., the alkynyl moiety of the arylalkenyl group is ($C_2$-$C_8$) alkynyl and the aryl moiety is ($C_6$-$C_{12}$) aryl. In still other aspects, an arylalkynyl group is ($C_8$-$C_{15}$) arylalkynyl, e.g., the alkynyl moiety of the arylalkynyl group is ($C_2$-$C_5$) alkynyl and the aryl moiety is ($C_6$-$C_{10}$) aryl.

"Carbohydrate derivative," refers to carbohydrates, of general formula $C_nH_{2n}O_n$ attached to a group of a chemical compound. In some embodiments a carbohydrate derivative typically contain five or six carbon atoms. In other embodiments, a carbohydrate derivative is a monosaccharide (e.g., glucose, fructose, galactose, ribose,). In still other embodiments, a carbohydrate derivative includes disaccharides (e.g., lactose, sucrose, maltose, cellobiose, chitobiose, gentobiose, etc.). In still other embodiments, a carbohydrate derivative includes oligosaccharides (e.g., oligofructose, oligogalactose, raffinose, plantose, veracose, etc.). In still other embodiments, a carbohydrate derivative includes polysaccharides (e.g., cellulose, amylose, starch, chitin, pectins, galactogen, etc.). In still other embodiments, a carbohydrate derivative includes protected carbohydrates, such as for example, esters (e.g., acetates or benzoates, etc.), silyl derivatives or carbohydrates protected with any other known other alcohol protecting groups.

"Compounds," refers to compounds encompassed by structural formulae disclosed herein and includes any specific compounds within these formulae whose structure is disclosed herein. Compounds may be identified either by their chemical structure and/or chemical name. The chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass the stereoisomerically pure form depicted in the structure (e.g., geometrically pure, enantiomerically pure or diastereomerically pure). The chemical structures depicted herein also encompass the enantiomeric and stereoisomeric derivatives of the compound depicted. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds disclosed herein include, but are not limited to, $^2H$, $^3H$, $^{11}C$, $^{13}C$, $^{14}C$, $^{15}N$, $^{18}O$, $^{17}O$, etc. Compounds may exist in unsolvated forms as well as solvated forms, including hydrated forms. In general, compounds may be hydrated or solvated. Certain compounds may exist in multiple crystalline or amorphous forms. In general, all physical forms are equivalent for the uses contemplated herein and are intended to be within the scope of the present disclosure. Further, it should be understood, when partial structures of the compounds are illustrated, that brackets indicate the point of attachment of the partial structure to the rest of the molecule.

"Cycloalkyl," by itself or as part of another substituent, refers to a saturated cyclic monovalent hydrocarbon radical derived by the removal of one hydrogen atom from a single carbon atom of a parent cycloalkane. Typical cycloalkyl groups include, but are not limited to, cyclopropyl, cyclobutyl, cyclopentyl cyclopentenyl; etc.; and the like. In some aspects, a cycloalkyl group comprises from 3 to 20 carbon atoms ($C_3$-$C_{15}$ cycloalkyl). In other aspects, a cycloalkyl group comprises from 3 to 10 carbon atoms ($C_3$-$C_{10}$ cycloalkyl). In still other aspects, a cycloalkyl group comprises from 3 to 8 carbon atoms ($C_3$-$C_8$ cycloalkyl). The term "cyclic monovalent hydrocarbon radical" also includes multicyclic hydrocarbon ring systems having a single radical and between 5 and 12 carbon atoms. Exemplary multicyclic cycloalkyl rings include, for example, norbornyl, pinyl, and adamantyl.

"Cycloalkenyl," by itself or as part of another substituent, refers to an unsaturated cyclic monovalent hydrocarbon radical derived by the removal of one hydrogen atom from a single carbon atom of a parent cycloalkene. Typical cycloalkenyl groups include, but are not limited to, cyclopropenyl, cyclobutenyl, cyclopentenyl; etc.; and the like. In some aspects, a cycloalkenyl group comprises from 3 to 20 carbon atoms ($C_3$-$C_{20}$ cycloalkenyl). In other aspects, a cycloalkenyl group comprises from 3 to 10 carbon atoms ($C_3$-$C_{10}$ cycloalkenyl). In still other aspects, a cycloalkenyl group comprises from 3 to 8 carbon atoms ($C_3$-$C_8$ cycloalkenyl).

"Cycloheteroalkyl," by itself or as part of another substituent, refers to a cycloalkyl group as defined herein in which one or more of the carbon atoms (and optionally any associated hydrogen atoms), are each, independently of one another, replaced with the same or different heteroatoms or heteroatomic groups as defined in "heteroalkyl" below. In some aspects, a cycloheteroalkyl group comprises from 3 to 20 carbon and hetero atoms (3-20 cycloheteroalkyl). In other aspects, a cycloheteroalkyl group comprises from 3 to 10 carbon and hetero atoms (3-10 cycloheteroalkyl). In still other aspects, a cycloheteroalkyl group comprises from 3 to 8 carbon and hetero atoms (3-8 cycloheteroalkyl). The term "cyclic monovalent heteroalkyl radical" also includes multicyclic heteroalkyl ring systems having a single radical and between 3 and 12 carbon and at least one hetero atom. Exemplary cycloheteroalkyl groups include, for example, azetidine, pyrrolidine, piperazine, piperidine, morpholine and tetrahydrofuran.

"Cycloheteroalkenyl," by itself or as part of another substituent, refers to a cycloalkenyl group as defined herein in which one or more of the carbon atoms (and optionally any associated hydrogen atoms), are each, independently of one another, replaced with the same or different heteroatoms or heteroatomic groups as defined in "heteroalkenyl" below. In some aspects, a cycloheteroalkenyl group comprises from 3 to 20 carbon and hetero atoms (3-20 cycloheteroalkenyl). In other aspects, a cycloheteroalkenyl group comprises from 3 to 10 carbon and hetero atoms (3-10) cycloheteroalkenyl). In still other aspects, a cycloheteroalkenyl group comprises from 3 to 8 carbon and heteroatoms (3-8 cycloheteroalkenyl). The term "cyclic monovalent heteroalkenyl radical" also includes multicyclic heteroalkenyl ring systems having a single radical and between 2 and 12 carbon and at least one hetero atom.

"DNA-damaging therapy" as used herein, includes, but is not limited to g-irradiation, alkylating agents such as nitrogen mustards (e.g., chlorambucil, cyclophosphamide, ifosfamide, melphalan), nitrosoureas (streptozocin, carmustine, lomustine), alkyl sulfonates (e.g., busulfan), triazines (dacarbazine, temozolomide) and ethylenimines (e.g., thiotepa, altretamine), platinum drugs such as, for example, cisplatin, carboplatin, oxalaplatin, antimetabolites such as, for example, 5-fluorouracil, 6-mercaptopurine, capecitabine, cladribine, clofarabine, cytarabine, floxuridine, fludarabine, gemcitabine, hydroxyurea, methotrexate, pemetrexed, pentostatin, thioguanine, anthracyclines such as, for example, daunorubicin, doxorubicin, epirubicin, idarubicin, anti-tumor antibiotics such as actinomycin-D, bleomycin, mitomycin-C, mitoxantrone, topoisomerase inhibitors such as topoisomerase I inhibitors (e.g., topotecan, irinotecan) and topoisomerase II inhibitors (e.g., etoposide, teniposide, mitoxantrone), mitotic inhibitors such as taxanes (e.g., paclitaxel, docetaxel), epothilones (e.g., ixabepilone), *vinca* alkaloids (e.g., vinblastine, vincristine, vinorelbine) and estramustine.

"Halo," by itself or as part of another substituent refers to a radical —F, —Cl, —Br or —I.

"Heteroalkyl," refer to an alkyl, group, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, $—S(O)_2—$, —S(O)NH—, $—S(O)_2NH—$ and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, —O—S—, $—NR^{501}R^{502}$, =N—N=, —N=N—, $—N=N—NR^{503}R^{404}$, $—PR^{505}—$, $—P(O)_2—$, $—POR^{506}—$, $—O—P(O)_2—$, —SO—, $—SO_2—$, $—SnR^{507}R^{508}$ and the like, where $R^{501}$, $R^{502}$, $R^{503}$, $R^{504}$, $R^{505}$, $R^{506}$, $R^{507}$ and $R^{508}$ are independently hydrogen, alkyl, aryl, substituted aryl, heteroalkyl, heteroaryl or substituted heteroaryl. In some aspects, an heteroalkyl group comprises from 1 to 20 carbon and hetero atoms ($_{1-20}$ heteroalkyl). In other aspects, an heteroalkyl group comprises from 1 to 10 carbon and hetero atoms ($_{1-10}$ heteroalkyl). In still other aspects, an heteroalkyl group comprises from 1 to 6 carbon and hetero atoms ($_{1-6}$ heteroalkyl).

"Heteroalkenyl," refers to an alkenyl group in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, $—S(O)_2—$, —S(O)NH—, $—S(O)_2NH—$ and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, —O—S—, $—NR^{501}R^{502}$, =N—N=, —N=N—, $—N=N—NR^{503}R^{404}$, $—PR^{505}—$, $—P(O)_2—$, $—POR^{506}—$, $—O—P(O)_2—$, —SO—, $—SO_2—$, $—SnR^{507}R^{508}$ and the like, where $R^{501}$, $R^{502}$, $R^{503}$, $R^{504}$, $R^{505}$, $R^{506}$, $R^{507}$ and $R^{508}$ are independently hydrogen, alkyl, aryl, substituted aryl, heteroalkyl, heteroaryl or substituted heteroaryl. In some aspects, an heteroalkenyl group comprises from 1 to 20 carbon and hetero atoms (1-20 heteroalkenyl). In other aspects, an heteroalkenyl group comprises from 1 to 10 carbon and hetero atoms ($_{1-10}$ heteroalkenyl). In still other aspects, an heteroalkenyl group comprises from 1 to 6 carbon and hetero atoms ($_{1-6}$ heteroalkenyl).

"Heteroaryl," by itself or as part of another substituent, refers to a monovalent heteroaromatic radical derived by the removal of one hydrogen atom from a single atom of a parent heteroaromatic ring system, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some aspects, the heteroaryl group comprises from 5 to 20 ring atoms (5-20 membered heteroaryl). In other aspects, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl," by itself or as part of another substituent refers to an acyclic alkyl group in which one of the hydrogen atoms bonded to a carbon atom, typically a terminal or $sp^3$ carbon atom, is replaced with a heteroaryl group. In some aspects, the heteroarylalkyl group is a 6-21 membered heteroarylalkyl, e.g., the alkyl moiety of the heteroarylalkyl is $(C_1-C_6)$ alkyl and the heteroaryl moiety is a 5-15-membered heteroaryl. In other aspects, the heteroarylalkyl is a 6-13 membered heteroarylalkyl, e.g., the alkyl moiety is $(C_1-C_3)$ alkyl and the heteroaryl moiety is a 5-10 membered heteroaryl.

"Heteroarylalkenyl," by itself or as part of another substituent refers to an acyclic alkenyl group in which one of the hydrogen atoms bonded to a carbon atom, is replaced with a heteroaryl group. In some aspects, the heteroarylalkenyl group is a 7-21 membered heteroarylalkenyl, e.g., the alkenyl moiety of the heteroarylalkenyl is $(C_2-C_6)$ alkenyl and the heteroaryl moiety is a 5-15-membered heteroaryl. In other aspects, the heteroarylalkenyl is a 7-13 membered heteroarylalkenyl, e.g., the alkenyl moiety is $(C_2-C_3)$ alkenyl and the heteroaryl moiety is a 5-10 membered heteroaryl.

"Heteroarylalkynyl," by itself or as part of another substituent refers to an acyclic alkenyl group in which one of the hydrogen atoms bonded to a carbon atom, is replaced with a heteroaryl group. In some aspects, the heteroarylalkynyl group is a 7-21 membered heteroarylalkynyl, e.g., the alkynyl moiety of the heteroarylalkynyl is $(C_2-C_6)$ alkynyl and the heteroaryl moiety is a 5-15-membered heteroaryl. In other aspects, the heteroarylalkynyl is a 7-13 membered heteroarylalkynyl, e.g., the alkynyl moiety is ($C_2$-$C_3$) alkynyl and the heteroaryl moiety is a 5-10 membered heteroaryl.

"Hydrates," refers to incorporation of water into to the crystal lattice of a compound described herein, in stoichiometric proportions, resulting in the formation of an adduct. Methods of making hydrates include, but are not limited to, storage in an atmosphere containing water vapor, dosage forms that include water, or routine pharmaceutical processing steps such as, for example, crystallization (i.e., from water or mixed aqueous solvents), lyophilization, wet granulation, aqueous film coating, or spray drying. Hydrates may also be formed, under certain circumstances, from crystalline solvates upon exposure to water vapor, or upon suspension of the anhydrous material in water. Hydrates may also crystallize in more than one form resulting in hydrate polymorphism. See e.g., (Guillory, K., Chapter 5, pp. 202-205 in Polymorphism in Pharmaceutical Solids, (Brittain, H. ed.), Marcel Dekker, Inc., New York, NY, 1999). The above methods for preparing hydrates are well within the ambit of those of skill in the art, are completely conventional and do not require any experimentation beyond what is typical in the art. Hydrates may be characterized and/or analyzed by methods well known to those of skill in the art such as, for example, single crystal X-ray diffraction, X-ray powder diffraction, polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205-208 in Polymorphism in Pharmaceutical Solids, (Brittain, H. ed.), Marcel Dekker, Inc. New York, 1999). In addition, many commercial companies routinely offer services that include preparation and/or characterization of hydrates such as, for example, HOLODIAG, Pharmaparc II, Voie de l'Innovation, 27 100 Val de Reuil, France (http://www.holodiag.com).

"N-oxide," refers to a compound containing an N—O bond with three additional hydrogen or side chains attached to the N, so that there is a positive charge on the nitrogen. The N-oxides of the present disclosure can be synthesized by oxidation procedures well known to those skilled in the a "Parent Aromatic Ring System," refers to an unsaturated cyclic or polycyclic ring system having a conjugated p electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System," refers to a parent aromatic ring system in which one or more carbon atoms (and optionally any associated hydrogen atoms) are each independently replaced with the same or different heteroatom. Typical heteroatoms to replace the carbon atoms include, but are not limited to, N, P, O, S, Si, etc. Specifically included within the definition of "parent heteroaromatic ring system" are fused ring systems in which one or more of the rings are aromatic and one or more of the rings are saturated or unsaturated, such as, for example, benzodioxan, benzofuran, chromane, chromene, indole, indoline, xanthene, etc. Typical parent heteroaromatic ring systems include, but are not limited to, arsindole, carbazole, b-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Pharmaceutically acceptable salt," refers to a salt of a compound which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Preventing," or "prevention," refers to a reduction in risk of acquiring a disease or disorder (i.e., causing at least one of the clinical symptoms of the disease not to develop in a patient that may be exposed to or predisposed to the disease but does not yet experience or display symptoms of the disease). The application of a therapeutic for preventing or prevention of a disease or disorder is known as 'prophylaxis.' In some aspects, the compounds provided herein provide superior prophylaxis because of lower long term side effects over long time periods.

"Prodrug," as used herein, refers to a derivative of a drug molecule that requires a transformation within the body to release the active drug. Prodrugs are frequently, although not necessarily, pharmacologically inactive until converted to the parent drug.

"Promoiety," as used herein, refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group," refers to a grouping of atoms that when attached to a reactive functional group in a molecule masks, reduces or prevents reactivity of the functional group during chemical synthesis. Examples of protecting groups can be found in Green et al., "Protective Groups in Organic Chemistry," (Wiley, $2^{nd}$ ed. 1991) and Harrison et al., "Compendium of Synthetic Organic Methods", Vols. 1-8

(John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Senescence," or "senescent cells," as used herein, refers to a state wherein cells have acquired one or more markers for senescence in response to some cellular stress. Such markers may typically include permanent withdrawal from the cell cycle, the expression of a bioactive secretome of inflammatory factors, altered methylation, senescence-associated heterochromatin foci (SAHF), expression markers for oxidative stress, expression of markers for DNA damage, protein and lipid modifications, morphological features of senescence, altered lysosome/vacuoles and expression of senescence-associated b-galactosidase (Galluzzi et al. (eds.), Cell Senescence: Methods and Protocols, Methods in Molecular Biology, vol. 965, DOI 10.1007/978-1-62703-239-1_4, © Springer Science+Business Media, L L C 2013).

"Senolytic agent," as used herein refers to an agent that "selectively" (preferentially or to a greater degree) destroys, kills, removes, or facilitates selective destruction of senescent cells. In other words, the senolytic agent destroys or kills a senescent cell in a biologically, clinically, and/or statistically significant manner compared with its capability to destroy or kill a non-senescent cell. A senolytic agent is used in an amount and for a time sufficient that selectively kills established senescent cells but is insufficient to kill a non-senescent cell in a clinically significant or biologically significant manner. In certain embodiments, the senolytic agents described herein alter at least one signaling pathway in a manner that induces (i.e., initiates, stimulates, triggers, activates, promotes) and results in death of the senescent cell.

"Solvates," refers to incorporation of solvents into to the crystal lattice of a compound described herein, in stoichiometric proportions, resulting in the formation of an adduct. Methods of making solvates include, but are not limited to, storage in an atmosphere containing a solvent, dosage forms that include the solvent, or routine pharmaceutical processing steps such as, for example, crystallization (i.e., from solvent or mixed solvents) vapor diffusion, etc. Solvates may also be formed, under certain circumstances, from other crystalline solvates or hydrates upon exposure to the solvent or upon suspension material in solvent. Solvates may crystallize in more than one form resulting in solvate polymorphism. See e.g., (Guillory, K., Chapter 5, pp. 202-205 in Polymorphism in Pharmaceutical Solids, (Brittain, H. ed.), Marcel Dekker, Inc., New York, NY, 1999)). The above methods for preparing solvates are well within the ambit of those of skill in the art, are completely conventional and do not require any experimentation beyond what is typical in the art. Solvates may be characterized and/or analyzed by methods well known to those of skill in the art such as, for example, single crystal X-ray diffraction, X-ray powder diffraction, polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205-208 in Polymorphism in Pharmaceutical Solids, (Brittain, H. ed.), Marcel Dekker, Inc. New York, 1999). In addition, many commercial companies routine offer services that include preparation and/or characterization of solvates such as, for example, HOLODIAG, Pharmaparc II, Voie de l'Innovation, 27 100 Val de Reuil, France (http://www.holodiag.com).

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include $R^a$, halo, —O—, =O, —$OR^b$, —$SR^b$, —$S^-$, =S, —$NR^cR^c$, —$NR^b$, =N—$OR^b$, trihalomethyl, —$CF_3$, —CN, —OCN, —SCN, —NO, —$NO_2$, —N—$OR^b$, —N—$NR^cR^c$, —$NR^bS(O)_2R^b$, =$N_2$, —$N_3$, —$S(O)_2R^b$, —$S(O)_2NR^bR^b$, —$S(O)_2O^-$, —$S(O)_2OR^b$, —$OS(O)_2R^b$, —$OS(O)_2O^-$, —$OS(O)_2OR^b$, —$OS(O)_2NR^cNR^c$, —$P(O)(O^-)_2$, —$P(O)(OR^b)(O^-)$, —$P(O)(OR^b)(OR^b)$, —$C(O)R^b$, —$C(O)NR^b$—$OR^b$—C(S) $R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —OC(S) $R^b$, —$OC(O)O^-$, —$OC(O)OR^b$, —$OC(O)NR^cR^c$, —OC(NCN) $NR^cR^c$—$OC(S)OR^b$, —$NR^bC(O)R^b$, —$NR^bC(S)R^b$, —$NR^bC(O)O$—, —$NR^bC(O)OR^b$, —$NR^bC(NCN)OR^b$, —$NR^bS(O)_2NR^cR^c$, —$NR^bC(S)OR^b$, —$NR^bC(O)NR^cR^c$, —$NR^bC(S)NR^cR^c$, —$NR^bC(S)NR^bC(O)R^a$, —$NR^bS(O)_2$ $OR^b$, —$NR^bS(O)_2R^b$, —$NR^bC$(NCN) $NR^cR^c$, —$NR_bC$ $(NR^b)R^b$ and —$NR^bC(NR^b)NR^cR^c$, where each $R^a$ is independently, substituted alkyl, substituted alkenyl, substituted alkynyl, aryl, substituted aryl, cycloalkyl, substituted cycloalkyl, cycloalkenyl, substituted cycloalkenyl, heteroalkyl, substituted heteroalkyl, heteroalkenyl, substituted heteroalkenyl, heteroalkynyl, substituted heteroalkynyl, heteroaryl or substituted heteroaryl; each $R^b$ is independently hydrogen, substituted alkyl, substituted alkenyl, substituted alkynyl, cycloalkyl, substituted cycloalkyl, cycloalkenyl, substituted cycloalkenyl, heteroalkyl, substituted heteroalkyl, heteroalkenyl, substituted heteroalkenyl, heteroalkynyl, substituted heteroalkynyl, arylalkyl, substituted arylalkyl, arylalkenyl, substituted arylalkenyl, arylalkynyl, substituted arylalkynyl, heteroarylalkyl, substituted heteroarylalkyl, heteroarylalkenyl, substituted heteroarylalkenyl, heteroarylalkynyl or substituted heteroarylalkynyl; and each $R^c$ is independently $R^b$ or alternatively, the two Res taken together with the nitrogen atom to which they are bonded form a 4-, 5-, 6- or 7 membered-cycloheteroalkyl, substituted cycloheteroalkyl, cycloheteroalkenyl, substituted cycloheteroalkenyl ring or a cycloheteroalkyl or cycloheteroalkenyl fused with an aryl group which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl. In other aspects, substituent groups useful for substituting saturated carbon atoms in the specified group or radical include $R^a$, halo, —$OR^b$, —$NR^cR^c$, trihalomethyl, —CN, —$NR^bS(O)_2R^b$, —$C(O)R^b$, —$C(O)NR^b$—$OR^b$, —$C(O)OR^b$, —$C(O)NR^cR^c$, —$OC(O)R^b$, —$OC(O)OR^b$, —$OS(O)_2NR^cNR^c$, —OC(O) $NR^cR^c$, and —$NR^cC$, $(O)OR^b$, where $R^a$, $R^b$ and $R^c$ are as previously defined. In still other aspects, substituent groups useful for substituting saturated carbon atoms in the specified group or radical include $R^a$, halo, —$OR^b$, —$NR^cR^c$, trihalomethyl, —CN, —$C(O)R^b$, —$C(O)OR^b$, —C(O)NR-$^cR^c$, —$OC(O)R^b$, —$OC(O)NR^cR^c$, and —$NR^bC(O)OR^b$, where $R^a$, $R^b$ and $R^c$ are as previously defined.

Substituent groups useful for substituting unsaturated carbon atoms in the specified group or radical include —$R^a$, halo, —O—, —$OR^b$, —$SR^b$, —S—, —$NR^cR^c$, trihalomethyl, —$CF_3$, —CN, —OCN, —SCN, —NO, —$NO_2$, —$N_3$, —$S(O)_2O^-$, —$S(O)_2OR^b$, —$OS(O)_2R^b$, —$OS(O)_2OR^b$, —$OS(O)_2O^-$, —$P(O)(O^-)_2$, —$P(O)(OR^b)(O^-)$, —$P(O)(OR^b)(OR^b)$, —$C(O)R^b$, —$C(S)R^b$, —$C(NR^b) R^b$, —$C(O) O^-$, —$C(O)OR^b$, —$C(S)OR^b$, —$C(O)NR^cR^c$, —$C(NR^b) NR^cR^c$, —$OC(O)R^b$, —$OC(S)R^b$, —$OC(O) O^-$, —$OC(O) OR^b$, —$OC(S)OR^b$, —$OC(O)NR^cR^c$, —$OS(O)_2NR^cNR^c$, —$NR^bC(O)R^b$, —$NR^bC(S)R^b$, —$NR^b C(O)O^-$, —$NR^bC(O) OR^b$, —$NR^bS(O)_2OR^a$, —$NR^bS(O)_2R^a$, —$NR^bC(S)OR^b$, —$NR^bC(O)NR^cR^c$, —$NR^bC(NR^b)R^b$, —$NR^bC(NR^b)NR^cR^c$ and —$C(NR^b) NR^bC(NR^b) NR^cR^c$ where $R^a$, $R^b$ and $R^c$ are as previously defined. In other aspects, substituent groups useful for substituting unsaturated carbon atoms in the specified group or radical include —$R^a$, halo, —$OR^b$, —$SR^b$, —$NR^cR^c$, trihalomethyl, —CN, —$S(O)_2OR^b$, —$C(O)R^b$, —$C(O)OR^b$, —$C(O)NR^cR^c$, —$OC(O)R^b$, —$OC(O)OR^b$, —$OS(O)_2NR^cNR^c$, —$NR^bC(O)R^b$ and —$NR^bC(O)OR^b$, where $R^a$, $R^b$ and $R^c$ are as previously defined. In still other aspects, substituent groups useful for substituting unsaturated carbon atoms in the specified group or radical include —$R^a$, halo, —$OR^b$, —$NR^cR^c$, trihalomethyl, —$S(O)_2OR^b$, —$C(O)R^b$, —$C(O)OR^b$, —$C(O)NR^cR^c$, —$OC(O)R^b$, —$NR^bC(O)R^b$ and —$NR^bC(O)OR^b$, where $R^a$, $R^b$ and $R^c$ are as previously defined.

Substituent groups useful for substituting nitrogen atoms in heteroalkyl and cycloheteroalkyl groups include, but are not limited to, —$R^a$, —O—, —$OR^b$, —$SR^b$, —S—, —$NR^cR^c$, trihalomethyl, —$CF_3$, —CN, —NO, —$NO_2$, —$S(O)_2R^b$, —$S(O)_2O$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$, —$NR^bC(NR^b)NR^cR^c$ and —$C(NR^b)NR^bC(NR^b)NR^cR^c$ where $R^a$, $R^b$ and $R^c$ are as previously defined. In some aspects, substituent groups useful for substituting nitrogen atoms in heteroalkyl and cycloheteroalkyl groups include, $R^a$, halo, —$OR^b$, —$NR^cR^c$, trihalomethyl, —CN, —$S(O)_2OR^b$, —$OS(O)_2R^b$, —$C(O)R^b$, —$C(NR^b)R^b$, —$C(O)OR^b$, —$C(O)NR^cR^c$, —$OC(O)R^b$, —$OC(O)OR^b$, —$OS(O)_2NR^cNR^c$, —$NR^bC(O)R^b$ and —$NR^bC(O)OR^b$, where $R^a$, $R^b$ and $R^c$ are as previously defined. In still other aspects, substituent groups useful for substituting nitrogen atoms in heteroalkyl and cycloheteroalkyl groups include, $R^a$, halo, —$OR^b$, —$NR^cR^c$, trihalomethyl, —CN, —$S(O)_2OR^b$, —$C(O)R^b$, —$C(NR^b) R^b$, —$C(O)OR^b$, —$C(O)NR^cR^c$, —$OC(O)R^b$, —$NR^b C(O)R^b$ and —$NR^bC(O)OR^b$, where $R^a$, $R^b$ and $R^c$ are as previously defined.

Substituent groups from the above lists useful for substituting other specified groups or atoms will be apparent to those of skill in the art.

The substituents used to substitute a specified group can be further substituted, typically with one or more of the same or different groups selected from the various groups specified above.

"Subject," "individual," or "patient," is used interchangeably herein and refers to a vertebrate, preferably a mammal. Mammals include, but are not limited to, murines, rodents, simians, humans, farm animals, sport animals and pets. In some aspects, the subject, individual, or patient is a member of the species *Homo sapiens*. In other aspects, the subject, individual, or patient includes all mammals except *Homo sapiens*.

"Treating," or "treatment," of any disease or disorder refers, in some aspects, to ameliorating the disease or disorder (i.e., arresting or reducing the development of the disease or at least one of the clinical symptoms thereof). Treatment may also be considered to include preemptive or prophylactic administration to ameliorate, arrest or prevent the development of the disease or at least one of the clinical symptoms. In a further feature the treatment rendered has lower potential for long-term side effects over multiple years. In other aspects "treating" or "treatment" refers to ameliorating at least one physical parameter, which may not be discernible by the patient. In yet other aspects, "treating" or "treatment" refers to inhibiting the disease or disorder, either physically (e.g., stabilization of a discernible symptom), physiologically (e.g., stabilization of a physical parameter) or both. In yet other aspects, "treating" or "treatment" refers to delaying the onset of the disease or disorder.

"Therapeutically effective amount," means the amount of a compound that, when administered to a patient for treating a disease, is sufficient to treat the disease. The "therapeutically effective amount" will vary depending on the compound, the disease and its severity and the age, weight, adsorption, distribution, metabolism and excretion etc., of the patient to be treated.

"Vehicle," refers to a diluent, excipient or carrier with which a compound is administered to a subject. In some aspects, the vehicle is pharmaceutically acceptable.

Compounds

In one aspect, a compound of Formula (I) which satisfies these and other needs is provided:

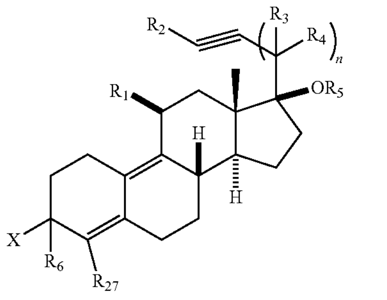

(I)

or pharmaceutically acceptable salts, hydrates or solvates thereof where $R_1$ is —$OR_{36}$, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl; $R_2$ is —H, —CN, —$CO_2R_7$, —$CONR_8R_9$, alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl; each $R_3$ and $R_4$ are independently, H, —F or alkyl; n is 1 or 2; $R_5$ is —H, —$CO_2R_{10}$, —C(O)$R_{11}$, —$CONR_{12}R_{13}$, alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl; $R_6$ is —H, alkyl, substituted alkyl, alkenyl, substituted alkenyl, alkynyl, substituted alkynyl, aryl, substituted aryl, arylalkyl, substituted arylalkyl, arylalkenyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, substituted arylalkenyl, arylalkynyl, substituted arylalkynyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl or is absent when X is =O or =$NR_{14}$; $R_{27}$ is hydrogen, halo, alkyl, substituted alkyl, heteroalkyl, substituted heteroalkyl, —$NR_{28}R_{29}$, —$NCONR_{30}R_{31}$, —$CONR_{32}R_{33}$, —$CO_2R_{34}$, —$NCO_2R_{35}$; X is =O, =$NR_{14}$ or —$OR_{15}$; $R_{14}$ is —$OR_{16}$, —$NR_{17}R_{18}$ or —$N^+R^{40}R_{41}R_{42}$; $R_7$-$R_{10}$, $R_{12}$, $R_{13}$, $R_{15}$ and $R_{28}$-$R_{36}$ are independently —H, alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl or optionally $R_8$ and $R_9$, $R_{12}$ and $R_{13}$, $R_{28}$ and $R_{29}$, $R_{30}$ and $R_{31}$, $R_{32}$ and $R_{33}$ together with the atoms to which they are attached from a cycloheteroalkyl ring or a substituted cycloheteroalkyl ring; $R_{11}$ is alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl; $R_{16}$ is —H, alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl, substituted heteroarylalkynyl or is a carbohydrate derivative; $R_{17}$ and $R_{18}$ are independently —H, alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl, substituted heteroarylalkynyl, a carbohydrate derivative, $R_{19}$CO—, $R_{20}R_{21}$NCO—, $R_{22}$OCO— or $R_{23}SO_2$—, provided that any substituted group is optionally substituted with a carbohydrate derivative and that both $R_{17}$ and $R_{18}$ are not $R_{19}$CO—, $R_{21}R_{20}$NCO—, $R_{22}$OCO— or $R_{23}SO_2$— or any combination thereof; $R_{19}$ is alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl, substituted heteroarylalkynyl or a carbohydrate derivative or optionally $R_{19}$ and $R_{17}$ together with the atoms to which they are attached form a cycloheteroalkyl ring or substituted cycloheteroalkyl ring provided that any substituted group is optionally substituted with a carbohydrate derivative; $R_{20}$ and $R_{21}$ are independently —H, alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl or a carbohydrate derivative or optionally $R_{20}$ and $R_{17}$ together with the atoms to which they are attached form a cycloheteroalkyl or substituted cycloheteroalkyl ring optionally substituted with =O or optionally $R_{20}$ and $R_{21}$ together with the atoms to which they are attached form a cycloheteroalkyl or substituted cycloheteroalkyl ring provided that any substituted group is optionally substituted with a carbohydrate derivative; $R_{22}$ is alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl, substituted heteroarylalkynyl or a carbohydrate derivative or optionally $R_{22}$ and $R_{17}$ together with the atoms to which they are attached form a cycloheteroalkyl ring or substituted cycloheteroalkyl ring provided that any substituted group is optionally substituted with a carbohydrate derivative; and $R_{23}$ is alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl provided that any substituted group is optionally substituted with a carbohydrate derivative or optionally $R_{23}$ and $R_{17}$ together with the atoms to which they are attached form a cycloheteroalkyl ring or substituted cycloheteroalkyl ring provided that any substituted group is optionally substituted with a carbohydrate derivative; and $R^{40}$, $R_{41}$ and $R_{42}$ are alkyl.

In some embodiments, when X is =O, n is 1, $R_1$ is not phenyl or substituted phenyl except $R_1$ may be phenyl substituted at the para position with —$OR_{25}$, $R_1$ may be phenyl substituted at the para position with —$OR_{25}$, $R_{25}$ is alkyl substituted with cycloalkyl, substituted cycloalkyl or —$CF_3$, cycloalkyl, substituted cycloalkyl or $R_{43}SO_2$—, where $R_{43}$ is alkyl or $CF_3$.

In other embodiments, when X is =O, n is 1, $R_3$ and $R_4$ are —F, $R_{27}$ is —H, $R_1$ is not phenyl or substituted phenyl except $R_1$ may be phenyl substituted at the para position with —$OR_{25}$, $R_{25}$ is alkyl substituted with cycloalkyl, substituted cycloalkyl or —$CF_3$, cycloalkyl, substituted cycloalkyl or $R_{43}SO_2$—, where $R_{43}$ is alkyl or $CF_3$.

In other embodiments, when X is =O, n is 1, $R_3$ and $R_4$ are —H, $R_{27}$ is —H, $R_1$ is not phenyl or substituted phenyl except $R_1$ may be phenyl substituted at the para position with cycloalkyl or substituted cycloalkyl.

In still other embodiments, when X is =O, n is 1, $R_1$ is not phenyl, substituted phenyl, —OH, alkyl, alkenyl or heteroaryl. In still other embodiments, when X is =O, n is 1, $R_1$ is not phenyl, substituted phenyl, alkyl, alkenyl or heteroaryl. In still other embodiments, when X is =O, n is 1, $R_1$ is not phenyl, substituted phenyl, alkyl or alkenyl. In still other embodiments, when X is =O, n is 1, $R_1$ is not phenyl, substituted phenyl or heteroaryl. In still other embodiments, when X is =O, n is 1 and $R_1$ is phenyl substituted at the para position with —$OR_{25}$, $R_{25}$ is not —H, alkyl, substituted alkyl, aryl substituted aryl, arylalkyl or substituted arylalkyl.

In some embodiments, when X is =O and n is 1, and $R_1$ is phenyl, the para position of the phenyl group is not substituted with alkyl, alkenyl, $R_{24}CO$—, cycloalkyl, cycloheteroalkyl, —CN, $R_{25}O$—, —$N(R_{26})_2$, —$CON(R_{26})_2$, —$S(O)_xR_{26}$ or —$(CH_2)p$-$CH_2$—Y; Y is —H, —$OR_{26}$—$SCH_3$, —$CF_3$, or —$N(R_{26})_2$; x is 0, 1 or 2; p is an integer from 1 to 18; $R_{24}$ is —$(C_1$-$C_{12})$ alkyl; $R_{25}$ is —H, alkyl, substituted alkyl, aryl substituted aryl, arylalkyl or substituted arylalkyl; $R_{26}$ is —H, alkyl or cycloalkyl; and $R_1$ is not

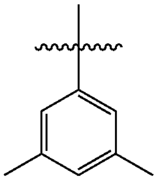
,
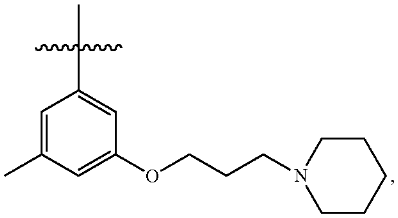
,
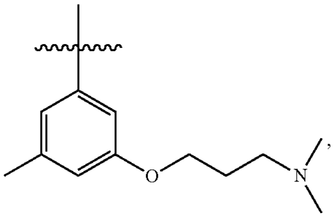
,
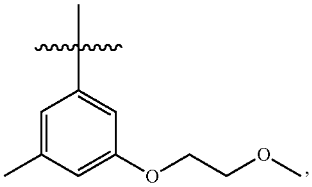
,
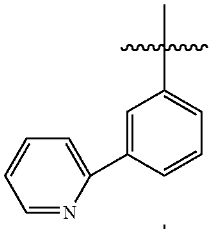
,
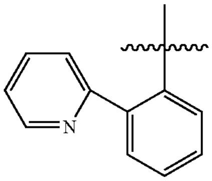
,
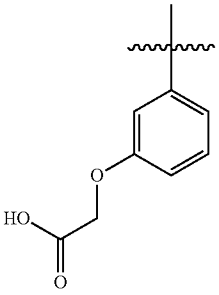
,
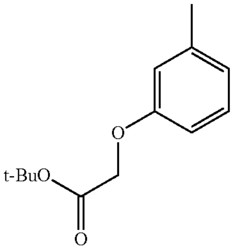
,
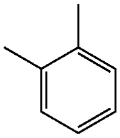
,
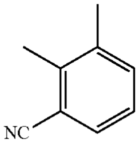
,
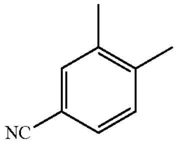
or -continued

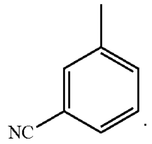

In other embodiments, when X is ═O and n is 1, $R_3$ and $R_4$ are —F, $R_{27}$ is —H, and $R_1$ is phenyl, the para position of the phenyl group is not substituted with alkyl, alkenyl, $R_{24}$CO—, cycloalkyl, cycloheteroalkyl, —CN, $R_{25}$O—, —$N(R_{26})_2$, —$CON(R_{26})_2$, —$S(O)_xR_{26}$ or —$(CH_2)$p-$CH_2$—Y; Y is —H, —$OR_{26}$—$SCH_3$, —$CF_3$, or —$N(R_{26})_2$; x is 0, 1 or 2; p is an integer from 1 to 18; $R_{24}$ is —($C_1$-$C_{12}$) alkyl; $R_{25}$ is —H, alkyl, substituted alkyl, aryl substituted aryl, arylalkyl or substituted arylalkyl; $R_{26}$ is —H, alkyl or cycloalkyl; and $R_1$ is not

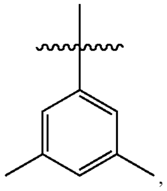

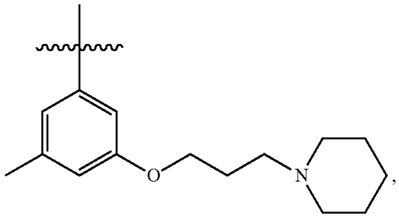

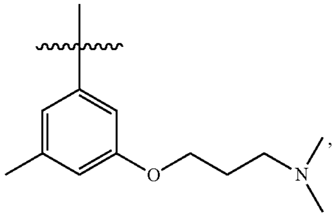

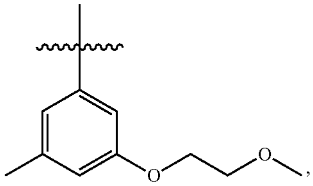

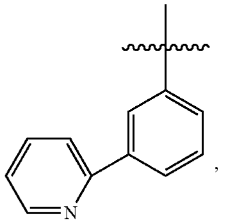

-continued

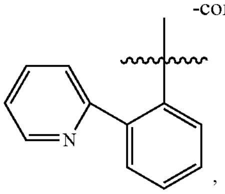

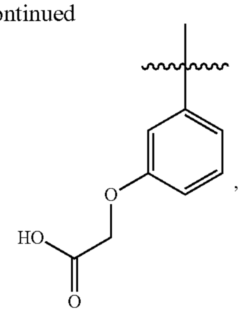

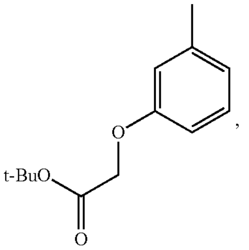

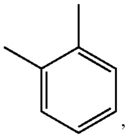

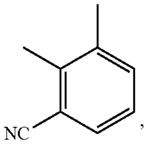

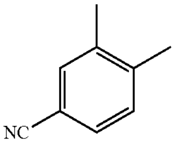

or

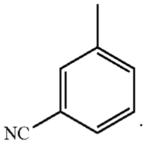

In some embodiments, when X is ═O, n is 1, $R_1$ is not phenyl or substituted phenyl. In other embodiments, when X is ═O, n is 1, $R_3$ and $R_4$ are —F, $R_1$ is not phenyl or substituted phenyl. In some embodiments, when X is ═O, n is 1, $R^3$ and $R^4$ are —F, $R^1$ is not phenyl or substituted phenyl except for phenyl substituted with

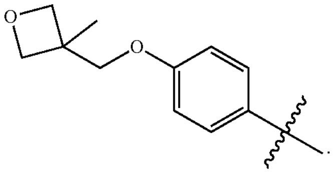 [SMILES: *c1ccc(OCC2(C)COC2)cc1]

In some embodiments, when X is ═O, n is 1, $R^3$ and $R^4$ are —H, $R^1$ is not phenyl or substituted phenyl except for phenyl substituted with

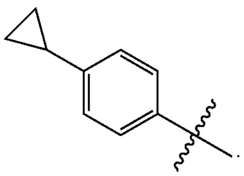

In some embodiments, when X is ═O, n is 1, $R^1$ is not phenyl or substituted phenyl except for phenyl substituted with

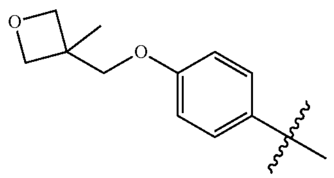
or
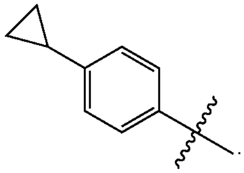 [SMILES: *c1ccc(C2CC2)cc1]

In still other embodiments, when X is ═O, n is 1, $R_1$ is not phenyl, substituted phenyl, —OH, alkyl, alkenyl or heteroaryl. In still other embodiments, when X is ═O, n is 1, $R_1$ is not phenyl, substituted phenyl, alkyl, alkenyl or heteroaryl. In still other embodiments, when X is ═O, n is 1, $R_1$ is not phenyl, substituted phenyl, alkyl or alkenyl. In still other embodiments, when X is ═O, n is 1, $R_1$ is not phenyl, substituted phenyl or heteroaryl. In still other embodiments, when X is ═O, n is 1 and $R_1$ is phenyl, the para position of the phenyl group is not substituted with —OH.

In some embodiments, when X is ═O and n is 1, and $R^1$ is phenyl, the para position of the phenyl group is not substituted with alkyl, alkenyl, $R_{24}CO$—, cycloalkyl, cycloheteroalkyl, —CN, $R_{25}O$—, —$N(R_{26})_2$, —$CON(R_{26})_2$, —$S(O)_xR_{26}$ or —$(CH_2)p$-$CH_2$—Y; Y is —H, —$OR_{26}$—$SCH_3$, —$CF_3$, or —$N(R_{26})_2$; x is 0, 1 or 2; p is an integer from 1 to 18; $R_{24}$ is —($C_1$-$C_{12}$)alkyl; $R_{25}$ is —H, alkyl, substituted alky, aryl substituted aryl, arylalkyl or substituted arylalkyl; $R_{26}$ is —H, alkyl or cycloalkyl; and $R_1$ is not

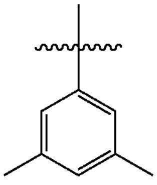
,
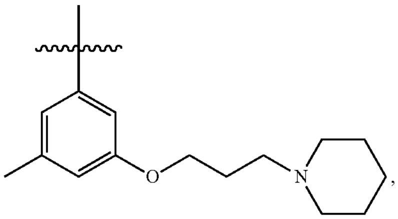
,
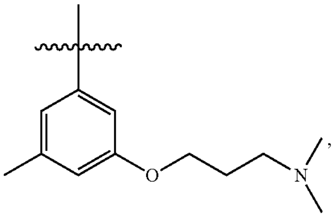
,
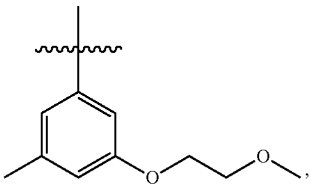
,
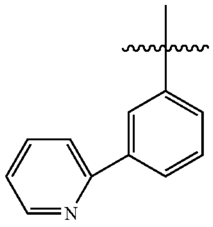
,

-continued

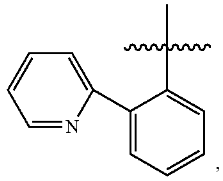
,
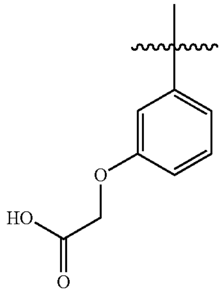
,
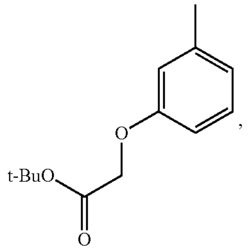
,
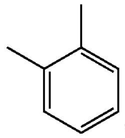
,
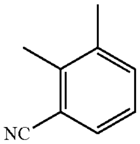
,
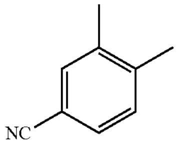
or
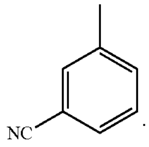
.

In some embodiments, $R^1$ is substituted aryl, heteroaryl or substituted heteroaryl. In other embodiments, $R_2$ is —H, —CN, —$CO_2R_7$, —$CONR_8R_9$, alkyl, alkenyl, aryl, substituted aryl, cycloalkyl, cycloalkenyl, cycloheteroalkyl, cycloheteroalkenyl, heteroalkyl, heteroalkenyl, heteroaryl or substituted heteroaryl. In still other embodiments, $R_3$ and $R_4$ are independently, H, or —F. In still other embodiments, $R_3$ and $R_4$ are independently, H, or —F provided that at least one of $R_3$ and $R_4$ is —F. In still other embodiments, $R_5$ is —H, —$CO_2R_{10}$, —$C(O)R_{11}$, —$CONR_{12}R_{13}$, alkyl, alkenyl, aryl, substituted aryl, cycloalkyl, cycloalkenyl, cycloheteroalkyl, cycloheteroalkenyl, heteroalkyl, heteroalkenyl, heteroaryl or substituted heteroaryl. In still other embodiments, $R_6$ is —H, alkyl, alkenyl, aryl, substituted aryl, cycloalkyl, cycloalkenyl, cycloheteroalkyl, cycloheteroalkenyl, heteroalkyl, heteroalkenyl, heteroaryl or substituted heteroaryl. In still other embodiments, $R_{27}$ is hydrogen, halo, —$NR_{28}R_{29}$, —$CONR_{32}R_{33}$ or —$CO_2R_{34}$. In still other embodiments, $R_7$-$R_{10}$, $R_{12}$, $R_{13}$, $R_{15}$, $R_{16}$ and $R_{28}$-$R_{36}$ are independently —H, alkyl, alkenyl, aryl, substituted aryl, cycloalkyl, cycloalkenyl, cycloheteroalkyl, cycloheteroalkenyl, heteroalkyl, heteroalkenyl, heteroaryl or substituted heteroaryl. In still other embodiments, $R_{11}$ is independently alkyl, alkenyl, aryl, substituted aryl, cycloalkyl, cycloalkenyl, heteroaryl. In still other embodiments, $R_{17}$ and $R_{18}$ are independently —H, alkyl, alkenyl, aryl, substituted aryl, cycloalkyl, cycloalkenyl, cycloheteroalkyl, cycloheteroalkenyl, heteroalkyl, heteroalkenyl, heteroaryl, substituted heteroaryl, a carbohydrate derivative, $R_{19}CO$—, $R_{20}R_{21}NCO$—, $R_{22}OCO$— or $R_{23}SO_2$—. In still other embodiments, $R_{19}$ is alkyl, alkenyl, aryl, substituted aryl, arylalkyl, cycloalkyl, substituted cycloalkyl, cycloalkenyl, cycloheteroalkyl, cycloheteroalkenyl, heteroalkyl, substituted heteroalkyl, substituted heteroalkenyl, heteroaryl, substituted heteroaryl, heteroarylalkyl, or a carbohydrate derivative or optionally $R_{19}$ and $R_{17}$ together with the atoms to which they are attached form a cycloheteroalkyl ring or substituted cycloheteroalkyl ring provided that any substituted group is optionally substituted with a carbohydrate derivative. In still other embodiments, $R_{20}$ and $R_{21}$ are independently alkyl, alkenyl, aryl, substituted aryl, arylalkyl, cycloalkyl, substituted cycloalkyl, cycloalkenyl, cycloheteroalkyl, cycloheteroalkenyl, heteroalkyl, substituted heteroalkyl, substituted heteroalkenyl, heteroaryl, substituted heteroaryl, heteroarylalkyl, or a carbohydrate derivative or optionally $R_{20}$ and $R_{21}$ together with the atoms to which they are attached form a cycloheteroalkyl or substituted cycloheteroalkyl ring provided that any substituted group is optionally substituted with a carbohydrate derivative. In still other embodiments, $R_{22}$ is alkyl, alkenyl, aryl, substituted aryl, arylalkyl, cycloalkyl, substituted cycloalkyl, cycloalkenyl, cycloheteroalkyl, cycloheteroalkenyl, heteroalkyl, substituted heteroalkyl, substituted heteroalkenyl, heteroaryl, substituted heteroaryl, heteroarylalkyl, or a carbohydrate derivative or optionally $R_{22}$ and $R_{17}$ together with the atoms to which they are attached form a cycloheteroalkyl ring or substituted cycloheteroalkyl ring provided that any substituted group is optionally substituted with a carbohydrate derivative. In still other embodiments, $R_{23}$ is alkyl, alkenyl, aryl, substituted aryl, arylalkyl, cycloalkyl, substituted cycloalkyl, cycloalkenyl, cycloheteroalkyl, cycloheteroalkenyl, heteroalkyl, substituted heteroalkyl, substituted heteroalkenyl, heteroaryl, substituted heteroaryl, heteroarylalkyl, or a carbohydrate derivative provided that any substituted group is optionally substituted with a carbohydrate derivative or optionally $R_{23}$ and $R_{17}$ together with the atoms to which they are attached form a cycloheteroalkyl ring or substituted cycloheteroalkyl ring provided that any substituted group is optionally substituted with a carbohydrate derivative.

In some embodiments, $R^1$ is substituted aryl, heteroaryl, substituted heteroaryl, $R_2$ is —H, —CN, —$CO_2R_7$, —$CONR_8R_9$, alkyl, alkenyl, aryl, substituted aryl, cycloalkyl, cycloalkenyl, heteroaryl; each $R_3$ and $R_4$ are independently, H, or —F provided that at least one of $R_3$ and $R_4$ is —F; $R_5$ is —H, —$CO_2R_{10}$, —C(O)$R_{11}$, —$CONR_{12}R_{13}$, alkyl, alkenyl, aryl, substituted aryl, cycloalkyl, cycloalkenyl, cycloheteroalkyl, cycloheteroalkenyl, heteroalkyl, heteroalkenyl, heteroaryl or substituted heteroaryl; $R_6$ is —H, alkyl, alkenyl, aryl, substituted aryl, cycloalkyl, cycloalkenyl, cycloheteroalkyl, cycloheteroalkenyl, heteroalkyl, heteroalkenyl, heteroaryl or substituted heteroaryl; $R_{27}$ is hydrogen, halo, —$NR_{28}R_{29}$, —$CONR_{32}R_{33}$ or —$CO_2R_{34}$; $R_7$-$R_{10}$, $R_{12}$, $R_{13}$, $R_{15}$ and $R_{28}$-$R_{36}$ are independently —H, alkyl, alkenyl, aryl, substituted aryl, cycloalkyl, cycloalkenyl, cycloheteroalkyl, cycloheteroalkenyl, heteroalkyl, heteroalkenyl, heteroaryl or substituted heteroaryl; $R_{11}$ is independently alkyl, alkenyl, aryl, substituted aryl, cycloalkyl, cycloalkenyl, cycloheteroalkyl, cycloheteroalkenyl, heteroalkyl, heteroalkenyl, heteroaryl or substituted heteroaryl; $R_{16}$ is —H, alkyl, alkenyl, alkynyl, aryl, cycloalkyl, cycloalkenyl, cycloheteroalkyl, cycloheteroalkenyl, heteroalkyl, heteroalkenyl, heteroaryl, substituted heteroaryl or is a carbohydrate derivative; $R_{17}$ and $R_{18}$ are independently —H, alkyl, alkenyl, aryl, substituted aryl, cycloalkyl, cycloalkenyl, cycloheteroalkyl, cycloheteroalkenyl, heteroalkyl, heteroalkenyl, heteroaryl, substituted heteroaryl, a carbohydrate derivative, $R_{19}$CO—, $R_{20}R_{21}$NCO—, $R_{22}$OCO— or $R_{23}SO_2$—; $R_{19}$ is alkyl, alkenyl, aryl, substituted aryl, arylalkyl, cycloalkyl, substituted cycloalkyl, cycloalkenyl, cycloheteroalkyl, cycloheteroalkenyl, heteroalkyl, substituted heteroalkyl, substituted heteroalkenyl, heteroaryl, substituted heteroaryl, heteroarylalkyl, or a carbohydrate derivative or optionally $R_{19}$ and $R_{17}$ together with the atoms to which they are attached form a cycloheteroalkyl ring or substituted cycloheteroalkyl ring provided that any substituted group is optionally substituted with a carbohydrate derivative; $R_{20}$ and $R_{21}$ are independently alkyl, alkenyl, aryl, substituted aryl, arylalkyl, cycloalkyl, substituted cycloalkyl, cycloalkenyl, cycloheteroalkyl, cycloheteroalkenyl, heteroalkyl, substituted heteroalkyl, substituted heteroalkenyl, heteroaryl, substituted heteroaryl, heteroarylalkyl, or a carbohydrate derivative or optionally $R_{20}$ and $R_{21}$ together with the atoms to which they are attached form a cycloheteroalkyl or substituted cycloheteroalkyl ring provided that any substituted group is optionally substituted with a carbohydrate derivative; $R_{22}$ is alkyl, alkenyl, aryl, substituted aryl, arylalkyl, cycloalkyl, substituted cycloalkyl, cycloalkenyl, cycloheteroalkyl, cycloheteroalkenyl, heteroalkyl, substituted heteroalkyl, substituted heteroalkenyl, heteroaryl, substituted heteroaryl, heteroarylalkyl, or a carbohydrate derivative or optionally $R_{22}$ and $R_{17}$ together with the atoms to which they are attached form a cycloheteroalkyl ring or substituted cycloheteroalkyl ring provided that any substituted group is optionally substituted with a carbohydrate derivative; and $R_{23}$ is alkyl, alkenyl, aryl, substituted aryl, arylalkyl, cycloalkyl, substituted cycloalkyl, cycloalkenyl, cycloheteroalkyl, cycloheteroalkenyl, heteroalkyl, substituted heteroalkyl, substituted heteroalkenyl, heteroaryl, substituted heteroaryl, heteroarylalkyl, or a carbohydrate derivative provided that any substituted group is optionally substituted with a carbohydrate derivative or optionally $R_{23}$ and $R_{17}$ together with the atoms to which they are attached form a cycloheteroalkyl ring or substituted cycloheteroalkyl ring provided that any substituted group is optionally substituted with a carbohydrate derivative.

In some embodiments, $R_1$ is substituted aryl or substituted phenyl. In other embodiments, $R_1$ is

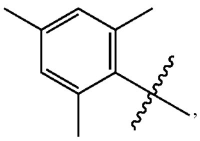
,
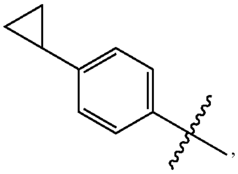
,
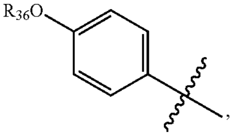
,
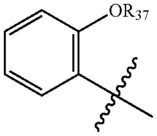
or
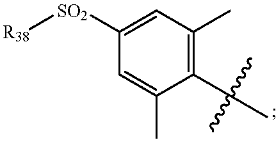
;

$R_{36}$ is alkyl, substituted alkyl, —$SO_2R_{39}$, arylalkyl, substituted arylalkyl; $R_{39}$ is alkyl or substituted alkyl; $R_{37}$ is alkyl; and $R_{38}$ is alkyl or substituted alkyl. In still other of the embodiments, $R_{36}$ is —$CH_3$, —$CH_2CF_3$, —$SO_2CF_3$, —$CH_2(CH_3)$-cyclobutyl or —$CH_2$Ph where Ph is substituted at the para position by —$SO_2CF_3$; $R_{37}$ is —$CH_3$; and $R_{38}$ is $CF_3$ or cyclopropyl. In still other embodiments, $R_1$ is

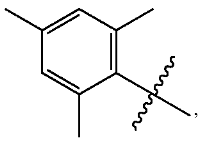 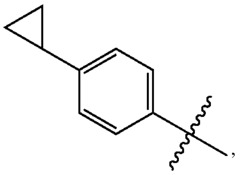

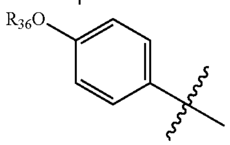 or

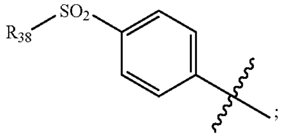

$R_{36}$ is alkyl, substituted alkyl, —$SO_2R_{39}$, arylalkyl, substituted arylalkyl; $R_{39}$ is alkyl or substituted alkyl; and $R_{38}$ is alkyl or substituted alkyl. In still other of the embodiments, $R_{36}$ is —$CH_3$, —$CH_2CF_3$, —$SO_2CF_3$ or —$CH_2(CH_3)$-cyclobutyl; $R_{37}$ is —$CH_3$; and $R_{38}$ is $CF_3$ or cyclopropyl.

In some embodiments, n is 1 and $R_3$ and $R_4$ are —F. In other embodiments, $R_2$ is —H. In still other embodiments, $R_5$ is —H. In still other of the above embodiments, X is ═O. In still other embodiments, X is —$OR_{15}$ and $R_6$ is —H or methyl. In still other embodiments, $R_{15}$ is —H or alkyl. In still other embodiments, X is ═$NR_{14}$. In still other embodiments, $R_{14}$ is —$OR_{16}$.

In some embodiments, $R_{16}$ is —H. In other embodiments, $R_{16}$ is alkyl. In still other embodiments, $R_{16}$ is $(C_1$-$C_4)$ alkyl. In still other embodiments, $R_{16}$ is —$CH_2CH_3$.

In some embodiments, $R_{16}$ is substituted alkyl. In other embodiments, $R_{16}$ is —$CH_2CF_3$, —$CH_2CO_2H$, —$CH_2CH_2OCH_3$, —$CH_2(CH_3)_2OH$, —$CH_2C(O)N(CH_3)_2$, —$CH_2CN$, —$CH_2CH_2OSi(CH_3)_3$, —$CH_2CH_2OH$, —$CH_2CH_2OCH_2CH_2OH$, —$CH_2CH_2OCH_2CH_2OCH_2CH_2OCH_3$,

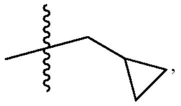 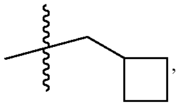

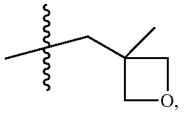 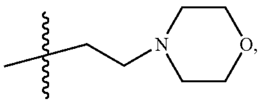

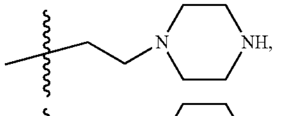

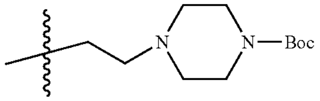 or

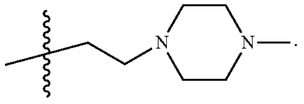

In some embodiments, $R_{16}$ is heteroarylalkyl. In other embodiments, $R_{16}$ is

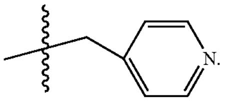 [SMILES: *Cc1ccncc1]

In some embodiments, $R_{16}$ is cycloheteroalkyl. In other embodiments, $R_{16}$ is

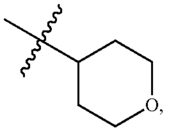 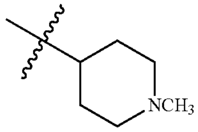 or

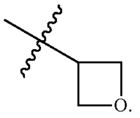

In some embodiments, $R_{16}$ is a carbohydrate derivative. In other embodiments, $R_{16}$ is

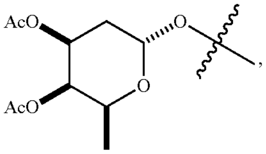 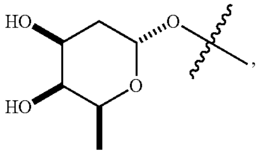

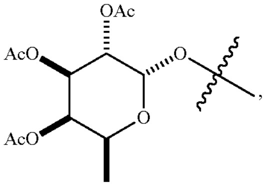 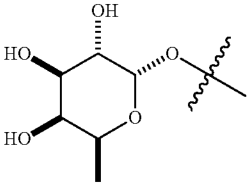

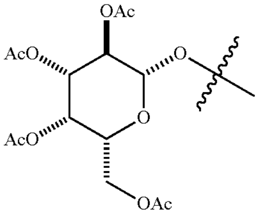 or

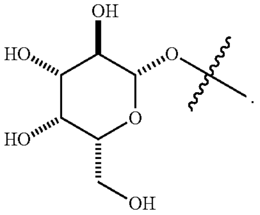

In some embodiments, $R_{14}$ is —$NR_{17}R_{18}$. In other embodiments, $R_{17}$ is —H, methyl, alkyl, cyclopropyl, cycloalkyl or —$C(O)CH_3$.

In some embodiments, $R_{18}$ is —H or methyl.

In some embodiments, $R_{18}$ is substituted arylalkyl. In other embodiments, $R_{18}$ is arylalkyl substituted with a carbohydrate derivative. In still other embodiments, $R_{18}$ is

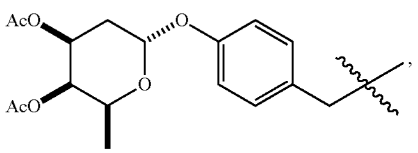

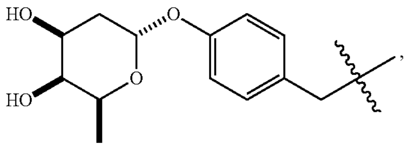

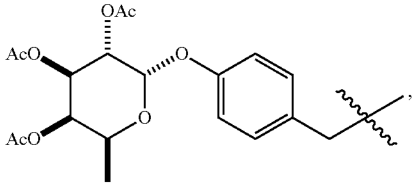

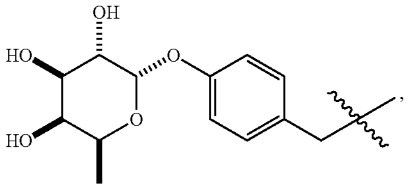

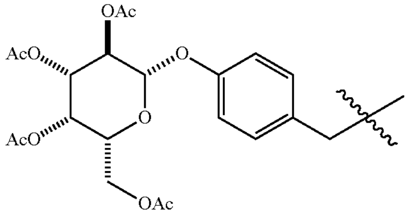

or

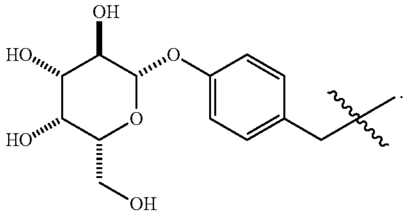

In some embodiments, $R_{17}$ is —H, methyl, alkyl, cyclopropyl, cycloalkyl or —$C(O)CH_3$ and $R_{18}$ is a carbohydrate derivative. In other embodiments, $R_{18}$ is

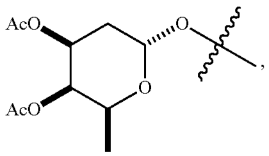

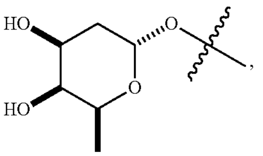

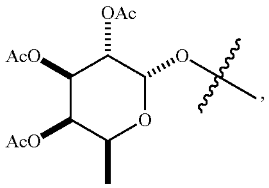

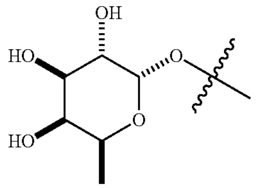

-continued

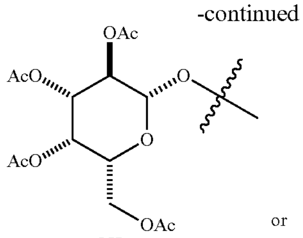

or

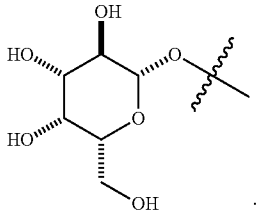

In some embodiments, $R_{17}$ is —H, methyl, alkyl, cyclopropyl, cycloalkyl or —$C(O)CH_3$ and $R_{18}$ is —H, substituted arylalkyl or arylalkyl substituted with a carbohydrate derivative. In other embodiments, $R_{18}$ is —H, substituted arylalkyl, arylalkyl substituted with a carbohydrate derivative or a carbohydrate derivative. In still other embodiments, $R_{17}$ is —H, methyl, alkyl, substituted alkyl, cyclopropyl, substituted cyclopropyl, cycloalkyl or substituted cycloalkyl and $R_{18}$ is $R_{19}CO$—.

In some embodiments, $R_{18}$ is $R_{19}CO$— In other embodiments, $R_{19}$ is alkyl. In still other embodiments, $R_{19}$ is —$CH_3$, —$CH(CH_3)_2$, —$CH_2CH(CH_3)_2$, —$C(CH_3)_3$— or —$CH_2CH_2CH_3$.

In some embodiments, $R_{19}$ is substituted alkyl. In other embodiments, $R_{19}$ is —$CH_2NH_2$, —$CH_2NHBoc$, —$CH_2OCH_3$, —$CH_2OH$, —$CH_2N(CH_3)_2$, —$CH_2CN$ or

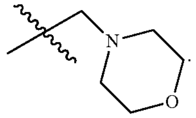 [SMILES: *CN1CCOCC1]

In some embodiments, $R_{19}$ is cycloalkyl or substituted cycloalkyl. In other embodiments, $R_{19}$ is cyclopropyl and substituted cyclopropyl.

In some embodiments, $R_{19}$ is heteroaryl or substituted heteroaryl. In other embodiments, $R_{19}$ is

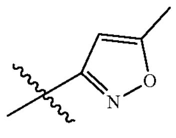

or

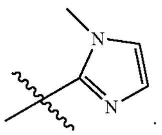

In some embodiments, $R_{19}$ is heteroarylalkyl. In other embodiments, $R_{19}$ is

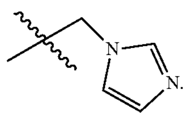 [SMILES: *Cn1ccnc1]

In some embodiments, $R_{19}$ is cycloalkyl. In other embodiments, $R_{19}$ is

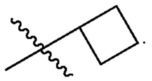 [SMILES: *C1CCC1]

In some embodiments, $R_{19}$ is cycloheteroalkyl. In other embodiments, $R_{19}$ is

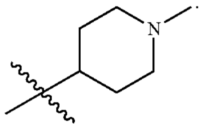 [SMILES: *C1CCN(C)CC1]

In some embodiments, $R_{19}$ and $R_{17}$ together with the atoms to which they are attached form a cycloheteroalkyl ring. In other embodiments, $R_{19}$ and $R_{17}$ together with the atoms to which they are attached form

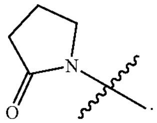 [SMILES: *N1CCCC1=O]

In some embodiments, $R_{17}$ is —H, methyl, alkyl, substituted alkyl, cyclopropyl, substituted cyclopropyl, cycloalkyl or substituted cycloalkyl and $R_{18}$ is $R_{20}R_{21}NCO$—.

In some embodiments, $R_{18}$ is $R_{20}R_{21}NCO$—. In other embodiments, $R_{20}$ is hydrogen or alkyl and $R_{21}$ is cycloalkyl or substituted cycloalkyl. In still other embodiments, $R_{20}$ is hydrogen or alkyl and $R_{21}$ is cyclopropyl or substituted cyclopropyl.

In some embodiments, $R_{20}$ is hydrogen or alkyl and $R_{21}$ is hydrogen or alkyl.

In some embodiments, $R_{20}$ is hydrogen or alkyl and $R_{21}$ is substituted alkyl.

In some embodiments, $R_{20}$ is hydrogen or alkyl and $R_{21}$ is a carbohydrate derivative. In other embodiments, $R_{21}$ is

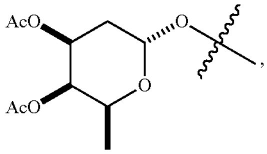,
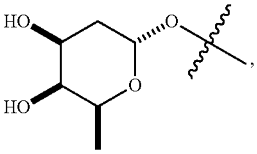,
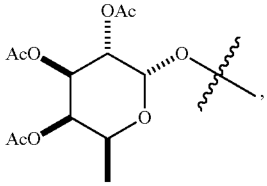,
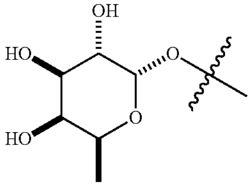
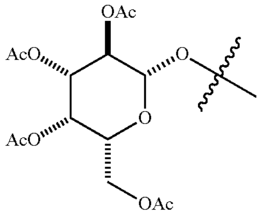

or

-continued

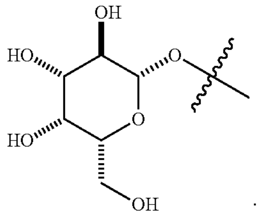

In some embodiments, $R_{17}$ is —H, methyl, alkyl, cyclopropyl, cycloalkyl, —$C(O)CH_3$, $R_{18}$ is —$R_{19}CO$—; and $R_{19}$ is alkyl, substituted alkyl, heteroaryl, substituted heteroaryl, substituted heteroarylalkyl, cycloalkyl, cycloheteroalkyl or $R_{19}$ and $R_{17}$ together with the atoms to which they are attached form a cycloheteroalkyl ring.

In some embodiments, $R_{18}$ is —$R_{19}CO$—, $R_{19}$ is alkyl, substituted alkyl, heteroaryl, substituted heteroaryl, substituted heteroarylalkyl, cycloalkyl, cycloheteroalkyl or optionally $R_{19}$ and $R_{17}$ together with the atoms to which they are attached form a cycloheteroalkyl ring.

In some embodiments, $R_{18}$ is $R_{22}OCO$—. In other embodiments, $R_{22}$ is arylalkyl substituted with a carbohydrate derivative. In still other embodiments, $R_{22}$ is

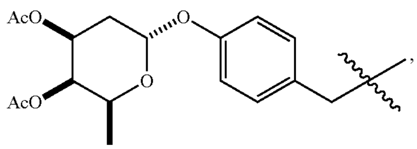,
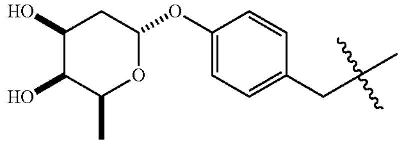,
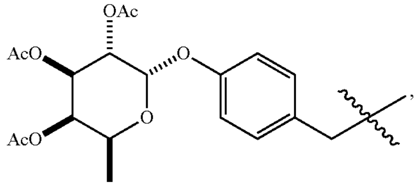,
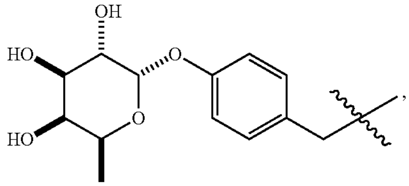,
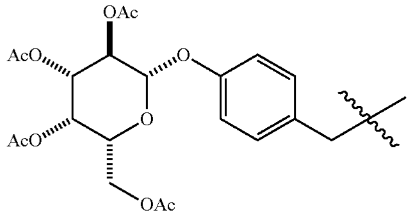

or

-continued

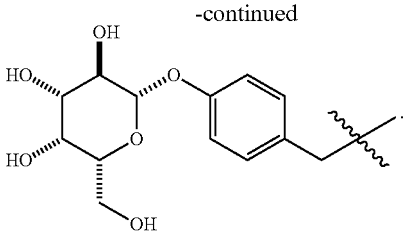

In some embodiments, $R_{22}$ is a carbohydrate derivative. In other embodiments, $R_{22}$ is

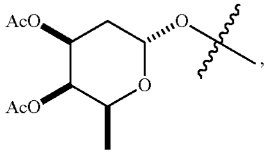,
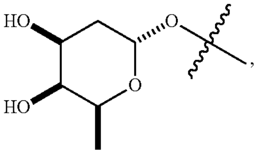,
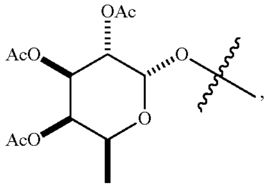,
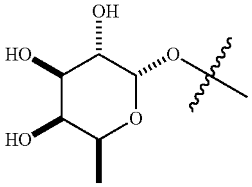
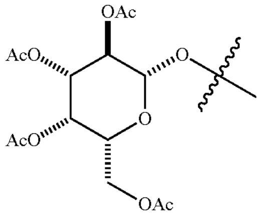 or
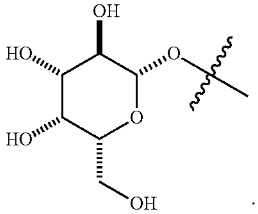.

In some embodiments, $R_{22}$ is alkyl. In other embodiments, $R_{22}$ is $-CH_3$, $-C_2H_5$ or $-C(CH_3)_3$.

In some embodiments, $R_{22}$ is substituted alkyl. In other embodiments, $R_{22}$ is $-CH_2CH_2OH$, $-CH_2CH_2OSi(CH_3)_3$ or $-CH_2CF_3$.

In some embodiments, $R_{22}$ and $R_{17}$ together with the atoms to which they are attached form a cycloheteroalkyl ring. In other embodiments, $R_{22}$ and $R_{17}$ together with the atoms to which they are attached form

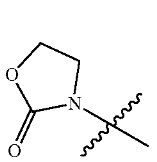 or 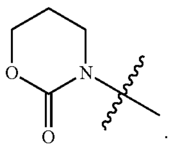.

In some embodiments, $R_{17}$ is —H, methyl, alkyl, cyclopropyl, cycloalkyl, $-C(O)CH_3$, $R_{18}$ is $R_{22}OCO$— and $R_{22}$ is arylalkyl substituted with a carbohydrate derivative, a carbohydrate derivative, alkyl, substituted alkyl or $R_{22}$ and $R_{17}$ together with the atoms to which they are attached form a cycloheteroalkyl ring.

In some embodiments, $R_{18}$ is $R_{22}OCO$— and $R_{22}$ is arylalkyl substituted with a carbohydrate derivative, a carbohydrate derivative, alkyl, substituted alkyl or $R_{22}$ and $R_{17}$ together with the atoms to which they are attached form a cycloheteroalkyl ring.

In some embodiments, $R_{18}$ is $R_{20}R_{21}NCO$—. In other embodiments, $R_{20}$ and $R_{17}$ together with the atoms to which they are attached form a cycloheteroalkyl or substituted cycloheteroalkyl ring optionally substituted with =O. In still other embodiments, $R_{20}$ and $R_{17}$ together with the atoms to which they are attached form

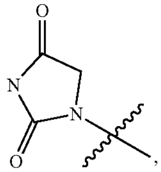, 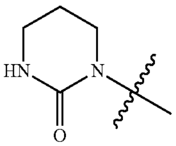 or
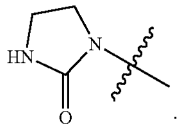.

In some embodiments, $R_{20}$ and $R_{21}$ together with the atoms to which they are attached form a cycloheteroalkyl or substituted cycloheteroalkyl ring. In other embodiments, $R_{20}$ and $R_{21}$ together with the atoms to which they are attached form,

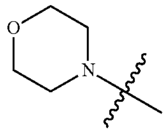, 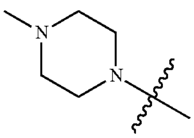 or
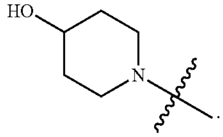.

In some embodiments, $R_{20}$ is aryl. In other embodiments, $R_{20}$ is

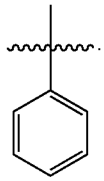

In some embodiments, $R_{20}$ is alkyl. In other embodiments, $R_{20}$ is $-CH(CH_3)_2$.

In some embodiments, $R_{20}$ is substituted alkyl. In other embodiments, $R_{20}$ is

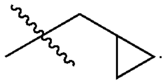

In some embodiments, $R_{20}$ is cycloalkyl. In other embodiments, $R_{20}$ is

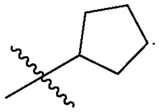 [SMILES: *C1CCCC1]

In some embodiments, $R_{20}$ is cycloheteroalkyl. In other embodiments, $R_{20}$ is

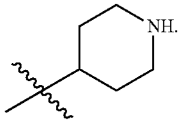 [SMILES: *C1CCNCC1]

In some embodiments, $R_{17}$ is —H, methyl, alkyl, cyclopropyl, cycloalkyl, —C(O)$CH_3$, $R_{18}$ is $R_{20}R_{21}$NCO—; and $R_{20}$ is alkyl, substituted alkyl, aryl, cycloalkyl, cycloheteroalkyl, $R_{20}$ and $R_{17}$ together with the atoms to which they are attached form a cycloheteroalkyl or substituted cycloheteroalkyl ring optionally substituted with =O, or $R_{20}$ and $R_{21}$ together with the atoms to which they are attached form a cycloheteroalkyl or substituted cycloheteroalkyl ring.

In some embodiments, $R_{18}$ is $R_{20}R_{21}$NCO— and $R_{20}$ is alkyl, substituted alkyl, aryl, cycloalkyl, cycloheteroalkyl, $R_{20}$ and $R_{17}$ together with the atoms to which they are attached form a cycloheteroalkyl or substituted cycloheteroalkyl ring optionally substituted with =O, or $R_{20}$ and $R_{21}$ together with the atoms to which they are attached form a cycloheteroalkyl or substituted cycloheteroalkyl ring.

In some embodiments, $R_{18}$ is $R_{23}SO_2$—.

In some embodiments, $R_{23}$ is alkyl. In other embodiments, $R_{23}$ is —$CH_2CH_2CH_3$ or —$CH(CH_3)_2$.

In some embodiments, $R_{23}$ is substituted alkyl. In other embodiments, $R_{23}$ is —$CH_2CH_2OCH_3$, —$CH_2CN$, —$CH_2SO_3CH_3$, or —$CH_2CF_3$,

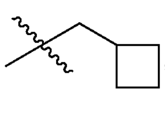,
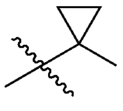

In some embodiments, $R_{23}$ is substituted aryl. In other embodiments, $R_{23}$ is

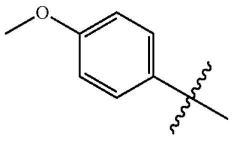
or
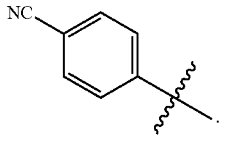

In some embodiment, $R_{23}$ is heteroaryl or substituted heteroaryl. In other embodiments, $R_{23}$ is

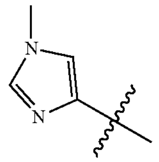
or
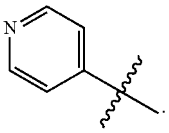

In some embodiments, $R_{23}$ is cycloalkyl. In other embodiments, $R_{23}$ is

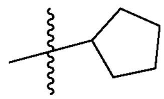
or
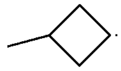

In some embodiments, $R_{23}$ is cycloheteroalkyl. In other embodiments, $R_{23}$ is

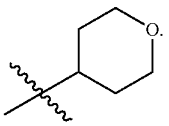 [SMILES: *C1CCOCC1]

In some embodiments, $R_{17}$ is —H, methyl, alkyl, cyclopropyl, cycloalkyl, —C(O)$CH_3$, $R_{18}$ is $R_{23}SO_2$— and $R_{23}$ is alkyl, substituted alkyl, substituted aryl, heteroaryl, substituted heteroaryl, cycloalkyl or cycloheteroalkyl. In other embodiments, $R_{18}$ is $R_{23}SO_2$— and $R_{23}$ is alkyl, substituted alkyl, substituted aryl, heteroaryl, substituted heteroaryl, cycloalkyl or cycloheteroalkyl.

In some embodiments, $R_{16}$ is —H, alkyl, substituted alkyl, heteroarylalkyl or cycloheteroalkyl, $R_{17}$ is —H, methyl, alkyl, cyclopropyl, cycloalkyl, —C(O) $CH_3$, $R_{18}$ is —H, substituted arylalkyl, arylalkyl substituted with a carbohydrate derivative, a carbohydrate derivative, —$R_{19}$CO—, $R_{20}R_{21}$NCO—, $R_{220}$CO—, or $R_{23}SO_2$—.

In some embodiments, $R_{19}$ is alkyl, substituted alkyl, heteroaryl, substituted heteroaryl, substituted heteroarylalkyl, cycloalkyl, cycloheteroalkyl or optionally $R_{19}$ and $R_{17}$ together with the atoms to which they are attached form a cycloheteroalkyl ring; $R_{20}$ is alkyl, substituted alkyl, aryl, cycloalkyl, cycloheteroalkyl or $R_{20}$ and $R_{17}$ together with the atoms to which they are attached form a cycloheteroalkyl or substituted cycloheteroalkyl ring optionally substituted with =O, or $R_{20}$ and $R_{21}$ together with the atoms to which they are attached form a cycloheteroalkyl or substituted cycloheteroalkyl ring; $R_{22}$ is arylalkyl substituted with a carbohydrate derivative, a carbohydrate derivative, alkyl, substituted alkyl or $R_{22}$ and $R_{17}$ together with the atoms to which they are attached form a cycloheteroalkyl ring; and $R_{23}$ is alkyl, substituted alkyl, substituted aryl, heteroaryl, substituted heteroaryl, cycloalkyl or cycloheteroalkyl.

In another aspect a compound of Formula (II) is provided:

(II)

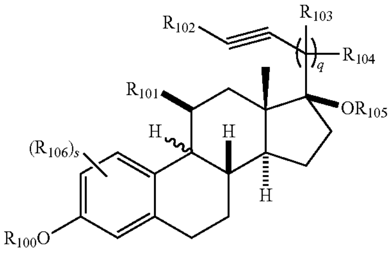

or pharmaceutically acceptable salts, hydrates or solvates thereof where $R_{100}$ is —H, —$CO_2R_{107}$, —$C(O)R_{108}$, —$CONR_{109}R_{110}$, alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl; $R_{101}$ is —$OR_{130}$, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl; $R_{102}$ is —H, —CN, —$CO_2R_{111}$, —$CONR_{112}R_{113}$, alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl; each $R_{103}$ and $R_{104}$ are independently, H, —F or alkyl provided that at least one of $R_{103}$ and $R_{104}$ is —F; q is 1 or 2; $R_{105}$ is —H, —$CO_2R_{114}$, —$C(O)R_{115}$, —$CONR_{116}R_{117}$, alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl; each $R_{106}$ is independently, —H, —$CO_2R_{118}$, —$C(O)R_{119}$, —$CONR_{120}R_{121}$, —$OR_{122}$, —$NR_{123}R_{124}$, —$NHR_{125}R_{126}C(O)R_{127}$, —$SO_2NR_{128}R_{130}$, alkyl, substituted alkyl, alkenyl, substituted alkenyl, alkynyl, substituted alkynyl, aryl, substituted aryl, arylalkyl, substituted arylalkyl, arylalkenyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, substituted arylalkenyl, arylalkynyl, substituted arylalkynyl, halo, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl; s is 0, 1 or 2; $R_{109}$-$R_{113}$, $R_{116}$-$R_{118}$, $R_{120}$-$R_{126}$ and $R_{128}$-$R_{130}$ are independently, —H, alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl; $R_{107}$, $R_{108}$, $R_{114}$, $R_{115}$ and $R_{127}$ are independently alkyl, substituted alkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroalkyl, substituted heteroalkyl, heteroalkenyl, substituted heteroalkenyl, heteroalkynyl, substituted heteroalkynyl, heteroaryl, substituted heteroaryl, heteroarylalkyl, substituted heteroarylalkyl, heteroarylalkenyl, substituted heteroarylalkenyl, heteroarylalkynyl or substituted heteroarylalkynyl.

In some embodiments, $R^{101}$ is substituted aryl, heteroaryl or substituted heteroaryl. In other embodiments, $R_{100}$ is —H, —$CO_2R_{107}$, —$C(O)R_{108}$, —$CONR_{109}R_{110}$, alkyl, alkenyl, aryl, substituted aryl, cycloalkyl, cycloalkenyl, cycloheteroalkyl, cycloheteroalkenyl, heteroalkyl, heteroalkenyl, heteroaryl or substituted heteroaryl. In still other embodiments, $R_{102}$ is —H, —CN, —$CO_2R_{111}$, —$CONR_{112}R_{113}$, alkyl, alkenyl, aryl, substituted aryl, cycloalkyl, cycloalkenyl, cycloheteroalkyl, cycloheteroalkenyl, heteroalkyl, heteroalkenyl, heteroaryl or substituted heteroaryl. In still other embodiments, each $R_{103}$ and $R_{104}$ are independently, —H, or —F. In still other embodiments, each $R_{103}$ and $R_{104}$ are independently, —H, or —F provided that at least one of $R_3$ and $R_4$ is —F. In still other embodiments, $R_{105}$ is —H, —$CO_2R_{114}$, —$C(O)R_{115}$, —$CONR_{116}R_{117}$, alkyl, alkenyl, aryl, substituted aryl, cycloalkyl, cycloalkenyl, cycloheteroalkyl, cycloheteroalkenyl, heteroalkyl, heteroalkenyl, heteroaryl or substituted heteroaryl. In still other embodiments, each $R_{106}$ is independently, —H, —$CO_2R_{118}$, —$C(O)R_{119}$, —$CONR_{120}R_{121}$, —$OR_{122}$, —$NR_{123}R_{124}$, alkyl, substituted alkyl, alkenyl, substituted alkenyl, aryl, substituted aryl, arylalkyl, substituted arylalkyl, halo, heteroaryl, substituted heteroaryl, heteroarylalkyl or substituted heteroarylalkyl. In still other embodiments, $R_{111}$-$R_{113}$ and $R_{116}$-$R_{124}$ are independently —H, alkyl, alkenyl, aryl, substituted aryl, cycloalkyl, cycloalkenyl, cycloheteroalkyl, cycloheteroalkenyl, heteroalkyl, heteroalkenyl, heteroaryl or substituted heteroaryl. In still other embodiments, $R_{114}$ and $R_{115}$ are independently alkyl, alkenyl, aryl, substituted aryl, cycloalkyl, cycloalkenyl, cycloheteroalkyl, cycloheteroalkenyl, heteroalkyl, heteroalkenyl, heteroaryl or substituted heteroaryl.

In some embodiments, $R_{100}$ is —H, —$CO_2R_{107}$, —C(O)$R_{108}$, —$CONR_{109}R_{110}$, alkyl, substituted alkyl, alkenyl, substituted alkenyl, aryl, substituted aryl, cycloalkyl, cycloalkenyl, cycloheteroalkyl, cycloheteroalkenyl, heteroalkyl, heteroalkenyl, heteroaryl or substituted heteroaryl; $R_{101}$ is —$OR_{130}$, substituted aryl, heteroaryl, substituted heteroaryl, $R_{102}$ is —H, —CN, —$CO_2R_{111}$, —$CONR_{112}R_{113}$, alkyl, alkenyl, aryl, substituted aryl, cycloalkyl, cycloalkenyl, cycloheteroalkyl, cycloheteroalkenyl, heteroalkyl, heteroalkenyl, heteroaryl or substituted heteroaryl; each $R_{103}$ and $R_{104}$ are independently H or —F provided that at least one of $R_{103}$ and $R_{104}$ is —F; $R_5$ is —H, —$CO_2R_{114}$, —C(O)$R_{115}$, —$CONR_{116}R_{117}$, alkyl, alkenyl, aryl, substituted aryl, cycloalkyl, cycloalkenyl, cycloheteroalkyl, cycloheteroalkenyl, heteroalkyl, heteroalkenyl, heteroaryl or substituted heteroaryl; $R_{106}$ is independently, —H, —$CO_2R_{118}$, —C(O)$R_{119}$, —$CONR_{120}R_{121}$, —$OR_{122}$, —$NR_{123}R_{124}$, alkyl, substituted alkyl, alkenyl, substituted alkenyl, aryl, substituted aryl, arylalkyl, substituted arylalkyl, halo, heteroaryl, substituted heteroaryl, heteroarylalkyl or substituted heteroarylalkyl; $R_{111}$-$R_{113}$, $R_{116}$-$R_{124}$ and $R_{130}$, are independently-H, alkyl, alkenyl, aryl, substituted aryl, cycloalkyl, cycloalkenyl, cycloheteroalkyl, cycloheteroalkenyl, heteroalkyl, heteroalkenyl, heteroaryl or substituted heteroaryl; and $R_{114}$ and $R_{115}$ are independently alkyl, alkenyl, aryl, substituted aryl, cycloalkyl, cycloalkenyl, cycloheteroalkyl, cycloheteroalkenyl, heteroalkyl, heteroalkenyl, heteroaryl or substituted heteroaryl.

In some embodiments, $R_{100}$ is —H, —$CO_2R_{107}$, alkyl, substituted alkyl, aryl, substituted aryl, cycloalkyl, cycloalkenyl, cycloheteroalkyl, cycloheteroalkenyl, heteroalkyl, substituted heteroalkyl, heteroalkenyl, heteroaryl or substituted heteroaryl.

In some embodiments, $R_{101}$ is substituted aryl or substituted phenyl. In other embodiments, $R_{101}$ is

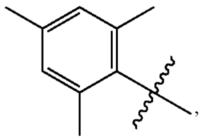
,
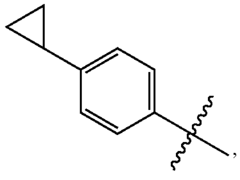
,
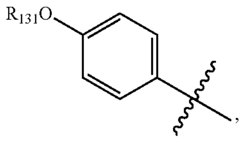
,
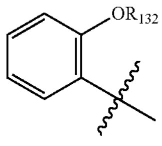
or
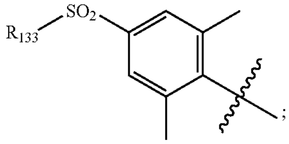
;

$R_{130}$ is alkyl, substituted alkyl, arylalkyl, substituted arylalkyl; $R_{133}$ is alkyl or substituted alkyl; $R_{131}$ is alkyl; and $R_{132}$ is alkyl or substituted alkyl.

In some embodiments, $R_{131}$ is —$CH_3$, —$CH_2CF_3$, —$SO_2CF_3$, —$CH_2$Ph where Ph is substituted at the para position by —$SO_2CF_3$; $R_{132}$ is —$CH_3$; and $R_{133}$ is $CF_3$.

In some embodiments, n is 1 and $R_3$ and $R_4$ are —F.

In some embodiments, $R_2$ is —H.

In some embodiments, $R_5$ is —H.

In some embodiments, $R_{100}$ is substituted alkyl. In other embodiments, $R_{100}$ is —$CH_2CF_3$, —$CH_2CO_2H$, —$CH_2CH_2OCH_3$, —$CH_2$ $(CH_3)_2OH$, —$CH_2C(O)N(CH_3)_2$, —$CH_2CN$, —$CH_2CH_2OSi(CH_3)_3$, —$CH_2CH_2OH$, —$CH_2CH_2OCH_2CH_2OH$, —$CH_2CH_2OCH_2CH_2OCH_2CH_2OCH_3$,

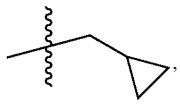
,
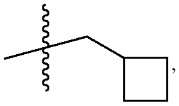
,
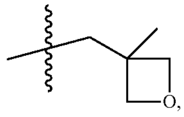
,
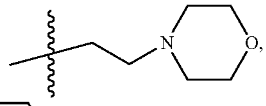
,
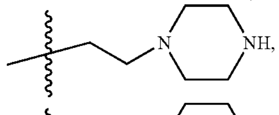
,
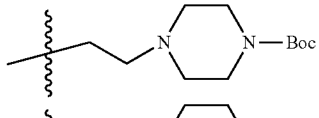
or
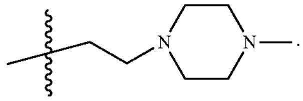
.

In some embodiments, a compound having the structure is provided:

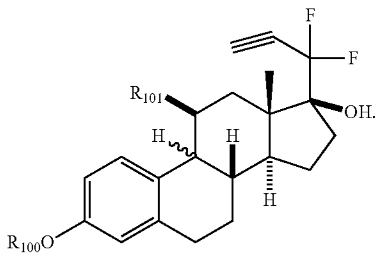

In some embodiments, $R_{100}$ is —H, —$CO_2R_{107}$, alkyl, substituted alkyl, heteroalkyl, heteroaryl or substituted heteroaryl.

In some embodiments, $R_{100}$ is —H, —$CO_2R_{107}$, alkyl, substituted alkyl, aryl, substituted aryl, cycloalkyl, cycloalkenyl, cycloheteroalkyl, cycloheteroalkenyl, heteroalkyl or substituted heteroalkyl.

Some exemplary compounds are depicted in Table1 below.

TABLE 1
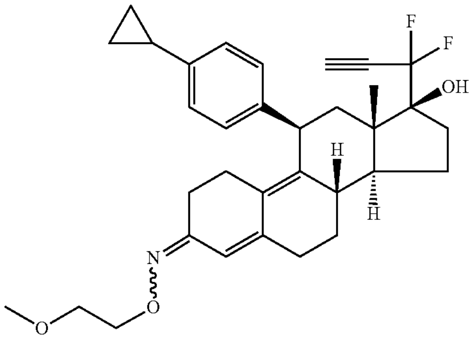
1
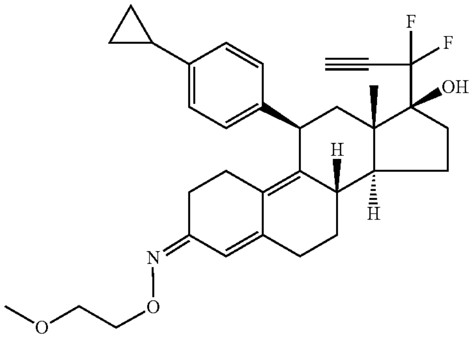
2
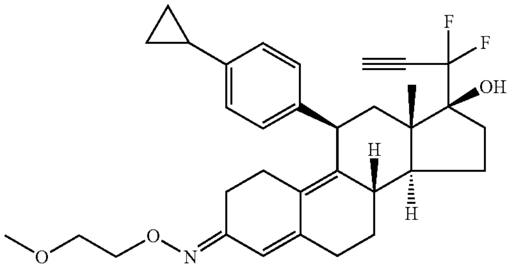
3
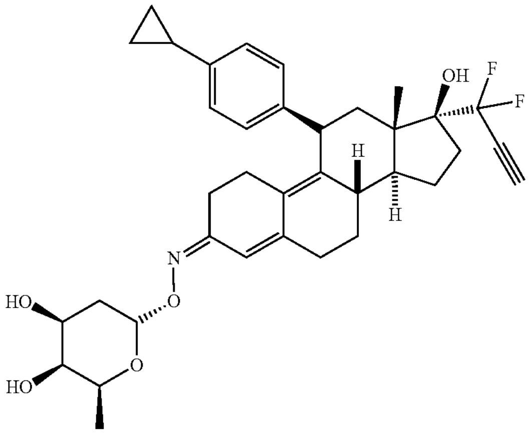
4

TABLE 1-continued
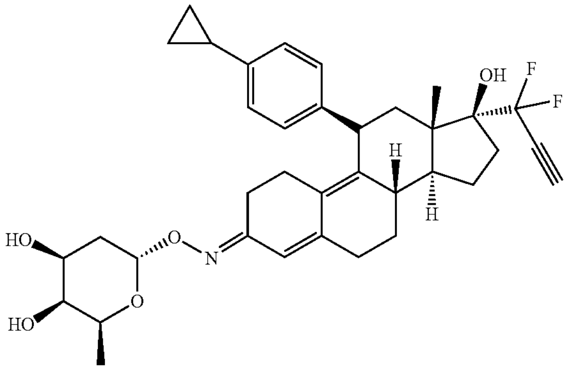
5
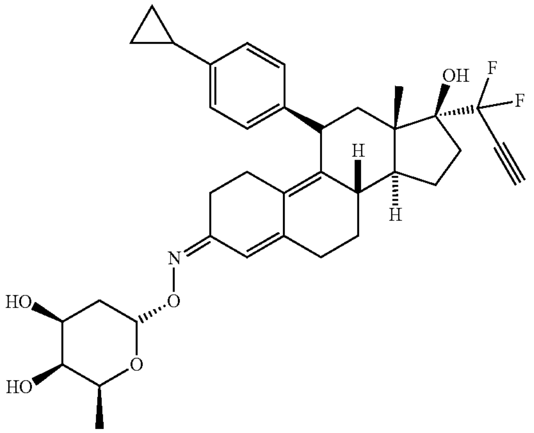
6
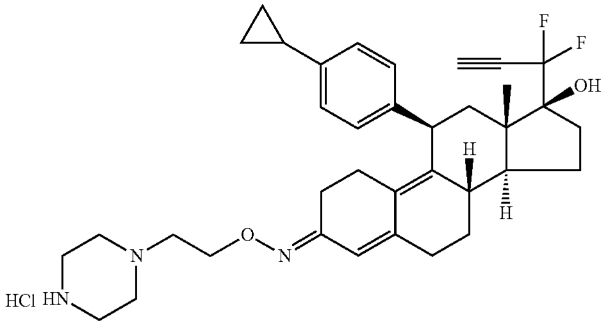
7
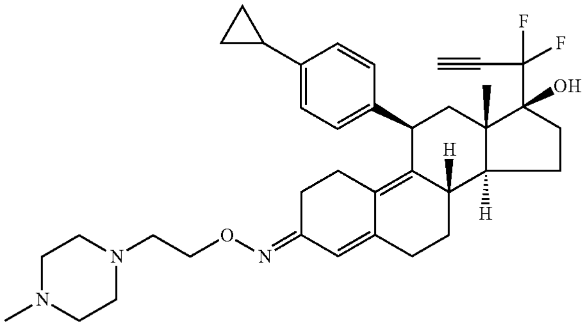
8

TABLE 1-continued
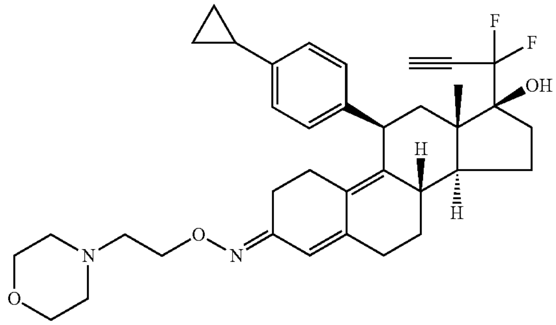
9
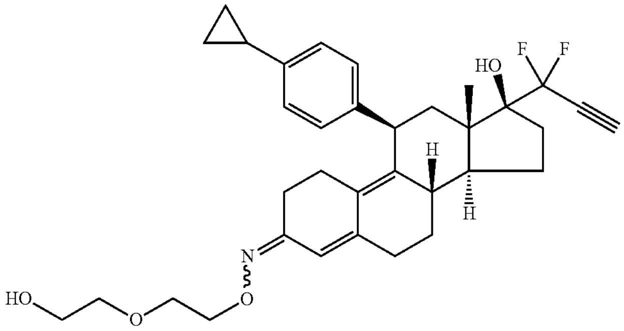
10
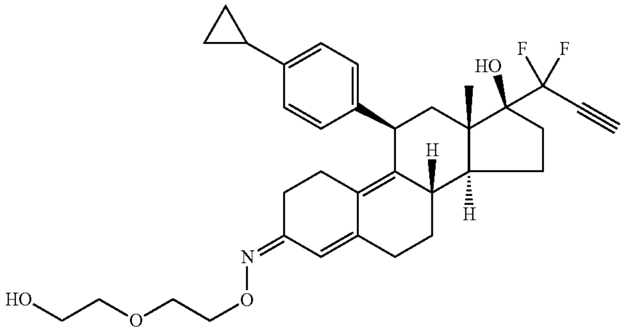
11
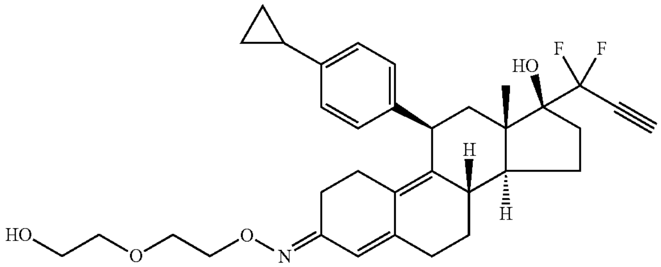
12
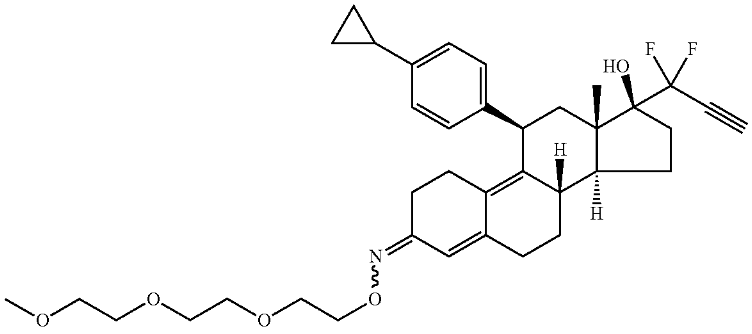
13

TABLE 1-continued
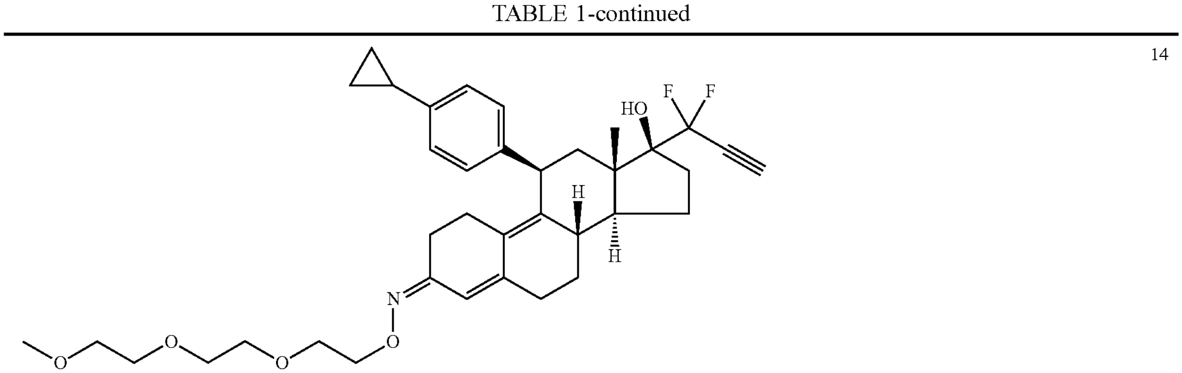
14
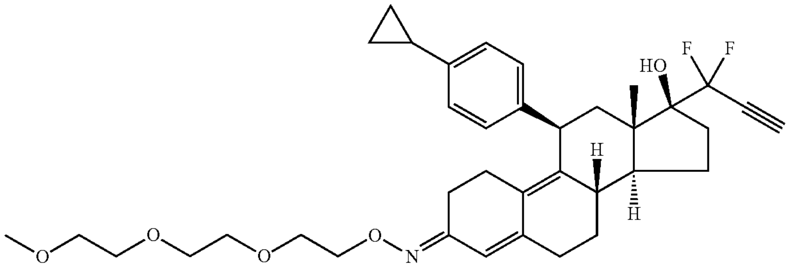
15
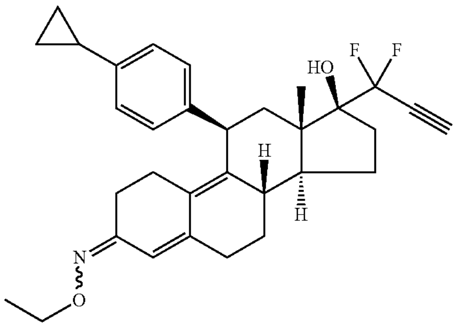
16
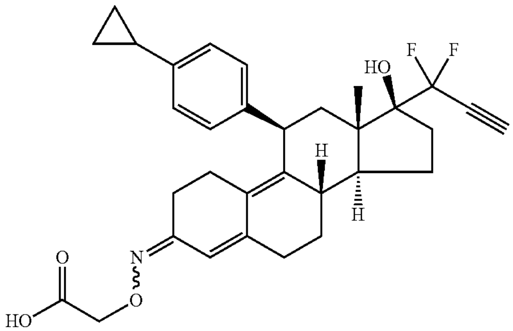
17
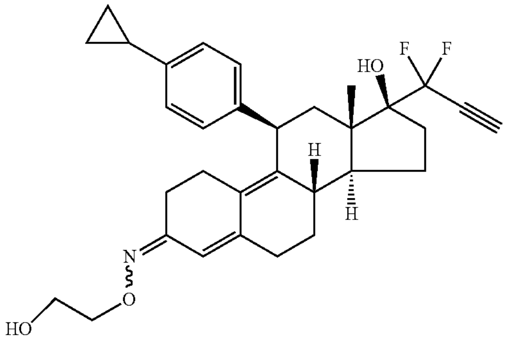
18

TABLE 1-continued
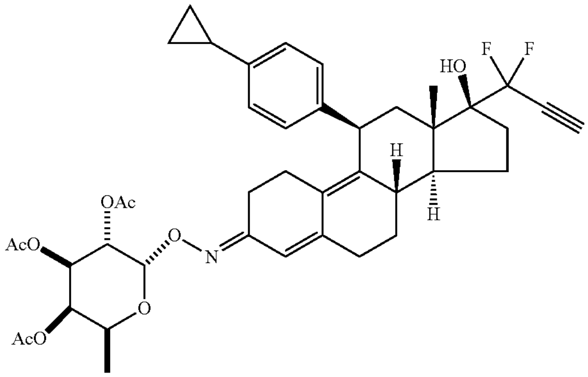
19
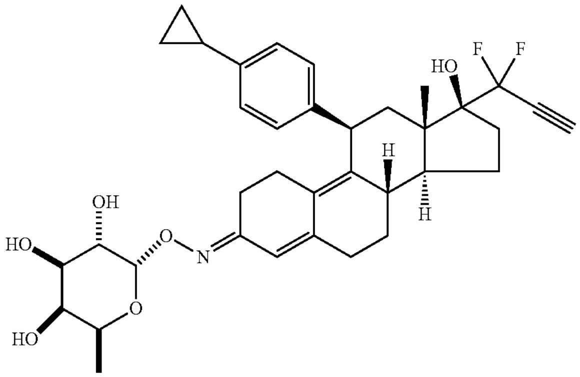
20
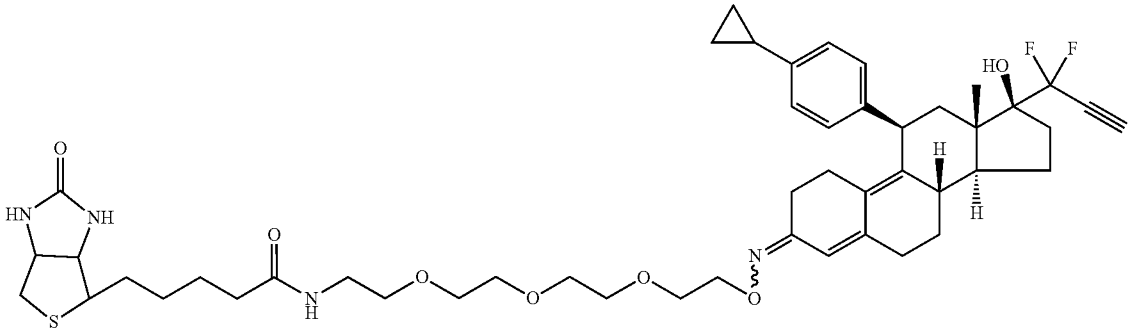
21
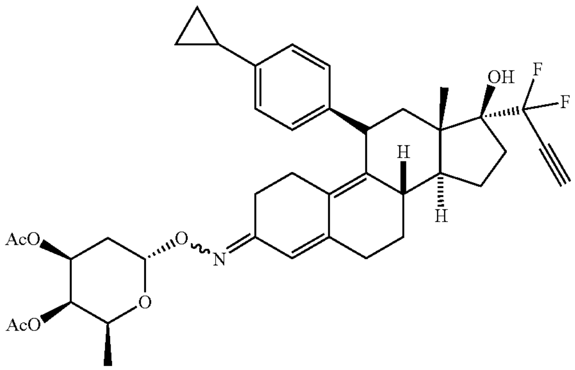
22

TABLE 1-continued
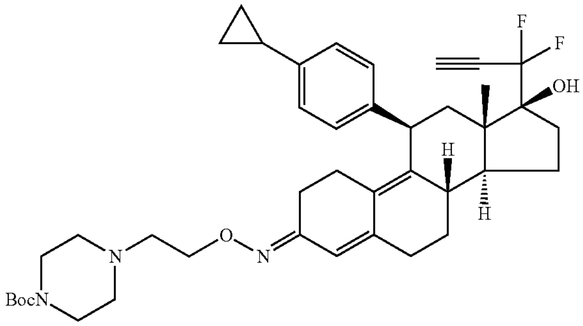
23
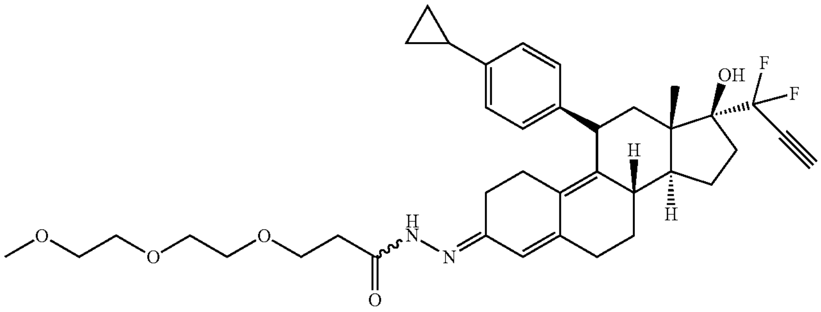
24
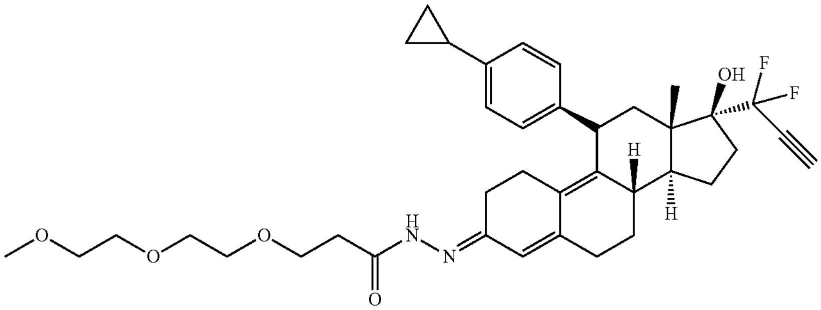
25
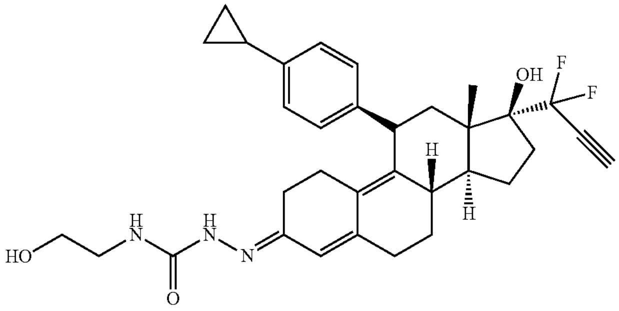
26
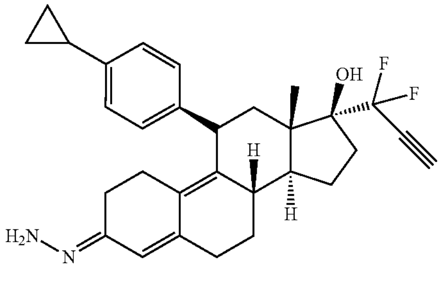
27

TABLE 1-continued
28
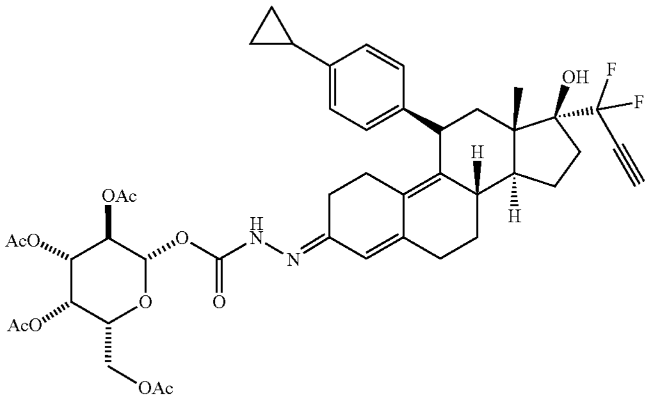
29
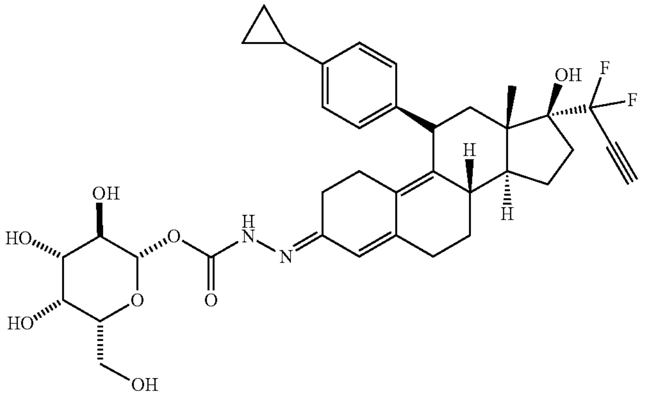
30
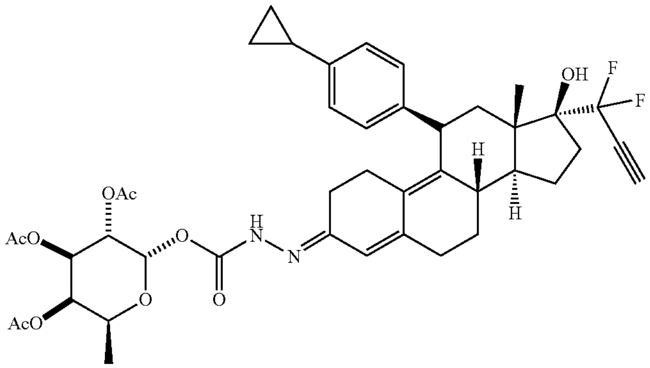
31
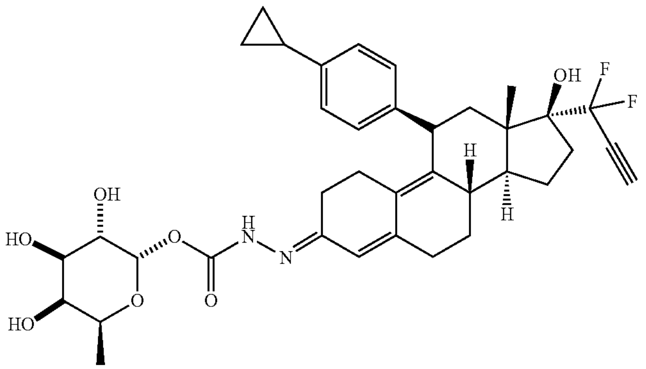

TABLE 1-continued
32
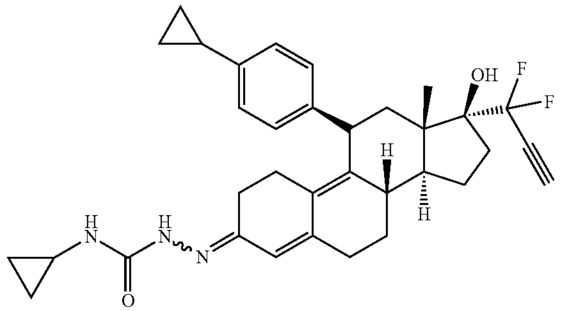
33
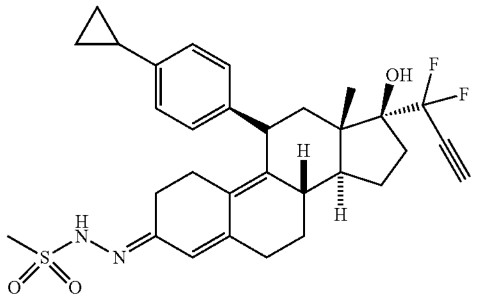
34
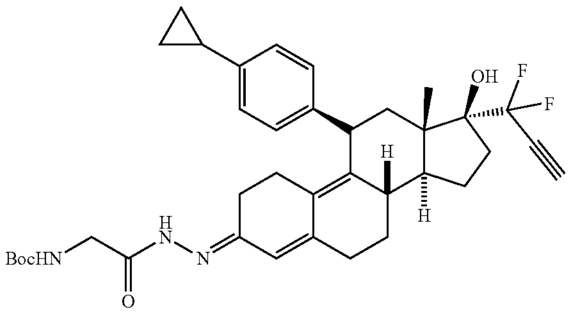
35
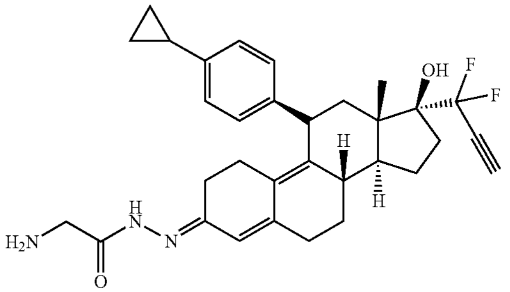
36
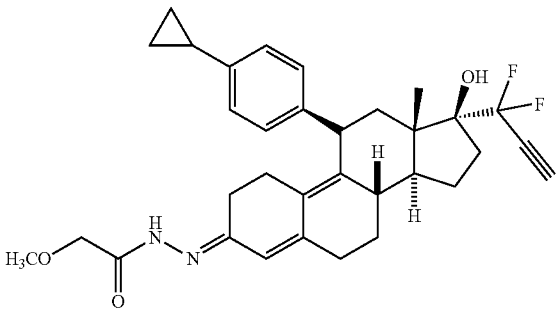

TABLE 1-continued
37
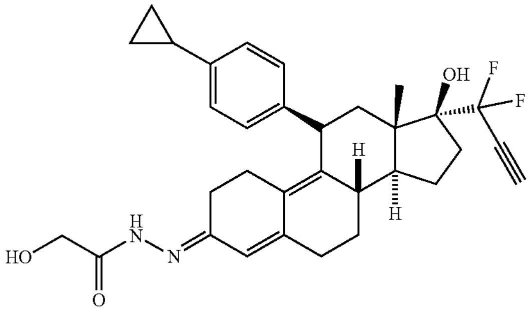
38
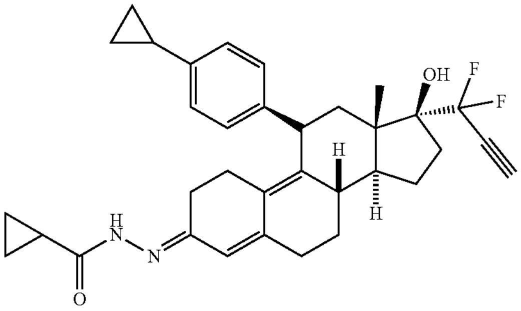
39
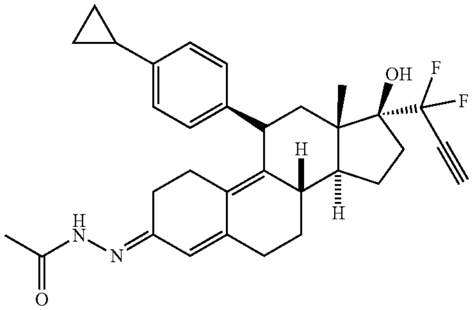
40
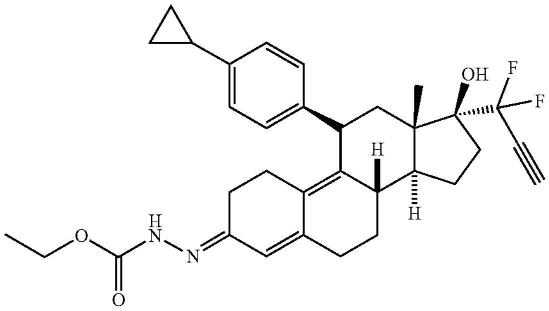
41
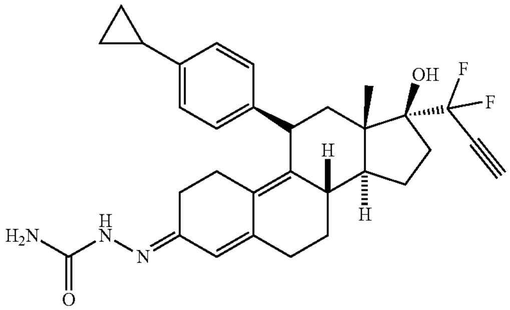

TABLE 1-continued
42
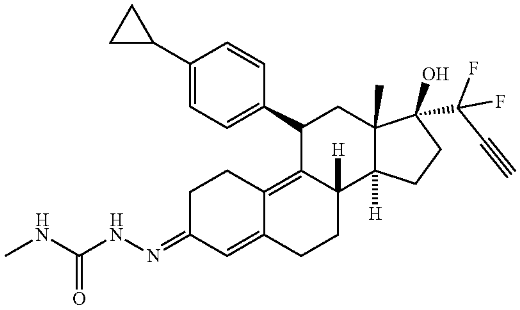
43
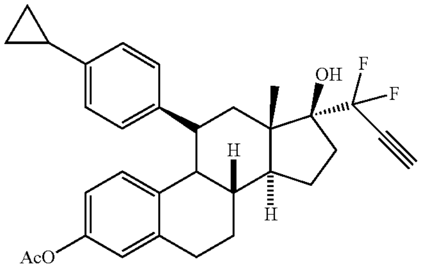
44
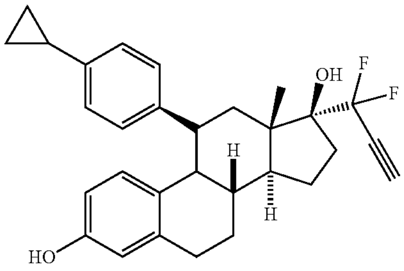
45
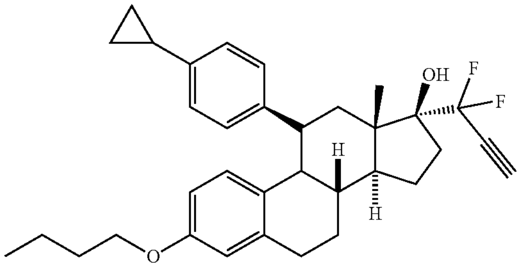
46
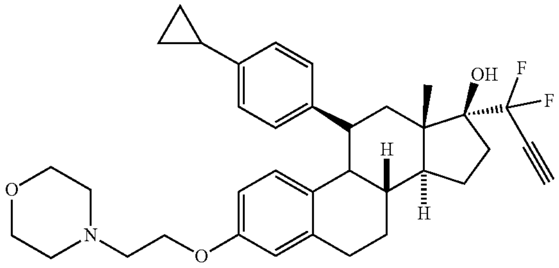

TABLE 1-continued
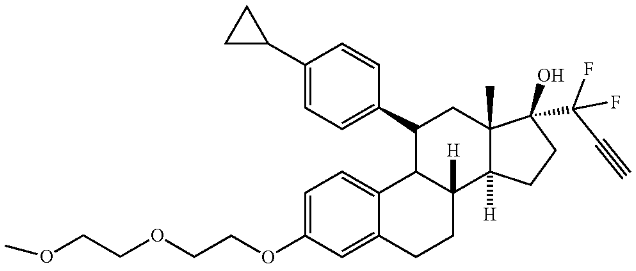
47
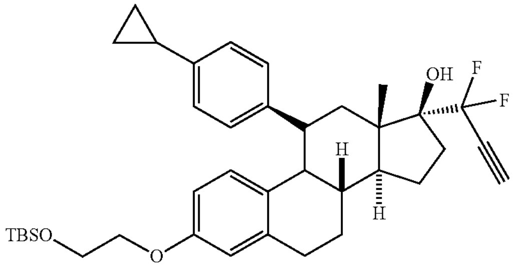
48
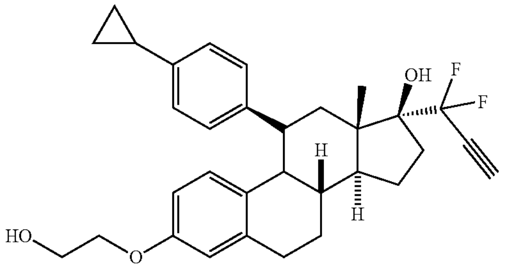
49
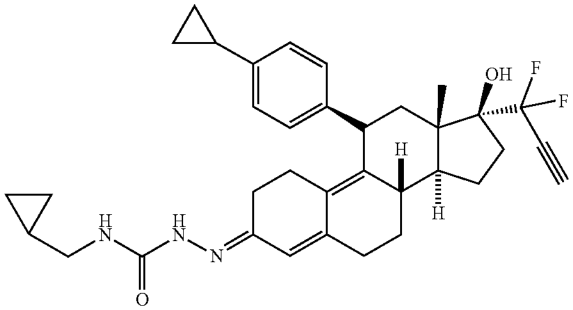
50
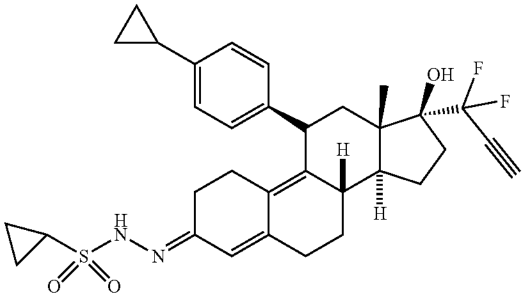
51

TABLE 1-continued
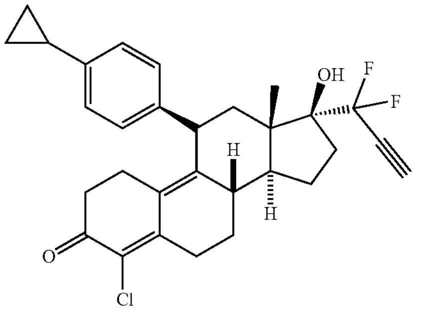
52
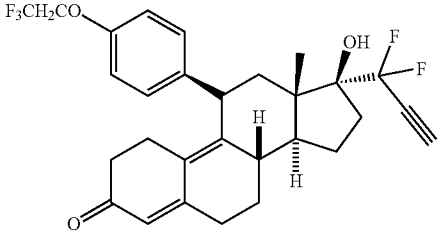
53
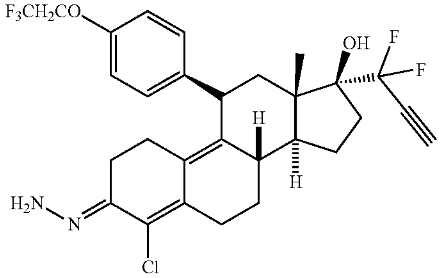
54
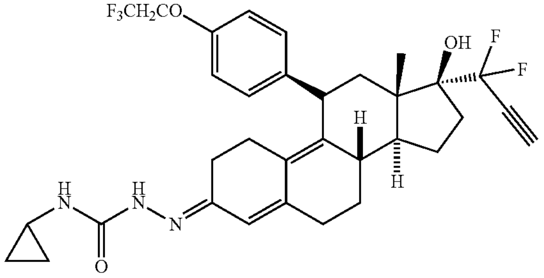
55
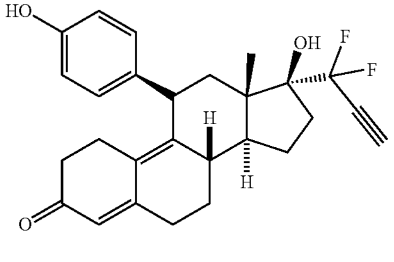
56

TABLE 1-continued
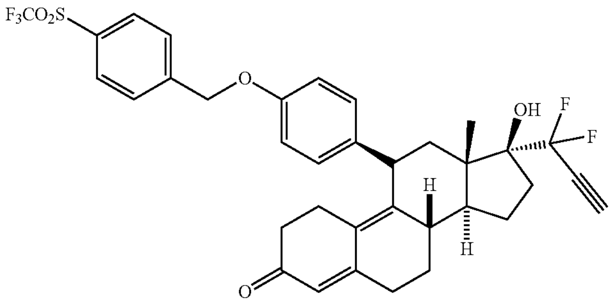
57
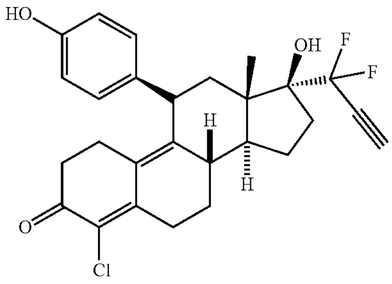
58
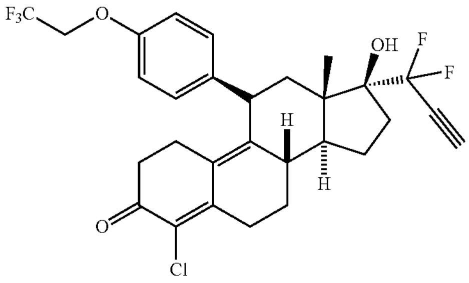
59
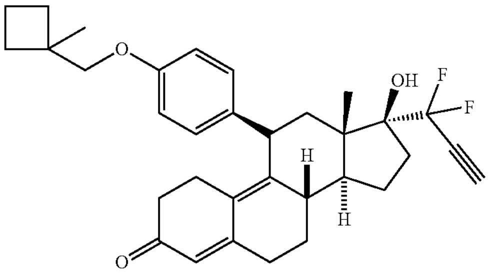
60
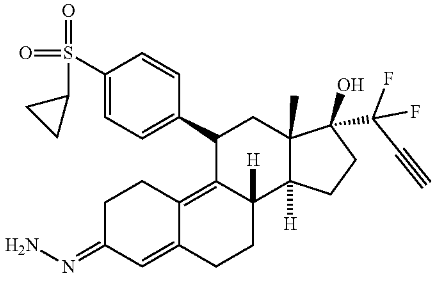
61

TABLE 1-continued
62
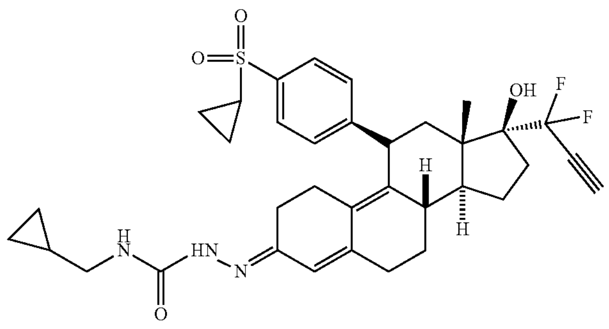
63
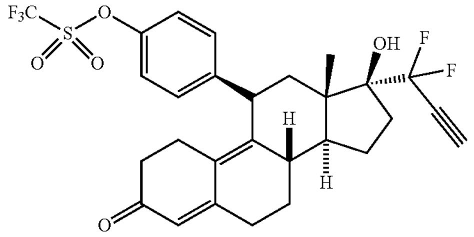
64
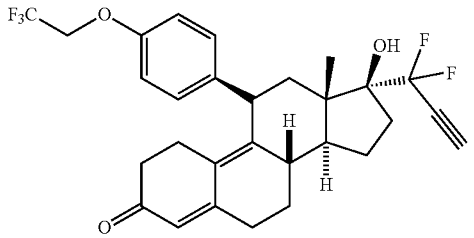
65
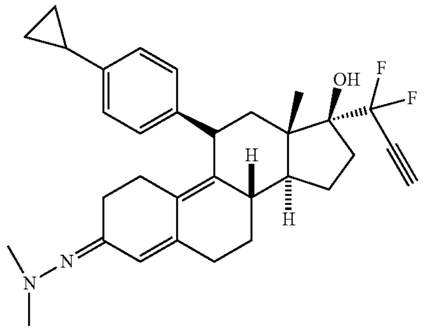
66
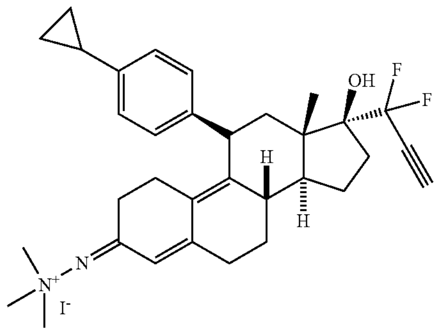

TABLE 1-continued
67
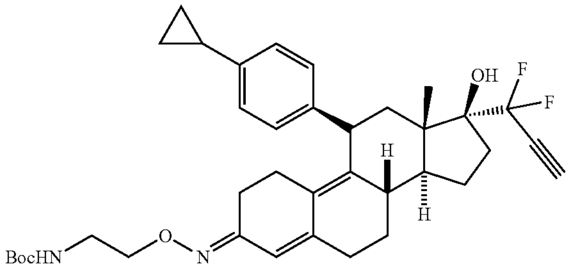
68
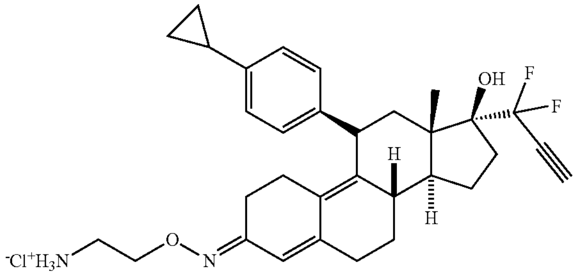
69
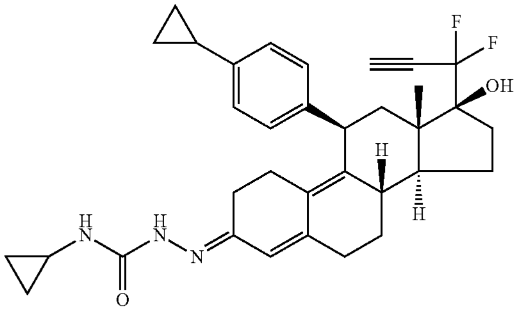
70
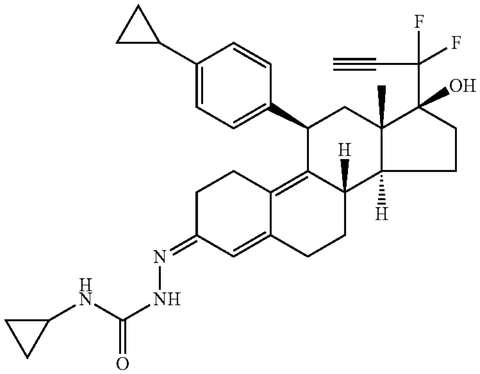
71
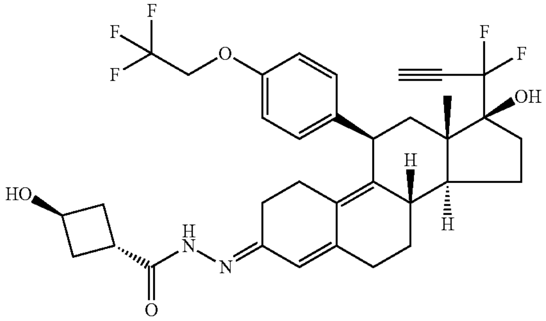

TABLE 1-continued
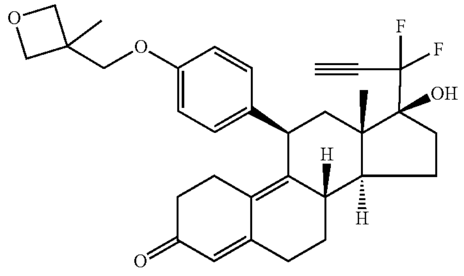
72
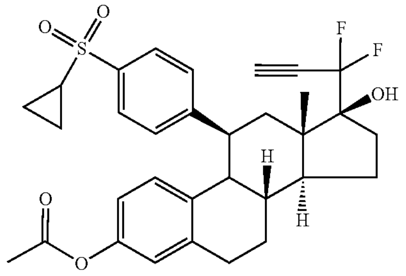
73
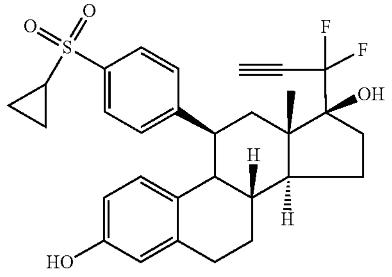
74
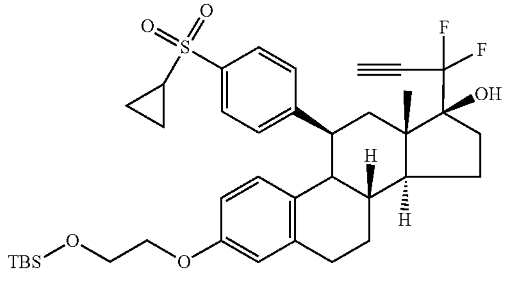
75
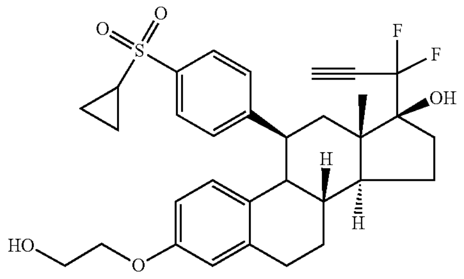
76

TABLE 1-continued

| | |
|---|---|
| 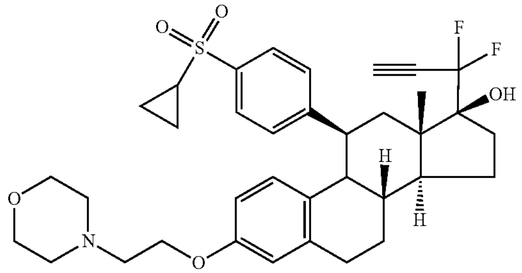 | 77 |
| 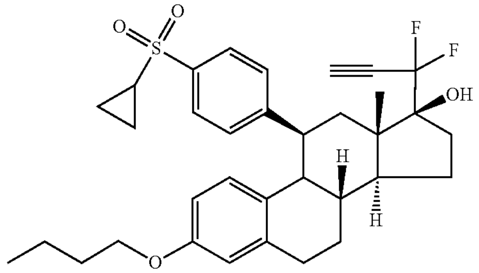 | 78 |
| 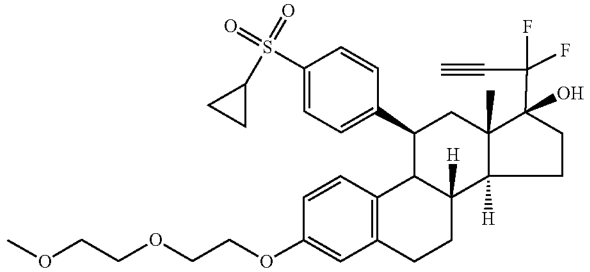 | 79 |
| 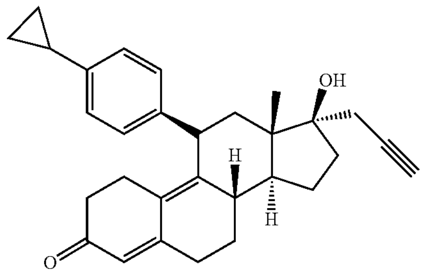 | 80 |

The compounds above can be made by well know procedures some of which are exemplified in the experimental section.

Methods for Characterizing and Identifying Senolytic Agents

Characterizing a senolytic agent can be determined using one or more cell-based assays and one or more animal models described herein or in the art and with which a person skilled in the art will be familiar. A senolytic agent may selectively kill one or more types of senescent cells (e.g., senescent preadipocytes, senescent endothelial cells, senescent fibroblasts, senescent neurons, senescent epithelial cells, senescent mesenchymal cells, senescent smooth muscle cells, senescent macrophages, or senescent chondrocytes). In certain embodiments, a senolytic agent is capable of selectively killing at least senescent fibroblasts.

Characterizing an agent as a senolytic agent can be accomplished using one or more cell-based assays and one or more animal models described herein or in the art. Those of skill in the art will readily appreciate that characterizing an agent as a senolytic agent and determining the level of killing by an agent can be accomplished by comparing the activity of a test agent with appropriate negative controls (e.g., vehicle or diluent only and/or a composition or compound known in the art not to kill senescent cells) and appropriate positive controls. In vitro cell-based assays for characterizing senolytic agents also include controls for determining the effect of the agent on non-senescent cells (e.g., quiescent cells or proliferating cells). A senolytic agent reduces (i.e., decreases) percent survival of a plurality of senescent cells (i.e., in some manner reduces the quantity of viable senescent cells in the animal or in the cell-based assay) compared with one or more negative controls. Conditions for a particular in vitro assay include temperature, buffers (including salts, cations, media), and other components, which maintain the integrity of the test agent and reagents used in the assay, are familiar to a person skilled in the art and/or which can be readily determined through routine experimentation.

The source of senescent cells for use in assays may be a primary cell culture, or culture-adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiable cell lines, transformed cell lines, and the like. In some embodiments, senescent cells are isolated from biological samples obtained from a host or subject who has a senescent cell associated disease or disorder. In other embodiments, non-senescent cells may be obtained from a subject or may be a culture adapted line and senescence is induced by methods described herein and, in the art, such as by exposure to irradiation or a chemotherapeutic agent (e.g., doxorubicin). Biological samples may be, for example, blood samples, biopsy specimens, body fluids (e.g., lung lavage, ascites, mucosal washings, synovial fluid, etc.), bone marrow, lymph nodes, tissue explants, organ cultures, or any other tissues or cell preparations obtained from a subject. The biological samples may be a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source. The subject may be a human or non-human animal.

Transgenic animal models as described herein and, in the art, may be used to determine killing or removal of senescent cells (see, e.g., Baker et al., Nature, 479 (2011) 232-236; International Application No. WO/2012/177927; International Application No. WO 2013/090645). Exemplary transgenic animal models contain a transgene that includes a nucleic acid that allows for controlled clearance of senescent cells (e.g., p16INK4a positive senescent cells) as a positive control. The presence and level of senescent cells in the transgenic animals can be determined by measuring the level of a detectable label or labels that are expressed in senescent cells of the animal. The transgene nucleotide sequence includes a detectable label, for example, one or more of a red fluorescent protein; a green fluorescent protein; and one or more luciferases to detect clearance of senescent cells.

Animal models that are described herein or in the art include art-accepted models for determining the effectiveness of a senolytic agent to treat or prevent (i.e., reduce the likelihood of occurrence of) a particular senescence associated disease or disorder, such as atherosclerosis models, osteoarthritis models, COPD models, IPF models, etc. As described herein, pulmonary disease murine models, such as a bleomycin pulmonary fibrosis model, and a chronic cigarette smoking model are applicable for diseases such as COPD and may be routinely practiced by a person skilled in the art. Animal models for determining the effectiveness of a senolytic agent to treat and/or prevent (i.e., reduce the likelihood of occurrence of) chemotherapy and radiotherapy side effect models or to treat or prevent (i.e., reduce the likelihood of occurrence of) metastasis are described in International Application Nos. WO 2013/090645 and WO 2014/205244. Animal models for determining the effectiveness of agents for treating eye diseases, particularly age-related macular degeneration is also routinely used in the art (see, e.g., Pennesi et al.; Mol. Aspects Med. 33 (2012) 487-509; Zeiss et al., Vet. Pathol. 47 (2010) 396-413; Chavala et al., J. Clin. Invest. 123 (2013) 4170-4181).

By way of non-limiting example and as described herein, osteoarthritis animal models have been developed. Osteoarthritis may be induced in the animal, for example, by inducing damage to a joint, for example, in the knee by surgical severing, incomplete or total, of the anterior cruciate ligament. Osteoarthritis animal models may be used for assessing the effectiveness of a senolytic agent to treat or prevent (i.e., reducing the likelihood of occurrence of) osteoarthritis and cause a decrease in proteoglycan erosion and to induce (i.e., stimulate, enhance) collagen (such as collagen type 2) production, and to reduce pain in an animal that has ACL surgery. Immunohistology may be performed to examine the integrity and composition of tissues and cells in a joint. Immunochemistry and/or molecular biology techniques may also be performed, such as assays for determining the level of inflammatory molecules (e.g., IL-6) and assays for determining the level of senescence markers as noted above, using methods and techniques described herein, which may be routinely practiced by a person skilled in the art.

By way of another non-limiting example and as described herein, atherosclerosis animal models have been developed. Atherosclerosis may be induced in the animal, for example, by feeding animals a high fat diet or by using transgenic animals highly susceptible to developing atherosclerosis. Animal models may be used for determining the effectiveness of a senolytic agent to reduce the amount of plaque or to inhibit formation of plaque in an atherosclerotic artery, to reduce the lipid content of an atherosclerotic plaque (i.e., reduce, decrease the amount of lipid in a plaque), and to cause an increase or to enhance fibrous cap thickness of a plaque. Sudan staining may be used to detect the level of lipid in an atherosclerotic vessel. Immunohistology and immunochemistry and molecular biology assays (e.g., for determining the level of inflammatory molecules (e.g., IL-6), and for determining the level of senescence markers as noted above), may all be performed according to methods described herein, which are routinely practiced in the art.

In still another non-limiting example, and as described herein, mouse models in which animals are treated with bleomycin have been described (see, e.g., Peng et al., PLOS One 8 (4) (2013) e59348. doi: 10.1371/journal.pone.0059348; Mouratis et al., Curr. Opin. Pulm. Med. 17 (2011) 355-361) for determining the effectiveness of an agent for treating IPF. In pulmonary disease animal models (e.g., a bleomycin animal model, smoke-exposure animal model, or the like), respiratory measurements may be taken to determine elastance, compliance, static compliance, and peripheral capillary oxygen saturation ($SpO_2$). Immunohistology and immunochemistry and molecular biology assays (e.g., for determining the level of inflammatory molecules (e.g., IL-6), and for determining the level of senescence markers as noted above), may all be performed according to methods described herein, which are routinely practiced in the art.

Determining the effectiveness of a senolytic agent to selectively kill senescent cells as described herein in an animal model may be performed using one or more statistical analyses with which those skilled in the art will be familiar. By way of example, statistical analyses such as two-way analysis of variance (ANOVA) may be used for determining the statistical significance of differences between animal groups treated with an agent and those that are not treated with the agent (i.e., negative control group, which may include vehicle only and/or a non-senolytic agent). Statistical packages such as SPSS, MINITAB, SAS, Statistika, Graphpad, GLIM, Genstat, and BMDP are readily available and are routinely used by a person skilled in the animal model art.

Those of skill in the art will readily appreciate that characterizing a senolytic agent and determining the level of killing by the senolytic agent can be accomplished by comparing the activity of a test agent with appropriate negative controls (e.g., vehicle only and/or a composition, agent, or compound known in the art not to kill senescent cells) and appropriate positive controls. In vitro cell-based assays for characterizing the agent also include controls for determining the effect of the agent on non-senescent cells (e.g., quiescent cells or proliferating cells). A senolytic agent that is useful reduces (i.e., decreases) percent survival of senescent cells (i.e., in some manner reduces the quantity of viable senescent cells in the animal or in the cell-based assay) compared with one or more negative controls. Accordingly, a senolytic agent selectively kills senescent cells compared with killing of non-senescent cells (which may be referred to herein as selectively killing senescent cells over non-senescent cells).

In certain embodiments (either in an in vitro assay or in vivo (in a human or non-human animal)), the at least one senolytic agent kills at least 20% of the senescent cells and kills no more than 5% of non-senescent cells. In other embodiments (either in an in vitro assay or in vivo (in a human or non-human animal)), the at least one senolytic agent kills at least about 25%, 30%, 35%, 40%, 45%, 50%, 55%, 60%, or 65% of the senescent cells and kills no more than about 5% or 10% of non-senescent cells. In still other embodiments (either in an in vitro assay or in vivo (in a human or non-human animal)), the at least one senolytic agent kills at least about 30%, 35%, 40%, 45%, 50%, 55%, 60%, or 65% of the senescent cells and kills no more than about 5%, 10%, or 15% of non-senescent cells. In still other embodiments (either in an in vitro assay or in vivo (in a human or non-human animal)), the at least one senolytic agent kills at least about 40%, 45%, 50%, 55%, 60%, or 65% of the senescent cells and kills no more than about 5%, 10%, 15%, 20%, or 25% of non-senescent cells. In still other embodiments (either in an in vitro assay or in vivo (in a human or non-human animal)), the at least one senolytic agent kills at least about 50%, 55%, 60%, or 65% of the senescent cells and kills no more than about 5%, 10%, 15%, 20%, 25%, or 30% of non-senescent cells. Stated another way, a senolytic agent has at least 5-25, 10-50, 10-100 or 100-1000 times greater selectively for killing senescent cells than for non-senescent cells.

With respect to specific embodiments of the methods described herein for treating a senescence-associated disease or disorder, the percent senescent cells killed may refer to the percent senescent cells killed in a tissue or organ that comprises senescent cells that contribute to onset, progression, and/or exacerbation of the disease or disorder. By way of non-limiting example, tissues of the brain, tissues and parts of the eye, pulmonary tissue, cardiac tissue, arteries, joints, skin, and muscles may comprise senescent cells that may be reduced in percent as described above by the senolytic agents described herein and thereby provide a therapeutic effect. Moreover, selectively removing at least 20% or at least 25% of senescent cells from an affected tissue or organ can have a clinically significant therapeutic effect.

With respect to specific embodiments of the methods described herein, such as for example, treating a cardiovascular disease or disorder associated with arteriosclerosis, such as atherosclerosis, by administering a senolytic agent (i.e., in reference to vivo methods above), the percent senescent cells killed may refer to the percent senescent cells killed in an affected artery containing plaque versus non-senescent cells killed in the arterial plaque. In certain embodiments, in the methods for treating the cardiovascular disease, such as atherosclerosis, as described herein, the at least one senolytic agent kills at least 20% of the senescent cells and kills no more than 5% of non-senescent cells in the artery. In other embodiments, the senolytic agent selectively kills at least 25% of the senescent cells in the arteriosclerotic artery.

In some embodiments, with respect to the methods described herein for treating osteoarthritis by administering a senolytic agent, the percent senescent cells killed may refer to the percent senescent cells killed in an osteoarthritic joint versus non-senescent cells killed in the osteoarthritic joint. In certain embodiments, in the methods for treating osteoarthritis as described herein, the at least one senolytic agent kills at least 20% of the senescent cells and kills no more than 5% of non-senescent cells in the osteoarthritic joint. In other embodiments, the senolytic agent selectively kills at least 25% of the senescent cells in the osteoarthritic joint.

In some embodiments, with respect to the methods described herein for treating senescence associated pulmonary disease or disorder (e.g., COPD, IPF) by administering at least one senolytic agent, the percent senescent cells killed may refer to the percent senescent cells killed in affected pulmonary tissue versus non-senescent cells killed in the affected pulmonary tissue of the lung. In certain embodiments, in the methods for treating senescence associated pulmonary diseases and disorders as described herein, a senolytic agent kills at least 20% of the senescent cells and kills no more than 5% of non-senescent cells in the affected pulmonary tissue. In other embodiments, the senolytic agent selectively kills at least 25% of the senescent cells in the affected pulmonary tissue.

In certain embodiments, methods are provided for identifying (i.e., screening for) agents that are useful senolytic agents for treating or preventing (i.e., reducing the likelihood of occurrence of) a senescence associated disease or disorder. In some embodiments, a method for identifying a senolytic agent for treating such diseases and disorders, comprises inducing cells to senesce to provide established senescent cells. Methods for inducing cells to senesce are described herein and in the art and include, for example, exposure to radiation (e.g., 10 Gy is typically sufficient) or a chemotherapeutic agent (e.g., doxorubicin or other anthracyclines). After exposure to the agent, the cells are cultured for an appropriate time and under appropriate conditions (e.g., media, temperature, $CO_2/O_2$ level appropriate for a given cell type or cell line) to allow senescence to be established. As discussed herein, senescence of cells may be determined by determining any number of characteristics, such as changes in morphology (as viewed by microscopy, for example); production of, for example, senescence-associated-galactosidase (SA-gal), p16INK4a, p21, or any one or more SASP factors (e.g., IL-6, MMP3). A sample of the senescent cells is then contacted with a candidate agent (i.e., mixed with, combined, or in some manner permitting the cells and the agent to interact). Persons skilled in the art will appreciate that the assay will include the appropriate controls, negative and positive, either historical or performed concurrently. For example, a sample of control non-senescent cells that have been cultured similarly as the senescent cells but not exposed to a senescence inducing agent are contacted with the candidate agent. The level of survival of the senescent cells is determined and compared with the level of survival of the non-senescent cells. A senolytic agent is identified when the level of survival of the senescent cells is less than the level of survival of the non-senescent cells.

In some embodiments, the above-described method to identify a senolytic agent may further comprise steps for identifying whether the senolytic agent is useful for treating osteoarthritis. The method may further comprise contacting the identified senolytic agent with cells capable of producing collagen; and determining the level of collagen produced by the cells. In some embodiments, the cells are chondrocytes and the collagen is Type 2 collagen. The method may further comprise administering a candidate senolytic agent to a non-human animal with arthritic lesions in a joint and determining one or more of (a) the level of senescent cells in the joint; (b) physical function of the animal; (c) the level of one or more markers of inflammation; (d) histology of the joint; and (e) the level of Type 2 collagen produced, thereby determining therapeutic efficacy of the senolytic agent wherein one or more of the following is observed in the treated animal compared with an animal not treated with the senolytic agent: (i) a decrease in the level of senescent cells in the joint of the treated animal; (ii) improved physical function of the treated animal; (iii) a decrease in the level of one or more markers of inflammation in the treated animal; (iv) increased histological normalcy in the joint of the treated animal; and (v) an increase in the level of Type 2 collagen produced in the treated animal. As described herein and in the art, the physical function of the animal may be determined by techniques that determine the sensitivity of a leg to an induced or natural osteoarthritic condition, for example, by the animal's tolerance to bear weight on an affected limb or the ability of the animal to move away from an unpleasant stimulus, such as heat or cold. Determining the effectiveness of an agent to kill senescent cells as described herein in an animal model may be performed using one or more statistical analyses with which a skilled person will be familiar. Statistical analyses as described herein and routinely practiced in the art may be applied to analyze data.

In other embodiments, the above-described method to identify a senolytic agent may further comprise steps for identifying whether the senolytic agent is useful for treating a cardiovascular disease caused by or associated with arteriosclerosis. Accordingly, the method may further comprise administering the senolytic candidate agent in non-human animals or in animal models for determining the effectiveness of an agent to reduce the amount of plaque, to inhibit formation of plaque in an atherosclerotic artery, to reduce the lipid content of an atherosclerotic plaque (i.e., reduce, decrease the amount of lipid in a plaque), and/or to cause an increase or to enhance fibrous cap thickness of a plaque. Sudan staining may be used to detect the level of lipid in an atherosclerotic vessel. Immunohistology, assays for determining the level of inflammatory molecules (e.g., IL-6), and/or assays for determining the level of senescence markers as noted above, may all be performed according to methods described herein and routinely practiced in the art.

In a specific embodiment, methods described herein for identifying a senolytic agent may further comprise administering a candidate senolytic agent to a non-human animal with atherosclerotic plaque and determining one or more of (a) the level of senescent cells in the artery; (b) physical function of the animal; (c) the level of one or more markers of inflammation; (d) histology of the affected blood vessel(s) (e.g., artery); and thereby determining therapeutic efficacy of the senolytic agent wherein one or more of the following is observed in the treated animal compared with an animal not treated with the senolytic agent: (i) a decrease in the level of senescent cells in the artery of the treated animal; (ii) improved physical function of the treated animal; (iii) a decrease in the level of one or more markers of inflammation in the treated animal; (iv) increased histological normalcy in the artery of the treated animal. As described herein and in the art, the physical function of the animal may be determined by measuring physical activity. Statistical analyses as described herein and routinely practiced in the art may be applied to analyze data.

In some embodiments, methods described herein for identifying a senolytic agent may comprise administering a candidate senolytic agent to a non-human animal pulmonary disease model such as a bleomycin model or a smoke-exposure animal model and determining one or more of (a) the level of senescent cells in a lung; (b) lung function of the animal; (c) the level of one or more markers of inflammation; (d) histology of pulmonary tissue, thereby determining therapeutic efficacy of the senolytic agent wherein one or more of the following is observed in the treated animal compared with an animal not treated with the senolytic agent: (i) a decrease in the level of senescent cells in the lungs and pulmonary tissue of the treated animal; (ii) improved lung function of the treated animal; (iii) a decrease in the level of one or more markers of inflammation in the treated animal; and (iv) increased histological normalcy in the pulmonary tissue of the treated animal. Respiratory measurements may be taken to determine elastance, compliance, static compliance, and peripheral capillary oxygen saturation ($SpO_2$). Lung function may be evaluated by determining any one of numerous measurements, such as expiratory reserve volume (ERV), forced vital capacity (FVC), forced expiratory volume (FEV) (e.g., FEV in one second, FEV1), FEV1/FEV ratio, forced expiratory flow 25% to 75%, and maximum voluntary ventilation (MVVpeak expiratory flow (PEF), slow vital capacity (SVC). Total lung volumes include total lung capacity (TLC), vital capacity (VC),), residual volume (RV), and functional residual capacity (FRC). Gas exchange across alveolar capillary membrane can be measured using diffusion capacity for carbon monoxide (DLCO). Peripheral capillary oxygen saturation (SpO.sub.2) can also be measured. Statistical analyses as described herein and routinely practiced in the art may be applied to analyze data.

Methods of Treatment and Prevention of Senescence-Associated Diseases and Disorders Methods are provided herein for treating conditions, diseases, or disorders related to, associated with, or caused by cellular senescence, including age-related diseases and disorders in a subject in need thereof. A senescence-associated disease or disorder may also be called herein a senescent cell-associated disease or disorder. Senescence-associated diseases and disorders include, for example, cardiovascular diseases and disorders, inflammatory diseases and disorders, autoimmune diseases and disorders, pulmonary diseases and disorders, eye diseases and disorders, metabolic diseases and disorders, neurological diseases and disorders (e.g., neurodegenerative diseases and disorders); age-related diseases and disorders induced by senescence; skin conditions; age-related diseases; dermatological diseases and disorders; and transplant related diseases and disorders. A prominent feature of aging is a gradual loss of function, or degeneration that occurs at the molecular, cellular, tissue, and organismal levels. Age-related degeneration gives rise to well-recognized pathologies, such as sarcopenia, atherosclerosis and heart failure, osteoporosis, pulmonary insufficiency, renal failure, neurodegeneration (including macular degeneration, Alzheimer's disease, and Parkinson's disease), and many others. Although different mammalian species vary in their susceptibilities to specific age-related pathologies, collectively, age-related pathologies generally rise with approximately exponential kinetics beginning at about the mid-point of the species-specific life span (e.g., 50-60 years of age for humans) (see, e.g., Campisi, Annu. Rev. Physiol. 75 (2013) 685-705; Naylor et al., Clin. Pharmacol. Ther. 93 (2013) 105-116).

Examples of senescence-associated conditions, disorders, or diseases that may be treated by administering any one of the senolytic agents described herein according to the methods described herein include, cognitive diseases (e.g., mild cognitive impairment (MCI), Alzheimer's disease and other dementias; Huntington's disease); cardiovascular disease (e.g., atherosclerosis, cardiac diastolic dysfunction, aortic aneurysm, angina, arrhythmia, cardiomyopathy, congestive heart failure, coronary artery disease, myocardial infarction, endocarditis, hypertension, carotid artery disease, peripheral vascular diseases, cardiac stress resistance, cardiac fibrosis); metabolic diseases and disorders (e.g., obesity, diabetes, metabolic syndrome); motor function diseases and disorders (e.g., Parkinson's disease, motor neuron dysfunction (MND); Huntington's disease); cerebrovascular disease; emphysema; osteoarthritis; benign prostatic hypertrophy; pulmonary diseases (e.g., idiopathic pulmonary fibrosis, chronic obstructive pulmonary disease (COPD), emphysema, obstructive bronchiolitis, asthma); inflammatory/autoimmune diseases and disorders (e.g., osteoarthritis, eczema, psoriasis, osteoporosis, mucositis, transplantation related diseases and disorders); ophthalmic diseases or disorders (e.g., age-related macular degeneration, cataracts, glaucoma, vision loss, presbyopia); diabetic ulcer; metastasis; a chemotherapeutic side effect, a radiotherapy side effect; aging-related diseases and disorders (e.g., kyphosis, renal dysfunction, frailty, hair loss, hearing loss, muscle fatigue, skin conditions, sarcopenia, and herniated intervertebral disc) and other age-related diseases that are induced by senescence (e.g., diseases/disorders resulting from irradiation, chemotherapy, smoking tobacco, eating a high fat/high sugar diet, and environmental factors); wound healing; skin nevi; fibrotic diseases and disorders (e.g., cystic fibrosis, renal fibrosis, liver fibrosis, pulmonary fibrosis, oral submucous fibrosis, cardiac fibrosis, and pancreatic fibrosis). In certain embodiments, any one or more of the diseases or disorders described above or herein may be excluded.

In some embodiments, methods are provided for treating a senescence-associated disease or disorder by killing senescent cells (i.e., established senescent cells) associated with the disease or disorder in a subject who has the disease or disorder by administering a senolytic agent, where the disease or disorder is osteoarthritis, idiopathic pulmonary fibrosis, chronic obstructive pulmonary disease (COPD), or atherosclerosis.

Cardiovascular Diseases and Disorders

In other embodiments, the senescence-associated disease or disorder treated by the methods described herein is a cardiovascular disease. The cardiovascular disease may be any one or more of angina, arrhythmia, atherosclerosis, cardiomyopathy, congestive heart failure, coronary artery disease (CAD), carotid artery disease, endocarditis, heart attack (coronary thrombosis, myocardial infarction [MI]), high blood pressure/hypertension, aortic aneurysm, brain aneurysm, cardiac fibrosis, cardiac diastolic dysfunction, hypercholesterolemia/hyperlipidemia, mitral valve prolapse, peripheral vascular disease (e.g., peripheral artery disease (PAD)), cardiac stress resistance and stroke.

In certain embodiments, methods are provided for treating senescence-associated cardiovascular disease that is associated with or caused by arteriosclerosis (i.e., hardening of the arteries). The cardiovascular disease may be any one or more of atherosclerosis (e.g., coronary artery disease (CAD) and carotid artery disease); angina, congestive heart failure, and peripheral vascular disease (e.g., peripheral artery disease (PAD)). The methods for treating a cardiovascular disease that is associated with or caused by arteriosclerosis may reduce the likelihood of occurrence of high blood pressure/hypertension, angina, stroke, and heart attack (i.e., coronary thrombosis, myocardial infarction (MI)). In certain embodiments, methods are provided for stabilizing atherosclerotic plaque(s) in a blood vessel (e.g., artery) of a subject, thereby reducing the likelihood of occurrence or delaying the occurrence of a thrombotic event, such as stroke or myocardial infraction. In certain embodiments, these methods comprising administration of a senolytic agent, reduce (i.e., cause decrease of) the lipid content of an atherosclerotic plaque in a blood vessel (e.g., artery) of the subject and/or increase the fibrous cap thickness (i.e., cause an increase, enhance or promote thickening of the fibrous cap).

Atherosclerosis is characterized by patchy intimal plaques (atheromas) that encroach on the lumen of medium-sized and large arteries; the plaques contain lipids, inflammatory cells, smooth muscle cells, and connective tissue. Atherosclerosis can affect large and medium-sized arteries, including the coronary, carotid, and cerebral arteries, the aorta and its branches, and major arteries of the extremities. In some embodiments, methods are provided for inhibiting the formation of atherosclerotic plaques (or reducing, diminishing, causing decrease in formation of atherosclerotic plaques) by administering a senolytic agent. In other embodiments, methods are provided for reducing (decreasing, diminishing) the amount (i.e., level) of plaque. Reduction in the amount of plaque in a blood vessel (e.g., artery) may be determined, for example, by a decrease in surface area of the plaque, or by a decrease in the extent or degree (e.g., percent) of occlusion of a blood vessel (e.g., artery), which can be determined by angiography or other visualizing methods used in the cardiovascular art. Also provided herein are methods for increasing the stability (or improving, promoting, enhancing stability) of atherosclerotic plaques that are present in one or more blood vessels (e.g., one or more arteries) of a subject, which methods comprise administering to the subject any one of the senolytic agents described herein.

Subjects suffering from cardiovascular disease can be identified using standard diagnostic methods known in the art for cardiovascular disease. Generally, diagnosis of atherosclerosis and other cardiovascular disease is based on symptoms (e.g., chest pain or pressure (angina), numbness or weakness in arms or legs, difficulty speaking or slurred speech, drooping muscles in face, leg pain, high blood pressure, kidney failure and/or erectile dysfunction), medical history, and/or physical examination of a patient. Diagnosis may be confirmed by angiography, ultrasonography, or other imaging tests. Subjects at risk of developing cardiovascular disease include those having any one or more of predisposing factors, such as a family history of cardiovascular disease and those having other risk factors (i.e., predisposing factors) such as high blood pressure, dyslipidemia, high cholesterol, diabetes, obesity and cigarette smoking, sedentary lifestyle, and hypertension. In certain embodiments, the cardiovascular disease that is a senescent cell associated disease/disorder is atherosclerosis.

The effectiveness of one or more senolytic agents for treating or preventing (i.e., reducing or decreasing the likelihood of developing or occurrence of) a cardiovascular disease (e.g., atherosclerosis) can readily be determined by a person skilled in the medical and clinical arts. One or any combination of diagnostic methods, including physical examination, assessment and monitoring of clinical symptoms, and performance of analytical tests and methods described herein and practiced in the art (e.g., angiography, electrocardiograman-stress test), may be used for monitoring the health status of the subject. The effects of the treatment of a senolytic agent or pharmaceutical composition comprising the same can be analyzed using techniques known in the art, such as comparing symptoms of patients suffering from or at risk of cardiovascular disease that have received the treatment with those of patients without such a treatment or with placebo treatment.

Inflammatory and Autoimmune Diseases and Disorders

In certain embodiments, a senescence-associated disease or disorder is an inflammatory disease or disorder, such as by way of non-limiting example, osteoarthritis, which may be treated or prevented (i.e., likelihood of occurrence is reduced) according to the methods described herein that comprise administration of a senolytic agent. Other inflammatory or autoimmune diseases or disorders that may be treated by administering a senolytic agent such as the inhibitors and antagonists described herein include osteoporosis, psoriasis, oral mucositis, rheumatoid arthritis, inflammatory bowel disease, eczema, kyphosis, herniated intervertebral disc, and the pulmonary diseases, COPD and idiopathic pulmonary fibrosis.

Osteoarthritis degenerative joint disease is characterized by fibrillation of the cartilage at sites of high mechanical stress, bone sclerosis, and thickening of the synovium and the joint capsule. Fibrillation is a local surface disorganization involving splitting of the superficial layers of the cartilage. The early splitting is tangential with the cartilage surface, following the axes of the predominant collagen bundles. Collagen within the cartilage becomes disorganized, and proteoglycans are lost from the cartilage surface. In the absence of protective and lubricating effects of proteoglycans in a joint, collagen fibers become susceptible to degradation, and mechanical destruction ensues. Predisposing risk factors for developing osteoarthritis include increasing age, obesity, previous joint injury, overuse of the joint, weak thigh muscles, and genetics. Symptoms of osteoarthritis include sore or stiff joints, particularly the hips, knees, and lower back, after inactivity or overuse; stiffness after resting that goes away after movement; and pain that is worse after activity or toward the end of the day. Osteoarthritis may also affect the neck, small finger joints, the base of the thumb, ankle, and big toe. Chronic inflammation is thought to be the main age-related factor that contributes to osteoarthritis. In combination with aging, joint overuse and obesity appear to promote osteoarthritis.

By selectively killing senescent cells a senolytic agent prevents (i.e., reduces the likelihood of occurrence), reduces or inhibits loss or erosion of proteoglycan layers in a joint, reduces inflammation in the affected joint, and promotes (i.e., stimulates, enhances, induces) production of collagen (e.g., type 2 collagen). Removal of senescent cells causes a reduction in the amount (i.e., level) of inflammatory cytokines, such as IL-6, produced in a joint and inflammation is reduced. Methods are provided herein for treating osteoarthritis, for selectively killing senescent cells in an osteoarthritic joint of a subject, and/or inducing collagen (such as Type 2 collagen) production in the joint of a subject by administering at least one senolytic agent (which may be combined with at least one pharmaceutically acceptable excipient to form a pharmaceutical composition) to the subject. A senolytic agent also may be used for decreasing (inhibiting, reducing) production of metalloproteinase 13 (MMP-13), which degrades collagen in a joint, and for restoring proteoglycan layer or inhibiting loss and/or degradation of the proteoglycan layer. Treatment with the senolytic agent thereby also prevents (i.e., reduces likelihood of occurrence of), inhibits, or decreases erosion, or slows (i.e., decreases rate) erosion of the bone. As described in detail herein, in certain embodiments, the senolytic agent is administered directly to an osteoarthritic joint (e.g., by intra-articularly, topical, transdermal, intradermal, or subcutaneous delivery). Treatment with a senolytic agent can also restore, improve, or inhibit deterioration of strength of a joint. In addition, the methods comprising administering a senolytic agent can reduce joint pain and are therefore useful for pain management of osteoarthritic joints.

The effectiveness of one or more senolytic agents for treatment or prophylaxis of osteoarthritis in a subject and monitoring of a subject who receives one or more senolytic agents can readily be determined by a person skilled in the medical and clinical arts. One or any combination of diagnostic methods, including physical examination (such as determining tenderness, swelling or redness of the affected joint), assessment and monitoring of clinical symptoms (such as pain, stiffness, mobility), and performance of analytical tests and methods described herein and practiced in the art (e.g., determining the level of inflammatory cytokines or chemokines; X-ray images to determine loss of cartilage as shown by a narrowing of space between the bones in a joint; magnetic resonance imaging (MRI), providing detailed images of bone and soft tissues, including cartilage), may be used for monitoring the health status of the subject. The effects of the treatment of one or more senolytic agents can be analyzed by comparing symptoms of patients suffering from or at risk of an inflammatory disease or disorder, such as osteoarthritis, who have received the treatment with those of patients who have not received such a treatment or who have received a placebo treatment.

In certain embodiments, senolytic agents may be used for treating and/or preventing (i.e., decreasing or reducing the likelihood of occurrence) rheumatoid arthritis (RA). Dysregulation of innate and adaptive immune responses characterize rheumatoid arthritis (RA), which is an autoimmune disease the incidence of which increases with age. Rheumatoid arthritis is a chronic inflammatory disorder that typically affects the small joints in hands and feet. Whereas osteoarthritis results from, at least in part, wear and tear of a joint, rheumatoid arthritis affects the lining of joints, resulting in a painful swelling that can lead to bone erosion and joint deformity. RA can sometimes also affect other organs of the body, such as the skin, eyes, lungs and blood vessels. RA can occur in a subject at any age; however, RA usually begins to develop after age 40. The disorder is much more common in women. In certain embodiments of the methods described herein, RA is excluded.

Chronic inflammation may also contribute to other age-related or aging related diseases and disorders, such as kyphosis and osteoporosis. Kyphosis is a severe curvature in the spinal column, and it is frequently seen with normal and premature aging (see, e.g., Katzman et al., J. Orthop. Sports Phys. Ther. 40 (2010) 352-360). Age-related kyphosis often occurs after osteoporosis weakens spinal bones to the point that they crack and compress. A few types of kyphosis target infants or teens. Severe kyphosis can affect lungs, nerves, and other tissues and organs, causing pain and other problems. Kyphosis has been associated with cellular senescence. Characterizing the capability of a senolytic agent for treating kyphosis may be determined in pre-clinical animal models used in the art. By way of example, TTD mice develop kyphosis (see, e.g., de Boer et al., Science 296 (2002) 1276-1279); other mice that may be used include BubR1$^{H/H}$ mice, which are also known to develop kyphosis (see, e.g., Baker et al., Nature 479 (2011) 232-236). Kyphosis formation is visually measured over time. The level of senescent cells decreased by treatment with the senolytic agent can be determined by detecting the presence of one or more senescent cell associated markers such as by SA-β-Gal staining.

Osteoporosis is a progressive bone disease that is characterized by a decrease in bone mass and density that may lead to an increased risk of fracture, which may be treated or prevented by administration of the senolytic agents described herein. Bone mineral density (BMD) is reduced, bone microarchitecture deteriorates, and the amount and variety of proteins in bone are altered. Osteoporosis is typically diagnosed and monitored by a bone mineral density test. Post-menopausal women or women who have reduced estrogen are most at risk. While both men and women over 75 are at risk, women are twice as likely to develop osteoporosis than men. The level of senescent cells decreased by treatment with the senolytic agent can be determined by detecting the presence of one or more senescent cell associated markers such as by SA-β-Gal staining.

In still other embodiments, an inflammatory/autoimmune disorder that may be treated or prevented (i.e., likelihood of occurrence is reduced) with the senolytic agents described herein includes irritable bowel syndrome (IBS) and inflammatory bowel diseases, such as ulcerative colitis and Crohn's disease. Inflammatory bowel disease (IBD) involves chronic inflammation of all or part of the digestive tract. In addition to life-threatening complications arising from IBD, the disease can be painful and debilitating. Ulcerative colitis is an inflammatory bowel disease that causes long-lasting inflammation in part of the digestive tract. Symptoms usually develop over time, rather than suddenly. Ulcerative colitis usually affects only the innermost lining of the large intestine (colon) and rectum. Crohn's disease is an inflammatory bowel disease that causes inflammation anywhere along the lining of your digestive tract, and often extends deep into affected tissues. This can lead to abdominal pain, severe diarrhea and malnutrition. The inflammation caused by Crohn's disease can involve different areas of the digestive tract. Diagnosis and monitoring of the diseases are performed according to methods and diagnostic tests routinely practiced in the art, including blood tests, colonoscopy, flexible sigmoidoscopy, barium enema, CT scan, MRI, endoscopy, and small intestine imaging.

Other inflammatory or autoimmune diseases that may be treated or prevented (i.e., likelihood of occurrence is reduced) by using a senolytic agent include eczema, psoriasis, osteoporosis, and pulmonary diseases (e.g., chronic obstructive pulmonary disease (COPD), idiopathic pulmonary fibrosis (IPF), asthma), inflammatory bowel disease, and mucositis (including oral mucositis, which in some instances is induced by radiation). Certain fibrosis or fibrotic conditions of organs such as renal fibrosis, liver fibrosis, pancreatic fibrosis, cardiac fibrosis, skin wound healing, and oral submucous fibrosis may be treated with the senolytic agents described herein.

In certain embodiments, the senescent cell associated disorder is an inflammatory disorder of the skin, such as by way of a non-limiting examples, psoriasis and eczema that may be treated or prevented (i.e., likelihood of occurrence is reduced) according to the methods described herein that comprise administration of a senolytic agent. Psoriasis is characterized by abnormally excessive and rapid growth of the epidermal layer of the skin. A diagnosis of psoriasis is usually based on the appearance of the skin. Skin characteristics typical for psoriasis are scaly red plaques, papules, or patches of skin that may be painful and itch. In psoriasis, cutaneous and systemic overexpression of various proinflammatory cytokines is observed such as IL-6, a key component of the SASP. Eczema is an inflammation of the skin that is characterized by redness, skin swelling, itching and dryness, crusting, flaking, blistering, cracking, oozing, or bleeding. The effectiveness of senolytic agents for treatment of psoriasis and eczema and monitoring of a subject who receives such a senolytic agent can be readily determined by a person skilled in the medical or clinical arts. One or any combination of diagnostic methods, including physical examination (such as skin appearance), assessment of monitoring of clinical symptoms (such as itching, swelling, and pain), and performance of analytical tests and methods described herein and practiced in the art (i.e., determining the level of pro-inflammatory cytokines).

Other immune disorders or conditions that may be treated or prevented (i.e., likelihood of occurrence is reduced) with senolytic agents described herein include conditions resulting from a host immune response to an organ transplant (e.g., kidney, bone marrow, liver, lung, or heart transplant), such as rejection of the transplanted organ. Senolytic agents described herein may also be used for treating or reducing the likelihood of occurrence of graft-vs-host disease.

Pulmonary Diseases and Disorders

In some embodiments, methods are provided for treating or preventing (i.e., reducing the likelihood of occurrence of) a senescence-associated disease or disorder that is a pulmonary disease or disorder by killing senescent cells (i.e., established senescent cells) associated with the disease or disorder in a subject who has the disease or disorder by administering senolytic agents described herein. Senescence associated pulmonary diseases and disorders include, for example, idiopathic pulmonary fibrosis (IPF), chronic obstructive pulmonary disease (COPD), asthma, cystic fibrosis, bronchiectasis, and emphysema.

COPD is a lung disease defined by persistently poor airflow resulting from the breakdown of lung tissue (emphysema) and the dysfunction of the small airways (obstructive bronchiolitis). Primary symptoms of COPD include shortness of breath, wheezing, chest tightness, chronic cough, and excess sputum production. Elastase from cigarette smoke-activated neutrophils and macrophages disintegrates the extracellular matrix of alveolar structures, resulting in enlarged air spaces and loss of respiratory capacity (see, e.g., Shapiro et al., Am. J. Respir. Cell Mol. Biol. 32 (2005) 367-372). COPD is most commonly caused by tobacco smoke (including cigarette smoke, cigar smoke, secondhand smoke, pipe smoke), occupational exposure (e.g., exposure to dust, smoke or fumes), and pollution, occurring over decades thereby implicating aging as a risk factor for developing COPD.

The processes involved in causing lung damage include, for example, oxidative stress produced by the high concentrations of free radicals in tobacco smoke; cytokine release due to inflammatory response to irritants in the airway; and impairment of anti-protease enzymes by tobacco smoke and free radicals, allowing proteases to damage the lungs. Genetic susceptibility can also contribute to the disease. In about 1% percent of people with COPD, the disease results from a genetic disorder that causes low level production of alpha-1-antitrypsin in the liver. The enzyme is normally secreted into the bloodstream to help protect the lungs.

Pulmonary fibrosis is a chronic and progressive lung disease characterized by stiffening and scarring of the lung, which may lead to respiratory failure, lung cancer, and heart failure. Fibrosis is associated with repair of epithelium. Fibroblasts are activated, production of extracellular matrix proteins is increased, and transdifferentiation to contractile myofibroblasts contribute to wound contraction. A provisional matrix plugs the injured epithelium and provides a scaffold for epithelial cell migration, involving an epithelial-mesenchymal transition (EMT). Blood loss associated with epithelial injury induces platelet activation, production of growth factors, and an acute inflammatory response. Normally, the epithelial barrier heals and the inflammatory response resolves. However, in fibrotic disease the fibroblast response continues, resulting in unresolved wound healing. Formation of fibroblastic foci is a feature of the disease, reflecting locations of ongoing fibrogenesis. As the name connotes, the etiology of IPF is unknown. The involvement of cellular senescence in IPF is suggested by the observations that the incidence of the disease increases with age and that lung tissue in IPF patients is enriched for SA-β-Gal-positive cells and contains elevated levels of the senescence marker p21 (see, e.g., Minagawa et al., Am. J. Physiol. Lung Cell. Mol. Physiol. 300 (2011) L391-L401; see also, e.g., Naylor et al., supra). Short telomeres are a risk factor common to both IPF and cellular senescence (see, e.g., Alder et al., Proc. Natl. Acad. Sci. USA 105 (2008) 13051-13056). Without wishing to be bound by theory, the contribution of cellular senescence to IPF is suggested by the report that SASP components of senescent cells, such as IL-6, IL-8, and IL-10, promote fibroblast-to-myofibroblast differentiation and epithelial-mesenchymal transition, resulting in extensive remodeling of the extracellular matrix of the alveolar and interstitial spaces (see, e.g., Minagawa et al., supra).

Subjects at risk of developing pulmonary fibrosis include those exposed to environmental or occupational pollutants, such as asbestosis and silicosis; who smoke cigarettes; having some typical connective tissue diseases such as rheumatoid arthritis, SLE and scleroderma; having other diseases that involve connective tissue, such as sarcoidosis and Wegener's granulomatosis; having infections; taking certain medications (e.g., amiodarone, bleomycin, busulfan, methotrexate, and nitrofurantoin); those subject to radiation therapy to the chest; and those whose family member has pulmonary fibrosis.

Symptoms of COPD may include any one of shortness of breath, especially during physical activities; wheezing; chest tightness; having to clear your throat first thing in the morning because of excess mucus in the lungs; a chronic cough that produces sputum that may be clear, white, yellow or greenish; blueness of the lips or fingernail beds (cyanosis); frequent respiratory infections; lack of energy; unintended weight loss (observed in later stages of disease). Subjects with COPD may also experience exacerbations, during which symptoms worsen and persist for days or longer. Symptoms of pulmonary fibrosis are known in the art and include shortness of breath, particularly during exercise; dry, hacking cough; fast, shallow breathing; gradual unintended weight loss; tiredness; aching joints and muscles; and clubbing (widening and rounding of the tips of the fingers or toes).

Subjects suffering from COPD or pulmonary fibrosis can be identified using standard diagnostic methods routinely practiced in the art. Monitoring the effect of one or more senolytic agents administered to a subject who has or who is at risk of developing a pulmonary disease may be performed using the methods typically used for diagnosis. Generally, one or more of the following exams or tests may be performed: physical exam, patient's medical history, patient's family's medical history, chest X-ray, lung function tests (such as spirometry), blood test (e.g., arterial blood gas analysis), bronchoalveolar lavage, lung biopsy, CT scan, and exercise testing.

Other pulmonary diseases or disorders that may be treated by using a senolytic agent include, for example, emphysema, asthma, bronchiectasis, and cystic fibrosis (see, e.g., Fischer et al., Am J Physiol Lung Cell Mol Physiol. 304 (6) (2013) L394-400). These diseases may also be exacerbated by tobacco smoke (including cigarette smoke, cigar smoke, secondhand smoke, pipe smoke), occupational exposure (e.g., exposure to dust, smoke or fumes), infection, and/or pollutants that induce cells into senescence and thereby contribute to inflammation. Emphysema is sometimes considered as a subgroup of COPD.

Bronchiectasis results from damage to the airways that causes them to widen and become flabby and scarred. Bronchiectasis usually is caused by a medical condition that injures the airway walls or inhibits the airways from clearing mucus. Examples of such conditions include cystic fibrosis and primary ciliary dyskinesia (PCD). When only one part of the lung is affected, the disorder may be caused by a blockage rather than a medical condition.

The methods described herein for treating or preventing (i.e., reducing the likelihood or occurrence of) a senescence associated pulmonary disease or disorder may also be used for treating a subject who is aging and has loss (or degeneration) of pulmonary function (i.e., declining or impaired pulmonary function compared with a younger subject) and/or degeneration of pulmonary tissue. The respiratory system undergoes various anatomical, physiological and immunological changes with age. The structural changes include chest wall and thoracic spine deformities that can impair the total respiratory system compliance resulting in increased effort to breathe. The respiratory system undergoes structural, physiological, and immunological changes with age. An increased proportion of neutrophils and lower percentage of macrophages can be found in bronchoalveolar lavage (BAL) of older adults compared with younger adults. Persistent low-grade inflammation in the lower respiratory tract can cause proteolytic and oxidant-mediated injury to the lung matrix resulting in loss of alveolar unit and impaired gas exchange across the alveolar membrane seen with aging. Sustained inflammation of the lower respiratory tract may predispose older adults to increased susceptibility to toxic environmental exposure and accelerated lung function decline. (See, for example, Sharma et al., Clinical Interventions in Aging 1 (2006) 253-260). Oxidative stress exacerbates inflammation during aging (see, e.g., Brod, Inflamm. Res. 49 (2000) 561-570; Hendel et al., Cell Death and Differentiation 17 (2010) 596-606). Alterations in redox balance and increased oxidative stress during aging precipitate the expression of cytokines, chemokines, and adhesion molecules, and enzymes (see, e.g., Chung et al., Ageing Res. Rev. 8 (2009) 18-30). Constitutive activation and recruitment of macrophages, T cells, and mast cells foster release of proteases leading to extracellular matrix degradation, cell death, remodeling, and other events that can cause tissue and organ damage during chronic inflammation (see, e.g., Demedts et al., Respir. Res. 7 (2006) 53-63). By administering a senolytic agent to an aging subject (which includes a middle-aged adult who is asymptomatic), the decline in pulmonary function may be decelerated or inhibited by killing and removing senescent cells from the respiratory tract.

The effectiveness of a senolytic agent can readily be determined by a person skilled in the medical and clinical arts. One or any combination of diagnostic methods, including physical examination, assessment and monitoring of clinical symptoms, and performance of analytical tests and methods described herein, may be used for monitoring the health status of the subject. The effects of the treatment of a senolytic agent or pharmaceutical composition comprising the agent can be analyzed using techniques known in the art, such as comparing symptoms of patients suffering from or at risk of the pulmonary disease that have received the treatment with those of patients without such a treatment or with placebo treatment. In addition, methods and techniques that evaluate mechanical functioning of the lung, for example, techniques that measure lung capacitance, elastance, and airway hypersensitivity may be performed. To determine lung function and to monitor lung function throughout treatment, any one of numerous measurements may be obtained, expiratory reserve volume (ERV), forced vital capacity (FVC), forced expiratory volume (FEV) (e.g., FEV in one second, FEV1), FEV1/FEV ratio, forced expiratory flow 25% to 75%, and maximum voluntary ventilation (MVV), peak expiratory flow (PEF), slow vital capacity (SVC). Total lung volumes include total lung capacity (TLC), vital capacity (VC), residual volume (RV), and functional residual capacity (FRC). Gas exchange across alveolar capillary membrane can be measured using diffusion capacity for carbon monoxide (DLCO). Peripheral capillary oxygen saturation ($SpO_2$) can also be measured; normal oxygen levels are typically between 95% and 100%. An $SpO_2$ level below 90% suggests the subject has hypoxemia. Values below 80% are considered critical and requiring intervention to maintain brain and cardiac function and avoid cardiac or respiratory arrest.

Neurological Diseases and Disorders

Senescence-associated diseases or disorders treatable by administering a senolytic agent described herein include neurological diseases or disorders. Such senescence-associated diseases and disorders include Parkinson's disease, Alzheimer's disease (and other dementias), motor neuron dysfunction (MND), mild cognitive impairment (MCI), Huntington's disease and diseases and disorders of the eyes, such as age-related macular degeneration. Other diseases of the eye that are associated with increasing age are glaucoma, vision loss, presbyopia, and cataracts.

Parkinson's disease (PD) is the second most common neurodegenerative disease. It is a disabling condition of the brain characterized by slowness of movement (bradykinesia), shaking, stiffness and in the later stages, loss of balance. Many of these symptoms are due to the loss of certain nerves in the brain, which results in the lack of dopamine. This disease is characterized by neurodegeneration, such as the loss of about 50% to 70% of the dopaminergic neurons in the substantia nigra pars *compacta*, a profound loss of dopamine in the striatum and/or the presence of intracytoplasmic inclusions (Lewy bodies), which are composed mainly of alpha-synuclein and ubiquitin. Parkinson's disease also features locomotor deficits, such as tremor, rigidity, bradykinesia and/or postural instability. Subjects at risk of developing Parkinson's disease include those having a family history of Parkinson's disease and those exposed to pesticides (e.g., rotenone or paraquat), herbicides (e.g., agent orange), or heavy metals. Senescence of dopamine-producing neurons is thought to contribute to the observed cell death in PD through the production of reactive oxygen species (see, e.g., Cohen et al., J. Neural Transm. Suppl. 19 (1983) 89-103); therefore, the methods and senolytic agents described herein are useful for treatment and prophylaxis of Parkinson's disease.

Methods for detecting, monitoring or quantifying neurodegenerative deficiencies and/or locomotor deficits associated with Parkinson's diseases are known in the art, such as histological studies, biochemical studies, and behavioral assessment (see, e.g., U.S. Application Publication No. 2012/0005765). Symptoms of Parkinson's disease are known in the art and include, but are not limited to, difficulty starting or finishing voluntary movements, jerky, stiff movements, muscle atrophy, shaking (tremors), and changes in heart rate, but normal reflexes, bradykinesia, and postural instability. There is a growing recognition that people diagnosed with Parkinson's disease may have cognitive impairment, including mild cognitive impairment, in addition to their physical symptoms.

Alzheimer's disease (AD) is a neurodegenerative disease that shows a slowly progressive mental deterioration with failure of memory, disorientation, and confusion, leading to profound dementia. Age is the single greatest predisposing risk factor for developing AD, which is the leading cause of dementia in the elderly (see, e.g., Hebert, et al., Arch. Neural. 60 (2003) 1119-1122). Early clinical symptoms show remarkable similarity to mild cognitive impairment (see below). As the disease progresses, impaired judgment, confusion, behavioral changes, disorientation, and difficulty in walking and swallowing occur.

Alzheimer's disease is characterized by the presence of neurofibrillary tangles and amyloid (senile) plaques in histological specimens. The disease predominantly involves the limbic and cortical regions of the brain. The argyrophilic plaques containing the amyloidogenic A□ fragment of amyloid precursor protein (APP) are scattered throughout the cerebral cortex and hippocampus. Neurofibrillary tangles are found in pyramidal neurons predominantly located in the neocortex, hippocampus, and nucleus basalis of Meynert. Other changes, such as granulovacuolar degeneration in the pyramidal cells of the hippocampus and neuron loss and gliosis in the cortex and hippocampus, are observed. Subjects at risk of developing Alzheimer's disease include those of advanced age, those with a family history of Alzheimer's disease, those with genetic risk genes (e.g., ApoE4) or deterministic gene mutations (e.g., APP, PS1, or PS2), and those with history of head trauma or heart/vascular conditions (e.g., high blood pressure, heart disease, stroke, diabetes, high cholesterol, etc.).

A number of behavioral and histopathological assays are known in the art for evaluating Alzheimer's disease phenotype, for characterizing therapeutic agents, and assessing treatment. Histological analyses are typically performed postmortem. Histological analysis of Aβ levels may be performed using Thioflavin-S, Congo red, or anti-A□ staining (e.g., 4G8, 10D5, or 6E10 antibodies) to visualize Aβ deposition on sectioned brain tissues (see, e.g., Holcomb et al., Nat. Med. 4 (1998) 97-100; Borchelt et al., Neuron 19 (1997) 939-945; Dickson et al., Am. J. Path. 132 (1998) 86-101). In vivo methods of visualizing Aβ deposition in transgenic mice have been also described. BSB ((trans, trans)-1-bromo-2,5-bis-(3-hydroxycarbonyl-4-hydroxy) styrylbenzene) and PET tracer $^{11}C$-labelled Pittsburgh Compound-B (PIB) bind to AP plaques (see, e.g., Skovronsky et al., Proc. Natl. Acad. Sci. USA 97 (2000) 7609-7614; Klunk et al., Ann. Neurol. 55 (2004) 306-319). $^{19}F$-containing amyloidophilic Congo red-type compound FSB ((E,E)-1-fluoro-2,5-bis-(3-hydroxycarbonyl-4-hydroxy) styrylbenzene) allows visualization of Aβ plaques by MRI (see, e.g., Higuchi et al., Nature Neurosci. 8 (2005) 527-533). Radiolabeled, putrescine-modified amyloid-beta peptide labels amyloid deposits in vivo in a mouse model of Alzheimer's disease (see, e.g., Wengenack et al., Nat. Biotechnol. 18 (2000) 868-872).

Increased glial fibrillary acidic protein (GFAP) by astrocytes is a marker for astroglial activation and gliosis during neurodegeneration. AP plaques are associated with GFAP-positive activated astrocytes, and may be visualized via GFAP staining (see, e.g., Nagele et al., Neurobiol. Aging 25 (2004) 663-674; Mandybur et al., Neurology 40 (1990) 635-639; Liang et al., J. Biol. Chem. 285 (2010) 27737-27744). Neurofibrillary tangles may be identified by immunohistochemistry using thioflavin-S fluorescent microscopy and Gallyas silver stains (see, e.g., Gotz et al., J. Biol. Chem. 276 (2001) 529-534; U.S. Pat. No. 6,664,443). Axon staining with electron microscopy and axonal transport studies may be used to visualize neuronal degeneration (see, e.g., Ishihara et al., Neuron 24 (1999) 751-762).

Subjects suffering from Alzheimer's disease can be identified using standard diagnostic methods known in the art for Alzheimer's disease. Generally, diagnosis of Alzheimer's disease is based on symptoms (e.g., progressive decline in memory function, gradual retreat from and frustration with normal activities, apathy, agitation or irritability, aggression, anxiety, sleep disturbance, dysphoria, aberrant motor behavior, disinhibition, social withdrawal, decreased appetite, hallucinations, dementia), medical history, neuropsychological tests, neurological and/or physical examination of a patient. Cerebrospinal fluid may also be evaluated for various proteins that have been associated with Alzheimer pathology, including tau, amyloid beta peptide, and AD7C-NTP. Genetic testing is also available for early-onset familial Alzheimer disease (eFAD), an autosomal-dominant genetic disease. Clinical genetic testing is available for individuals with AD symptoms or at-risk family members of patients with early-onset disease. In the U.S., mutations for PS2, and APP may be evaluated in a clinical or federally approved laboratory under the Clinical Laboratory Improvement Amendments. A commercial test for PS1 mutations is also available (Elan Pharmaceuticals).

The effectiveness of one or more senolytic agents described herein and monitoring of a subject who receives one or more senolytic agents can readily be determined by a person skilled in the medical and clinical arts. One or any combination of diagnostic methods, including physical examination, assessment and monitoring of clinical symptoms, and performance of analytical tests and methods described herein, may be used for monitoring the health status of the subject. The effects of administering one or more senolytic agents can be analyzed using techniques known in the art, such as comparing symptoms of patients suffering from or at risk of Alzheimer's disease that have received the treatment with those of patients without such a treatment or with placebo treatment.

Mild Cognitive Impairment (MCI) is a brain-function syndrome involving the onset and evolution of cognitive impairments beyond those expected based on age and education of the individual, but which are not significant enough to interfere with the daily activities of an individual. MCI is an aspect of cognitive aging that is considered to be a transitional state between normal aging and the dementia into which it may convert (see, Pepeu, Dialogues in Clinical Neuroscience 6 (2004) 369-377). MCI that primarily affects memory is known as "amnestic MCI." A person with amnestic MCI may start to forget important information that he or she would previously have recalled easily, such as recent events. Amnestic MCI is frequently seen as prodromal stage of Alzheimer's disease. MCI that affects thinking skills other than memory is known as "non-amnestic MCI." This type of MCI affect thinking skills such as the ability to make sound decisions, judge the time or sequence of steps needed to complete a complex task, or visual perception. Individuals with non-amnestic MCI are believed to be more likely to convert to other types of dementias (e.g., dementia with Lewy bodies).

Persons in the medical art have a growing recognition that people diagnosed with Parkinson's disease may have MCI in addition to their physical symptoms. Recent studies show 20-30% of people with Parkinson's disease have MCI and that their MCI tends to be non-amnestic. Parkinson's disease patients with MCI sometimes go on to develop full blown dementia (Parkinson's disease with dementia).

Methods for detecting, monitoring, quantifying or assessing neuropathological deficiencies associated with MCI are known in the art, including astrocyte morphological analyses, release of acetylcholine, silver staining for assessing neurodegeneration, and PiB PET imaging to detect beta amyloid deposits (see, e.g., U.S. Application Publication No. 2012/0071468; Pepeu, (2004), supra). Methods for detecting, monitoring, quantifying or assessing behavioral deficiencies associated with MCI are also known in the art, including eight-arm radial maze paradigm, non-matching-to-sample task, allocentric place determination task in a water maze, Morris maze test, visuospatial tasks, delayed response spatial memory task, and the olfactory novelty test.

Motor Neuron Dysfunction (MND) is a group of progressive neurological disorders that destroy motor neurons, the cells that control essential voluntary muscle activity such as speaking, walking, breathing and swallowing. It is classified according to whether degeneration affects upper motor neurons, lower motor neurons, or both. Examples of MNDs include but are not limited to Amyotrophic Lateral Sclerosis (ALS), also known as Lou Gehrig's Disease, progressive bulbar palsy, pseudobulbar palsy, primary lateral sclerosis, progressive muscular atrophy, lower motor neuron disease, and spinal muscular atrophy (SMA) (e.g., SMA1 also called Werdnig-Hoffmann Disease, SMA2, SMA3 also called Kugelberg-Welander Disease, and Kennedy's disease), post-polio syndrome, and hereditary spastic paraplegia. In adults, the most common MND is amyotrophic lateral sclerosis (ALS), which affects both upper and lower motor neurons. It can affect the arms, legs, or facial muscles. Primary lateral sclerosis is a disease of the upper motor neurons, while progressive muscular atrophy affects only lower motor neurons in the spinal cord. In progressive bulbar palsy, the lowest motor neurons of the brain stem are most affected, causing slurred speech and difficulty chewing and swallowing. There are almost always mildly abnormal signs in the arms and legs. Patients with MND exhibit a phenotype of Parkinson's disease (e.g., having tremor, rigidity, bradykinesia, and/or postural instability). Methods for detecting, monitoring or quantifying locomotor and/or other deficits associated with Parkinson's diseases, such as MND, are known in the art (see, e.g., U.S. Application Publication No. 2012/0005765).

Methods for detecting, monitoring, quantifying or assessing motor deficits and histopathological deficiencies associated with MND are known in the art, including histopathological, biochemical, and electrophysiological studies and motor activity analysis (see, e.g., Rich et al., J. Neurophysiol. 88 (2002) 3293-3304; Appel et al., Proc. Natl. Acad.

Sci. USA 88 (1991) 647-651). Histopathologically, MNDs are characterized by death of motor neurons, progressive accumulation of detergent-resistant aggregates containing SOD1 and ubiquitin and aberrant neurofilament accumulations in degenerating motor neurons. In addition, reactive astroglia and microglia are often detected in diseased tissue. Patients with an MND show one or more motor deficits, including muscle weakness and wasting, uncontrollable twitching, spasticity, slow and effortful movements, and overactive tendon reflexes.

Ophthalmic Diseases and Disorders

In certain embodiments, a senescence-associated disease or disorder is an ocular disease, disorder, or condition, for example, presbyopia, macular degeneration, or cataracts. In other certain embodiments, the senescence-associated disease or disorder is glaucoma. Macular degeneration is a neurodegenerative disease that causes the loss of photoreceptor cells in the central part of retina, called the macula. Macular degeneration generally is classified into two types: dry type and wet type. The dry form is more common than the wet, with about 90% of age-related macular degeneration (ARMD or AMD) patients diagnosed with the dry form. The wet form of the disease usually leads to more serious vision loss. While the exact causes of age-related macular degeneration are still unknown, the number of senescent retinal pigmented epithelial (RPE) cells increases with age. Age and certain genetic factors and environmental factors are risk factors for developing ARMD (see, e.g., Lyengar et al., Am. J. Hum. Genet. 74 (2004) 20-39; Kenealy et al., Mol. Vis. 10 (2004) 57-61; Gorin et al., Mol. Vis. 5 (1999) 29). Environment predisposing factors include omega-3 fatty acids intake (see, e.g., Christen et al., Arch. Ophthalmol. 129 (2011) 921-929); estrogen exposure (see, e.g., Feshanich et al., Arch. Ophthalmol. 126 (4) (2008) 519-524); and increased serum levels of vitamin D (see, e.g., Millen, et al., Arch. Ophthalmol. 129 (4) (2011) 481-89). Genetic predisposing risk factors include reduced levels Dicer1 (enzyme involved in maturation of micro-RNA) in eyes of patients with dry AMD and decreased micro RNAs contributes to a senescent cell profile.

Dry ARMD is associated with atrophy of RPE layer, which causes loss of photoreceptor cells. The dry form of ARMD may result from aging and thinning of macular tissues and from deposition of pigment in the macula. Senescence appears to inhibit both replication and migration of RPE, resulting in permanent RPE depletion in the macula of dry AMD patients (see, e.g., Iriyama et al., J. Biol. Chem. 283 (2008) 11947-11953). With wet ARMD, new blood vessels grow beneath the retina and leak blood and fluid. This abnormal leaky choroidal neovascularization causes the retinal cells to die, creating blind spots in central vision. Different forms of macular degeneration may also occur in younger patients. Non-age-related etiology may be linked to heredity, diabetes, nutritional deficits, head injury, infection, or other factors. Declining vision noticed by the patient or by an ophthalmologist during a routine eye exam may be the first indicator of macular degeneration. The formation of exudates, or "drusen," underneath the Bruch's membrane of the macula is often the first physical sign that macular degeneration may develop. Symptoms include perceived distortion of straight lines and, in some cases, the center of vision appears more distorted than the rest of a scene; a dark, blurry area or "white-out" appears in the center of vision; and/or color perception changes or diminishes. Diagnosing and monitoring of a subject with macular degeneration may be accomplished by a person skilled in the ophthalmic art according to art-accepted periodic eye examination procedures and report of symptoms by the subject.

Presbyopia is an age-related condition where the eye exhibits a progressively diminished ability to focus on near objects as the speed and amplitude of accommodation of a normal eye decrease with advancing age. Loss of elasticity of the crystalline lens and loss of contractility of the ciliary muscles have been postulated as its cause (see, e.g., Heys et al., Mol. Vis. 10 (2004) 956-963; Petrash, Invest. Ophthalmol. Vis. Sci. 54 (2013) ORSF54-ORSF59). Age-related changes in the mechanical properties of the anterior lens capsule and posterior lens capsule suggest that the mechanical strength of the posterior lens capsule decreases significantly with age (see, e.g., Krag et al., Invest. Ophthalmol. Vis. Sci. 44 (2003) 691-696; Krag et al., Invest. Ophthalmol. Vis. Sci. 38 (1997) 357-363).

The laminated structure of the capsule also changes and may result, at least in part, from a change in the composition of the tissue (see, e.g., Krag et al., 1997, supra, and references cited therein). The major structural component of the lens capsule is basement membrane type IV collagen that is organized into a three-dimensional molecular network (see, e.g., Cummings et al., Connect. Tissue Res. 55 (2014) 8-12; Veis et al., Coll. Relat. Res. 1 (1981) 269-286). Type IV collagen is composed of six homologous a chains (a 1-6) that associate into heterotrimeric collagen IV protomers with each comprising a specific chain combination of a 112, a 345, or a 556 (see, e.g., Khoshnoodi et al., Microsc. Res. Tech. 71 (2008) 357-370). Protomers share structural similarities of a triple-helical collagenous domain with the triplet peptide sequence of Gly-X-Y (Timpl et al., Eur. J. Biochem. 95 (1979) 255-263), ending in a globular C-terminal region termed the non-collagenous 1 (NC1) domain. The N-termini are composed of a helical domain termed the 7S domain (see, e.g., Risteli et al., Eur. J. Biochem. 108 (1980) 239-250), which is also involved in protomer-protomer interactions.

Research has suggested that collagen IV influences cellular function which is inferred from the positioning of basement membranes underneath epithelial layers, and data support the role of collagen IV in tissue stabilization (see, e.g., Cummings et al., supra). Posterior capsule opacification (PCO) develops as a complication in approximately 20-40% of patients in subsequent years after cataract surgery (see, e.g., Awasthi et al., Arch. Ophthalmol. 127 (2009) 555-562). PCO results from proliferation and activity of residual lens epithelial cells along the posterior capsule in a response akin to wound healing. Growth factors, such as fibroblast growth factor, transforming growth factor, epidermal growth factor, hepatocyte growth factor, insulin-like growth factor, and interleukins IL-1 and IL-6 may also promote epithelial cell migration, (see, e.g., Awasthi et al, supra; Raj et al., supra). As discussed herein, production of these factors and cytokines by senescent cells contribute to the SASP. In contrast, in vitro studies show that collagen IV promotes adherence of lens epithelial cells (see, e.g., Olivero et al., Invest. Ophthalmol. Vis. Sci. 34 (1993) 2825-2834). Adhesion of the collagen IV, fibronectin, and laminin to the intraocular lens inhibits cell migration and may reduce the risk of PCO (see, e.g., Raj et al, Int. J. Biomed. Sci. 3 (2007) 237-250).

Without wishing to be bound by any particular theory, selective killing of senescent cells by the senolytic agents described herein may slow or impede (delay, inhibit, retard) the disorganization of the type IV collagen network. Removal of senescent cells and thereby removing the inflammatory effects of SASP may decrease or inhibit epithelial cell migration and may also delay (suppress) the onset of presbyopia or decrease or slow the progressive severity of the condition (such as slow the advancement from mild to moderate or moderate to severe). The senolytic agents described herein may also be useful for post-cataract surgery to reduce the likelihood of occurrence of PCO.

While no direct evidence for the involvement of cellular senescence with the development of cataracts has been obtained from human studies, BubR1 hypomorphic mice develop posterior subcapsular cataracts bilaterally early in life, suggesting that senescence may play a role (see, e.g., Baker et al., Nat. Cell Biol. 10 (2008) 825-836). Cataracts are a clouding of the lens of an eye, causing blurred vision, and if left untreated can result in blindness. Surgery is effective and routinely performed to remove cataracts. Administration of one or more of the senolytic agents described herein may result in decreasing the likelihood of occurrence of a cataract or may slow or inhibit progression of a cataract. The presence and severity of a cataract can be monitored by eye exams using methods routinely performed by a person skilled in the ophthalmology art.

In certain embodiments, at least one senolytic agent described herein may be administered to a subject who is at risk of developing presbyopia, cataracts, or macular degeneration. Treatment with a senolytic agent may be initiated when a human subject is at least 40 years of age to delay or inhibit onset or development of cataracts, presbyopia, and macular degeneration. Because almost all humans develop presbyopia, in certain embodiments, the senolytic agent may be administered in a manner as described herein to a human subject after the subject reaches the age of 40 to delay or inhibit onset or development of presbyopia.

In certain embodiments, the senescence associated disease or disorder is glaucoma. Glaucoma is a broad term used to describe a group of diseases that causes visual field loss, often without any other prevailing symptoms. The lack of symptoms often leads to a delayed diagnosis of glaucoma until the terminal stages of the disease. Even if subjects afflicted with glaucoma do not become blind, their vision is often severely impaired. Normally, clear fluid flows into and out of the front part of the eye, known as the anterior chamber. In individuals who have open/wide-angle glaucoma, this fluid drains too slowly, leading to increased pressure within the eye. If left untreated, this high pressure subsequently damages the optic nerve and can lead to complete blindness. The loss of peripheral vision is caused by the death of ganglion cells in the retina. Ganglion cells are a specific type of projection neuron that connects the eye to the brain. When the cellular network required for the outflow of fluid was subjected to SA-β-Gal staining, a fourfold increase in senescence has been observed in glaucoma patients (see, e.g., Liton et al., Exp. Gerontol. 40 (2005) 745-748).

For monitoring the effect of a therapy on inhibiting progression of glaucoma, standard automated perimetry (visual field test) is the most widely used technique. In addition, several algorithms for progression detection have been developed (see, e.g., Wesselink et al., Arch. Ophthalmol. 127 (3) (2009) 270-274, and references therein). Additional methods include gonioscopy (examines the trabecular meshwork and the angle where fluid drains out of the eye); imaging technology, for example scanning laser tomography (e.g., HRT3), laser polarimetry (e.g., GDX), and ocular coherence tomography); ophthalmoscopy; and pachymeter measurements that determine central corneal thickness.

Metabolic Diseases or Disorders

Senescence-associated diseases or disorders treatable by administering a senolytic agent include metabolic diseases or disorders. Such senescent cell associated diseases and disorders include diabetes, metabolic syndrome, diabetic ulcers, and obesity.

Diabetes is characterized by high levels of blood glucose caused by defects in insulin production, insulin action, or both. The great majority (90 to 95%) of all diagnosed cases of diabetes in adults are type 2 diabetes, characterized by the gradual loss of insulin production by the pancreas. Diabetes is the leading cause of kidney failure, nontraumatic lower-limb amputations, and new cases of blindness among adults in the U.S. Diabetes is a major cause of heart disease and stroke and is the seventh leading cause of death in the U.S. (see, e.g., Centers for Disease Control and Prevention, National diabetes fact sheet: national estimates and general information on diabetes and pre-diabetes in the United States, 2011 ("Diabetes fact sheet")). Senolytic agents described herein may be used for treating type 2 diabetes, particularly age-, diet- and obesity-associated type 2 diabetes.

Involvement of senescent cells in metabolic disease, such as obesity and type 2 diabetes, has been suggested as a response to injury or metabolic dysfunction (see, e.g., Tchkonia et al., Aging Cell 9 (2010) 667-684). Fat tissue from obese mice showed induction of the senescence markers SA-β-Gal, p53, and p21 (see, e.g., Tchkonia et al., supra; Minamino et al., Nat. Med. 15 (2009) 1082-1087). A concomitant up-regulation of pro-inflammatory cytokines, such as tumor necrosis factor and Ccl2/MCP1, was observed in the same fat tissue (see, e.g., Minamino et al., supra). Induction of senescent cells in obesity potentially has clinical implications because pro-inflammatory SASP components are also suggested to contribute to type 2 diabetes (see, e.g., Tchkonia et al., supra). A similar pattern of up-regulation of senescence markers and SASP components are associated with diabetes, both in mice and in humans (see, e.g., Minamino et al., supra). Accordingly, the methods described herein that comprise administering a senolytic agent may be useful for treatment or prophylaxis of type 2 diabetes, as well as obesity and metabolic syndrome. Without wishing to be bound by theory, contact of senescent pre-adipocytes with a senolytic agent thereby killing the senescent pre-adipocytes may provide clinical and health benefit to a person who has any one of diabetes, obesity, or metabolic syndrome.

Subjects suffering from type 2 diabetes can be identified using standard diagnostic methods known in the art for type 2 diabetes. Generally, diagnosis of type 2 diabetes is based on symptoms (e.g., increased thirst and frequent urination, increased hunger, weight loss, fatigue, blurred vision, slow-healing sores or frequent infections, and/or areas of darkened skin), medical history, and/or physical examination of a patient. Subjects at risk of developing type 2 diabetes include those who have a family history of type 2 diabetes and those who have other risk factors such as excess weight, fat distribution, inactivity, race, age, prediabetes, and/or gestational diabetes.

The effectiveness of a senolytic agent can readily be determined by a person skilled in the medical and clinical arts. One or any combination of diagnostic methods, including physical examination, assessment and monitoring of clinical symptoms, and performance of analytical tests and methods, such as those described herein, may be used for monitoring the health status of the subject. A subject who is receiving one or more senolytic agents described herein for treatment or prophylaxis of diabetes can be monitored, for example, by assaying glucose and insulin tolerance, energy expenditure, body composition, fat tissue, skeletal muscle, and liver inflammation, and/or lipotoxicity (muscle and liver lipid by imaging in vivo and muscle, liver, bone marrow, and pancreatic-cell lipid accumulation and inflammation by histology). Other characteristic features or phenotypes of type 2 diabetes are known and can be assayed as described herein and by using other methods and techniques known and routinely practiced in the art.

Obesity and obesity-related disorders are used to refer to conditions of subjects who have a body mass that is measurably greater than ideal for their height and frame. Body Mass Index (BMI) is a measurement tool used to determine excess body weight and is calculated from the height and weight of a subject. A human is considered overweight when the person has a BMI of 25-29; a person is considered obese when the person has a BMI of 30-39, and a person is considered severely obese when the person has a BMI of >40. Accordingly, the terms obesity and obesity-related refer to human subjects with body mass index values of greater than 30, greater than 35, or greater than 40. A category of obesity not captured by BMI is called "abdominal obesity" in the art, which relates to the extra fat found around a subject's middle, which is an important factor in health, even independent of BMI. The simplest and most often used measure of abdominal obesity is waist size. Generally abdominal obesity in women is defined as a waist size 35 inches or higher, and in men as a waist size of 40 inches or higher. More complex methods for determining obesity require specialized equipment, such as magnetic resonance imaging or dual energy X-ray absorptiometry machines.

A condition or disorder associated with diabetes and senescence is a diabetic ulcer (i.e., diabetic wound). An ulcer is a breakdown in the skin, which may extend to involve the subcutaneous tissue or even muscle or bone. These lesions occur, particularly, on the lower extremities. Patients with diabetic venous ulcer exhibit elevated presence of cellular senescence at sites of chronic wounds (see, e.g., Stanley et al., J. Vas. Surg. 33 (2001) 1206-1211). Chronic inflammation is also observed at sites of chronic wounds, such as diabetic ulcers (see, e.g., Goren et al., Am. J. Pathol. 168 (2006) 65-77) suggesting that the proinflammatory cytokine phenotype of senescent cells has a role in the pathology.

Subjects who have type 2 diabetes or who are at risk of developing type 2 diabetes may have metabolic syndrome. Metabolic syndrome in humans is typically associated with obesity and characterized by one or more of cardiovascular disease, liver steatosis, hyperlipidemia, diabetes, and insulin resistance. A subject with metabolic syndrome may present with a cluster of metabolic disorders or abnormalities which may include, for example, one or more of hypertension, type-2 diabetes, hyperlipidemia, dyslipidemia (e.g., hypertriglyceridemia, hypercholesterolemia), insulin resistance, liver steatosis (steatohepatitis), hypertension, atherosclerosis, and other metabolic disorders.

Renal Dysfunction

Nephrological pathologies, such as glomerular disease, arise in the elderly and may be treated by the administration of senolytic compounds described herein. Glomerulonephritis is characterized by inflammation of the kidney and by the expression of two proteins, IL1α and IL1β (see, e.g., Niemir et al., Kidney Int. 52 (1997) 393-403). IL1α and IL1β are considered master regulators of SASP (see, e.g., Coppe et al., PLOS. Biol. 6 (2008) 2853-2868). Glomerular disease is associated with elevated presence of senescent cells, especially in fibrotic kidneys (see, e.g., Sis et al., Kidney Int. 71 (2007) 218-226).

Dermatological Diseases or Disorders

Diseases or disorders treatable by administering a compound described herein include dermatological diseases or disorders. Such diseases and disorders include psoriasis and eczema, which are also inflammatory diseases and are discussed in greater detail above. Other dermatological diseases and disorders include rhytides (wrinkles due to aging); pruritis (linked to diabetes and aging); dysesthesia (chemotherapy side effect that is linked to diabetes and multiple sclerosis); psoriasis (as noted) and other papulosquamous disorders, for example, erythroderma, lichen planus, and lichenoid dermatosis; atopic dermatitis (a form of eczema and associated with inflammation); eczematous eruptions (often observed in aging patients and linked to side effects of certain drugs). Other dermatological diseases and disorders associated with senescence include eosinophilic dermatosis (linked to certain kinds of hematologic cancers); reactive neutrophilic dermatosis (associated with underlying diseases such as inflammatory bowel syndrome); pemphigus (an autoimmune disease in which autoantibodies form against desmoglein); pemphigoid and other immunobullous dermatosis (autoimmune blistering of skin); fibrohistiocytic proliferations of skin, which is linked to aging; and cutaneous lymphomas that are more common in older populations. Another dermatological disease that may be treatable according to the methods described herein includes cutaneous lupus, which is a symptom of lupus erythematosus. Late onset lupus may be linked to decreased (i.e., reduced) function of T-cell and B-cells and cytokines (immunosenescence). Still other dermatology indications which may be treated using the compounds described herein include, but are not limited to plaque psoriasis, dermatitis and alopecia induced by cancer therapy (chemotherapy or radiation), vitiligo, alopecia areata, hidradenitis suppurativa, chronic spontaneous urticaria, actinic keratosis and seborrheic keratosis.

Metastasis

In some embodiments, methods are provided for treating or preventing (i.e., reducing the likelihood of occurrence or development of) a senescent cell associated disease (or disorder or condition), which is metastasis. The senolytic agents described herein may also be used according to the methods described herein for treating or preventing (i.e., reducing the likelihood of occurrence of) metastasis (i.e., the spreading and dissemination of cancer or tumor cells) from one organ or tissue to another organ or tissue in the body.

A senescent cell-associated disease or disorder includes metastasis, and a subject who has a cancer may benefit from administration of a senolytic agent as described herein for inhibiting metastasis. Such a senolytic agent when administered to a subject who has a cancer according to the methods described herein may inhibit tumor proliferation. Metastasis of a cancer occurs when the cancer cells (i.e., tumor cells) spread beyond the anatomical site of origin and initial colonization to other areas throughout the body of the subject. Tumor proliferation may be determined by tumor size, which can be measured in various ways familiar to a person skilled in the art, such as by PET scanning, MRI, CAT scan, biopsy, for example. The effect of the therapeutic agent on tumor proliferation may also be evaluated by examining differentiation of the tumor cells.

As used herein and in the art, the terms cancer or tumor are clinically descriptive terms that encompass diseases typically characterized by cells exhibiting abnormal cellular proliferation. The term cancer is generally used to describe a malignant tumor or the disease state arising from the tumor. Alternatively, an abnormal growth may be referred to in the art as a neoplasm. The term tumor, such as in reference to a tissue, generally refers to any abnormal tissue growth that is characterized, at least in part, by excessive and abnormal cellular proliferation. A tumor may be metastatic and capable of spreading beyond its anatomical site of origin and initial colonization to other areas throughout the body of the subject. A cancer may comprise a solid tumor or may comprise a "liquid" tumor (e.g., leukemia and other blood cancers).

Cells are induced to senesce by cancer therapies, such as radiation and certain chemotherapy drugs. The presence of senescent cells increases secretion of inflammatory molecules, promotes tumor progression, which may include promoting tumor growth and increasing tumor size, promoting metastasis, and altering differentiation. When senescent cells are destroyed, tumor progression is significantly inhibited, resulting in tumors of small size and with little or no observed metastatic growth (see, e.g., International Publication No. WO 2013/090645).

In some embodiments, methods are provided for preventing (i.e., reducing the likelihood of occurrence of), inhibiting, or retarding metastasis in a subject who has a cancer by administering a senolytic agent as described herein. In other embodiments, the senolytic agent is administered on one or more days within a treatment window (i.e., treatment course) of no longer than 7 days or 14 days. In still other embodiments, the treatment course is no longer than 2, 3, 4, 5, 6, 7, 8, 9, 10, 11, 12, 13, 14, 15, 16, 17, 18, 19, 20, or no longer than 21 days. In still other embodiments, the treatment course is a single day. In still other embodiments, the senolytic agent is administered on two or more days within a treatment window of no longer than 7 days or 14 days.

Because cells may be induced to senesce by cancer therapies, such as radiation and certain chemotherapy drugs (e.g., doxorubicin; paclitaxel; gemcitabine; pomalidomide; lenalidomide), a senolytic agent described herein may be administered after the chemotherapy or radiotherapy to kill (or facilitate killing) of these senescent cells. As discussed herein and understood in the art, establishment of senescence, such as shown by the presence of a senescence-associated secretory phenotype (SASP), occurs over several days; therefore, administering a senolytic agent to kill senescent cells, and thereby reduce the likelihood of occurrence or reduce the extent of metastasis, is initiated when senescence has been established. As discussed herein, the following treatment courses for administration of the senolytic agent may be used in methods described herein for treating or preventing (i.e., reducing the likelihood of occurrence, or reducing the severity) a chemotherapy or radiotherapy side effect.

In certain embodiments, when chemotherapy or radiotherapy is administered in a treatment cycle of at least one day on-therapy (i.e., chemotherapy or radiotherapy)) followed by at least 3, 4, 5, 6, 7, 8, 9, 10, 11, 12, 13, 14 (or about 2 weeks), 15, 16, 17, 18, 19, 20, 21 (or about 3 weeks) days, or about 4 weeks (about one month) off-therapy (i.e., off chemo-or radio-therapy), the senolytic agent is administered on one or more days during the off-therapy time interval (time period) beginning on or after the second day of the off-therapy time interval and ending on or before the last day of the off-therapy time interval. By way of illustrative example, if n is the number of days off-therapy, then the senolytic agent is administered on at least one day and no more than n-1 days of the off-therapy time interval. In some embodiments when chemotherapy or radiotherapy is administered in a treatment cycle of at least one day on-therapy (i.e., chemotherapy or radiotherapy) followed by at least one week off-therapy, the senolytic agent is administered on one or more days during the off-therapy time interval beginning on or after the second day of the off-therapy time interval and ending on or before the last day of the off-therapy time interval.

A chemotherapy may be referred to as a chemotherapy, chemotherapeutic, or chemotherapeutic drug. Many chemotherapeutics are compounds referred to as small organic molecules. Chemotherapy is a term that is also used to describe a combination of chemotherapeutic drugs that are administered to treat a particular cancer. As understood by a person skilled in the art, a chemotherapy may also refer to a combination of two or more chemotherapeutic molecules that are administered coordinately and which may be referred to as combination chemotherapy. Numerous chemotherapeutic drugs are used in the oncology art and include, without limitation, alkylating agents; antimetabolites; anthracyclines, plant alkaloids; and topoisomerase inhibitors.

A cancer that may metastasize may be a solid tumor or may be a liquid tumor (e.g., a blood cancer, for example, a leukemia). Cancers that are liquid tumors are classified in the art as those that occur in blood, bone marrow, and lymph nodes and include generally, leukemias (myeloid and lymphocytic), lymphomas (e.g., Hodgkin lymphoma), and melanoma (including multiple myeloma). Leukemias include for example, acute lymphoblastic leukemia (ALL), acute myeloid leukemia (AML), chronic lymphocytic leukemia (CLL), chronic myelogenous leukemia (CML), and hairy cell leukemia. Cancers that are solid tumors and occur in greater frequency in humans include, for example, prostate cancer, testicular cancer, breast cancer, brain cancer, pancreatic cancer, colon cancer, thyroid cancer, stomach cancer, lung cancer, ovarian cancer, Kaposi's sarcoma, skin cancer (including squamous cell skin cancer), renal cancer, head and neck cancers, throat cancer, squamous carcinomas that form on the moist mucosal linings of the nose, mouth, throat, etc.), bladder cancer, osteosarcoma (bone cancer), cervical cancer, endometrial cancer, esophageal cancer, liver cancer, and kidney cancer. In certain specific embodiments, the senescent cell-associated disease or disorder treated or prevented (i.e., likelihood of occurrence or development is reduced) by the methods described herein is metastasis of melanoma cells, prostate cancer cells, testicular cancer cells, breast cancer cells, brain cancer cells, pancreatic cancer cells, colon cancer cells, thyroid cancer cells, stomach cancer cells, lung cancer cells, ovarian cancer cells, Kaposi's sarcoma cells, skin cancer cells, renal cancer cells, head or neck cancer cells, throat cancer cells, squamous carcinoma cells, bladder cancer cells, osteosarcoma cells, cervical cancer cells, endometrial cancer cells, esophageal cancer cells, liver cancer cells, or kidney cancer cells.

The methods described herein are also useful for inhibiting, retarding or slowing progression of metastatic cancer of any one of the types of tumors described in the medical art. Types of cancers (tumors) include the following: adrenocortical carcinoma, childhood adrenocortical carcinoma, aids-related cancers, anal cancer, appendix cancer, basal cell carcinoma, childhood basal cell carcinoma, bladder cancer, childhood bladder cancer, bone cancer, brain tumor, childhood astrocytomas, childhood brain stem glioma, childhood central nervous system atypical teratoid/rhabdoid tumor, childhood central nervous system embryonal tumors, childhood central nervous system germ cell tumors, childhood craniopharyngioma brain tumor, childhood ependymoma brain tumor, breast cancer, childhood bronchial tumors, carcinoid tumor, childhood carcinoid tumor, gastrointestinal carcinoid tumor, carcinoma of unknown primary, childhood carcinoma of unknown primary, childhood cardiac (heart) tumors, cervical cancer, childhood cervical cancer, childhood chordoma, chronic myeloproliferative disorders, colon cancer, colorectal cancer, childhood colorectal cancer, extrahepatic bile duct cancer, ductal carcinoma in situ (DCIS), endometrial cancer, esophageal cancer, childhood esophageal cancer, childhood esthesioneuroblastoma, eye cancer, malignant fibrous histiocytoma of bone, gallbladder cancer, gastric (stomach) cancer, childhood gastric (stomach) cancer, gastrointestinal stromal tumors (GIST), childhood gastrointestinal stromal tumors (GIST), childhood extracranial germ cell tumor, extragonadal germ cell tumor, gestational trophoblastic tumor, glioma, head and neck cancer, childhood head and neck cancer, hepatocellular (liver) cancer, hypopharyngeal cancer, kidney cancer, renal cell kidney cancer, Wilms tumor, childhood kidney tumors, Langerhans cell histiocytosis, laryngeal cancer, childhood laryngeal cancer, leukemia, acute lymphoblastic leukemia (ALL), acute myeloid leukemia (AML), chronic lymphocytic leukemia (CLL), chronic myelogenous leukemia (CML), hairy cell leukemia, lip cancer, liver cancer (primary), childhood liver cancer (primary), lobular carcinoma in situ (LCIS), lung cancer, non-small cell lung cancer, small cell lung cancer, lymphoma, aids-related lymphoma, Burkitt lymphoma, cutaneous T-cell lymphoma, Hodgkin lymphoma, non-Hodgkin lymphoma, primary central nervous system lymphoma (CNS), melanoma, childhood melanoma, intraocular (eye) melanoma, Merkel cell carcinoma, malignant mesothelioma, childhood malignant mesothelioma, metastatic squamous neck cancer with occult primary, midline tract carcinoma involving the NUT gene, mouth cancer, childhood multiple endocrine neoplasia syndromes, mycosis fungoides, myelodysplastic syndromes, myelodysplastic neoplasms, myeloproliferative neoplasms, multiple myeloma, nasal cavity cancer, nasopharyngeal cancer, childhood nasopharyngeal cancer, neuroblastoma, oral cancer, childhood oral cancer, oropharyngeal cancer, ovarian cancer, childhood ovarian cancer, epithelial ovarian cancer, low malignant potential tumor ovarian cancer, pancreatic cancer, childhood pancreatic cancer, pancreatic neuroendocrine tumors (islet cell tumors), childhood papillomatosis, paraganglioma, paranasal sinus cancer, parathyroid cancer, penile cancer, pharyngeal cancer, pheochromocytoma, pituitary tumor, plasma cell neoplasm, childhood pleuropulmonary blastoma, prostate cancer, rectal cancer, renal pelvis transitional cell cancer, retinoblastoma, salivary gland cancer, childhood salivary gland cancer, Ewing sarcoma family of tumors, Kaposi Sarcoma, osteosarcoma, rhabdomyosarcoma, childhood rhabdomyosarcoma, soft tissue sarcoma, uterine sarcoma, Sezary syndrome, childhood skin cancer, nonmelanoma skin cancer, small intestine cancer, squamous cell carcinoma, childhood squamous cell carcinoma, testicular cancer, childhood testicular cancer, throat cancer, thymoma and thymic carcinoma, childhood thymoma and thymic carcinoma, thyroid cancer, childhood thyroid cancer, ureter transitional cell cancer, urethral cancer, endometrial uterine cancer, vaginal cancer, vulvar cancer, and Waldenstrom macroglobulinemia.

Chemotherapy and Radiotherapy Side Effects

In other embodiments, the senescence cell associated disorder or condition is a chemotherapeutic side effect or a radiotherapy side effect. Examples of chemotherapeutic agents that induce non-cancer cells to senesce include anthracyclines (such as doxorubicin, daunorubicin); taxols (e.g., paclitaxel); gemcitabine; pomalidomide; and lenalidomide. One or more of the senolytic agents administered as described herein may be used for treating and/or preventing (i.e., reducing the likelihood or occurrence of) a chemotherapeutic side effect or a radiotherapy side effect. Removal or destruction of senescent cells may ameliorate acute toxicity, including acute toxicity comprising energy imbalance, of a chemotherapy or radiotherapy. Acute toxic side effects include but are not limited to gastrointestinal toxicity (e.g., nausea, vomiting, constipation, anorexia, diarrhea), peripheral neuropathy, fatigue, malaise, low physical activity, hematological toxicity (e.g., anemia), hepatotoxicity, alopecia (hair loss), pain, infection, mucositis, fluid retention, dermatological toxicity (e.g., rashes, dermatitis, hyperpigmentation, urticaria, photosensitivity, nail changes), mouth (e.g., oral mucositis), gum or throat problems, or any toxic side effect caused by a chemotherapy or radiotherapy. For example, toxic side effects caused by radiotherapy or chemotherapy may be ameliorated by the methods described herein. Accordingly, in certain embodiments, methods are provided herein for ameliorating (reducing, inhibiting, or preventing occurrence (i.e., reducing the likelihood of occurrence)) acute toxicity or reducing severity of a toxic side effect (i.e., deleterious side effect) of a chemotherapy or radiotherapy or both in a subject who receives the therapy, wherein the method comprises administering to the subject an agent that selectively kills, removes, or destroys or facilitates selective destruction of senescent cells. Administration of senolytic agents described herein for treating or reducing the likelihood of occurrence or reducing the severity of a chemotherapy or radiotherapy side effect may be accomplished by the same treatment courses described above for treatment/prevention of metastasis. As described for treating or preventing (i.e., reducing the likelihood of occurrence of) metastasis, the senolytic agent is administered during the off-chemotherapy or off-radiotherapy time interval or after the chemotherapy or radiotherapy treatment regimen has been completed.

In more specific embodiments, the acute toxicity is an acute toxicity comprising energy imbalance and may comprise one or more of weight loss, endocrine change(s) (e.g., hormone imbalance, change in hormone signaling), and change(s) in body composition. In certain embodiments, an acute toxicity comprising energy imbalance relates to decreased or reduced ability of the subject to be physically active, as indicated by decreased or diminished expenditure of energy than would be observed in a subject who did not receive the medical therapy. By way of non-limiting example, such an acute toxic effect that comprises energy imbalance includes low physical activity. In other embodiments, energy imbalance comprises fatigue or malaise.

In some embodiments, a chemotherapy side effect to be treated or prevented (i.e., likelihood of occurrence is reduced) by a senolytic agent described herein is cardiotoxicity. A subject who has a cancer that is being treated with an anthracycline (such as doxorubicin, daunorubicin) may be treated with one or more senolytic agents described herein that reduce, ameliorate, or decrease the cardiotoxicity of the anthracycline. As is well understood in the medical art, because of the cardiotoxicity associated with anthracyclines, the maximum lifetime dose that a subject can receive is limited even if the cancer is responsive to the drug. Administration of one or more of the senolytic agents may reduce the cardiotoxicity such that additional amounts of the anthracycline can be administered to the subject, resulting in an improved prognosis related to cancer disease. In some embodiments, the cardiotoxicity results from administration of an anthracycline, such as doxorubicin. Doxorubicin is an anthracycline topoisomerase inhibitor that is approved for treating patients who have ovarian cancer after failure of a platinum-based therapy; Kaposi's sarcoma after failure of primary systemic chemotherapy or intolerance to the therapy; or multiple myeloma in combination with bortezomib in patients who have not previously received bortezomib or who have received at least one prior therapy. Doxorubicin may cause myocardial damage that could lead to congestive heart failure if the total lifetime dose to a patient exceeds 550 mg/$m^2$. Cardiotoxicity may occur at even lower doses if the patient also receives mediastinal irradiation or another cardiotoxic drug.

In other embodiments, a senolytic agent described herein may be used in the methods as provided herein for ameliorating chronic or long-term side effects. Chronic toxic side effects typically result from multiple exposures to or administrations of a chemotherapy or radiotherapy over a longer period of time. Certain toxic effects appear long after treatment (also called late toxic effects) and result from damage to an organ or system by the therapy. Organ dysfunction (e.g., neurological, pulmonary, cardiovascular, and endocrine dysfunction) has been observed in patients who were treated for cancers during childhood (see, e.g., Hudson et al., JAMA 309 92013) 2371-2381). Without wishing to be bound by any particular theory, by destroying senescent cells, particular normal cells that have been induced to senescence by chemotherapy or radiotherapy, the likelihood of occurrence of a chronic side effect may be reduced, or the severity of a chronic side effect may be reduced or diminished, or the time of onset of a chronic side effect may be delayed. Chronic and/or late toxic side effects that occur in subjects who received chemotherapy or radiation therapy include by way of non-limiting example, cardiomyopathy, congestive heart disease, inflammation, early menopause, osteoporosis, infertility, impaired cognitive function, peripheral neuropathy, secondary cancers, cataracts and other vision problems, hearing loss, chronic fatigue, reduced lung capacity, and lung disease.

In addition, by killing or removing senescent cells in a subject who has a cancer by administering a senolytic agent, the sensitivity to the chemotherapy or the radiotherapy may be enhanced in a clinically or statistically significant manner than if the senolytic agent was not administered. In other words, development of chemotherapy or radiotherapy resistance may be inhibited when a senolytic agent is administered to a subject treated with the respective chemotherapy or radiotherapy.

Age-Related Diseases and Disorders

A senolytic agent described herein selectively kills senescent cells. In this way, targeting senescent cells during the course of aging may be a preventative strategy. Accordingly, administration of a senolytic agent described herein to a subject may prevent comorbidity and delay mortality in an older subject. Further, selective killing of senescent cells may boost the immune system, extend the health span, and improve the quality of life in a subject.

A senolytic agent may also be useful for treating or preventing (i.e., reducing the likelihood of occurrence) of an age-related disease or disorder that occurs as part of the natural aging process or that occurs when the subject is exposed to a senescence inducing agent or factor (e.g., irradiation, chemotherapy, smoking tobacco, high fat/high sugar diet, other environmental factors). An age-related disorder or disease or an age-sensitive trait may be associated with a senescence-inducing stimulus. The efficacy of a method of treatment described herein may be manifested by reducing the number of symptoms of an age-related disorder or age-sensitive trait associated with a senescence-inducing stimulus, decreasing the severity of one or more symptoms, or delaying the progression of an age-related disorder or age-sensitive trait associated with a senescence-inducing stimulus. In other embodiments, preventing an age-related disorder or age-sensitive trait associated with a senescence-inducing stimulus refers to preventing (i.e., reducing the likelihood of occurrence) or delaying onset of an age-related disorder or age-sensitive trait associated with a senescence-inducing stimulus, or reoccurrence of one or more age-related disorder or age-sensitive trait associated with a senescence-inducing stimulus. Age related diseases or conditions include, for example, renal dysfunction, kyphosis, herniated intervertebral disc, frailty, hair loss, hearing loss, vision loss (blindness or impaired vision), muscle fatigue, skin conditions, skin nevi, diabetes, metabolic syndrome, and sarcopenia. Vision loss refers to the absence of vision when a subject previously had vision. Various scales have been developed to describe the extent of vision and vision loss based on visual acuity. Age-related diseases and conditions also include dermatological conditions, for example without limitation, treating one or more of the following conditions: wrinkles, including superficial fine wrinkles; hyperpigmentation; scars; keloid; dermatitis; psoriasis; eczema (including seborrheic eczema); rosacea; vitiligo; ichthyosis vulgaris; dermatomyositis; and actinic keratosis. Frailty has been defined as a clinically recognizable state of increased vulnerability resulting from aging-associated decline in reserve and function across multiple physiologic systems that compromise a subject's ability to cope with every day or acute stressors. Frailty may be characterized by compromised energetics characteristics such as low grip strength, low energy, slowed walking speed, low physical activity, and/or unintentional weight loss. Studies have suggested that a patient may be diagnosed with frailty when three of five of the foregoing characteristics are observed (see, e.g., Fried et al., J. Gerontol. A Biol. Sci. Med, Sci. 56 (3) (2001) M146-M156; Xue, Clin. Geriatr. Med. 27 (1) (2001) 1-15). In certain embodiments, aging and diseases and disorders related to aging may be treated or prevented (i.e., the likelihood of occurrence of is reduced) by administering a senolytic agent. The senolytic agent may inhibit senescence of adult stem cells or inhibit accumulation, kill, or facilitate removal of adult stem cells that have become senescent. The importance of preventing senescence in stem cells to maintain regenerative capacity of tissues is discussed, e.g., in Park et al., J. Clin. Invest. 113 (2004) 175-179; and Sousa-Victor, Nature 506 (2014) 316-321.

Methods of measuring aging are known in the art. For example, aging may be measured in the bone by incident non-vertebral fractures, incident hip fractures, incident total fractures, incident vertebral fractures, incident repeat fractures, functional recovery after fracture, bone mineral density decrease at the lumbar spine and hip, rate of knee buckling, NSAID use, number of joints with pain, and osteoarthritis. Aging may also be measured in the muscle by functional decline, rate of falls, reaction time and grip strength, muscle mass decrease at upper and lower extremities, and dual tasking 10-meter gait speed. Further, aging may be measured in the cardiovascular system by systolic and diastolic blood pressure change, incident hypertension, major cardiovascular events such as myocardial infarction, stroke, congestive heart disease, and cardiovascular mortality. Additionally, aging may be measured in the brain by cognitive decline, incident depression, and incident dementia. Also, aging may be measured in the immune system by rate of infection, rate of upper respiratory infections, rate of flu-like illness, incident severe infections that lead to hospital admission, incident cancer, rate of implant infections, and rate of gastrointestinal infections. Other indications of aging may include, but not limited to, decline in oral health, tooth loss, rate of GI symptoms, change in fasting glucose and/or insulin levels, body composition, decline in kidney function, quality of life, incident disability regarding activities of daily living, and incident nursing home admission. Methods of measuring skin aging are known in the art and may include trans-epidermal water loss (TEWL), skin hydration, skin elasticity, area ratio analysis of crow's feet, sensitivity, radiance, roughness, spots, laxity, skin tone homogeneity, softness, and relief (variations in depth).

Administration of a senolytic agent described herein can prolong prolonging survival when compared to expected survival if a subject were not receiving treatment. Subjects in need of treatment include those who already have the disease or disorder as well as subjects prone to have or at risk of developing the disease or disorder, and those in which the disease, condition, or disorder is to be treated prophylactically. A subject may have a genetic predisposition for developing a disease or disorder that would benefit from clearance of senescent cells or may be of a certain age wherein receiving a senolytic agent would provide clinical benefit to delay development or reduce severity of a disease, including an age-related disease or disorder.

In other embodiments, a method is provided for treating a senescence-associated disease or disorder that further comprises identifying a subject who would benefit from treatment with a senolytic agent described herein (i.e., phenotyping; individualized treatment). This method comprises first detecting the level of senescent cells in the subject, such as in a particular organ or tissue of the subject. A biological sample may be obtained from the subject, for example, a blood sample, serum or plasma sample, biopsy specimen, body fluids (e.g., lung lavage, ascites, mucosal washings, synovial fluid, vitreous fluid, spinal fluid), bone marrow, lymph nodes, tissue explant, organ culture, or any other tissue or cell preparation from a subject. The level of senescent cells may be determined according to any of the in vitro assays or techniques described herein. For example, senescent cells may be detected by morphology (as viewed by microscopy, for example); production of senescence associated markers such as, senescence-associated □-galactosidase (SA-β-gal), p16INK4a, p21, PAI-1, or any one or more SASP factors (e.g., IL-6, MMP3). The senescent cells and non-senescent cells of the biological sample may also be used in an in vitro cell assay in which the cells are exposed to any one of the senolytic agents described herein to determine the capability of the senolytic agent to kill the subject's senescent cells without undesired toxicity to non-senescent cells. In addition, these methods may be used to monitor the level of senescent cells in the subject before, during, and after treatment with a senolytic agent. In certain embodiments, the presence of senescent cells, may be detected (e.g., by determining the level of a senescent cell marker expression of mRNA, for example), and the treatment course and/or non-treatment interval can be adjusted accordingly.

Methods of Treatment and Prevention of GPX4 Diseases and Disorders

Methods of treating, preventing, or ameliorating symptoms of a glutathione peroxidase 4 (GPX4)-associated disease in a subject, comprises administering an effective amount of one or more compounds disclosed herein or the compositions disclosed herein are provided. In some embodiments, the GPX4-associated disease is cancer, neurotic disorder, neurodegenerative disorder, spondylometaphyseal dysplasia, mixed cerebral palsy, pontocerebellar hypoplasia or male infertility.

In some embodiments, the GPX4-associated disease is a cancer. Non limiting examples of cancer include hepatocellular carcinoma, sarcoma, glioma, renal cell carcinoma, ovarian cancer, prostate cancer, breast cancer, pancreatic cancer, melanoma, colon cancer, diffuse large B cell lymphoma, leukemia, lung cancer, clear-cell carcinoma or non-small cell lung carcinoma. In some embodiments, the cancer is hepatocellular carcinoma. In other embodiments, the cancer is metastatic. In still other embodiments, the cancer is hypersensitive to ferroptosis. In still other embodiments, the cancer is refractory to standard cancer treatment. In still other embodiments, the cancer has mesenchymal features. In still other embodiments, the cancer is a multiple therapy resistant cancer.

Also provided herein is a method for modulating the activity of GPX4 in a subject comprising administering an effective amount of one or more compounds disclosed herein or the compositions disclosed herein. In some embodiments, the modulation comprises inhibiting GPX4 activity.

Also provided herein is a method for increasing the level of peroxide in a subject comprising administering an effective amount of one or more compounds disclosed herein or the compositions disclosed herein. Non-limiting examples of peroxide include hydrogen peroxide, organic hydroperoxide, lipid peroxide, and combinations thereof.

Also provided herein is a method for inducing ferroptosis in a cell, comprising contacting the cell with an effective amount of one or more compounds disclosed herein or the compositions disclosed herein. The cell may have aberrant lipid accumulation. In some embodiments, the cell is a cancer cell which includes but is not limited to hepatocellular carcinoma, sarcoma, glioma, renal cell carcinoma, ovarian cancer, prostate cancer, breast cancer, pancreatic cancer, melanoma, colon cancer, diffuse large B cell lymphoma, leukemia, lung cancer, clear-cell carcinoma, or non-small cell lung carcinoma cell. In other embodiments, the cancer cell is a hepatocellular carcinoma cell.

In some embodiments, the cancer cell is metastatic. In other embodiments, the cancer cell is hypersensitive to ferroptosis. In still other embodiments, the cancer has mesenchymal features. In still other embodiments the cancer is a multiple therapy resistant cancer.

The hypersensitivity to ferropotosis may be identified by NADPH abundance, GCH1 expression, NF2-YAP activity, EMT signature, and GPX4 expression. In some embodiments, the cancer cell is selected from the group consisting of hepatocellular carcinoma, sarcoma, glioma, renal cell carcinoma, ovarian cancer, prostate cancer, breast cancer, pancreatic cancer, melanoma, colon cancer, diffuse large B cell lymphoma, leukemia, lung cancer, clear-cell carcinoma or non-small cell lung carcinoma cell. In some embodiments, the cancer is a hepatocellular carcinoma cell.

Pharmaceutical Compositions and Methods of Administration

Also provided herein are pharmaceutical compositions that comprise a senolytic agent as described herein and at least one pharmaceutically acceptable excipient, which may also be called a pharmaceutically suitable excipient or carrier (i.e., a non-toxic material that does not interfere with the activity of the active ingredient). A pharmaceutical composition may be a sterile aqueous or non-aqueous solution, suspension or emulsion (e.g., a microemulsion). The excipients described herein are examples and are in no way limiting. An effective amount or therapeutically effective amount refers to an amount of the one or more senolytic agents administered to a subject, either as a single dose or as part of a series of doses, which is effective to produce a desired therapeutic effect.

When two or more senolytic agents are administered to a subject for treatment of a disease or disorder described herein, each of the senolytic agents may be formulated into separate pharmaceutical compositions. A pharmaceutical preparation may be prepared that comprises each of the separate pharmaceutical compositions (which may be referred to for convenience, for example, as a first pharmaceutical composition and a second pharmaceutical composition comprising each of the first and second senolytic agents, respectively). Each of the pharmaceutical compositions in the preparation may be administered at the same time (i.e., concurrently) and via the same route of administration or may be administered at different times by the same or different administration routes. Alternatively, two or more senolytic agents may be formulated together in a single pharmaceutical composition.

In other embodiments, a combination of at least one senolytic agent and at least one inhibitor of an mTOR, NF-□B, or PI3K pathway may be administered to a subject in need thereof. When at least one senolytic agent and an inhibitor of one or more of mTOR, NF-□B, or PI3K pathways are both used together in the methods described herein for selectively killing senescent cells, each of the agents may be formulated into the same pharmaceutical composition or formulated in separate pharmaceutical compositions. A pharmaceutical preparation may be prepared that comprises each of the separate pharmaceutical compositions, which may be referred to for convenience, for example, as a first pharmaceutical composition and a second pharmaceutical composition comprising each of the senolytic agent and the inhibitor of one or more of mTOR, NF-□B, or PI3K pathways, respectively. Each of the pharmaceutical compositions in the preparation may be administered at the same time and via the same route of administration or may be administered at different times by the same or different administration routes.

Pharmacokinetics of a senolytic agent (or one or more metabolites thereof) that is administered to a subject may be monitored by determining the level of the senolytic agent in a biological fluid, for example, in the blood, blood fraction (e.g., serum), and/or in the urine, and/or other biological sample or biological tissue from the subject. Any method practiced in the art and described herein to detect the agent may be used to measure the level of the senolytic agent during a treatment course.

The dose of a senolytic agent described herein for treating a senescence cell associated disease or disorder may depend upon the subject's condition, that is, stage of the disease, severity of symptoms caused by the disease, general health status, as well as age, gender, and weight, and other factors apparent to a person skilled in the medical art. Pharmaceutical compositions may be administered in a manner appropriate to the disease to be treated as determined by persons skilled in the medical arts. In addition to the factors described herein and above related to use of the senolytic agent for treating a senescence-associated disease or disorder, suitable duration and frequency of administration of the senolytic agent may also be determined or adjusted by such factors as the condition of the patient, the type and severity of the patient's disease, the particular form of the active ingredient, and the method of administration. Optimal doses of an agent may generally be determined using experimental models and/or clinical trials. The optimal dose may depend upon the body mass, weight, or blood volume of the subject. The use of the minimum dose that is sufficient to provide effective therapy is usually preferred. Design and execution of pre-clinical and clinical studies for a senolytic agent (including when administered for prophylactic benefit) described herein are well within the skill of a person skilled in the relevant art. When two or more senolytic agents are administered to treat a senescence-associated disease or disorder, the optimal dose of each senolytic agent may be different, such as less, than when either agent is administered alone as a single agent therapy. In certain embodiments, two senolytic agents in combination make act synergistically or additively, and either agent may be used in a lesser amount than if administered alone. An amount of a senolytic agent that may be administered per day may be, for example, between about 0.01 mg/kg and 100 mg/kg (e.g., between about 0.1 to 1 mg/kg, between about 1 to 10 mg/kg, between about 10-50 mg/kg, between about 50-100 mg/kg body weight. In other embodiments, the amount of a senolytic agent that may be administered per day is between about 0.01 mg/kg and 1000 mg/kg, between about 100-500 mg/kg, or between about 500-1000 mg/kg body weight. The optimal dose (per day or per course of treatment) may be different for the senescence-associated disease or disorder to be treated and may also vary with the administrative route and therapeutic regimen.

Pharmaceutical compositions comprising a senolytic agent can be formulated in a manner appropriate for the delivery method by using techniques routinely practiced in the art. The composition may be in the form of a solid (e.g., tablet, capsule), semi-solid (e.g., gel), liquid, or gas (aerosol). In other certain specific embodiments, the senolytic agent (or pharmaceutical composition comprising same) is administered as a bolus infusion. In certain embodiments when the senolytic agent is delivered by infusion, the senolytic agent is delivered to an organ or tissue comprising senescent cells to be killed via a blood vessel in accordance with techniques routinely performed by a person skilled in the medical art.

Pharmaceutical acceptable excipients are well known in the pharmaceutical art and described, for example, in Rowe et al., Handbook of Pharmaceutical Excipients: A Comprehensive Guide to Uses, Properties, and Safety, $5^{th}$ Ed., 2006, and in Remington: The Science and Practice of Pharmacy (Gennaro, $21^{st}$ Ed. Mack Pub. Co., Easton, Pa. (2005)). Exemplary pharmaceutically acceptable excipients include sterile saline and phosphate buffered saline at physiological pH. Preservatives, stabilizers, dyes, buffers, and the like may be provided in the pharmaceutical composition. In addition, antioxidants and suspending agents may also be used. In general, the type of excipient is selected based on the mode of administration, as well as the chemical composition of the active ingredient(s). Alternatively, compositions described herein may be formulated as a lyophilizate. A composition described herein may be lyophilized or otherwise formulated as a lyophilized product using one or more appropriate excipient solutions for solubilizing and/or diluting the agent(s) of the composition upon administration. In other embodiments, the agent may be encapsulated within liposomes using technology known and practiced in the art. Pharmaceutical compositions may be formulated for any appropriate manner of administration described herein and, in the art., A pharmaceutical composition may be delivered to a subject in need thereof by any one of several routes known to a person skilled in the art. By way of non-limiting example, the composition may be delivered orally, intravenously, intraperitoneally, by infusion (e.g., a bolus infusion), subcutaneously, enteral, rectal, intranasal, by inhalation, buccal, sublingual, intramuscular, transdermal, intradermal, topically, intraocular, vaginal, rectal, or by intracranial injection, or any combination thereof. In certain embodiments, administration of a dose, as described above, is via intravenous, intraperitoneal, directly into the target tissue or organ, or subcutaneous route. In certain embodiments, a delivery method includes drug-coated or permeated stents for which the drug is the senolytic agent. Formulations suitable for such delivery methods are described in greater detail herein.

In certain embodiments, a senolytic agent (which may be combined with at least one pharmaceutically acceptable excipient to form a pharmaceutical composition) is administered directly to the target tissue or organ comprising senescent cells that contribute to the manifestation of the disease or disorder. In specific embodiments when treating osteoarthritis, the at least one senolytic agent is administered directly to an osteoarthritic joint (i.e., intra-articularly) of a subject in need thereof. In other specific embodiments, a senolytic agent(s) may be administered to the joint via topical, transdermal, intradermal, or subcutaneous route. In other certain embodiments, methods are provided herein for treating a cardiovascular disease or disorder associated with arteriosclerosis, such as atherosclerosis by administering directly into an artery. In other embodiments, a senolytic agent (which may be combined with at least one pharmaceutically acceptable excipient to form a pharmaceutical composition) for treating a senescent-associated pulmonary disease or disorder may be administered by inhalation, intranasally, by intubation, or intrathecally, for example, to provide the senolytic agent more directly to the affected pulmonary tissue. By way of another non-limiting example, the senolytic agent (or pharmaceutical composition comprising the senolytic agent) may be delivered directly to the eye either by injection (e.g., intraocular or intravitreal) or by conjunctival application underneath an eyelid of a cream, ointment, gel, or eye drops. In more particular embodiments, the senolytic agent or pharmaceutical composition comprising the senolytic agent may be formulated as a timed release (also called sustained release, controlled release) composition or may be administered as a bolus infusion.

A pharmaceutical composition (e.g., for oral administration or for injection, infusion, subcutaneous delivery, intramuscular delivery, intraperitoneal delivery or other method) may be in the form of a liquid. A liquid pharmaceutical composition may include, for example, one or more of the following: a sterile diluent such as water, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral composition can be enclosed in ampoules, disposable syringes or multiple dose vials made of glass or plastic. The use of physiological saline is preferred, and an injectable pharmaceutical composition is preferably sterile. In other embodiments, for treatment of an ophthalmological condition or disease, a liquid pharmaceutical composition may be applied to the eye in the form of eye drops. A liquid pharmaceutical composition may be delivered orally.

For oral formulations, at least one of the senolytic agents described herein can be used alone or in combination with appropriate additives to make tablets, powders, granules or capsules, and if desired, with diluents, buffering agents, moistening agents, preservatives, coloring agents, and flavoring agents. The compounds may be formulated with a buffering agent to provide for protection of the compound from low pH of the gastric environment and/or an enteric coating. A senolytic agent included in a pharmaceutical composition may be formulated for oral delivery with a flavoring agent, e.g., in a liquid, solid or semi-solid formulation and/or with an enteric coating.

A pharmaceutical composition comprising any one of the senolytic agents described herein may be formulated for sustained or slow release (also called timed release or controlled release). Such compositions may generally be prepared using well known technology and administered by, for example, oral, rectal, intradermal, or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible and may also be biodegradable; preferably the formulation provides a relatively constant level of active component release. The amount of active agent contained within a sustained release formulation depends upon the site of implantation, the rate and expected duration of release, and the nature of the condition, disease or disorder to be treated or prevented.

In certain embodiments, the pharmaceutical compositions comprising a senolytic agent are formulated for transdermal, intradermal, or topical administration. The compositions can be administered using a syringe, bandage, transdermal patch, insert, or syringe-like applicator, as a powder/talc or other solid, liquid, spray, aerosol, ointment, foam, cream, gel, paste. This preferably is in the form of a controlled release formulation or sustained release formulation administered topically or injected directly into the skin adjacent to or within the area to be treated (intradermally or subcutaneously). The active compositions can also be delivered via iontophoresis. Preservatives can be used to prevent the growth of fungi and other microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, thimerosal, and combinations thereof.

Pharmaceutical compositions comprising a senolytic agent can be formulated as emulsions for topical application. An emulsion contains one liquid distributed the body of a second liquid. The emulsion may be an oil-in-water emulsion or a water-in-oil emulsion. Either or both of the oil phase and the aqueous phase may contain one or more surfactants, emulsifiers, emulsion stabilizers, buffers, and other excipients. The oil phase may contain other oily pharmaceutically approved excipients. Suitable surfactants include, but are not limited to, anionic surfactants, non-ionic surfactants, cationic surfactants, and amphoteric surfactants. Compositions for topical application may also include at least one suitable suspending agent, antioxidant, chelating agent, emollient, or humectant.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Liquid sprays may be delivered from pressurized packs, for example, via a specially shaped closure. Oil-in-water emulsions can also be used in the compositions, patches, bandages and articles. These systems are semisolid emulsions, micro-emulsions, or foam emulsion systems.

Controlled or sustained release transdermal or topical formulations can be achieved by the addition of time-release additives, such as polymeric structures, matrices, which are available in the art. For example, the compositions may be administered through use of hot-melt extrusion articles, such as bioadhesive hot-melt extruded film. The formulation can comprise a cross-linked polycarboxylic acid polymer formulation. A cross-linking agent may be present in an amount that provides adequate adhesion to allow the system to remain attached to target epithelial or endothelial cell surfaces for a sufficient time to allow the desired release of the compound.

An insert, transdermal patch, bandage or article can comprise a mixture or coating of polymers that provide release of the active agents at a constant rate over a prolonged period of time. In some embodiments, the article, transdermal patch or insert comprises water-soluble pore forming agents, such as polyethylene glycol (PEG) that can be mixed with water insoluble polymers to increase the durability of the insert and to prolong the release of the active ingredients.

A polymer formulation can also be utilized to provide controlled or sustained release. Bioadhesive polymers described in the art may be used. By way of example, a sustained-release gel and the compound may be incorporated in a polymeric matrix, such as a hydrophobic polymer matrix. Examples of a polymeric matrix include a microparticle. The microparticles can be microspheres, and the core may be of a different material than the polymeric shell. Alternatively, the polymer may be cast as a thin slab or film, a powder produced by grinding or other standard techniques, or a gel such as a hydrogel. The polymer can also be in the form of a coating or part of a bandage, stent, catheter, vascular graft, or other device to facilitate delivery of the senolytic agent. The matrices can be formed by solvent evaporation, spray drying, solvent extraction and other methods known to those skilled in the art.

Kits with unit doses of one or more of the agents described herein, usually in oral or injectable doses, are provided. Such kits may include a container containing the unit dose, an informational package insert describing the use and attendant benefits of the drugs in treating the senescent cell associated disease, and optionally an appliance or device for delivery of the composition.

Combination Therapy

The compounds and compositions disclosed herein may also be used in combination with one or more other active ingredients. In certain aspects, the compounds may be administered in combination, or sequentially, with another therapeutic agent. Such other therapeutic agents include those known for treatment, prevention, or amelioration of one or more symptoms disclosed herein. Many such therapeutic agents are known in the art.

It should be understood that any suitable combination of the compounds and compositions provided herein with one or more of the above therapeutic agents and optionally one or more further pharmacologically active substances are considered to be within the scope of the present disclosure. In some aspects, the compounds and compositions provided herein are administered prior to or subsequent to the one or more additional active ingredients.

Examples of compounds which may be administered with the compounds disclosed herein include, but are not limited to, dasatinib, quercetin, fisetin, leeutolin, curcumin, curcumin analog EF24, Navioclax (ABT253), A1331852, A1155463, Geldamycin, Tanespimycin, Alvespimycin, piperlongumeine, FOXO-4 peptide, Nutlin3a, cardiac glycosides (e.g., Ouabain, Proscillaridin A, Digoxin, etc.), HSP-90 inhibitors, triptolide, EF-24, Procyanidin C1, Azithromycin, Roxithromycin, 25-hydroxycholesterol, SSK1, BIRC5 knockout, BCL-2 inhibitors, Src inhibitors, PD-1, CTLA-4 ipilimumab, pembrolizumab, nivolumab, atezolizumab, avelumab, durvalumab, cemiplimab, ofatumumab, blinatumomab, daratumumab, elotuzumab, obinutuzumab, talimogene laberparepvec, necitumumab, lenalidomide, dinutuximab and combinations thereof.

Finally, it should be noted that there are alternative ways of implementing the present invention. Accordingly, the present aspects are to be considered as illustrative and not restrictive, and the invention is not to be limited to the details given herein but may be modified within the scope and equivalents of the appended claims.

All publications and patents cited herein are incorporated by reference in their entirety.

The following examples are provided for illustrative purposes only and are not intended to limit the scope of the invention.

EXAMPLES

Scheme 1 illustrated the preparation of compounds 1, 2 and 3.

Scheme 1

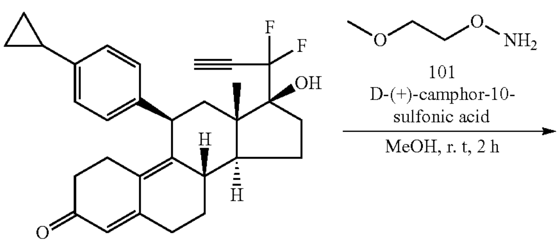

100

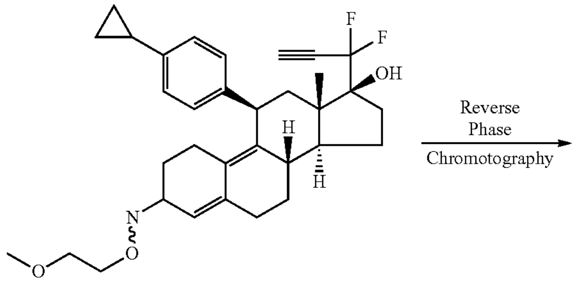

1

-continued

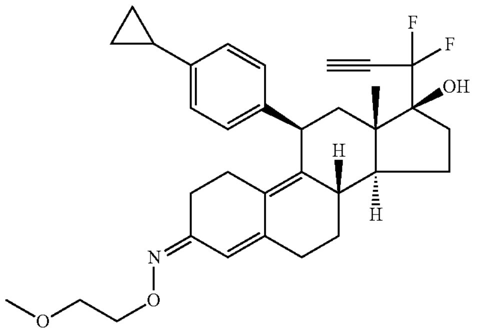

+

2

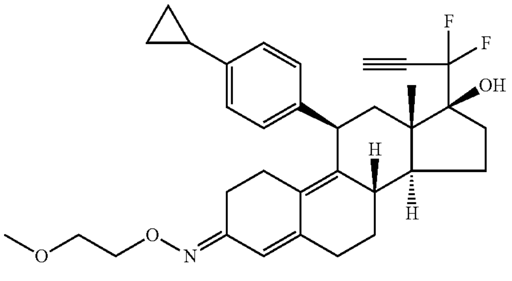

3

Example 1: (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one O-(2-methoxyethyl)oxime (1)

1

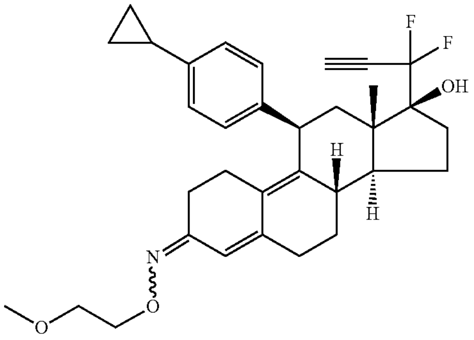

To a stirred solution of (11S,13S, 17S)-11-(4-cyclopropylphenyl)-17-(1,1-difluoroprop-2-yn-1-yl)-17-hydroxy-13-methyl-1,2,6,7,8,11,12,13, 14, 15, 16, 17-dodecahydro-1H-cyclopenta[a]phenanthren-3-one (100) (35 mg, 0.08 mmol, 1.0 equiv) in methanol (1 mL, 0.1M) was added O-(2-methoxyethyl)hydroxylamine (101) (0.15 mmol, 2.0 equiv) followed by D-(+)-camphor-10-sulfonic acid (4 mg, 0.015 mmol, 0.2 equiv) at ambient temperature. The reaction mixture was stirred at room temperature for 2 h until the reaction was complete by LCMS analysis. The mixture was concentrated by rotary evaporation to provide compound 1 as a mixture of E and Z isomers.

Example 2: (8S,11R,13S,14S,17S,Z)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one O-(2-methoxyethyl)oxime (2) and (8S,11R,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one O-(2-methoxyethyl)oxime (3)

2

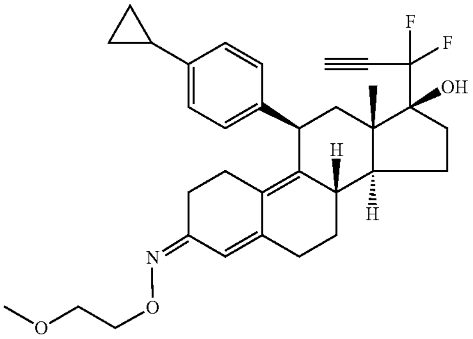

3

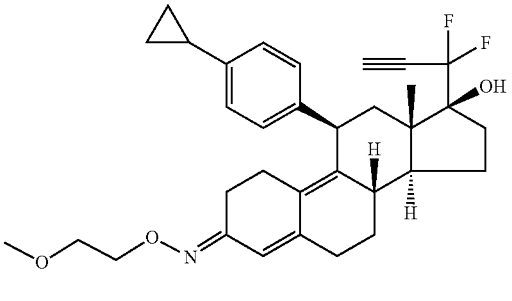

Compound 1 was purified by reverse phase HPLC (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to yield pure geometric isomers 2 (5 mg, 12% yield) and 3 (14.6 mg, 36% yield).

Compound 2: $^1$H NMR (500 MHZ, DMSO-d6): δ 7.02 (d, J=8.3 Hz, 2H), 6.97-6.92 (m, 2H), 6.28 (s, 1H), 5.42 (s, 1H), 4.29 (d, J=6.8 Hz, 1H), 4.24 (t, J=5.2, 5.2 Hz, 1H), 4.04-3.99 (m, 2H), 3.51-3.47 (m, 2H), 3.23 (s, 3H), 2.59-2.53 (m, 1H), 2.39 (d, J=13.3 Hz, 2H), 2.26-2.04 (m, 4H), 1.96-1.89 (m, 1H), 1.82 (m, 2H), 1.76-1.57 (m, 3H), 1.34 (m, 1H), 1.23 (m, 1H), 0.92-0.83 (m, 2H), 0.62-0.56 (m, 2H), 0.45 (s, 3H). Calculated mass: 535.29, Mass (ESI+) observed: 536.5 [M+H]

Compound 3: $^1$H NMR (500 MHZ, DMSO-d6): δ 7.02 (d, J=8.2 Hz, 2H), 6.94 (d, J=8.4 Hz, 2H), 5.77 (s, 1H), 4.28 (d, J=6.8 Hz, 1H), 4.26-4.21 (m, 1H), 4.07-4.01 (m, 2H), 3.51-3.45 (m, 2H), 3.43 (s, 2H), 3.20 (s, 3H), 2.65 (dd, J=11.5, 5.5 Hz, 2H), 2.40 (s, 3H), 2.18-2.03 (m, 3H), 1.96-1.89 (m, 1H), 1.82 (m, 2H), 1.76-1.56 (m, 4H), 1.35-1.20 (m, 2H), 0.92-0.85 (m, 2H), 0.62-0.55 (m, 2H), 0.43 (s, 3H). Calculated mass: 535.29, Mass (ESI+) observed: 536.5 [M+H].

Scheme 2

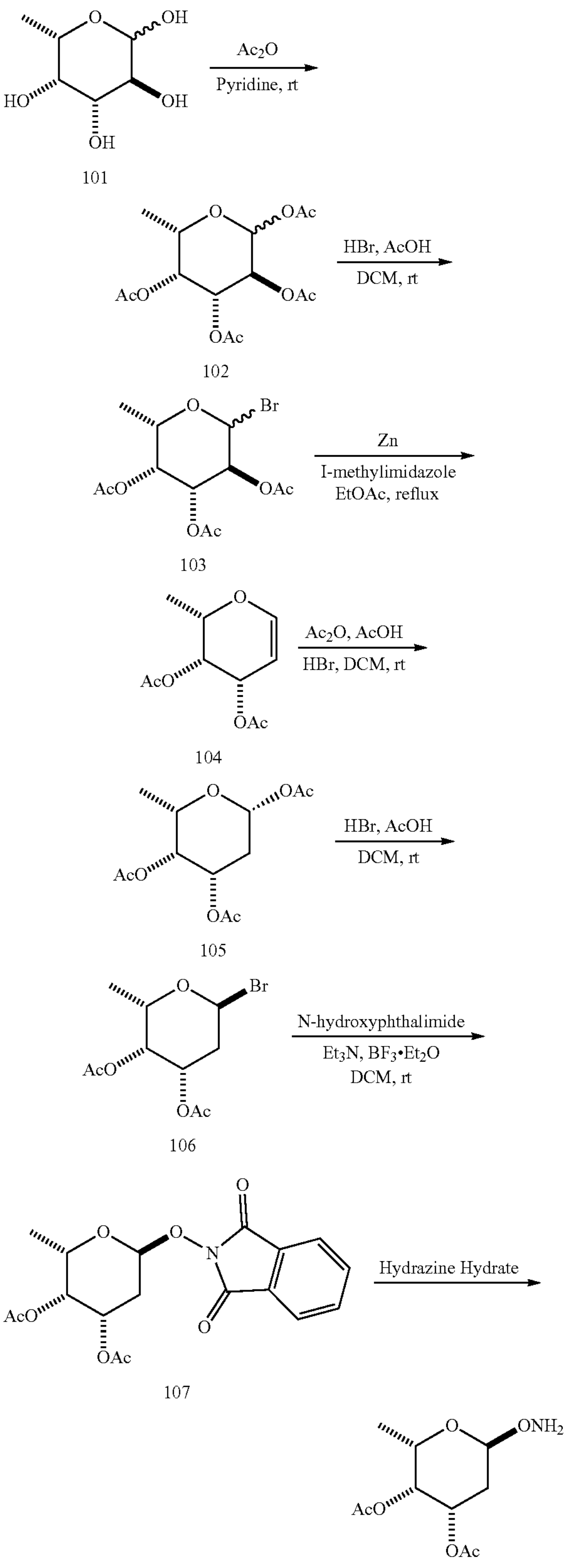

101

102

103

104

105

106

107

108

Scheme 2 illustrate preparation of key intermediate 108.

Preparation of 1,2,3,4-Tetra-O-acetyl-L-fucose (102)

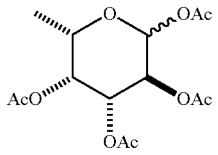

102

L-Fucose (101) (50 g, 0.3 mol) was dissolved in a solution of acetic anhydride (400 mL, 4.23 mol) and pyridine (800 mL, 9.9 mol). The reaction mixture was stirred at room temperature overnight, concentrated under reduced pressure, diluted with EtOAc (2000 mL), washed with water (1000 mL), 10% aqueous citric acid (3×700 mL), water (1000 mL), brine (1000 mL), dried over anhydrous $Na_2SO_4$, filtered and concentrated under reduced pressure. The residue was azeotroped with toluene (200 mL) and dried under high vacuum to afford the crude product 1,2,3,4-tetra-O-acetyl-L-fucose (102) (100 g, quant.) which was used in the next step without any further purification.

Preparation of (2S,3R,4R,5S)-4,5-bis (acetyloxy)-6-bromo-2-methyloxan-3-yl acetate (103)

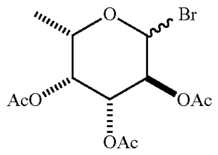

103

1,2,3,4-tetra-O-acetyl-L-fucose (102) (101 g, 0.3 mol) was dissolved in anhydrous dichloromethane (500 mL) and cooled to 0° C. Then, HBr (33% in AcOH, 135 mL) was added and the reaction mixture was allowed to warm to room temperature with stirring for 2 h, poured into an ice/water mixture and the organic layer was separated. The aqueous phase was extracted with $CH_2Cl_2$ (200 mL). The organic layer was washed with saturated $NaHCO_3$ (100 mL), brine (150 mL), dried over anhydrous $Na_2SO_4$, and concentrated under reduced pressure to yield (2S,3R,4R,5S)-4,5-bis (acetyloxy)-6-bromo-2-methyloxan-3-yl acetate, (103) (115 g, quant) as a yellow oil. The crude material was used in the next step without further purification.

Preparation of (2S,3R,4S)-4-(acetyloxy)-2-methyl-3,4-dihydro-2H-pyran-3-yl acetate (104)

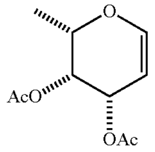

104

To a stirring solution of Zn (111 g, 1.7 mol) and 1-methylimidazole (25 mL, 0.31 mol) in anhydrous ethyl acetate (1200 mL) at reflux, was added a solution of (2S,3R,4R,5S)-4,5-bis (acetyloxy)-6-bromo-2-methyloxan-3-yl acetate (103) (100 g, 0.28 mol) in anhydrous ethyl acetate (200 mL) drop wise in 40 min. The reaction mixture was heated at reflux for 3 h until TLC analysis showed that the reaction was complete. The reaction mixture was cooled to room temperature, stirred for another 30 min and then filtered through a pad of celite. Concentration under reduced pressure afforded a crude product which was purified by silica gel flash chromatography (0-10% EtOAc in hexanes) to afford desired product (2S,3R,4S)-4-(acetyloxy)-2-methyl-3,4-dihydro-2H-pyran-3-yl acetate, (104) (38 g, 63% yield).

Preparation of (2S,3R,4S)-4,6-bis (acetyloxy)-2-methyloxan-3-yl acetate (105)

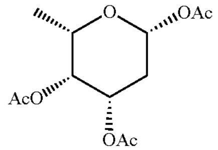 [SMILES: CC(=O)O[C@@H]1C[C@H](OC(C)=O)[C@H](OC(C)=O)[C@H](C)O1]

To a cold solution (ice/water bath) of (2S,3R,4S)-4-(acetyloxy)-2-methyl-3,4-dihydro-2H-pyran-3-yl acetate (104) (75 g, 0.35 mol) in anhydrous dichloromethane (500 mL) was added acetic acid (190 mL, 3.3 mol) and acetic anhydride (290 mL, 3 mol). The reaction mixture was stirred for 15 minutes, 33% HBr solution in AcOH (19 mL) was added and stirring continued for an additional 30 min until the solution turned light yellow. TLC analysis showed complete consumption of starting material (lower spot, 25% EtOAc/hexanes). An ice/water mixture was added to quench the reaction. The organic layer was thoroughly washed with water (2×1 L) followed by cold saturated aqueous $NaHCO_3$ solution (1 L), water (1 L) and brine (1 L). The organic layer was dried over anhydrous $Na_2SO_4$, and concentrated in vacuo to provide a crude product which was purified by silica gel flash chromatography (0-20% EtOAc in hexanes) to afford desired product (2S,3R,4S)-4,6-bis (acetyloxy)-2-methyloxan-3-yl acetate, (105) as a white solid (83 g, 86.2% yield).

Preparation of (2S,3R,4S,6S)-4-(acetyloxy)-6-bromo-2-methyloxan-3-yl acetate (106)

106

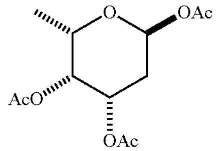

To a solution of (2S,3R,4S)-4,6-bis (acetyloxy)-2-methyloxan-3-yl acetate (105) (82 g, 0.3 mol) in anhydrous dichloromethane (700 mL) was added 33% HBr in AcOH (80 mL) at 0° C. The reaction mixture was stirred for 15 minutes and then ice-cold water (300 mL) was added to quench the reaction. The aqueous phase was extracted with dichloromethane (3×700 mL) and the combined organic layers were washed with brine (2×500 mL), dried over anhydrous sodium sulfate and concentrated in vacuo to give (2S,3R,4S,6S)-4-(acetyloxy)-6-bromo-2-methyloxan-3-yl acetate, (106) as sticky oil. The crude material was taken forward into next step without any further purification as soon as possible.

Preparation of (2S,3R,4S,6S)-4-(acetyloxy)-6-[(1,3-dioxo-2,3-dihydro-1H-isoindol-2-yl)oxy]-2-methyloxan-3-yl acetate (107)

107

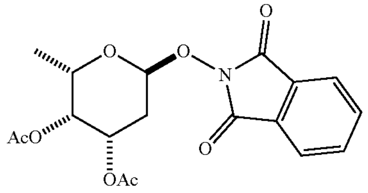

To a solution of crude (2S,3R,4S,6S)-4-(acetyloxy)-6-bromo-2-methyloxan-3-yl acetate (106) and N-hydroxyphthalimide (54 g, 0.33 mol) in anhydrous dichloromethane (600 mL) was added triethylamine (55 mL, 0.33 mol) followed by $BF_3$·$OEt_2$ (92 mL, 0.75 mol) at 0° C. The reaction mixture was brought to room temperature and stirred for 1h until a greenish gray color formed. Cold saturated aqueous $NaHCO_3$ solution (500 mL) was added and the organic layer was separated. The aqueous later was extracted with dichloromethane (3×500 mL) and the combined organic layers were dried over anhydrous sodium sulfate and concentrated under reduced pressure to obtain crude material. Silica gel flash chromatography (10%-60% EtOAc in hexanes) provided (2S,3R,4S,6S)-4-(acetyloxy)-6-[(1,3-dioxo-2,3-dihydro-1H-isoindol-2-yl)oxy]-2-methyloxan-3-yl acetate (107) as white foamy solid (75 g, 66% yield over two steps).

LC/MS (Method B): RT=4.32 Min; m/z=377.1, found=378.2 $[M^{+}H]^{+}$. Total time=12 min. $^{1}H$ NMR (500 MHZ, Chloroform d3) δ 7.85 (ddd, J=5.5, 3.3, 0.6 Hz, 2H), 7.76 (ddd, J=5.9, 2.9, 0.8 Hz, 2H), 5.62-5.52 (m, 1H), 5.43 (ddd, J=12.5, 5.3, 3.0 Hz, 1H), 5.38-5.23 (m, 1H), 4.97 (td, J=6.7, 6.7, 5.6 Hz, 1H), 2.35-2.18 (m, 2H), 2.17 (s, 3H), 2.03 (d, J=0.6 Hz, 3H), 1.14 (dd, J=6.5, 0.6 Hz, 3H).

Preparation of (2S,3R,4S,6S)-4-(acetyloxy)-6-(aminooxy)-2-methyloxan-3-yl acetate (108)

108

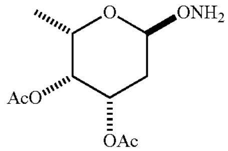

A solution of (2S,3R,4S,6S)-4-(acetyloxy)-6-[(1,3-dioxo-2,3-dihydro-1H-isoindol-2-yl)oxy]-2-methyloxan-3-yl acetate (107) (25 g, 0.066 mol) in methanol (500 mL) was cooled to 0° C. under an ice/water bath. Hydrazine hydrate (5.5 mL, 0.066 mol) was added slowly and the resulting reaction mixture was stirred for additional 30 min at 0° C. The precipitate was filtered and the filtrate was diluted with dichloromethane (500 mL), washed with cold aqueous $NaHCO_3$ (2×350 mL), water (350 mL), brine (350 mL), dried over anhydrous $Na_2SO_4$ and concentrated under reduced pressure to afford crude (2S,3R,4S,6S)-4-(acetyloxy)-6-(aminooxy)-2-methyloxan-3-yl acetate, (108), (12 g, 78% yield) as an off white foamy solid. LC/MS: m/z=247.2, found=248.3 $[M+H]^+$. Total time=6 min.

Scheme 3 illustrated the preparation of compounds 4, 5, 6 and 22.

Scheme 3

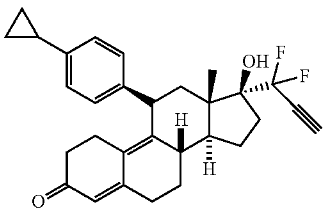

100

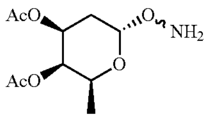

108

PTSA, Pyridine

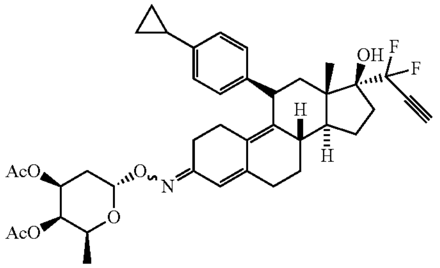

22

TEA

MeOH, $H_2O$

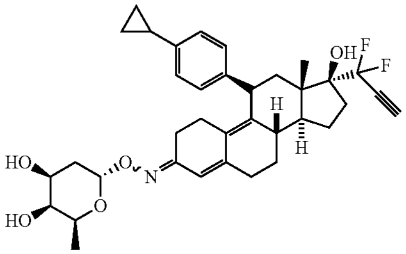

4

Reverse Phase

Chromotography

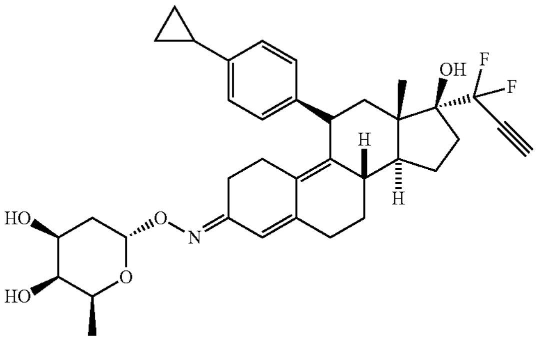

+

5

-continued

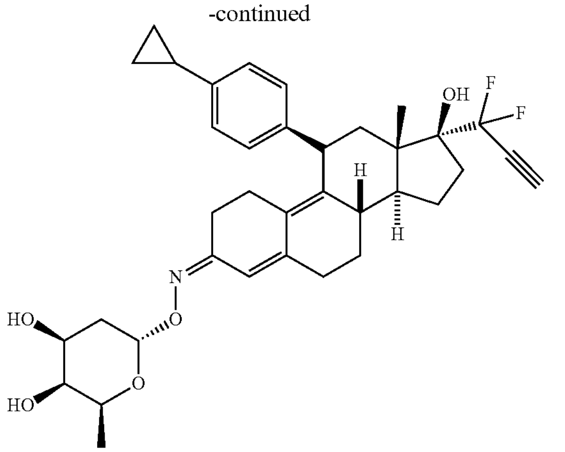

6

Example 3: (2S,3R,4S,6S)-6-((((11S,13S,17S,E:Z)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)amino)oxy)-2-methyltetrahydro-2H-pyran-3,4-diyl diacetate (22)

22

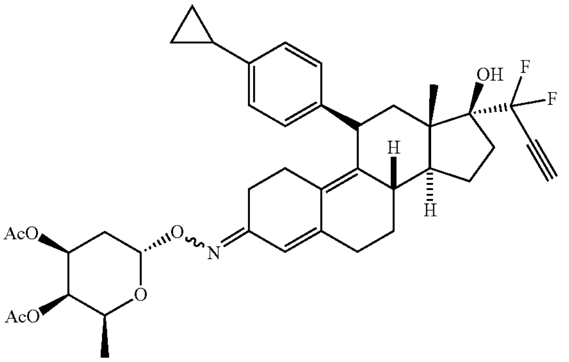

To a stirred solution of (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (52 mg, 0.11 mmol, 1.0 equiv) in pyridine (1.1 mL, 0.1M) was added (2S,3R,4S,6S)-6-(aminooxy)-2-methyltetrahydro-2H-pyran-3,4-diyl diacetate (31.0 mg, 0.12 mmol, 1.1 equiv) followed by p-toluenesulfonic acid monohydrate (11.0 mg, 0.05 mmol, 0.5 equiv) at ambient temperature. The reaction mixture was stirred at room temperature for 3 h when the reaction was complete by LCMS analysis. The reaction mixture was concentrated and dried to afford (2S,3R,4S,6S)-6-((((11S,13S,17S,E:Z)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)amino)oxy)-2-methyltetrahydro-2H-pyran-3,4-diyl diacetate (22) (78 mg, 100% yield).

Example 4: (8S,11S,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one O-((2S,4S,5S,6S)-4,5-dihydroxy-6-methyltetrahydro-2H-pyran-2-yl) oxime (4)

4

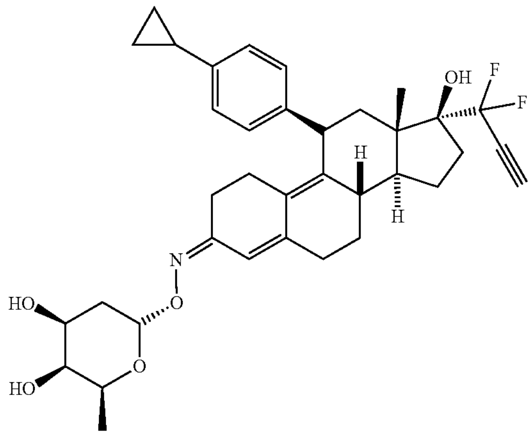

To a stirred solution of (2S,3R,4S,6S)-6-((((11S,13S,17S, E: Z)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene) amino)oxy)-2-methyltetrahydro-2H-pyran-3,4-diyl diacetate (22) (78 mg, 0.11 mmol, 1.0 equiv) in methanol (1.6 mL) and water (0.4 mL) was added trimethylamine (73 μL, 0.56 mmol, 5.0 equiv) at ambient temperature. The reaction mixture was stirred at room temperature for 16 h the reaction was complete by LCMS analysis to afford (8S,11S,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one O-((2S,4S,5S,6S)-4,5-dihydroxy-6-methyltetrahydro-2H-pyran-2-yl) oxime (4).

Example 5: (8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one O-((2S,4S,5S,6S)-4,5-dihydroxy-6-methyltetrahydro-2H-pyran-2-yl) oxime (5) and (8S,11S,13S,14S,17S,Z)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one O-((2S,4S,5S,6S)-4,5-dihydroxy-6-methyltetrahydro-2H-pyran-2-yl) oxime (6)

5

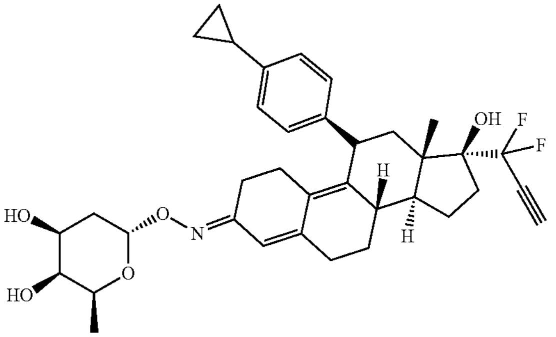

-continued

6

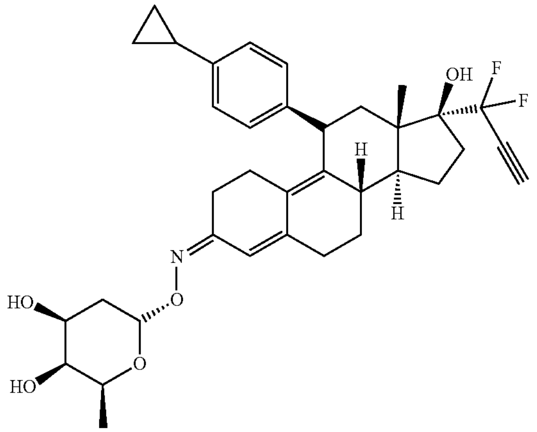

Compound 4 was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to yield pure geometric isomers 5 (22.7 mg, 33% yield) and 6 (5.9 mg, 8.6% yield).

Compound 5: $^1$H NMR (500 MHZ, DMSO-d6): δ 7.03 (d, J=8.4 Hz, 2H), 6.95 (d, J=8.5 Hz, 2H), 5.81 (s, 1H), 5.41 (s, 1H), 5.30-5.26 (m, 1H), 4.55 (d, J=6.2 Hz, 1H), 4.31-4.26 (m, 2H), 4.23 (t, J=5.3, 5.3 Hz, 1H), 3.72-3.63 (m, 2H), 2.67 (dt, J=16.8, 5.7, 5.7 Hz, 1H), 2.42 (d, J=13.3 Hz, 4H), 2.23-2.04 (m, 3H), 1.97-1.90 (m, 1H), 1.86-1.78 (m, 2H), 1.78-1.65 (m, 3H), 1.62 (dt, J=11.6, 5.7, 5.7 Hz, 2H), 1.36-1.19 (m, 2H), 1.02 (d, J=6.5 Hz, 3H), 0.93-0.83 (m, 2H), 0.62-0.56 (m, 2H), 0.44 (s, 3H). Calculated mass: 607.3, Mass (ESI+) observed: 608.5 [M+H].

Compound 6: $^1$H NMR (500 MHZ, DMSO-d6): δ 7.03 (d, J=8.2 Hz, 2H), 6.95 (d, J=8.5 Hz, 2H), 6.31 (s, 1H), 5.41 (s, 1H), 5.30-5.24 (m, 1H), 4.56 (d, J=6.1 Hz, 1H), 4.29 (t, J=5.2, 5.2 Hz, 2H), 4.24 (t, J=5.2, 5.2 Hz, 1H), 3.80 (dt, J=12.0, 8.1, 8.1 Hz, 1H), 3.69 (q, J=7.0, 6.5, 6.5 Hz, 1H), 2.39 (d, J=12.6 Hz, 2H), 2.25-2.04 (m, 4H), 1.96-1.89 (m, 1H), 1.88-1.78 (m, 3H), 1.72 (dd, J=25.7, 9.0 Hz, 2H), 1.62 (dd, J=12.4, 4.9 Hz, 2H), 1.34 (q, J=11.5, 11.5, 11.5 Hz, 1H), 1.28-1.18 (m, 1H), 1.03 (d, J=6.6 Hz, 3H), 0.91-0.86 (m, 2H), 0.62-0.56 (m, 2H), 0.45 (s, 3H). Calculated mass: 607.3, Mass (ESI+) observed: 608.5 [M+H].

Scheme 4 illustrated the preparation of intermediate 114.

Scheme 4

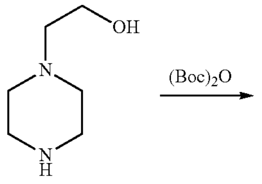

110

-continued

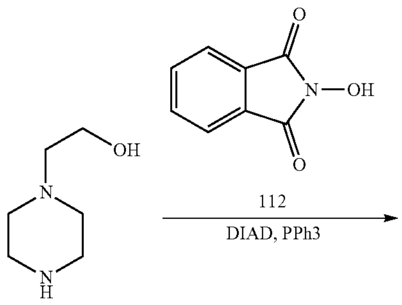

112

111

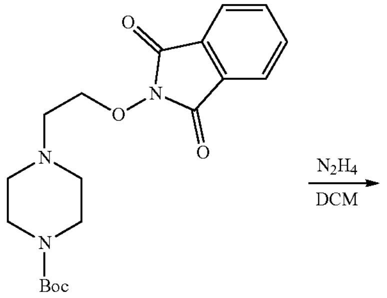

113

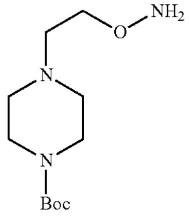

114

Preparation of tert-butyl 4-(2-hydroxyethyl)piperazine-1-carboxylate (111)

111

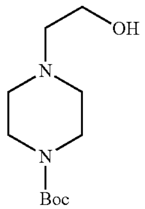

To a stirred solution of 2-(piperazin-1-yl) ethan-1-ol (110) (1.0 g, 7.68 mmol, 1.0 equiv) in THF (76 mL) was added di-tert-butyl dicarbonate (1.84 g, 8.44 mmol, 1.1 equiv) at 0° C. The reaction mixture was stirred at 0° C. for 10 min, then warmed to room temperature for 6 h when the reaction was complete by LCMS analysis. The reaction mixture was quenched with water (76 mL) and extracted with ethyl acetate (2×200 mL). The combined organic layers were dried over $Na_2SO_4$, filtered, concentrated and dried to afford tert-butyl 4-(2-hydroxyethyl)piperazine-1-carboxylate (111) (1.76 g, 100% yield).

Preparation of tert-butyl 4-(2-((1,3-dioxoisoindolin-2-yl)oxy)ethyl)piperazine-1-carboxylate (113)

113

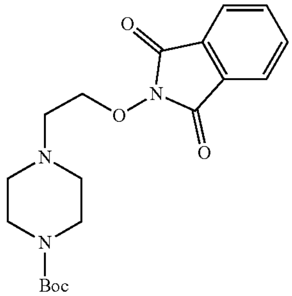

To a stirred solution of tert-butyl 4-(2-hydroxyethyl) piperazine-1-carboxylate (111) (1.7 g, 7.39 mmol, 1.0 equiv) in THF (74 mL) was added N-hydroxypthalamide (112) (1.2 g, 7.39 mmol, 1.0 equiv), triphenylphosphine (2.13 g, 8.13 mmol, 1.1 equiv) followed by diisopropyl azodicarboxylate at room temperature. The reaction mixture was stirred room temperature for 16 h when the reaction was complete by LCMS analysis. The reaction mixture was quenched with water (76 mL) and extracted with ethyl acetate (2×200 mL). The combined organic layers were dried over $Na_2SO_4$, filtered and concentrated. The crude material was diluted with diethyl ether (30 mL) and hexane (70 mL) and stirred at rt for 1 h. The mixture was filtered through a sintered funnel to remove most of the triphenylphosphine oxide. The filtrate was purified by normal phase silica gel (0-60% EtOAc in hexanes) to afford tert-butyl 4-(2-((1,3-dioxoisoindolin-2-yl)oxy)ethyl)piperazine-1-carboxylate (113) as a white solid (2.16 g, 78%).

Preparation of tert-butyl 4-(2-(aminooxy)ethyl)piperazine-1-carboxylate (114)

114

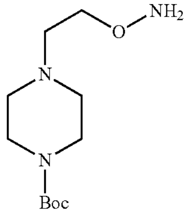

To a stirred solution of tert-butyl 4-(2-((1,3-dioxoisoindolin-2-yl)oxy)ethyl)piperazine-1-carboxylate (113) (0.2 g, 0.52 mmol, 1.0 equiv) in THF (74 mL) was added hydrazine monohydrate (0.12 mL, 1.6 mmol, 3.0 equiv) at room temperature. The reaction mixture was stirred room temperature for 1 h when the reaction was complete by LCMS analysis. The reaction mixture was filtered through a celite pad and the filtrate was concentrated to afford tert-butyl 4-(2-(aminooxy)ethyl)piperazine-1-carboxylate (114) (0.13 g, 100%).

Scheme 5 illustrated the preparation of compounds 7 and 23.

Scheme 5

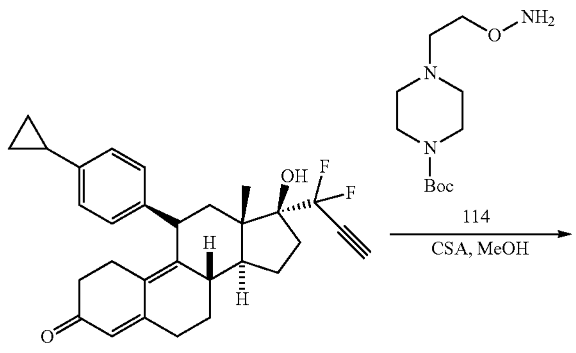

100

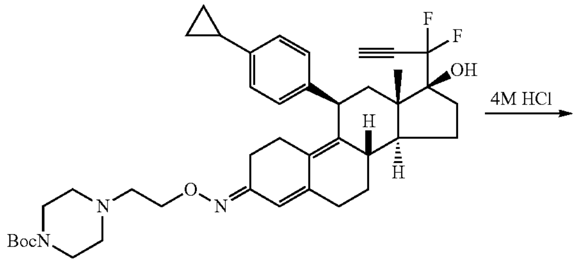

23

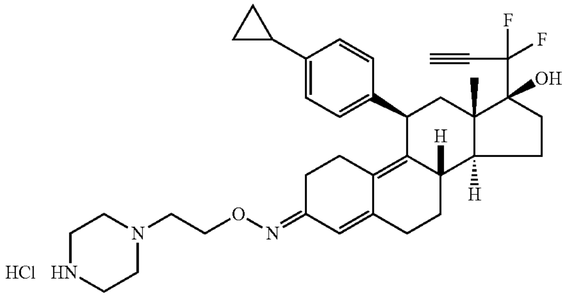

7

Example 6: tert-butyl 4-(2-((((8S,11R,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)amino)oxy)ethyl)piperazine-1-carboxylate (23)

23

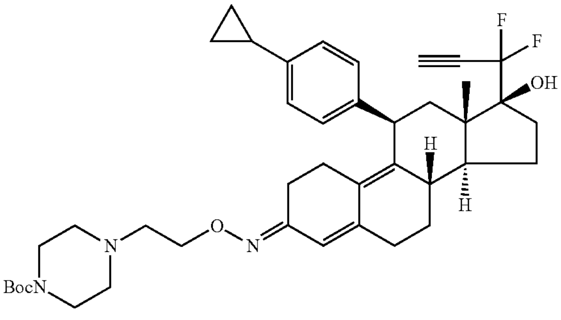

To a stirred solution of (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (0.1 g, 0.216 mmol, 1.0 equiv) in methanol (3 mL) was added tert-butyl 4-(2-(aminooxy)ethyl)piperazine-1-carboxylate (114) (0.16 g, 0.43 mmol, 2.0 equiv) followed by D-(+)-camphor-10-sulfonic acid (10 mg, 0.08 mmol, 0.4 equiv) at ambient temperature. The reaction mixture was stirred at room temperature for 16 h when the reaction was complete by LCMS analysis. The mixture was concentrated by rotary evaporation. The residue was purified by reverse phase HPLC (CLIPEUS C-18 10 um (Higgins Analytical Inc) 20 ×250 mm; ELSD and 254 UV detection; mobile phase A: 10 mmol ammonium bicarbonate in water; mobile phase B: 5% aqueous acetonitrile to 90% aqueous acetonitrile over 40 min) to afford tert-butyl 4-(2-((((8S,11R,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)amino)oxy)ethyl)piperazine-1-carboxylate (23) (59 mg, 50% yield).

Example 7: (8S,11R,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one O-(2-(piperazin-1-yl)ethyl)oxime (7)

7

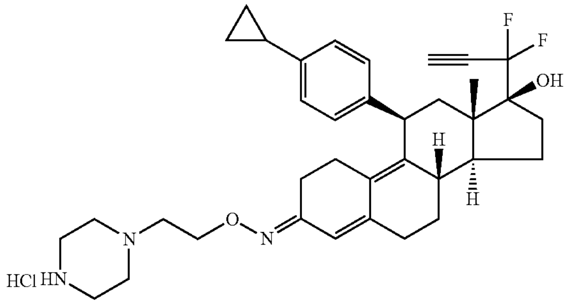

To tert-butyl 4-(2-((((8S,11R,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)amino)oxy)ethyl)piperazine-1-carboxylate (23) (10 mg, 0.014 mmol) was added 4M HCl (in dioxane) (0.5 mL) at room temperature. The reaction mixture was stirred room temperature for 2 h when the reaction was complete by LCMS analysis. The reaction mixture was concentrated to afford (8S,11R,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16, 17-dodecahydro-3H-cyclopenta[a]phenanthren-3-one O-(2-(piperazin-1-yl)ethyl)oxime (7) (13 mg, 100%).

$^1$H NMR (500 MHZ, DMSO-d6): δ 7.03 (dd, J=8.3, 3.9 Hz, 2H), 6.95 (d, J=7.4 Hz, 2H), 6.36 (s, 1H), 4.31 (d, J=6.8 Hz, 3H), 4.24 (t, J=5.6, 5.6 Hz, 1H), 3.73-3.63 (m, 2H), 3.50-3.44 (m, 3H), 2.45 (s, 2H), 2.43-2.37 (m, 2H), 2.29-2.21 (m, 1H), 2.18 (s, 1H), 2.15 (dd, J=9.0, 5.7 Hz, 1H), 2.13-2.04 (m, 1H), 1.94 (dt, J=12.6, 4.3, 4.3 Hz, 1H), 1.83 (ddd, J=10.4, 8.4, 5.1 Hz, 2H), 1.76-1.57 (m, 3H), 1.39-1.17 (m, 3H), 0.93-0.86 (m, 2H), 0.59 (tq, J=4.5, 4.5, 2.7, 2.1, 2.1 Hz, 2H), 0.45 (d, J=5.0 Hz, 3H). Calculated mass: 589.35, Mass (ESI+) observed: 590.5 [M+H].

Scheme 6 illustrates the synthesis of intermediate 118.

Scheme 6

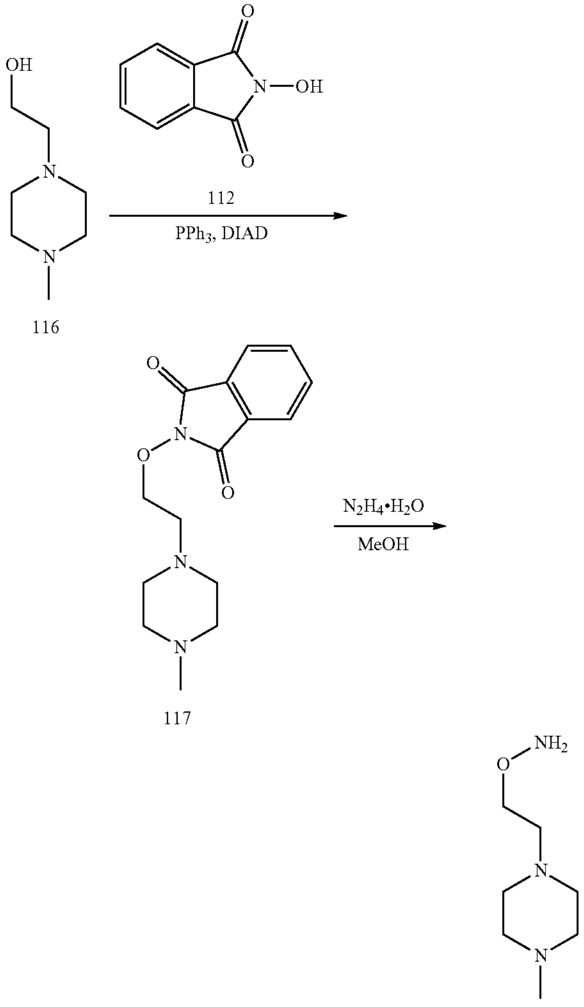

112

116

117

118

Preparation of 2-(2-(4-methylpiperazin-1-yl)ethoxy) isoindoline-1,3-dione (117)

117

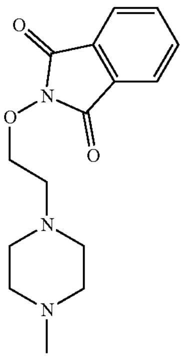

To a stirred solution of 2-hydroxyisoindoline-1,3-dione (112) (1.12 g, 6.9 mmol, 1 equiv) and triphenylphosphine (2.0 g, 7.6 mmol, 1.1 equiv) in THF (25 ml) at 0° C. was added 2-(4-methylpiperazin-1-yl) ethanol (116) (1.0 g, 6.9 mmol, 1.01 equiv) dropwise. The mixture was then stirred at 0° C. for 30 min before DIAD (1.5 mL, 7.6 mmol, 1.1 equiv) was added dropwise. The reaction was stirred for a further 30 min at 0° C. before being warmed to rt and stirred for 16 h. The solvent was removed under reduced pressure and the residue re-dissolved in EtOAc (35 mL). The organic layer was washed with saturated $NaHCO_3$ (2x25 mL), dried over $Na_2SO_4$, filtered and concentrated under reduced pressure to approximately 15 mL. The organic layer was cooled to 0° C. and cold 1 M aqueous HCl solution (15 mL) was added. After complete addition, the mixture was warmed to rt and stirred for 20 min. The layers were separated and the aqueous layer washed with $Et_2O$ (2x15 mL). After cooling to 0° C., the aqueous layer was basified by slow addition of a saturated $NaHCO_3$ solution before being extracted with $CHCl_3$ (3x25 mL). The organic extracts were combined, dried over $Na_2SO_4$, filtered and concentrated under reduced pressure to afford 2-(2-(4-methylpiperazin-1-yl)ethoxy) isoindoline-1,3-dione (117) as a beige solid (1.1 g, 55%). Calculated mass: 289.14, Mass (ESI+) observed: 290.1 [M+H].

Preparation of O-(2-(4-methylpiperazin-1-yl)ethyl) hydroxylamine (118)

118

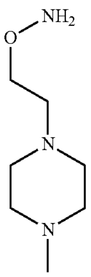

To a stirred solution of 2-(2-(4-methylpiperazin-1-yl) ethoxy)isoindoline-1,3-dione (117) (200 mg, 0.69 mmol) in MeOH: DCM (2:1, 3 mL) at 0° C. was added hydrazine monohydrate (0.1 mL, 2.1 mmol, 3 equiv) and stirring was continued at 0° C. for 1 h. After completion of the reaction, solvent was removed under vacuum, the residue was redissolved in ethyl acetate, washed twice with water (2x3 mL), dried with $Na_2SO_4$ and concentrated to provide O-(2-(4-methylpiperazin-1-yl)ethyl)hydroxylamine (118), which used for the next step without further purification (110 mg, crude). Calculated mass: 159.13, Mass (ESI+) observed: 160.0 [M+H].

Scheme 7 illustrates preparation of compound 8.

Scheme 7

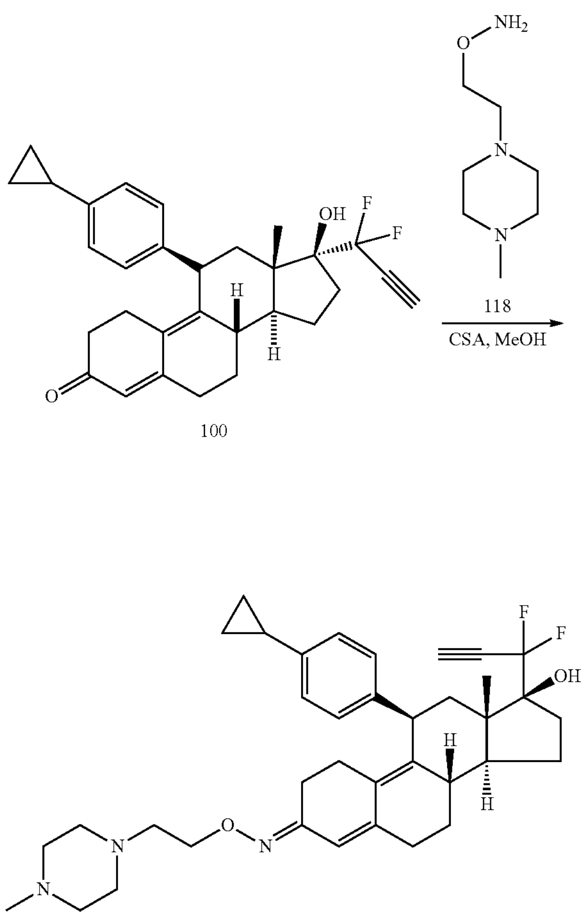

100

8

Example 8: (8S,11R,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one O-(2-(4-methylpiperazin-1-yl)ethyl)oxime (8)

8

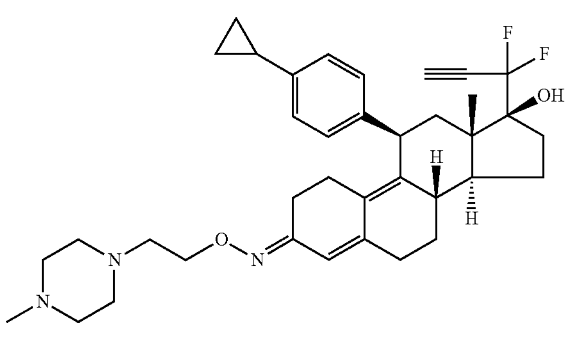

To a stirred solution of (8S,11R,13S,14S, 17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (35 mg, 0.07 mmol, 1.0 equiv) in methanol (0.7 mL, 0.1M) was added O-(2-(4-methylpiperazin-1-yl)ethyl)hydroxylamine (118) (36 mg, 0.22 mmol, 3.0 equiv) followed by D-(+)-camphor-10-sulfonic acid (3.5 mg, 0.01 mmol, 0.2 equiv) at ambient temperature. The reaction mixture was stirred at room temperature for 2 h when the reaction was complete by LCMS analysis. The volatiles were concentrated by rotary evaporation. The residue was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to afford (8S,11R,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one O-(2-(4-methylpiperazin-1-yl)ethyl)oxime (8) (3.9 mg, 8.5% yield).

$^1$H NMR (500 MHZ, DMSO-d6): δ 7.07-7.00 (m, 2H), 6.97-6.91 (m, 2H), 5.96 (s, 1H), 5.71 (s, 1H), 5.40 (d, J=6.0 Hz, 1H), 4.31-4.20 (m, 2H), 2.87 (s, 1H), 2.71 (s, 1H), 2.42-2.32 (m, 5H), 2.20-2.01 (m, 3H), 1.93 (ddt, J=17.1, 11.8, 5.5, 5.5 Hz, 2H), 1.86-1.55 (m, 5H), 1.38-1.17 (m, 2H), 0.92-0.83 (m, 2H), 0.62-0.56 (m, 2H), 0.44 (d, J=5.5 Hz, 3H). Calculated mass: 603.364, Mass (ESI+) observed: 605.5 $[M+H]^+$.

Scheme 8 illustrates preparation of compound 9.

Scheme 8

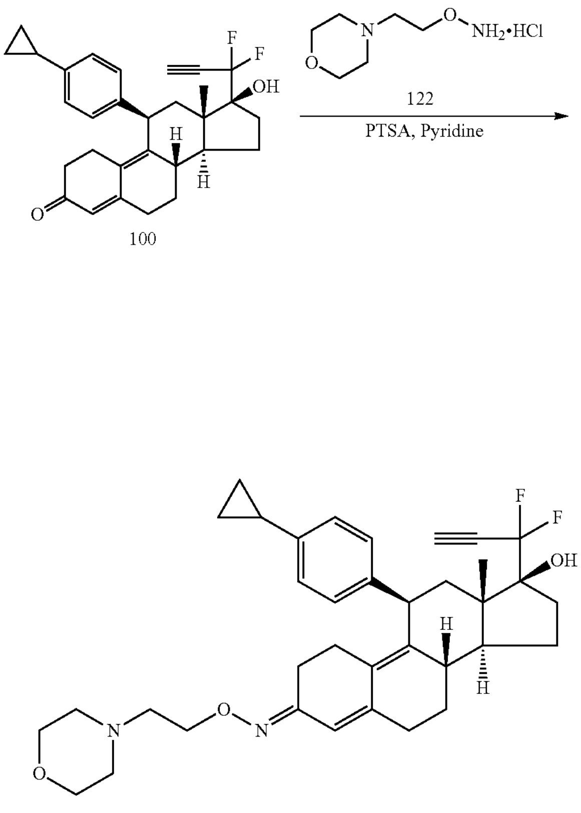

100

9

Example 9: (8S,11R,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one O-(2-morpholinoethyl)oxime (9)

9

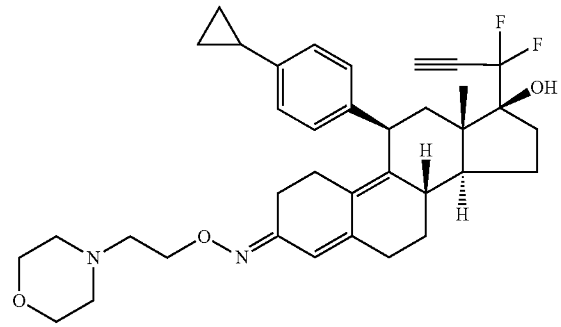

To a stirred solution of (11S,13S,17S)-11-(4-cyclopropylphenyl)-17-(1,1-difluoroprop-2-yn-1-yl)-17-hydroxy-13-methyl-6,7,8,11,12,13,14,15,16,17-dodecahydro-1H-cyclopenta[a]phenanthren-3 (2H)-one (100) (35 mg, 0.08 mmol, 1.0 equiv) in pyridine (0.7 mL, 0.1M) was added O-(2-morpholinoethyl)hydroxylamine (122) (42 mg, 0.23 mmol, 3.0 equiv) followed by p-toluenesulfonic acid mono hydrate (7.3 mg, 0.04 mmol, 0.5 equiv) at ambient temperature. The reaction mixture was stirred at room temperature for 16 h when the reaction was complete by LCMS analysis. The reaction mixture was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to afford (8S,11R,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one O-(2-morpholinoethyl)oxime (9) (8.5 mg, 19% yield).

$^1$H NMR (500 MHZ, DMSO-d6): δ 7.02 (d, J=8.3 Hz, 2H), 6.94 (d, J=8.5 Hz, 2H), 5.77 (s, 1H), 5.41 (s, 1H), 4.28 (d, J=6.8 Hz, 1H), 4.23 (t, J=5.2, 5.2 Hz, 1H), 4.05 (t, J=5.9, 5.9 Hz, 2H), 3.50 (t, J=4.7, 4.7 Hz, 4H), 2.67-2.59 (m, 2H), 2.43-2.31 (m, 9H), 2.19-2.03 (m, 3H), 2.02-1.88 (m, 1H), 1.82 (m, 1H), 1.77-1.56 (m, 4H), 1.36-1.19 (m, 2H), 0.92-0.85 (m, 2H), 0.62-0.55 (m, 2H), 0.43 (s, 3H). Calculated mass: 590.33, Mass (ESI+) observed: 591.7 [M+H].

Scheme 9 illustrates the preparation of compounds 10, 11 and 12.

Scheme 9

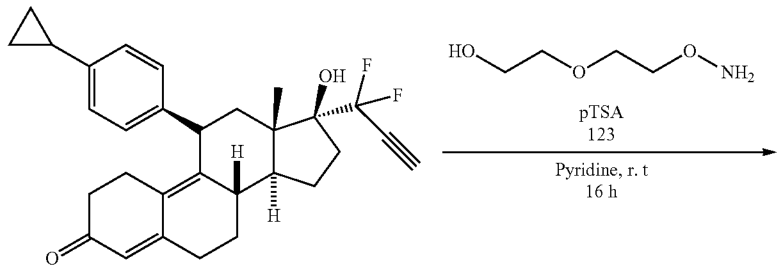

100

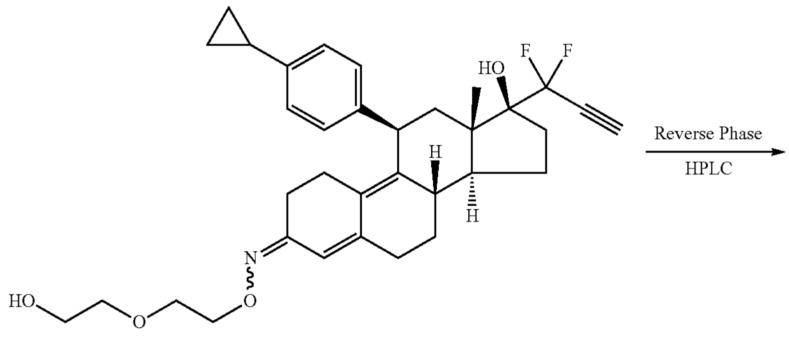

10

-continued

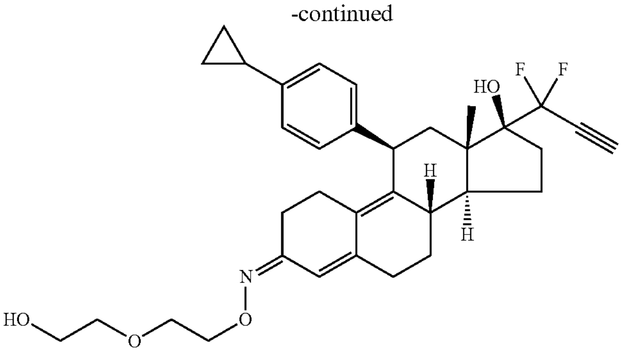

+

11

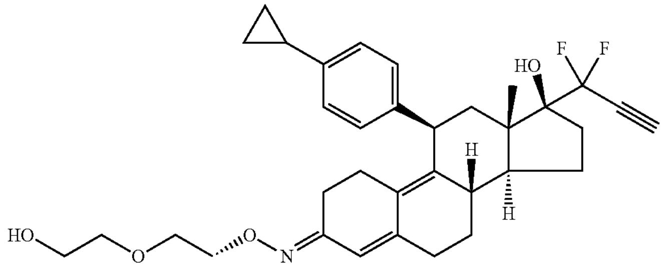

12

Example 10: (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one O-(2-(2-hydroxyethoxy)ethyl)oxime (10)

10

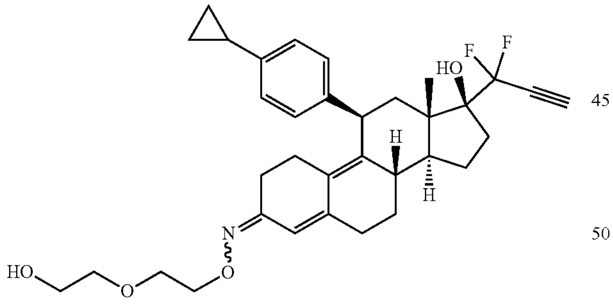

To a stirred solution of (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (35 mg, 0.08 mmol, 1.0 equiv) in pyridine (0.7 mL, 0.1M) was added 2-(2-(aminooxy)ethoxy)ethanol (123) (27 mg, 0.23 mmol, 3.0 equiv) followed by p-toluenesulfonic acid mono hydrate (7.3 mg, 0.04 mmol, 0.5 equiv) at ambient temperature. The reaction mixture was stirred at room temperature for 16 h at which time the reaction was complete by LCMS analysis to afford compound 10.

Example 11: (8S,11R,13S,14S,17S,Z)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one O-(2-(2-hydroxyethoxy)ethyl)oxime (11) and (8S,11R,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one O-(2-(2-hydroxyethoxy)ethyl)oxime (12)

11

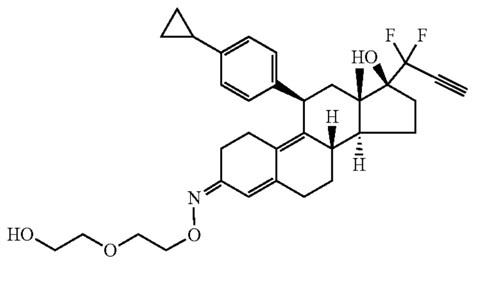

+

12

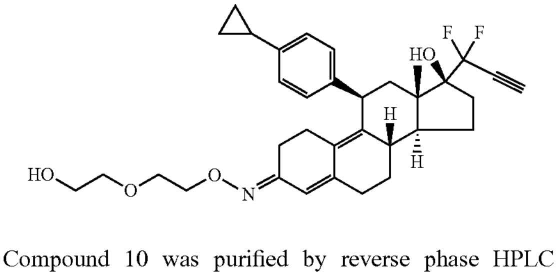

Compound 10 was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to yield pure geometric isomers 11 (4 mg, 10% yield) and 12 (18 mg, 42% yield).

Compound 11: $^1$H NMR (500 MHZ, Chloroform-d3): δ 7.05 (d, J=7.9 Hz, 2H), 7.02-6.92 (m, 2H), 6.45 (s, 1H), 4.32 (d, J=7.4 Hz, 1H), 4.23-4.18 (m, 2H), 3.80-3.75 (m, 2H), 3.73 (m, 2H), 3.65-3.58 (m, 2H), 2.89 (t, J=5.4, 5.4 Hz, 1H), 2.60-2.25 (m, 10H), 2.13-2.06 (m, 1H), 2.05 (s, 1H), 1.99 (m, 1H), 1.85 (m, 2H), 1.79-1.70 (m, 2H), 1.49-1.33 (m, 2H), 0.93 (m, 2H), 0.69-0.62 (m, 2H), 0.59 (s, 3H). Calculated mass: 565.3, Mass (ESI+) observed: 566.2 [M+H].

Compound 12: $^1$H NMR (500 MHZ, DMSO-d6): δ 7.03 (d, J=8.3 Hz, 2H), 6.96 (d, J=8.5 Hz, 2H), 5.79 (s, 1H), 5.42 (s, 1H), 4.53 (t, J=5.5, 5.5 Hz, 1H), 4.30 (d, J=7.3 Hz, 1H), 4.24 (t, J=5.4, 5.4 Hz, 1H), 4.05 (dd, J=5.9, 4.0 Hz, 2H), 3.60-3.55 (m, 2H), 3.45 (m, 2H), 3.41-3.37 (m, 2H), 2.69-2.62 (m, 1H), 2.42 (d, J=13.4 Hz, 3H), 2.19-2.06 (m, 6H), 1.97-1.90 (m, 1H), 1.83 (m, 1H), 1.76-1.57 (m, 4H), 1.37-1.19 (m, 2H), 0.94-0.84 (m, 2H), 0.66-0.54 (m, 2H), 0.45 (s, 3H). Calculated mass: 565.3, Mass (ESI+) observed: 566.5 [M+H].

Scheme 10 illustrates the preparation of compounds 13, 14 and 15.

Scheme 10

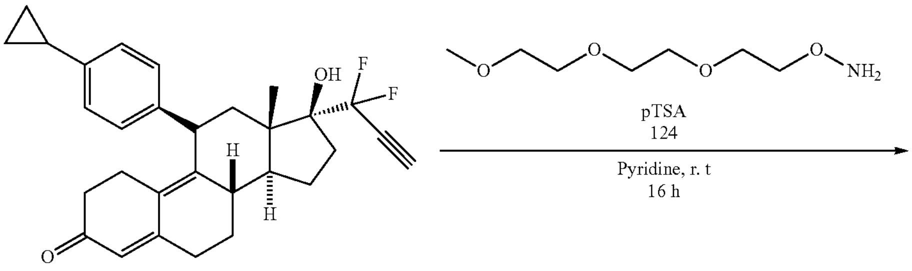

100

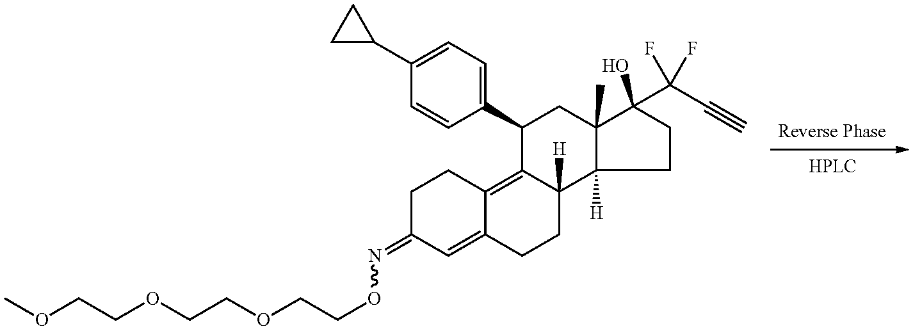

13

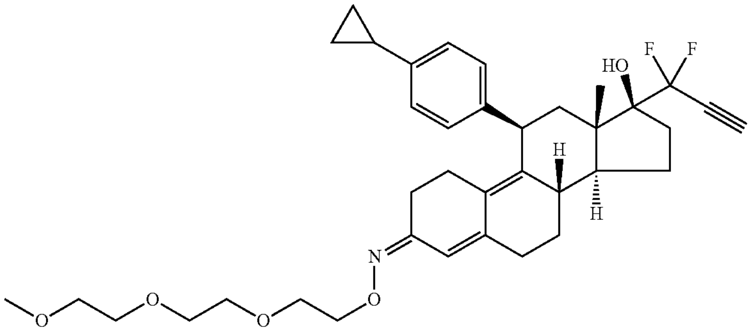

+

14

-continued

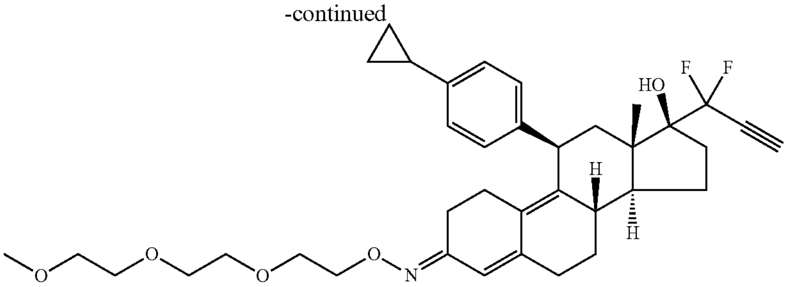

15

Example 12: (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one O-(2-(2-(2-methoxyethoxy)ethoxy)ethyl)oxime (13)

13

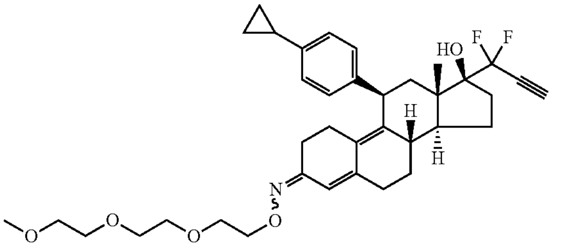

To a stirred solution of (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (35 mg, 0.07 mmol, 1.0 equiv) in pyridine (0.7 mL, 0.1M) was added O-(2-(2-methoxyethoxy)ethyl)hydroxylamine (124) (20.0 mg, 0.15 mmol, 2.0 equiv) followed by p-toluenesulfonic acid monohydrate (7.2 mg, 0.03 mmol, 0.5 equiv) at ambient temperature. The reaction mixture was stirred at room temperature for 16 h at which time the reaction was by LCMS analysis to provide compound 13.

Example 13: (8S,11R,13S,14S,17S,Z)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one O-(2-(2-(2-methoxyethoxy)ethoxy)ethyl)oxime (14) and (8S,11R,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one O-(2-(2-(2-methoxyethoxy)ethoxy)ethyl)oxime (15)

14

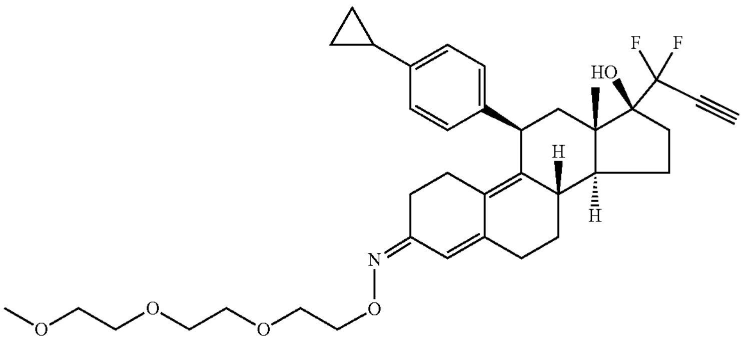

+

15

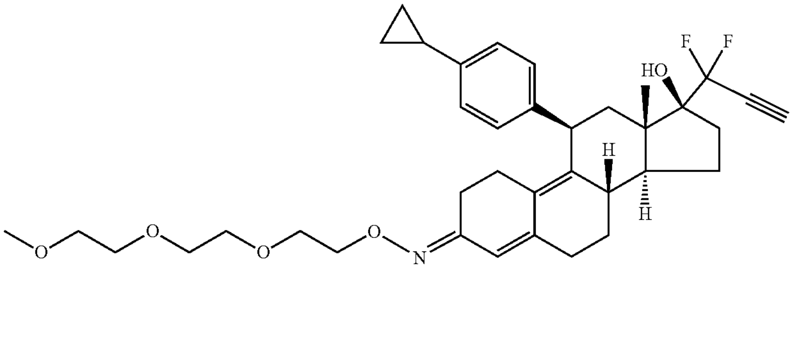

Compound 13 was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to yield pure geometric isomers 14 (5.4 mg, 13% yield) and 15 (13.3 mg, 33% yield).

Compound 14: $^1$H NMR (500 MHZ, DMSO-d6): δ 7.03 (d, J=8.3 Hz, 2H), 6.95 (d, J=8.4 Hz, 2H), 6.29 (s, 1H), 5.42 (s, 1H), 4.30 (d, J=7.2 Hz, 1H), 4.25 (t, J=5.5, 5.5 Hz, 1H), 4.02 (dd, J=5.7, 4.2 Hz, 2H), 3.58 (t, J=5.0, 5.0 Hz, 2H), 3.53-3.49 (m, 2H), 3.44-3.40 (m, 2H), 3.23 (s, 3H), 2.58 (d, J=5.4 Hz, 1H), 2.40 (d, J=13.3 Hz, 2H), 2.27-2.05 (m, 4H), 1.97-1.90 (m, 1H), 1.83 (tt, J=8.4, 8.4, 5.1, 5.1 Hz, 2H), 1.77-1.58 (m, 3H), 1.35 (q, J=11.5, 11.5, 11.5 Hz, 1H), 1.24 (qd, J=12.4, 12.2, 12.2, 5.4 Hz, 1H), 0.93-0.84 (m, 2H), 0.63-0.57 (m, 2H), 0.46 (s, 3H). Calculated mass: 579.3, Mass (ESI+) observed: 580.3 [M+H].

Compound 15: $^1$H NMR (500 MHZ, DMSO-d6): δ 7.03 (d, J=8.3 Hz, 2H), 6.95 (d, J=8.4 Hz, 2H), 5.79 (s, 1H), 5.42 (s, 1H), 4.30 (d, J=7.3 Hz, 1H), 4.24 (t, J=5.4, 5.4 Hz, 1H), 4.05 (dd, J=5.9, 4.0 Hz, 2H), 3.57 (t, J=4.9, 4.9 Hz, 2H), 3.51-3.46 (m, 2H), 3.39 (dd, J=5.7, 3.8 Hz, 2H), 3.20 (s, 3H), 2.70-2.62 (m, 1H), 2.58-2.53 (m, 1H), 2.42 (d, J=13.7 Hz, 3H), 2.19-2.06 (m, 3H), 1.97-1.90 (m, 1H), 1.83 (tt, J=8.3, 8.3, 5.1, 5.1 Hz, 1H), 1.78-1.58 (m, 4H), 1.37-1.19 (m, 2H), 0.93-0.86 (m, 2H), 0.62-0.57 (m, 2H), 0.45 (s, 3H). Calculated mass: 579.3, Mass (ESI+) observed: 580.6 [M+H].

Scheme 11 illustrates the preparation of compound 16.

Scheme 11

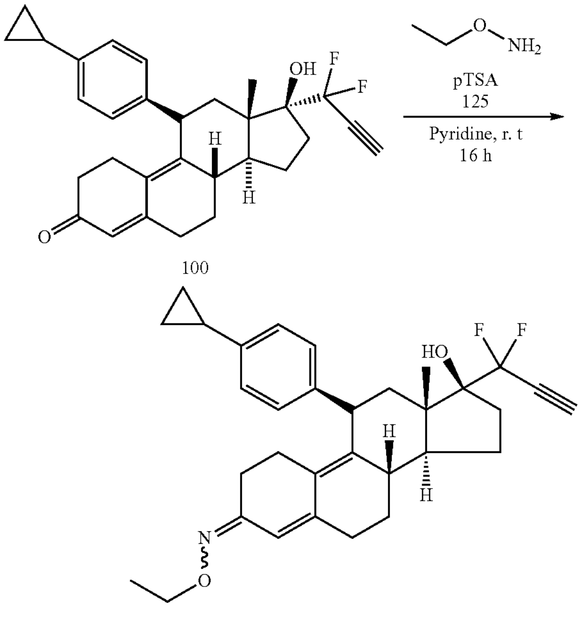

100

16

Example 14: (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one O-ethyl oxime (16)

To a stirred solution of (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (35 mg, 0.07 mmol, 1.0 equiv) in pyridine (0.7 mL, 0.1M) was added O-ethylhydroxylamine hydrochloride (125) (22 mg, 0.22 mmol, 3.0 equiv) followed by p-toluenesulfonic acid mono hydrate (7.2 mg, 0.04 mmol, 0.5 equiv) at ambient temperature. The reaction mixture was stirred at room temperature for 16 h when the reaction was complete by LCMS analysis. The reaction mixture was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to afford (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one O-ethyl oxime (16) (6.7 mg, 17% yield).

$^1$H NMR (500 MHZ, DMSO-d6): δ 7.02 (dd, J=8.3, 2.4 Hz, 2H), 6.97-6.92 (m, 2H), 5.41 (s, 1H), 4.28 (s, 1H), 4.24 (d, J=5.0 Hz, 1H), 3.96 (dq, J=12.1, 7.0, 7.0, 7.0 Hz, 2H), 2.68-2.59 (m, 1H), 2.44-2.35 (m, 3H), 2.25-2.04 (m, 3H), 1.92 (dt, J=12.4, 4.3, 4.3 Hz, 1H), 1.82 (tt, J=8.5, 8.5, 5.1, 5.1 Hz, 1H), 1.76-1.57 (m, 3H), 1.38-1.18 (m, 2H), 1.14 (td, J=7.1, 7.0, 4.9 Hz, 3H), 0.92-0.85 (m, 2H), 0.59 (dddd, J=6.3, 5.4, 4.1, 1.2 Hz, 2H), 0.44 (d, J=6.7 Hz, 3H). Calculated mass: 505.2792, Mass (ESI+) observed: 506.5 [M+H].

Scheme 12 illustrates the preparation of compound 17.

Scheme 12

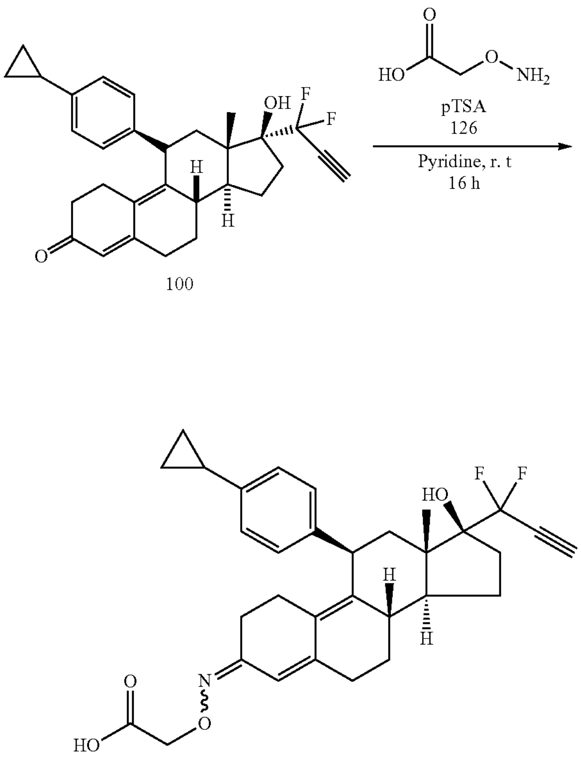

100

17

Example 15:2-((((8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)amino)oxy)acetic acid (17)

17

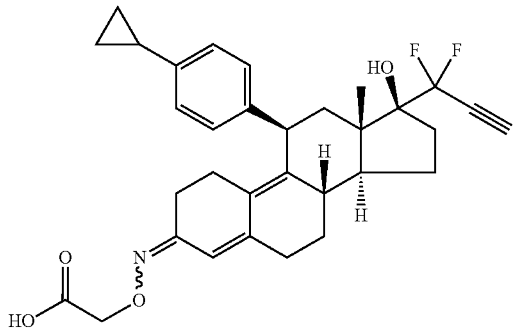

To a stirred solution of (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (35 mg, 0.08 mmol, 1.0 equiv) in pyridine (0.7 mL, 0.1M) was added 2-(aminooxy)acetic acid (126) (22 mg, 0.23 mmol, 3.0 equiv) followed by p-toluenesulfonic acid mono hydrate (7.3 mg, 0.04 mmol, 0.5 equiv) at ambient temperature. The reaction mixture was stirred at room temperature for 16 h when the reaction was complete by LCMS analysis. The reaction mixture was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to afford 2-((((8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)amino)oxy)acetic acid (17) (3.6 mg, 9% yield).

$^1$H NMR (500 MHZ, DMSO-d6): δ 7.03 (d, J=8.3 Hz, 2H), 6.95 (d, J=8.4 Hz, 2H), 5.75 (s, 1H), 5.41 (s, 1H), 4.38 (d, J=6.8 Hz, 2H), 4.30 (d, J=6.6 Hz, 1H), 4.24 (t, J=5.4, 5.4 Hz, 1H), 2.70 (m, 1H), 2.56 (d, J=5.7 Hz, 1H), 2.45-2.35 (m, 4H), 2.23-2.03 (m, 3H), 1.97-1.89 (m, 1H), 1.82 (m, 1H), 1.78-1.54 (m, 4H), 1.37-1.27 (m, 1H), 1.27-1.18 (m, 1H), 0.92-0.83 (m, 2H), 0.63-0.56 (m, 2H), 0.45 (d, J=6.0 Hz, 3H). Calculated mass: 535.25, Mass (ESI+) observed: 536.2 [M+H].

Scheme 13 illustrates the preparation of compound 18.

Scheme 13

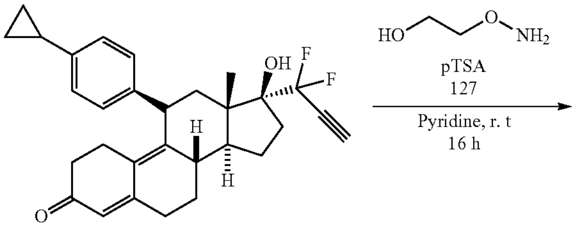

100

-continued

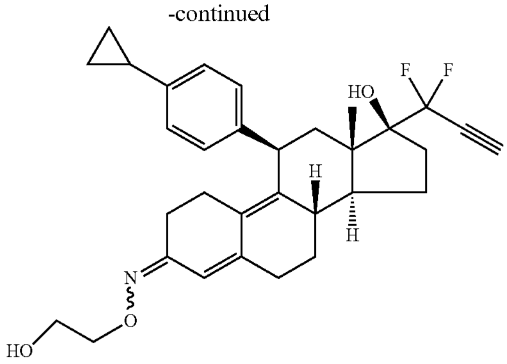

18

Example 16: (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one O-(2-hydroxyethyl)oxime (18)

18

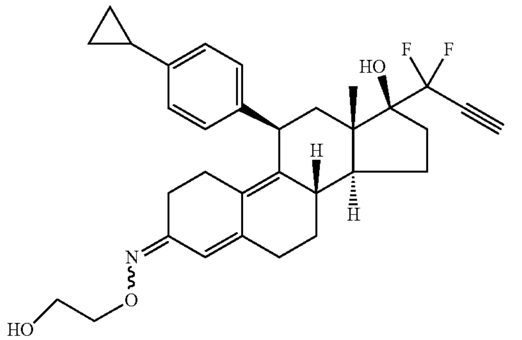

To a stirred solution of (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (0.8 g, 1.73 mmol, 1.0 equiv) in methanol (57 mL, 0.03M) was added 2-(aminoxy)ethanol (127) (0.4 g, 5.19 mmol, 3.0 equiv) followed by D-(+)-camphor-10-sulfonic acid (0.16 g, 6.92 mmol, 0.4 equiv) at ambient temperature. The reaction mixture was stirred at room temperature for 2 h when the reaction was complete by LCMS analysis. The mixture was concentrated by rotary evaporation and the residue was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to afford (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one O-(2-hydroxyethyl)oxime (18) (0.6 g, 66% yield).

$^1$H NMR (500 MHZ, Chloroform-d3): 7.05 (t, J=8.7, 8.7 Hz, 2H), 6.95 (dd, J=8.4, 2.8 Hz, 2H), 5.84 (s, 1H), 4.32 (d, J=6.8 Hz, 1H), 4.16 (ddd, J=4.4, 2.9, 1.1 Hz, 2H), 3.90-3.83 (m, 2H), 2.88 (t, J=5.4, 5.4 Hz, 1H), 2.79 (ddd, J=16.8, 6.2, 4.5 Hz, 1H), 2.61-2.43 (m, 5H), 2.41-2.23 (m, 4H), 2.13-1.80 (m, 6H), 1.74 (dd, J=12.9, 9.2 Hz, 3H), 1.49-1.33 (m, 3H), 0.97-0.89 (m, 2H), 0.71-0.61 (m, 2H), 0.58 (d, J=3.2 Hz, 3H). Calculated mass: 522.4, Mass (ESI+) observed: 522.4 [M+H].

Scheme 14 illustrates the preparation of compounds 19 and 20.
Scheme 14
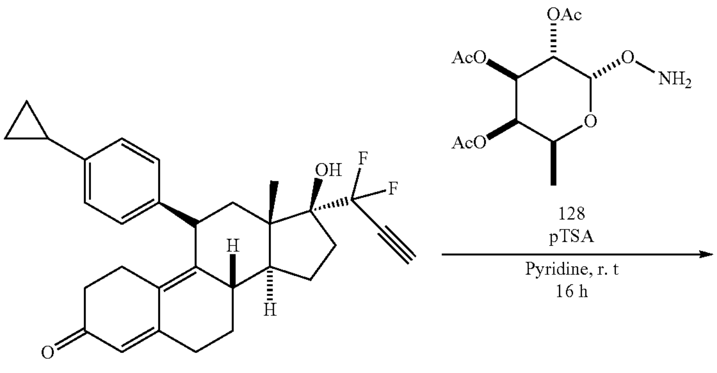
100
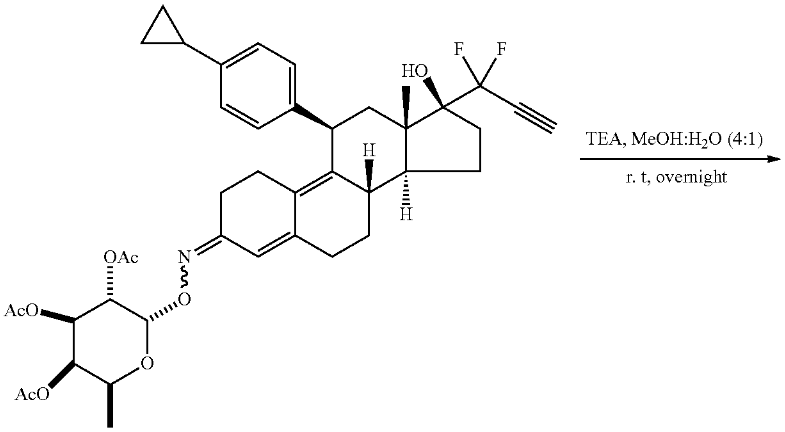
19
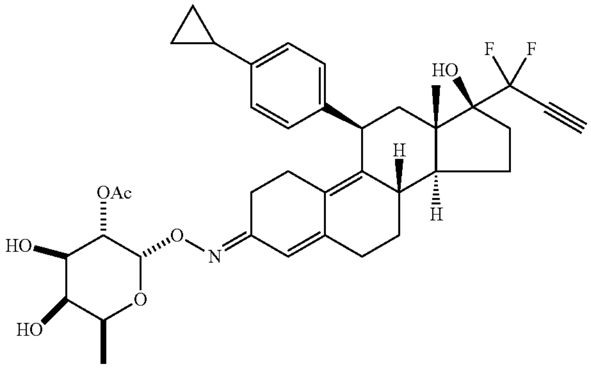
20

Example 17: (2S,3S,4R,5R,6S)-2-((((8S,11R,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)amino)oxy)-6-methyltetrahydro-2H-pyran-3,4,5-triyl triacetate (19)

19

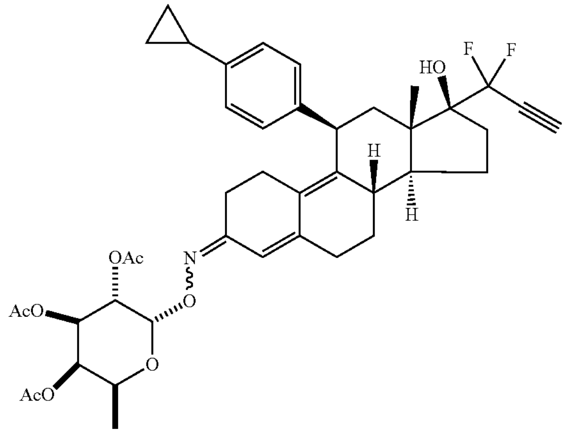

To a stirred solution of (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (60 mg, 0.13 mmol, 1.0 equiv) in pyridine (1 mL, 0.1M) was added (2S,3S,4R,5S,6S)-2-(aminooxy)-6-methyltetrahydro-2H-pyran-3,4,5-triacetate (128) (80 mg, 0.27 mmol, 2.0 equiv) followed by p-toluenesulfonic acid mono hydrate (13 mg, 0.07 mmol, 0.5 equiv) at ambient temperature. The reaction mixture was stirred at room temperature for 16 h when the reaction was complete by LCMS analysis. After completion of the reaction, the solvent was removed under vacuum to provide (2S,3S,4R,5R,6S)-2-((((8S,11R,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)amino)oxy)-6-methyltetrahydro-2H-pyran-3,4,5-triyl triacetate (19).

Example 18: (8S,11R,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one O-((2S,3S,4R,5S,6S)-3,4,5-trihydroxy-6-methyltetrahydro-2H-pyran-2-yl) oxime (20)

20

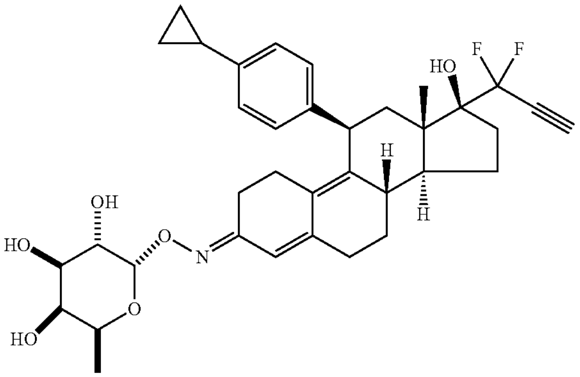

(8S,11R,13S,14S,17S,E: Z)-11-(4-cyclopropylphenyl)-17-(1,1-difluoroprop-2-yn-1-yl)-17-hydroxy-13-methyl-6,7,8,11,12,13,14,15,16,17-decahydro-1H-cyclopenta[a]phenanthrene-3 (2H)-one-O-((2S,3S,4R,5S,6S)-3,4,5-triacetoxy-6-methyltetrahydro-2H-pyran-2-yl) oxime (19) was dissolved in MeOH/$H_2O$ (4:1) (5 mL), TEA (0.09 mL) was added and the mixture stirred at room temperature overnight, when the reaction was complete by LCMS analysis. The crude reaction mixture was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to afford (8S,11R,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one O-((2S,3S,4R,5S,6S)-3,4,5-trihydroxy-6-methyltetrahydro-2H-pyran-2-yl) oxime (20) (10.5 mg, 14% yield).

$^1$H NMR (500 MHZ, DMSO-d6): δ 7.04 (d, J=8.3 Hz, 2H), 6.96 (d, J=8.5 Hz, 2H), 6.41-6.37 (m, 1H), 5.42 (s, 1H), 5.12 (d, J=3.5 Hz, 1H), 4.65 (d, J=5.9 Hz, 1H), 4.56 (d, J=5.5 Hz, 1H), 4.42 (d, J=4.6 Hz, 1H), 4.31 (d, J=7.0 Hz, 1H), 4.25 (t, J=5.5, 5.5 Hz, 1H), 3.77 (m, 1H), 3.69-3.60 (m, 2H), 3.51 (t, J=4.5, 4.5 Hz, 1H), 2.56 (s, 1H), 2.41 (d, J=13.2 Hz, 2H), 2.28-2.05 (m, 4H), 1.98-1.91 (m, 1H), 1.84 (m, 2H), 1.78-1.58 (m, 3H), 1.40-1.19 (m, 2H), 1.03 (d, J=6.5 Hz, 3H), 0.93-0.86 (m, 2H), 0.63-0.58 (m, 2H), 0.46 (s, 3H). Calculated mass: 623.31, Mass (ESI+) observed: 624.4 [M+H].

Scheme 15 illustrates the preparation of compound 21.

Scheme 15

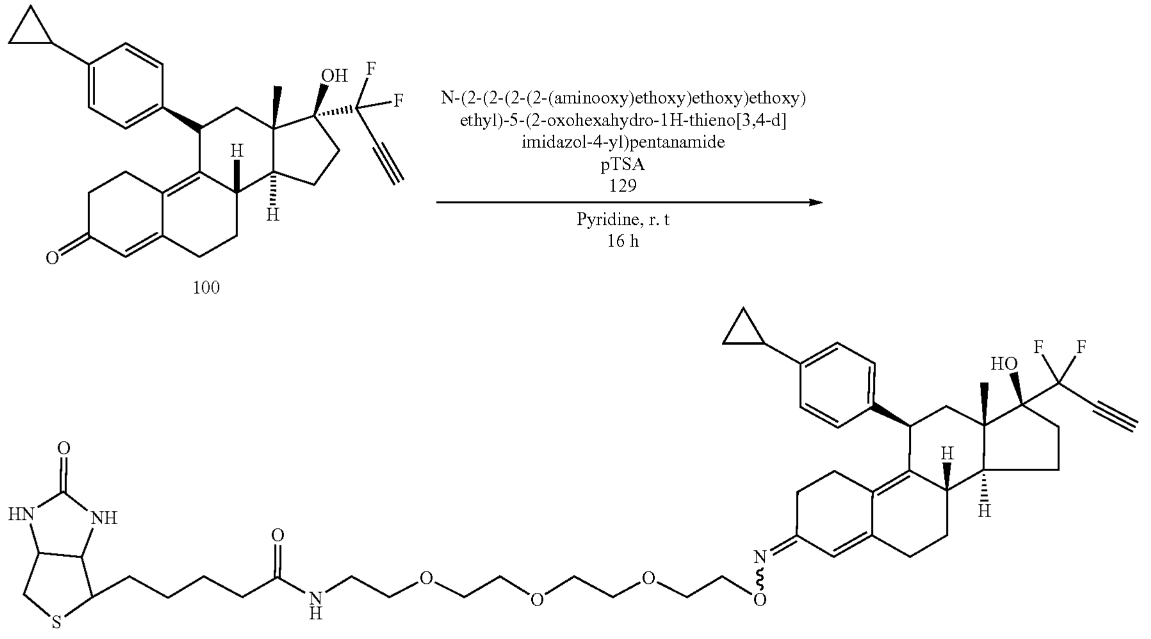

100

21

Example 19: N-(2-(2-(2-(2-((((8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)amino)oxy)ethoxy)ethoxy)ethoxy)ethyl)-5-(2-oxohexahydro-1H-thieno[3,4-d]imidazol-4-yl)pentanamide (21)

21

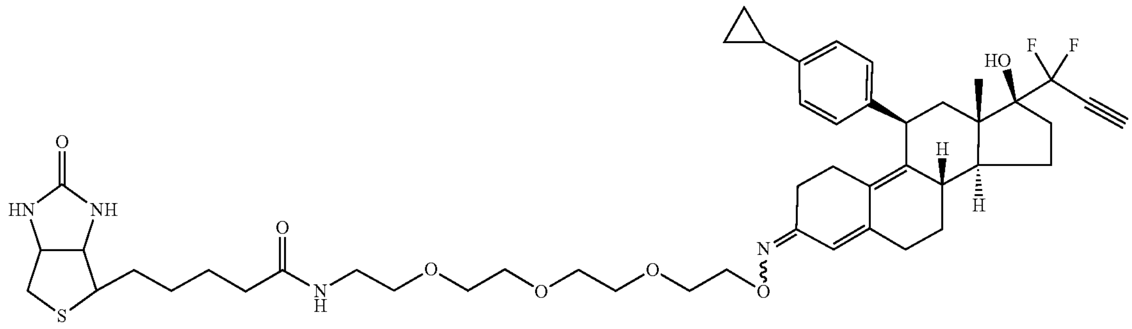

To a stirred solution of (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (35 mg, 0.07 mmol, 1.0 equiv) in pyridine (0.7 mL, 0.1M) was added N-(2-(2-(2-(2-(aminooxy)ethoxy)ethoxy)ethoxy)ethyl)-5-(2-oxohexahydro-1H-thieno[3,4-d]imidazol-4-yl)pentanamide (129) (71.0 mg, 0.15 mmol, 2.0 equiv) followed by p-toluenesulfonic acid monohydrate (7.2 mg, 0.03 mmol, 0.5 equiv) at ambient temperature. The reaction mixture was stirred at room temperature for 16 h when the reaction was complete by LCMS analysis. The reaction mixture was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to afford N-(2-(2-(2-(2-((((8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)amino)oxy)ethoxy)ethoxy)ethoxy)ethyl)-5-(2-oxohexahydro-1H-thieno[3,4-d]imidazol-4-yl)pentanamide (21) (13.4 mg, 22% yield).

$^1$H NMR (500 MHZ, DMSO-d6): 7.79 (t, J=5.5, 5.5 Hz, 1H), 7.03 (d, J=8.4 Hz, 2H), 6.95 (d, J=8.4 Hz, 2H), 6.39 (s, 1H), 6.33 (s, 1H), 5.78 (s, 1H), 5.42 (s, 1H), 4.29 (t, J=6.3, 6.3 Hz, 2H), 4.24 (d, J=5.5 Hz, 1H), 4.11 (dd, J=9.1, 3.2 Hz, 1H), 4.05 (t, J=5.0, 5.0 Hz, 2H), 3.57 (t, J=4.9, 4.9 Hz, 2H), 3.50-3.45 (m, 8H), 3.15 (d, J=5.7 Hz, 2H), 2.80 (dd, J=12.4, 5.1 Hz, 1H), 2.67 (d, J=5.2 Hz, 1H), 2.57 (d, J=12.2 Hz, 2H), 2.40 (s, 3H), 2.19-2.07 (m, 3H), 2.04 (t, J=7.5, 7.5 Hz, 2H), 1.97-1.90 (m, 1H), 1.83 (td, J=8.4, 8.4, 4.3 Hz, 1H), 1.77-1.55 (m, 5H), 1.52-1.39 (m, 3H), 1.35-1.20 (m, 4H), 0.93-0.86 (m, 2H), 0.63-0.56 (m, 2H), 0.44 (s, 3H). Calculated mass: 878.4, Mass (ESI+) observed: 879.7 [M+H].

Scheme 16 illustrates the preparation of intermediate 132.

Scheme 16

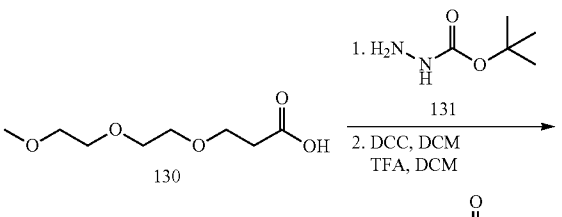

131

130

132

Preparation of intermediate 132

132

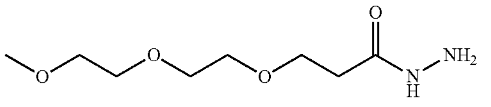

To a stirred solution of 3-(2-(2-methoxyethoxy)ethoxy) propanoic acid (130) (500 mg, 2.60 mmol, 1.0 equiv) in dichloromethane (20 mL) was added tert-butyl hydrazinecarboxylate (131) (380 mg, 2.87 mmol, 1.1 equiv) (131) followed by N,N'-Dicyclohexylcarbodiimide (590 mg, 2.87 mmol, 1.1 equiv) at ambient temperature. The reaction mixture was stirred at room temperature for 1 h when the reaction was complete by LCMS analysis. The white precipitate was filtered and the mixture was concentrated by rotary evaporation. The residue was purified by Combi Flash chromatography to afford tert-butyl 4-oxo-7,10,13-trioxa-2,3-diazatetradecan-1-oate (690 mg, 87 yield).

To a stirred solution of tert-butyl 4-oxo-7,10,13-trioxa-2,3-diazatetradecan-1-oate (690 mg, 2.8 mmol, 1.0 equiv) in dichloromethane (20 mL) was added trifluoroacetic acid (1.7 mL, 11.27 mmol, 5.0 equiv) at ambient temperature. The reaction mixture was stirred at room temperature for 3 h when the reaction was complete by LCMS analysis. The reaction mixture was concentrated by rotary evaporation to afford 3-(2-(2-methoxyethoxy)ethoxy)propanehydrazide (132) (410 mg, 88% yield) and used for next step without further purification.

Scheme 17 illustrates the preparation of compounds 24 and 25.

Scheme 17

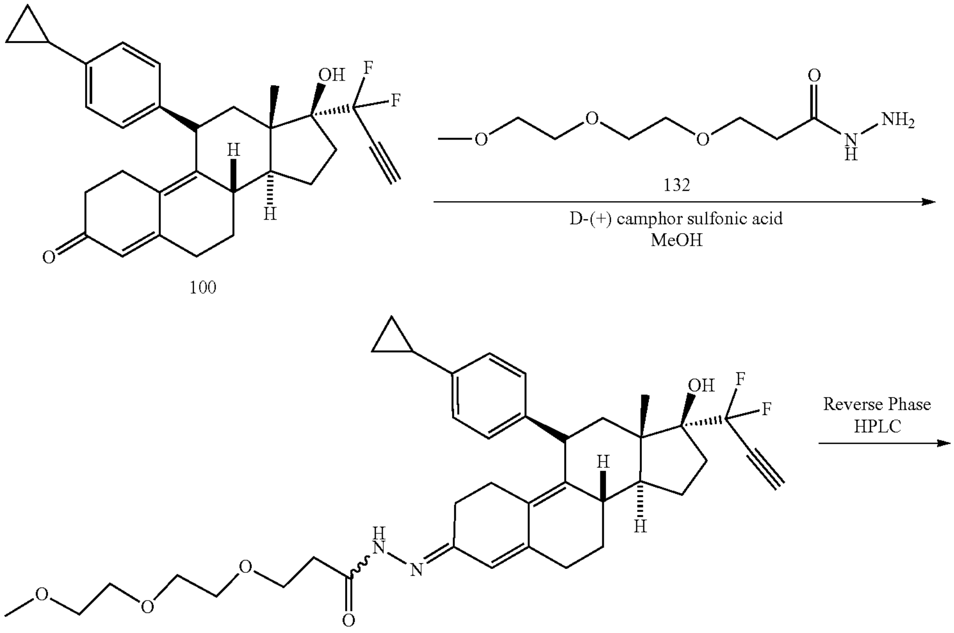

100

132

24

-continued

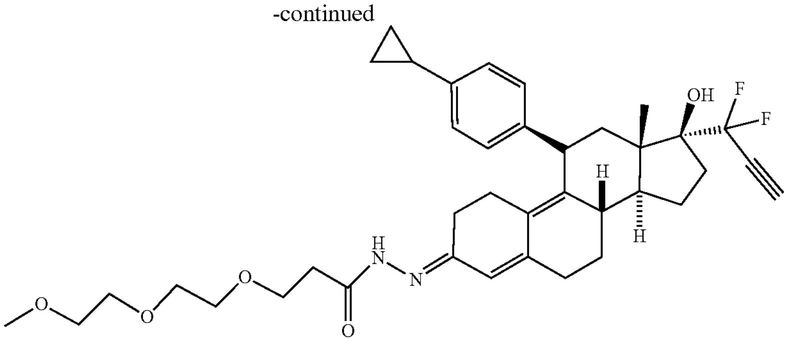

25

Example 19: N'-((8S,11S,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)-3-(2-(2-methoxyethoxy)ethoxy) propanehydrazide (24)

24

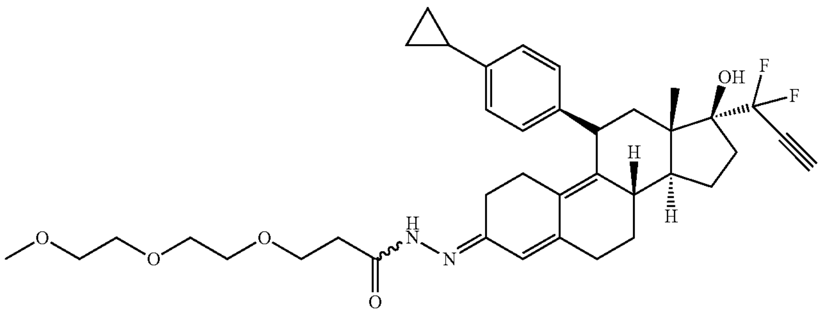

To a stirred solution of (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (0.615 g, 1.32 mmol, 1.0 equiv) in methanol (49 mL, 0.03M) was added 3-(2-(2-methoxyethoxy)ethoxy)propanehydrazide (132) (0.410 g, 2.0 mmol, 1.5 equiv) followed by D-(+)-camphor-10-sulfonic acid (124 mg, 0.54 mmol, 0.4 equiv) at ambient temperature. The reaction mixture was stirred at room temperature for 2 h when the reaction was complete by LCMS analysis. The solvent was removed to provide N'-((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)-3-(2-(2-methoxyethoxy)ethoxy)propanehydrazide (24).

Example 20: N'-((8S,11S,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)-3-(2-(2-methoxyethoxy)ethoxy) propanehydrazide (24) and N'-((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)-3-(2-(2-methoxyethoxy)ethoxy)propanehydrazide (25)

24

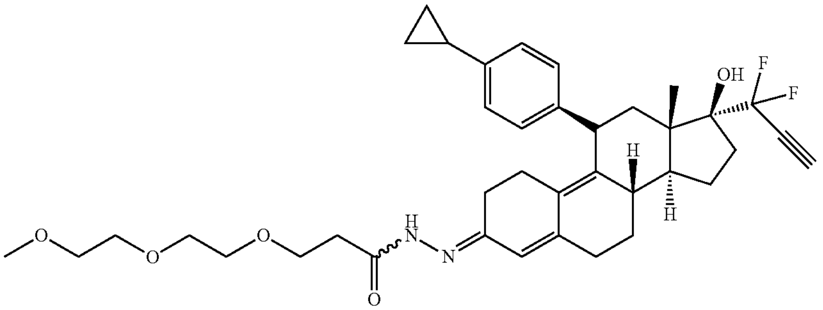

+

25

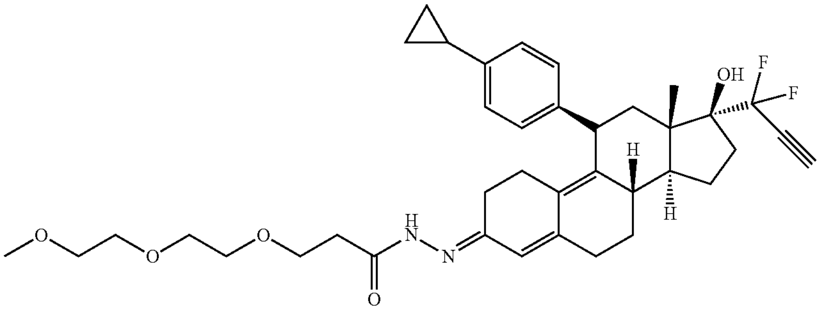

Compound 24 was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to yield 24 (235.1 mg, 27% yield) and 25 (130 mg, 15% yield).

Compound 24: $^1$H NMR (500 MHZ, DMSO-d6): δ 7.03 (t, J=6.5, 6.5 Hz, 2H), 6.95 (dd, J=8.5, 3.3 Hz, 2H), 5.84 (d, J=16.0 Hz, 1H), 5.44 (s, 1H), 4.30 (dd, J=32.6, 7.0 Hz, 2H), 3.61 (dt, J=18.5, 6.5, 6.5 Hz, 2H), 3.49-3.43 (m, 6H), 3.41-3.34 (m, 3H), 3.19 (d, J=16.0 Hz, 3H), 2.74 (t, J=6.7, 6.7 Hz, 1H), 2.61-2.51 (m, 2H), 2.47-2.35 (m, 5H), 2.11 (ddd, J=30.9, 13.1, 7.0 Hz, 3H), 1.93 (dd, J=8.3, 4.1 Hz, 1H), 1.86-1.70 (m, 3H), 1.70-1.56 (m, 2H), 1.38-1.17 (m, 2H), 0.92-0.85 (m, 2H), 0.62-0.55 (m, 2H), 0.44 (s, 3H). Calculated mass: 650.3, Mass (ESI+) observed: 651.4.

Compound 25: $^1$H NMR (500 MHZ, DMSO-d6): δ 7.02 (d, J=7.4 Hz, 2H), 6.94 (d, J=8.5 Hz, 2H), 5.45 (d, J=2.9 Hz, 1H), 4.29 (dd, J=22.9, 5.7 Hz, 2H), 3.61 (td, J=6.6, 6.3, 3.3 Hz, 2H), 3.50-3.42 (m, 7H), 3.41-3.35 (m, 3H), 3.20 (d, J=6.5 Hz, 3H), 2.75-2.69 (m, 1H), 2.56 (d, J=14.8 Hz, 2H), 2.46-2.36 (m, 4H), 2.34-2.24 (m, 1H), 2.22-2.14 (m, 2H), 2.09 (dt, J=15.7, 8.5, 8.5 Hz, 1H), 1.95 (d, J=8.4 Hz, 1H), 1.82 (tt, J=8.7, 8.7, 4.9, 4.9 Hz, 2H), 1.77-1.58 (m, 3H), 1.33 (t, J=9.8, 9.8 Hz, 1H), 1.28-1.19 (m, 1H), 0.92-0.85 (m, 2H), 0.59 (dt, J=4.6, 2.3, 2.3 Hz, 2H), 0.45 (d, J=3.5 Hz, 3H). Calculated mass: 650.3, Mass (ESI+) observed: 651.4 [M+H].

Scheme 18 illustrates the preparation of key intermediate 135.

Scheme 18

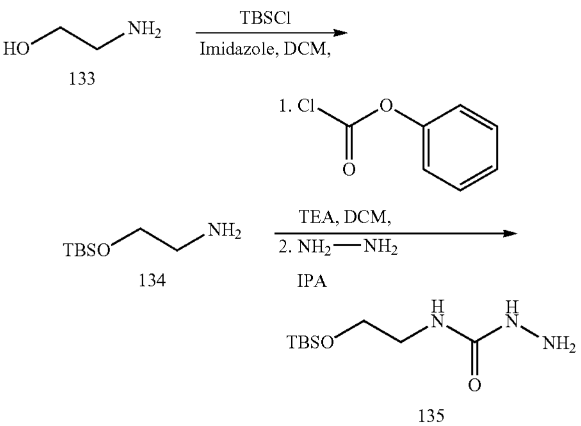

Preparation of 2-((tert-butyldimethylsilyl)oxy)ethan-1-amine (134)

134

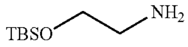

To a stirred solution of 2-aminoethanol (133) (2.5 g, 41 mmol, 1.0 equiv) in dichloromethane (50 mL) were added imidazole (5.6 g, 82 mmol, 2.0 equiv) and tert-butyldimethylsilyl chloride (6.8 g, 45 mmol) at 0° C. The reaction mixture was stirred at room temperature for 16 h. After the reaction was complete, water (20 mL) was added to the reaction mixture and the mixture was extracted with dichloromethane (200 mL×3). The combined organic extracts were dried over anhydrous $Na_2SO_4$, filtered, and concentrated under reduced pressure. The resulting residue was subjected to flash column chromatography on silica gel (MeOH/DCM, 1:9) to give 2-((tert-butyldimethylsilyl)oxy)ethan-1-amine (134) (5.26 g, 73%, yellow oil). Calculated mass: 175.343, Mass (ESI+) observed: 176.3 [M+H].

Preparation of (2-((tert-butyldimethylsilyl)oxy)ethyl)carbamate (135)

135

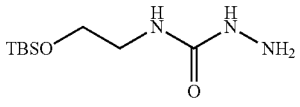

To a stirred solution of 2-((tert-butyldimethylsilyl)oxy) ethanamine (134) (5.26 g, 30 mmol, 1.0 equiv) in dichloromethane (50 mL) were added triethylamine (8.4 mL, 60 mmol, 2.0 equiv) and phenyl chloroformate (4.9 mL, 39 mmol) at 0° C. The reaction mixture was stirred at room temperature for 16 h. After the reaction was complete, water (30 mL) was added to the reaction mixture and the mixture was extracted with dichloromethane (200 mL×3). The combined organic extracts were dried over anhydrous sodium sulfate, filtered and concentrated under reduced pressure afforded the target compound phenyl (2-((tert-butyldimethylsilyl)oxy)ethyl)carbamate (135) (5.26 g, 73%, yellow oil). Calculated mass: 295.16, Mass (ESI+) observed: 296.4 [M+H].

Scheme 19 illustrates the preparation of compound 26.

Scheme 19

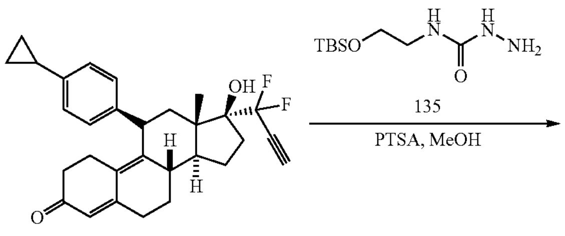

100

-continued

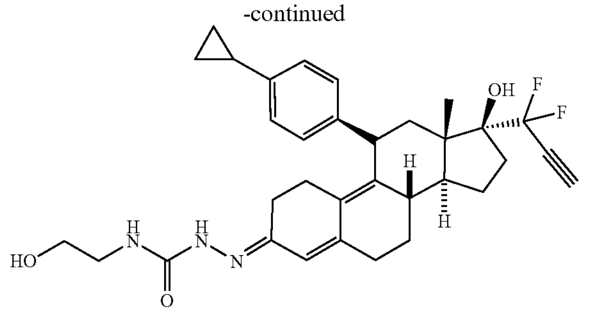

26

Example 21: (E)-2-((8S,11S,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)-N-(2-hydroxyethyl)hydrazine-1-carboxamide (26)

26

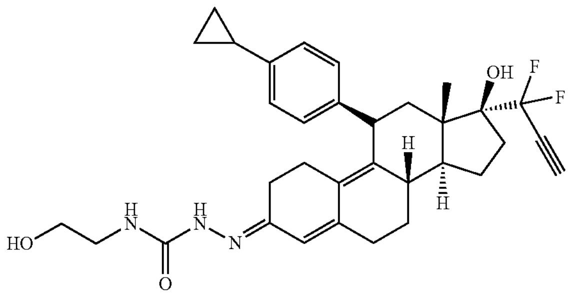

To a stirred solution of (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (0.67 g, 1.45 mmol, 1.0 equiv) in methanol (50 mL) was added N-(2-((tert-butyldimethylsilyl)oxy)ethyl)hydrazinecarboxamide (0.40 g, 1.74 mmol, 1.2 equiv) followed by p-toluenesulfonic acid monohydrate (0.27 g, 1.45 mmol, 1 equiv) at ambient temperature. The reaction mixture was stirred at room temperature for 1 h when the reaction was complete by LCMS analysis. The reaction mixture was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to afford (E)-2-((8S,11S,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)-N-(2-hydroxyethyl)hydrazine-1-carboxamide (26) (0.42 g, 51% yield).

$^1$H NMR (500 MHz, DMSO-d6): δ 9.47 (s, 1H), 7.03 (dd, J=8.4, 2.3 Hz, 2H), 6.94 (d, J=8.4 Hz, 2H), 6.62 (dt, J=27.7, 5.9, 5.9 Hz, 1H), 6.45 (s, 1H), 5.41 (d, J=5.4 Hz, 1H), 4.67 (dt, J=10.6, 5.2, 5.2 Hz, 1H), 4.29 (d, J=7.4 Hz, 1H), 4.23 (t, J=5.5, 5.5 Hz, 1H), 3.39 (p, J=5.9, 5.9, 5.7, 5.7 Hz, 2H), 3.15 (p, J=6.1, 6.1, 6.0, 6.0 Hz, 2H), 2.59-2.50 (m, 2H), 2.45-2.36 (m, 3H), 2.27 (ddd, J=14.5, 11.2, 5.2 Hz, 1H), 2.20-2.04 (m, 3H), 1.97-1.90 (m, 1H), 1.82 (tt, J=8.4, 8.4, 5.1, 5.1 Hz, 2H), 1.77-1.56 (m, 3H), 1.36-1.20 (m, 2H), 0.92-0.83 (m, 2H), 0.62-0.55 (m, 2H), 0.45 (d, J=2.2 Hz, 3H). Calculated mass: 563.296, Mass (ESI+) observed: 564.7 [M+H].
Scheme 20 illustrates the preparation of compounds 27, 28 and 29.
Scheme 20
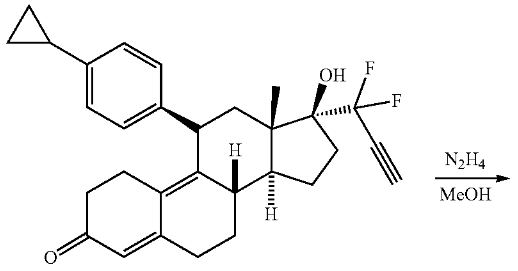
100
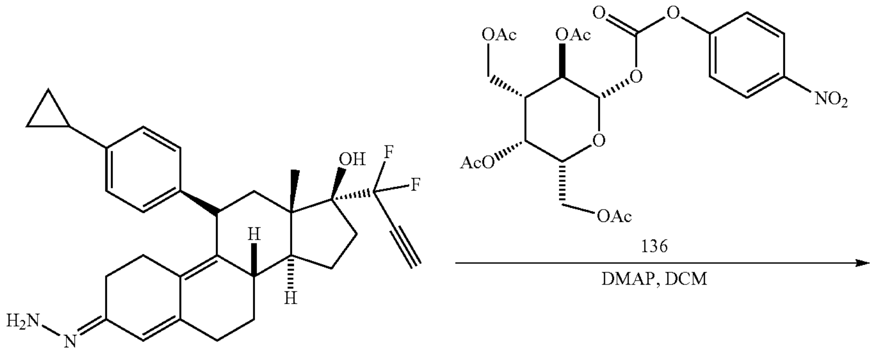
136
27
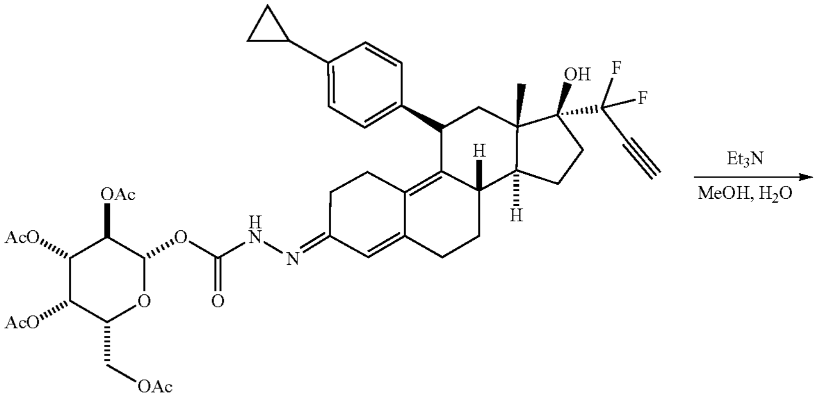
28
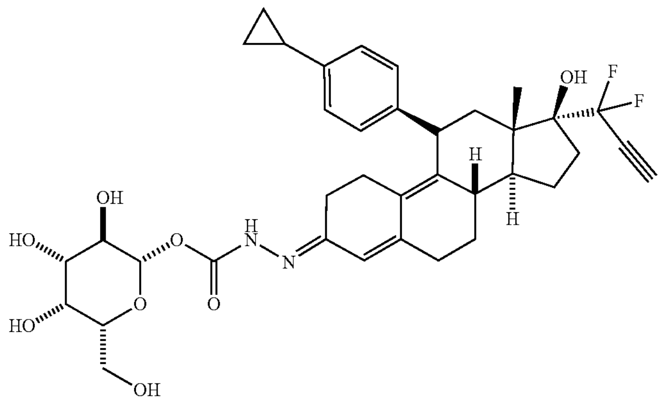
29

Example 22: (8S,11S,13S,14S,17S,E)-11-(4-cyclopropylphenyl)-17-(1,1-difluoroprop-2-yn-1-yl)-3-hydrazineylidene-13-methyl-2,3,6,7,8,11,12,13,14,15,16,17-dodecahydro-1H-cyclopenta[a]phenanthren-17-ol (27)

27

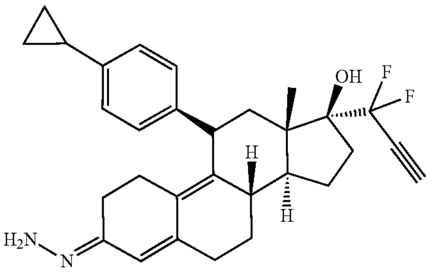

To a stirred solution of (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (76 mg, 0.16 mmol, 1.0 equiv) in methanol (1.6 mL, 0.1M) was added hydrazine hydrate (50.0 mg, 0.96 mmol, 6.0 equiv) at ambient temperature. The reaction mixture was stirred at room temperature for 2 h when the reaction was complete by LCMS analysis. The reaction mixture was concentrated and the residue was dissolved in dichloromethane (5 mL), concentrated and dried to afford (8S,11S,13S,14S,17S,E)-11-(4-cyclopropylphenyl)-17-(1,1-difluoroprop-2-yn-1-yl)-3-hydrazineylidene-13-methyl-2,3,6,7,8,11,12,13,14,15,16,17-dodecahydro-1H-cyclopenta[a]phenanthren-17-ol (27) (78 mg, 100% yield).

Example 23: (2R,3S,4S,5R,6S)-2-(acetoxymethyl)-6-((2-((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)hydrazine-1-carbonyl)oxy)tetrahydro-2H-pyran-3,4,5-triyl triacetate (28)

28

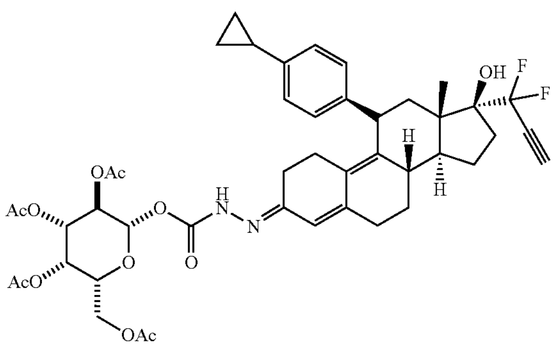

To a stirred solution of (8S,11S,13S,14S,17S,E)-11-(4-cyclopropylphenyl)-17-(1,1-difluoroprop-2-yn-1-yl)-3-hydrazineylidene-13-methyl-2,3,6,7,8,11,12,13,14,15,16,17-dodecahydro-1H-cyclopenta[a]phenanthren-17-ol (27) (78 mg, 1.0 equiv) in dichloromethane (1.6 mL) was added (2S,3R,4S,5S,6S)-2-(acetoxymethyl)-6-(((4-nitrophenoxy)carbonyl)oxy) tetrahydro-2H-pyran-3,4,5-triyl triacetate (136) (27) (102.0 mg, 0.198 mmol, 1.2 equiv) at room temperature. The mixture was stirred at room temperature for 1 h. Then DMAP (24.2 mg, 0.198 mmol, 1.2 equiv) was added and the mixture was stirred at room temperature for 16 h when the reaction was complete by LCMS analysis. The reaction mixture was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to afford (2R,3S,4S,5R,6S)-2-(acetoxymethyl)-6-((2-((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)hydrazine-1-carbonyl)oxy) tetrahydro-2H-pyran-3,4,5-triyl triacetate (28) (72.6 mg, 52% yield).

$^1$H NMR 500 MHZ, DMSO-d6): 7.04 (d, J=8.4 Hz, 2H), 6.99-6.93 (m, 2H), 5.92 (d, J=8.3 Hz, 1H), 5.85 (s, 1H), 5.42 (d, J=6.5 Hz, 1H), 5.35-5.28 (m, 1H), 5.28-5.25 (m, 1H), 5.13 (dt, J=10.4, 8.0, 8.0 Hz, 1H), 4.40 (t, J=6.3, 6.3 Hz, 1H), 4.33 (d, J=7.4 Hz, 1H), 4.25 (t, J=5.2, 5.2 Hz, 1H), 4.08-4.02 (m, 1H), 3.98 (dd, J=11.4, 6.8 Hz, 1H), 2.41 (d, J=13.1 Hz, 2H), 2.16 (d, J=11.5 Hz, 2H), 2.14-2.05 (m, 4H), 1.91 (d, J=4.6 Hz, 3H), 1.88-1.55 (m, 5H), 1.38-1.21 (m, 2H), 0.93-0.84 (m, 2H), 0.60 (dtd, J=6.3, 4.3, 4.2, 1.7 Hz, 2H), 0.46 (d, J=5.9 Hz, 3H). Calculated mass: 850.3, Mass (ESI+) observed: 851.5 [M+H].

Example 24: (2S,3R,4S,5R,6R)-3,4,5-trihydroxy-6-(hydroxymethyl)tetrahydro-2H-pyran-2-yl (E)-2-((8S,11S,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)hydrazine-1-carboxylate (29)

29

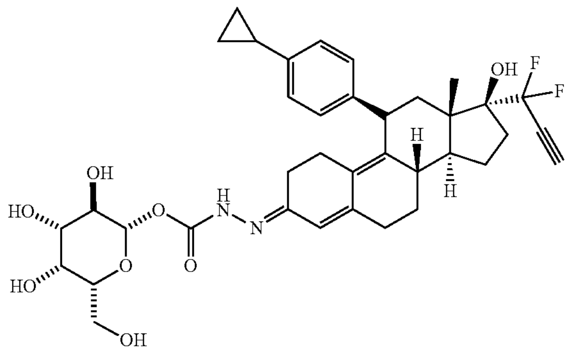

To a stirred solution of (2R,3S,4S,5R,6S)-2-(acetoxymethyl)-6-((2-((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)hydrazine-1-carbonyl)oxy)tetrahydro-2H-pyran-3,4,5-triyl triacetate (28) (70 mg,0.05 mmol, 1.0 equiv) in methanol (0.7 mL) $H_2O$ (0.1 mL) was added trimethylamine (60 μL, 0.4 mmol, 8.0 equiv) at room temperature. The mixture was stirred at room temperature for 16 h when the reaction was complete by LCMS analysis. The reaction mixture was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to afford (2S,3R,4S,5R,6R)-3,4,5-trihydroxy-6-(hydroxymethyl)tetrahydro-2H-pyran-2-yl (E)-2-((8S,11S,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)hydrazine-1-carboxylate (29) (3.9 mg, 7% yield).

$^1$H NMR (500 MHZ, Chloroform-d3): 7.01 (s, 2H), 6.93 (s, 2H), 4.25 (s, 1H), 3.75 (s, 3H), 3.11 (s, 1H), 2.37 (d, J=61.6 Hz, 6H), 1.81 (s, 21H), 1.26 (s, 2H), 0.88 (d, J=7.3 Hz, 2H), 0.58 (d, J=35.4 Hz, 5H). Calculated mass: 682.3, Mass (ESI+) observed: 683.5 [M+H].

Scheme 21 illustrate the preparation of compounds 30 and 31.

Scheme 21

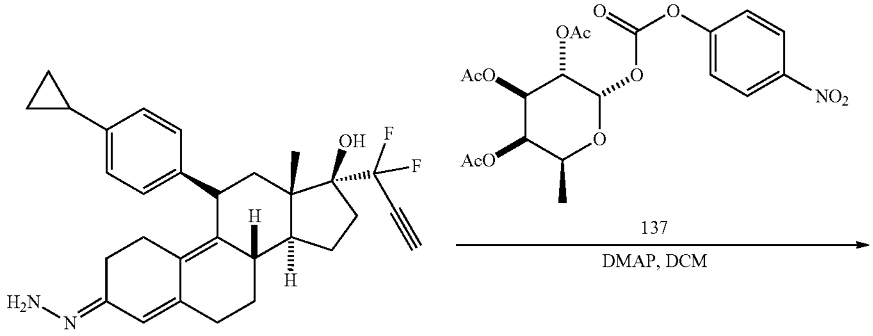

27

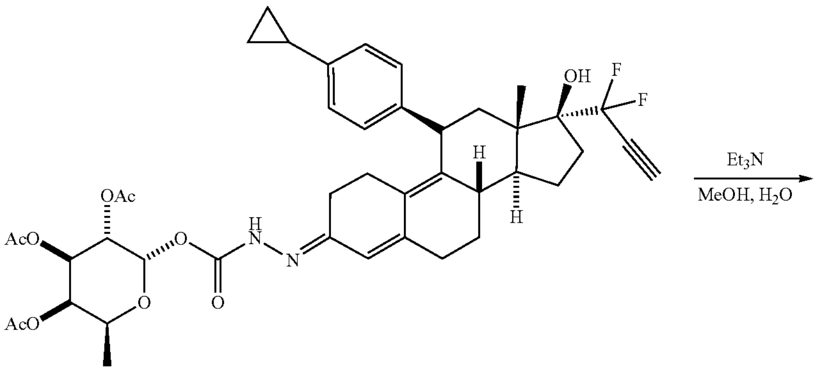

30

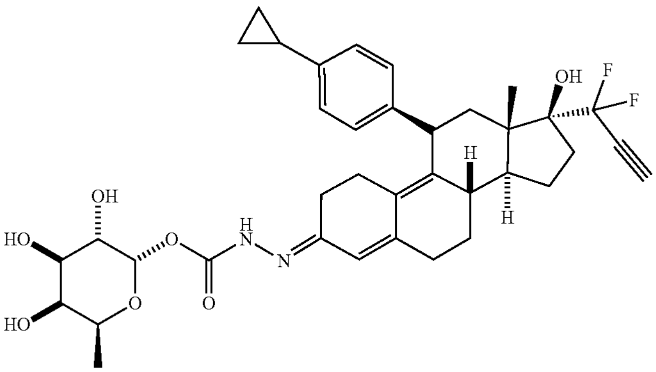

31

Example 25: (2S,3S,4R,5R,6S)-2-((2-((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)hydrazine-1-carbonyl)oxy)-6-methyltetrahydro-2H-pyran-3,4,5-triyl triacetate (30)

30

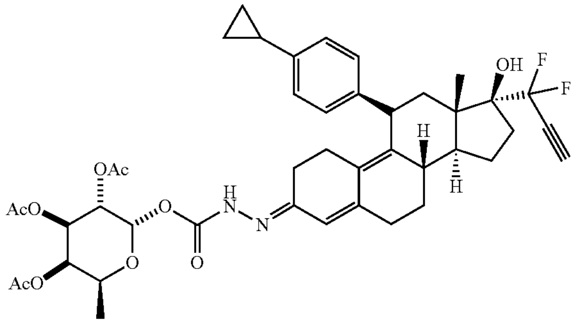

To a stirred solution of (8S,11S,13S,14S,17S,E)-11-(4-cyclopropylphenyl)-17-(1,1-difluoroprop-2-yn-1-yl)-3-hydrazineylidene-13-methyl-2,3,6,7,8,11,12,13,14,15,16,17-dodecahydro-1H-cyclopenta[a]phenanthren-17-ol (27) (47.6 mg, 0.1 mmol, 1.0 equiv) in dichloromethane (1 mL) was added compound 137 (55 mg, 0.12 mmol, 1.2 equiv) at room temperature. The mixture was stirred at room temperature for 1 h. Then DMAP (14.6 mg, 0.12 mmol, 1.2 equiv) was added and the mixture was stirred at room temperature for 16 h when the reaction was complete by LCMS analysis. The reaction mixture was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to afford (2S,3S,4R,5R,6S)-2-((2-((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)hydrazine-1-carbonyl)oxy)-6-methyltetrahydro-2H-pyran-3,4,5-triyl triacetate (30) (45.3 mg, 64% yield).

$^1$H NMR 500 MHz, DMSO-d6): δ 10.09 (s, 1H), 7.04 (t, J=7.1, 7.1 Hz, 4H), 6.96 (dd, J=8.5, 3.6 Hz, 4H), 6.09 (s, 1H), 5.87 (s, 1H), 5.32 (d, J=11.5 Hz, 1H), 5.25 (d, J=8.4 Hz, 1H), 5.08 (dt, J=10.7, 4.0, 4.0 Hz, 1H), 4.34 (d, J=6.6 Hz, 2H), 4.24 (s, 1H), 2.24-2.06 (m, 10H), 1.97 (dd, J=17.4, 10.2 Hz, 9H), 1.83 (td, J=8.4, 8.4, 4.1 Hz, 2H), 1.70 (dd, J=30.6, 15.9 Hz, 2H), 1.63 (s, 1H), 1.37-1.29 (m, 1H), 1.24 (d, J=14.0 Hz, 1H), 1.05 (t, J=6.7, 6.7 Hz, 4H), 0.92-0.88 (m, 3H), 0.62-0.58 (m, 3H), 0.46 (d, J=8.2 Hz, 5H). Calculated mass: 792.3, Mass (ESI+) observed: 793.6 [M+H].

Example 26: (2S,3S,4R,5S,6S)-3,4,5-trihydroxy-6-methyltetrahydro-2H-pyran-2-yl (E)-2-((8S,11S,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)hydrazine-1-carboxylate (31)

31

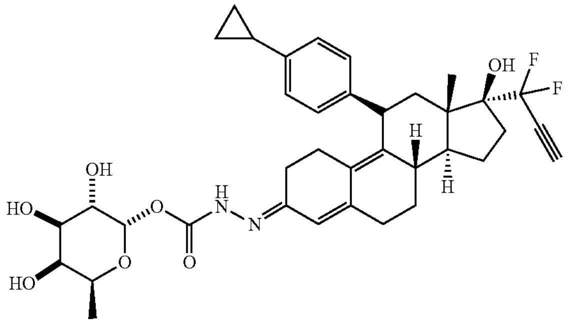

To a stirred solution of (2S,3S,4R,5R,6S)-2-((2-((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)hydrazine-1-carbonyl)oxy)-6-methyltetrahydro-2H-pyran-3,4,5-triyl triacetate (30) (39.6 mg, 0.05 mmol, 1.0 equiv) in methanol (0.7 mL) $H_2O$ (0.1 mL) was added trimethylamine (60 μL, 0.4 mmol, 8.0 equiv) at room temperature. The mixture was stirred at room temperature for 8 days when the reaction was complete by LCMS analysis. The reaction mixture was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to afford (2S,3S,4R,5S,6S)-3,4,5-trihydroxy-6-methyltetrahydro-2H-pyran-2-yl (E)-2-((8S,11S,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)hydrazine-1-carboxylate (31) (2.8 mg, 8% yield).

$^1$H NMR (500 MHZ, DMSO-d6): δ 7.03 (d, J=8.4 Hz, 2H), 6.96 (d, J=8.5 Hz, 2H), 6.58 (dd, J=30.9, 7.4 Hz, 1H), 5.95 (s, 1H), 5.43 (d, J=6.2 Hz, 1H), 5.31-5.21 (m, 1H), 5.16 (d, J=7.2 Hz, 1H), 4.59 (dd, J=16.0, 11.7 Hz, 1H), 4.42 (dd, J=15.9, 5.9 Hz, 1H), 4.34 (dd, J=23.1, 6.8 Hz, 1H), 4.26 (d, J=5.5 Hz, 1H), 4.16 (d, J=6.7 Hz, 1H), 3.87 (t, J=6.6, 6.6 Hz, 1H), 2.67-2.54 (m, 2H), 2.42 (d, J=13.5 Hz, 3H), 2.32-2.04 (m, 3H), 1.97 (dd, J=8.4, 4.3 Hz, 1H), 1.87-1.56 (m, 5H), 1.41-1.17 (m, 3H), 1.15-0.99 (m, 3H), 0.93-0.81 (m, 2H), 0.63-0.56 (m, 2H), 0.46 (d, J=7.6 Hz, 3H). Calculated mass: 666.3, Mass (ESI+) observed: 667.6 [M+H].

Scheme 22 illustrates the preparation of key intermediate 141.

Scheme 22

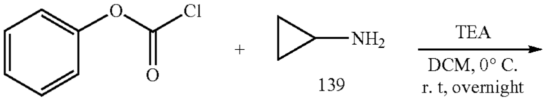

138

139

-continued

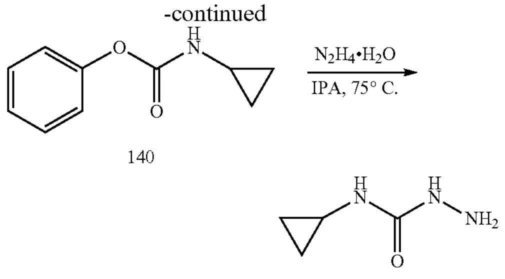

140

141

Preparation of Phenyl Cyclopropylcarbamate (140)

140

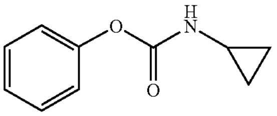

Intermediate 140 was prepared from 138 and 139 following the procedure in Xi et al., International Publication Number WO 201744434.

Preparation of N-cyclopropylhydrazinecarboxamide (141)

141

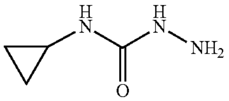

To a stirred solution of phenyl cyclopropylcarbamate (140) (3.7 g, 21 mmol, 1.0 equiv) in 2-propanol (20 mL) was added hydrazine monohydrate (8.2 mL, 105 mmol, 5.0 equiv) and the mixture was stirred at reflux overnight. After completion of the reaction, the reaction mixture was cooled to room temperature, the solvent removed under vacuum, the residue redissolved in ethyl acetate, washed twice with 0.1% NaOH, the organic layer was dried with $Na_2SO_4$ and concentrated to provide N-cyclopropylhydrazinecarboxamide (141), which was used in the next step without further purification. Calculated mass: 115.07, Mass (ESI+) observed: 116.1 $[M+H]^+$.

Scheme 23 illustrated the preparation of compound 32.

Scheme 23

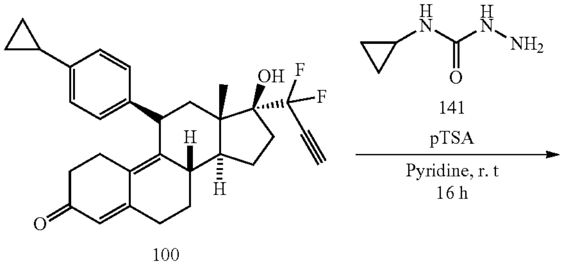

100

-continued

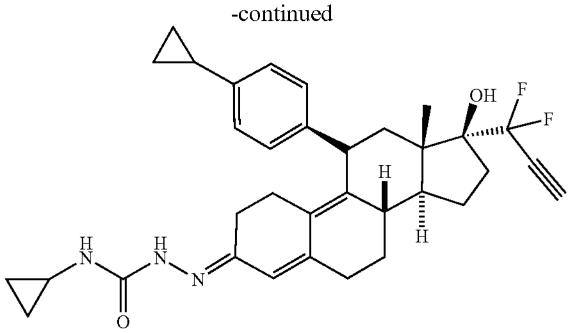

32

Example 27: N-cyclopropyl-2-((8S,11S,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)hydrazine-1-carboxamide (32)

32

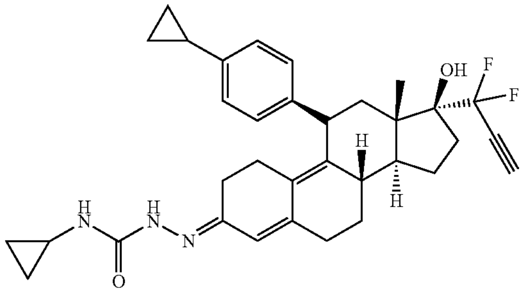

To a stirred solution of (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (0.7 g, 1.51 mmol, 1.0 equiv) in pyridine (14 mL, 0.1M) was added N-cyclopropylhydrazinecarboxamide (141) (32) (0.87 g, 7.6 mmol, 5.0 equiv) followed by p-toluenesulfonic acid mono hydrate (144 mg, 0.76 mmol, 0.5 equiv) at ambient temperature. The reaction mixture was stirred at room temperature for 16 when the reaction was complete by LCMS analysis. The reaction mixture was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min.) to afford N-cyclopropyl-2-((8S,11S,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)hydrazine-1-carboxamide (32) (350 mg, 46% yield).

$^1H$ NMR (500 MHZ, DMSO-d6): δ 9.14 (s, 1H), 7.04 (d, J=8.4 Hz, 2H), 6.95 (d, J=8.4 Hz, 2H), 6.63 (d, J=3.5 Hz, 1H), 5.82 (s, 1H), 4.31 (d, J=7.8 Hz, 1H), 4.24 (t, J=5.4, 5.4 Hz, 1H), 2.40 (d, J=12.8 Hz, 3H), 2.20-2.03 (m, 4H), 1.97-1.90 (m, 2H), 1.83 (m, 1H), 1.79-1.57 (m, 4H), 1.38-1.18 (m, 3H), 0.93-0.86 (m, 3H), 0.63-0.54 (m, 4H), 0.45 (d, J=2.3 Hz, 5H). Calculated mass: 559.3, Mass (ESI+) observed: 560.2 [M+H].

Scheme 24 illustrates the preparation of compound 33.

Scheme 24

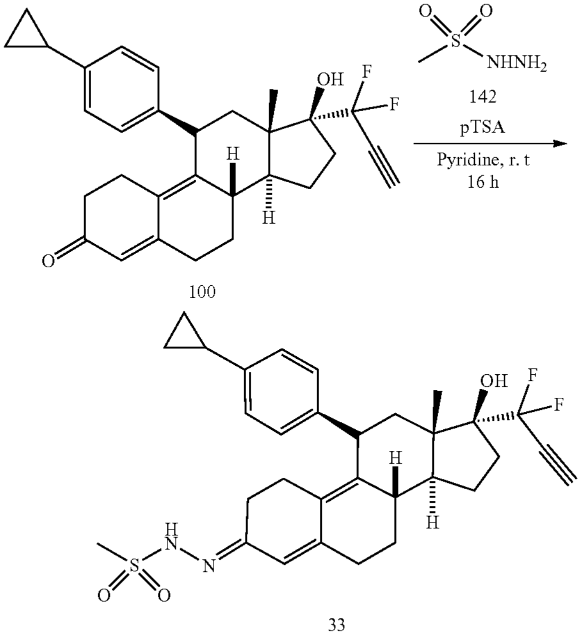

100

33

Example 28: N'-((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene) methanesulfonohydrazide (33)

33

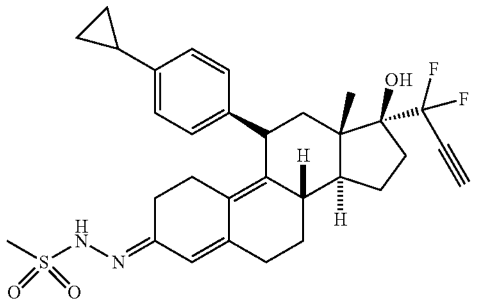

To a stirred solution of (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (35 mg, 0.08 mmol, 1.0 equiv) in pyridine (0.7 mL, 0.1M) was added N-methylhydrazinecarboxamide (142) (Helvetica Chimica Acta 1989, 72, 1383) (21 mg, 0.23 mmol, 3.0 equiv) followed by p-toluenesulfonic acid mono hydrate (7.3 mg, 0.04 mmol, 0.5 equiv) at ambient temperature. The reaction mixture was stirred at room temperature for 16 h when the reaction was complete by LCMS analysis. The reaction mixture was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min.) to afford N'-((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene) methanesulfonohydrazide (33) (15 mg, 36% yield).

$^1$H NMR (500 MHZ, DMSO-d6): δ 9.64 (s, 1H), 7.04 (d, J=8.3 Hz, 2H), 6.96 (d, J=8.4 Hz, 2H), 5.84 (s, 1H), 5.42 (s, 1H), 4.33 (d, J=7.2 Hz, 1H), 4.25 (t, J=5.5, 5.5 Hz, 1H), 2.92 (s, 3H), 2.57 (t, J=5.1, 5.1 Hz, 1H), 2.42 (d, J=13.4 Hz, 3H), 2.21-2.05 (m, 4H), 1.98-1.91 (m, 1H), 1.88-1.73 (m, 3H), 1.73-1.57 (m, 2H), 1.39-1.21 (m, 2H), 0.93-0.85 (m, 2H), 0.63-0.57 (m, 2H), 0.46 (s, 3H). Calculated mass: 554.2, Mass (ESI+) observed: 555.1 [M+H].

Scheme 25 illustrates the preparation of compounds 34 and 35.

Scheme 25

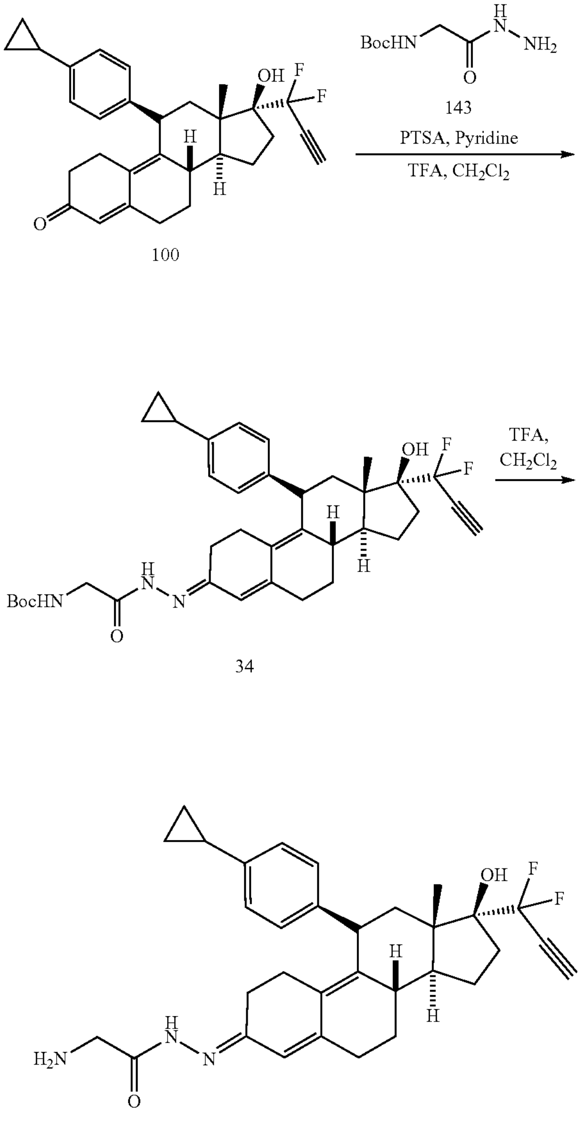

100

34

35

Example 29: tert-butyl (2-(2-((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)hydrazineyl)-2-oxoethyl) carbamate (34)

34

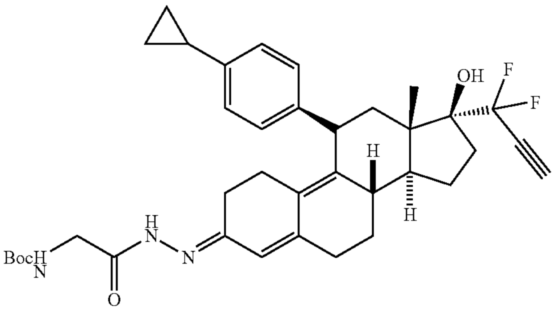

To a stirred solution of (8S,11R,13S,14S, 17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (55.5 mg, 0.12 mmol, 1.0 equiv) in pyridine (1.2 mL, 0.1M) was added compound 143 (68.0 mg, 0.36 mmol, 3.0 equiv) followed by p-toluenesulfonic acid monohydrate (11.4 mg, 0.06 mmol, 0.5 equiv) at ambient temperature. The reaction mixture was stirred at room temperature for 16 h when the reaction was complete by LCMS analysis. The reaction mixture was concentrated, the residue was dissolved in ethyl acetate (30 mL), washed with sat $NaHCO_3$ (10 mL) and brine (10 mL). The organic layer was dried over $Na_2SO_4$, filtered and concentrated to afford tert-butyl (2-(2-((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)hydrazineyl)-2-oxoethyl)carbamate (34) (76 mg, 100% yield).

Example 30:2-amino-N'-((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)acetohydrazide (35)

35

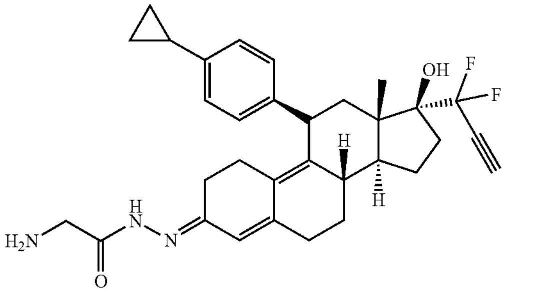

To a stirred solution of tert-butyl (2-(2-((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)hydrazineyl)-2-oxoethyl)carbamate (34) (76 mg, 0.12 mmol) in dichloromethane (0.9 mL) was added trifluoroacetic acid (0.3 mL) at room temperature. The reaction mixture was stirred at room temperature for 3 h when the reaction was complete by LCMS analysis. The reaction mixture was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to afford 2-amino-N'-((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene) acetohydrazide (35) (12.9 mg, 20% yield).

$^1$H NMR (500 MHZ, Chloroform-d3): 7.06 (dt, J=11.7, 5.9, 5.9 Hz, 2H), 6.96 (dt, J=8.5, 2.3, 2.3 Hz, 2H), 4.32 (d, J=7.2 Hz, 1H), 3.81-3.73 (m, 1H), 3.54 (d, J=13.3 Hz, 1H), 2.90 (q, J=5.2, 4.1, 4.1 Hz, 1H), 2.68-2.44 (m, 6H), 2.42-2.26 (m, 3H), 2.23-1.80 (m, 10H), 1.79-1.68 (m, 2H), 1.41 (qd, J=17.2, 14.9, 14.9, 9.0 Hz, 2H), 1.00-0.86 (m, 2H), 0.65 (qd, J=7.2, 7.2, 6.1, 3.5 Hz, 2H), 0.59 (d, J=4.0 Hz, 3H). Calculated mass: 534.26, Mass (ESI+) observed: 535.3 [M+H].

Scheme 26 illustrates the preparation of compound 36.

Scheme 26

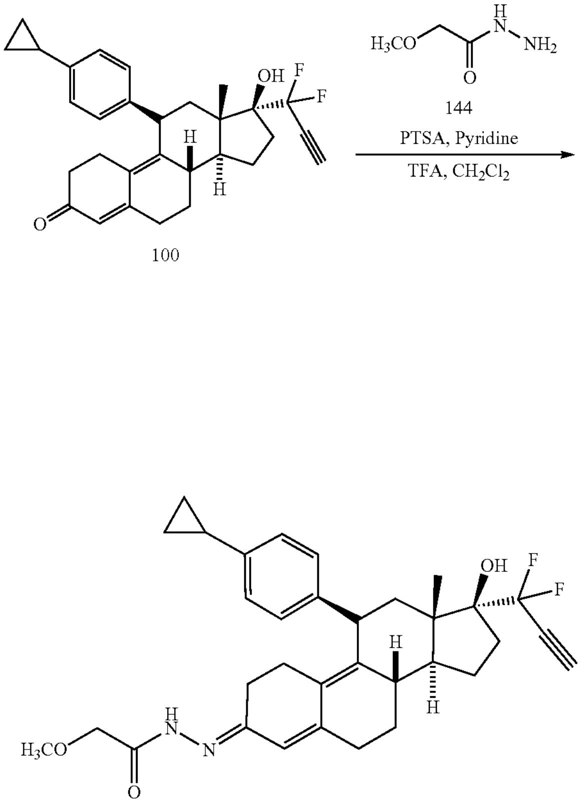

144

100

36

Example 31: N'-((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)-2-methoxyacetohydrazide (36)

36

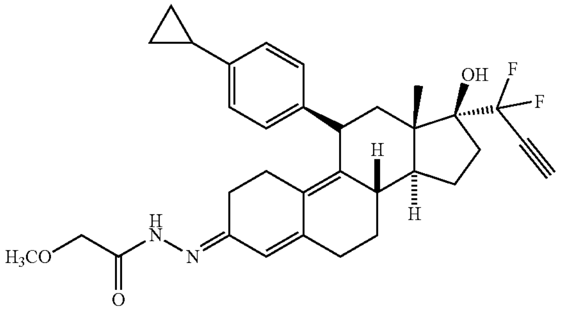

To a stirred solution of (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (35 mg, 0.07 mmol, 1.0 equiv) in pyridine (0.7 mL, 0.1M) was added 2-methoxyacetohydrazide (144) (24.0 mg, 0.22 mmol, 3.0 equiv) followed by p-toluenesulfonic acid monohydrate (7.2 mg, 0.03 mmol, 0.5 equiv) at ambient temperature. The reaction mixture was stirred at room temperature for 16 h when the reaction was complete by LCMS analysis. The reaction mixture was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to afford N'-((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)-2-methoxyacetohydrazide (36) (10.3 g, 27% yield).

$^1$H NMR (500 MHZ, DMSO-d6): 9.76 (s, 1H), 7.03 (d, J=8.3 Hz, 2H), 6.95 (d, J=8.4 Hz, 2H), 5.82 (s, 1H), 5.41 (s, 1H), 4.32 (d, J=6.8 Hz, 1H), 4.24 (t, J=5.5, 5.5 Hz, 1H), 2.64-2.51 (m, 2H), 2.46 (s, 2H), 2.41 (d, J=13.7 Hz, 2H), 2.20-2.04 (m, 3H), 1.99-1.89 (m, 1H), 1.86-1.71 (m, 3H), 1.70-1.57 (m, 2H), 1.38-1.19 (m, 2H), 1.04-0.92 (m, 4H), 0.91-0.85 (m, 2H), 0.62-0.56 (m, 2H), 0.45 (s, 3H). Calculated mass: 548.2, Mass (ESI+) observed: 549.4 [M+H].

Scheme 27 illustrates the preparation of compound 37.

Scheme 27

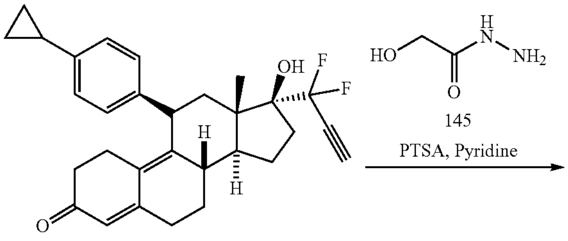

100

-continued

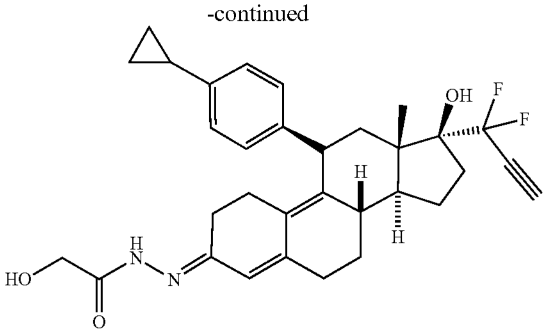

37

Example 32: N'-((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)-2-hydroxyacetohydrazide (37)

37

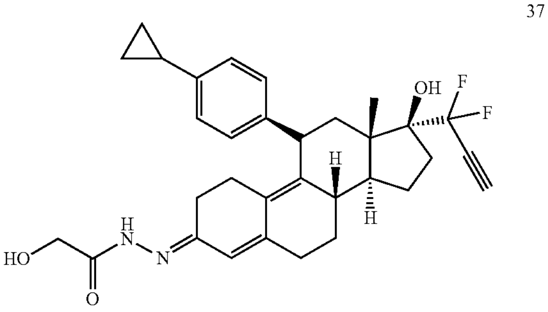

To a stirred solution of (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (37 mg, 0.08 mmol, 1.0 equiv) in pyridine (0.8 mL, 0.1M) was added 2-hydroxyacetohydrazide (145) (22.0 mg, 0.24 mmol, 3.0 equiv) followed by p-toluenesulfonic acid monohydrate (7.6 mg, 0.04 mmol, 0.5 equiv) at ambient temperature. The reaction mixture was stirred at room temperature for 16 h when the reaction was complete by LCMS analysis. The reaction mixture was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to afford N'-((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)-2-hydroxyacetohydrazide (37) (3.3 mg, 8% yield).

$^1$H NMR (500 MHZ, Chloroform-d3): 7.03 (d, J=4.5 Hz, 2H), 6.96 (d, J=8.2 Hz, 2H), 5.43 (s, 1H), 4.32 (s, 1H), 4.23 (q, J=10.0, 7.7, 7.7 Hz, 2H), 3.92 (d, J=5.7 Hz, 1H), 3.39 (s, 4H), 2.40 (d, J=13.3 Hz, 2H), 2.26-2.03 (m, 2H), 1.94 (s, 1H), 1.88-1.56 (m, 4H), 1.29 (dd, J=49.9, 11.8 Hz, 1H), 0.93-0.85 (m, 2H), 0.65-0.56 (m, 2H), 0.46 (d, J=6.8 Hz, 3H). Calculated mass: 534.26, Mass (ESI+) observed: 535.3 [M+H].

Scheme 28 illustrates the preparation of compound 38.

Scheme 28

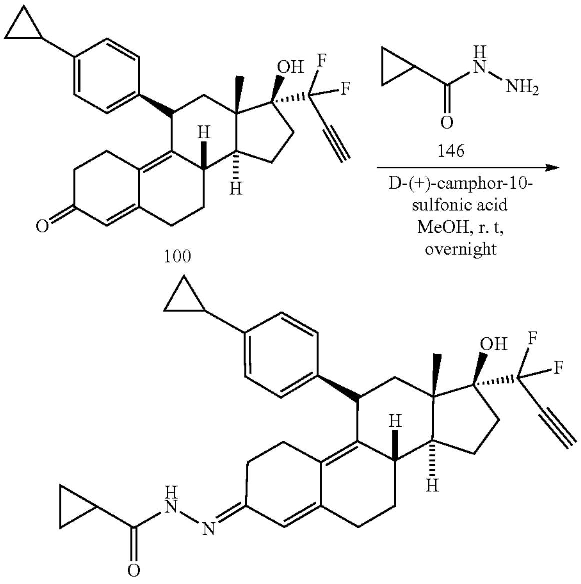

100 146 38

Example 33: N'-((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)cyclopropanecarbohydrazide (38)

38

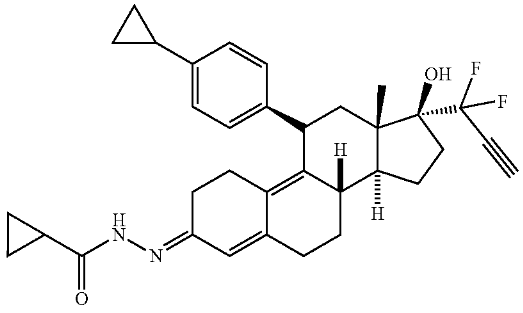

To a stirred solution of (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (0.8 g, 1.72 mmol, 1.0 equiv) in methanol (60 mL, 0.1M) was added cyclopropanecarbohydrazide (146) (146) (146) (0.52 g, 5.2 mmol, 3.0 equiv) followed by D-(+)-camphor-10-sulfonic acid (160 mg, 0.69 mmol, 0.4 equiv) at ambient temperature. The reaction mixture was stirred at room temperature overnight when the reaction was complete by LCMS analysis. The reaction mixture was concentrated and the residue was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to afford N'-((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene) cyclopropanecarbohydrazide (38) (625 mg, 66% yield).

$^1$H NMR (500 MHZ, DMSO-d6): δ 7.03 (d, J=8.3 Hz, 2H), 6.98-6.92 (m, 2H), 5.85 (s, 1H), 5.45 (s, 1H), 4.33 (d, J=17.3 Hz, 1H), 4.27 (d, J=5.1 Hz, 1H), 2.64-2.50 (m, 3H), 2.45 (s, 1H), 2.39 (d, J=12.6 Hz, 2H), 2.35-2.23 (m, 1H), 2.16 (t, J=9.4, 9.4 Hz, 2H), 2.09 (dt, J=15.9, 8.6, 8.6 Hz, 1H), 2.00-1.90 (m, 1H), 1.90-1.56 (m, 6H), 1.33 (d, J=8.2 Hz, 1H), 1.25 (t, J=13.4, 13.4 Hz, 1H), 0.92-0.85 (m, 2H), 0.76 (dd, J=13.5, 7.7 Hz, 2H), 0.69 (d, J=3.7 Hz, 2H), 0.59 (dt, J=6.5, 3.2, 3.2 Hz, 2H), 0.45 (d, J=7.3 Hz, 3H). Calculated mass: 544.2, Mass (ESI+) observed: 545.5 [M+H].

Scheme 29 illustrates the preparation of compound 39.

Scheme 29

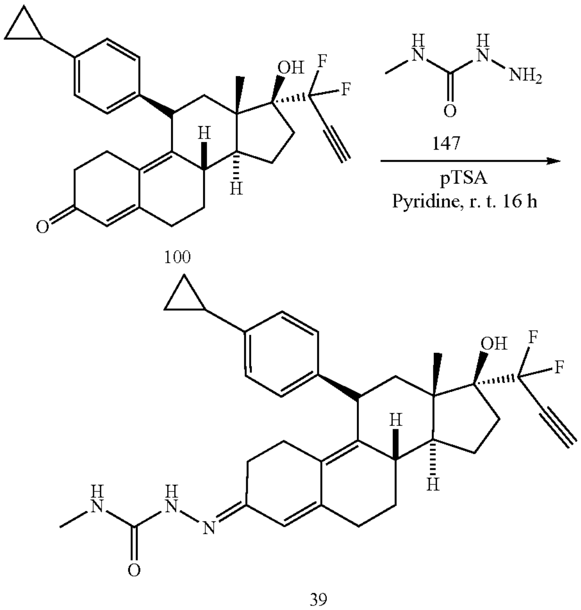

147 100 39

Example 34: N'-((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)acetohydrazide (39)

39

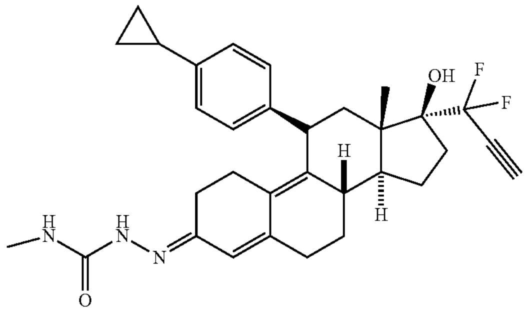

To a stirred solution of (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (35 mg, 0.08 mmol, 1.0 equiv) in pyridine (0.7 mL, 0.1M) was added N-methylhydrazinecarboxamide (147) (21 mg, 0.23 mmol, 3.0 equiv) followed by p-toluenesulfonic acid mono hydrate (7.3 mg, 0.04 mmol, 0.5 equiv) at ambient temperature. The reaction mixture was stirred at room temperature for 16 h when the reaction was complete by LCMS analysis. The reaction mixture was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to afford N'-((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)acetohydrazide (39) (14 mg, 35% yield).

$^1$H NMR (500 MHZ, Chloroform-d3): δ 7.53 (s, 1H), 7.06 (d, J=8.2 Hz, 2H), 6.96 (d, J=8.4 Hz, 2H), 6.14 (q, J=5.0, 4.9, 4.9 Hz, 1H), 5.86 (s, 1H), 4.32 (d, J=7.2 Hz, 1H), 2.89 (d, J=5.0 Hz, 4H), 2.62 (m, 1H), 2.53-2.45 (m, 4H), 2.42-2.30 (m, 3H), 2.26-2.13 (m, 2H), 2.03 (m, 2H), 1.93-1.80 (m, 2H), 1.79-1.70 (m, 2H), 1.48-1.32 (m, 2H), 0.98-0.87 (m, 2H), 0.68-0.62 (m, 2H), 0.58 (s, 3H). Calculated mass: 533.2, Mass (ESI+) observed: 534.2 [M+H].

Scheme 30 illustrates the preparation of compound 40.

Scheme 30

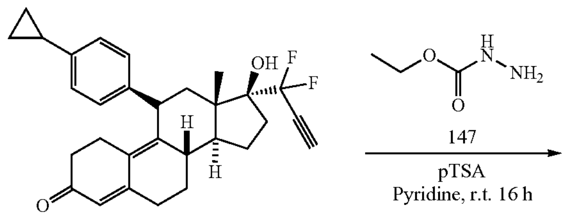

100

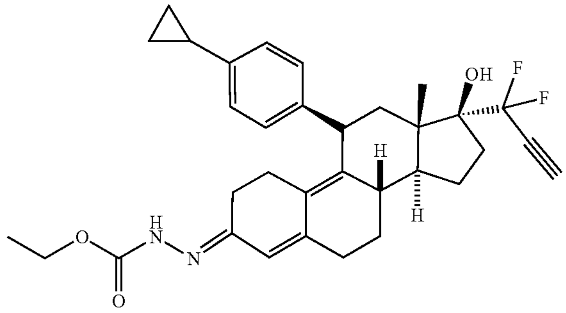

40

Example 35: ethyl (E)-2-((8S,11S,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)hydrazine-1-carboxylate (40)

40

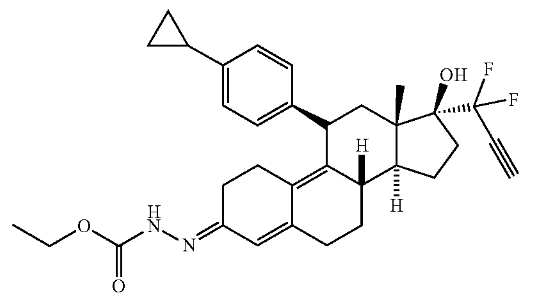

To a stirred solution of (8S,11R,13S,14S, 17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (20 mg, 0.04 mmol, 1.0 equiv) in pyridine (0.4 mL, 0.1M) was added ethyl carbazate (148) (13.5 mg, 0.13 mmol, 3.0 equiv) followed by p-toluenesulfonic acid mono hydrate (4.1 mg, 0.02 mmol, 0.5 equiv) at ambient temperature. The reaction mixture was stirred at room temperature for 16 h when the reaction was complete by LCMS analysis. The reaction mixture was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to afford ethyl (E)-2-((8S,11S,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)hydrazine-1-carboxylate (40) (5.9 mg, 27% yield).

$^1$H NMR (500 MHZ, Chloroform-d3): 7.05 (dd, J=11.2, 8.2 Hz, 2H), 6.96 (dd, J=8.4, 3.8 Hz, 2H), 4.34-4.21 (m, 3H), 3.49 (s, 1H), 2.89 (td, J=5.3, 5.2, 1.4 Hz, 1H), 2.66-2.27 (m, 9H), 2.24-2.09 (m, 1H), 2.06 (s, 1H), 2.03-1.94 (m, 1H), 1.93-1.81 (m, 2H), 1.80-1.69 (m, 2H), 1.60 (s, 1H), 1.48-1.35 (m, 2H), 1.32 (s, 3H), 0.97-0.89 (m, 2H), 0.70-0.62 (m, 2H), 0.58 (d, J=4.4 Hz, 3H). Calculated mass: 548.66, Mass (ESI+) observed: 549.4 [M+H].

Scheme 31 illustrates the preparation of compound 41.

Scheme 31

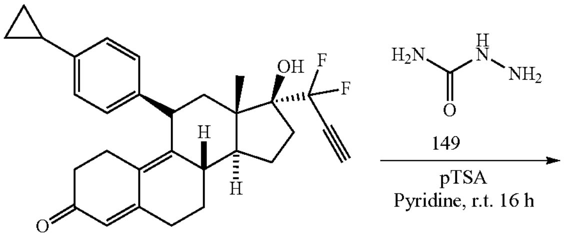

100

-continued

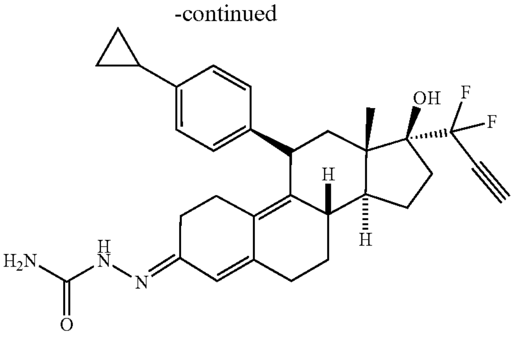

41

Example 36: (E)-2-((8S,11S,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)hydrazine-1-carboxamide (41)

41

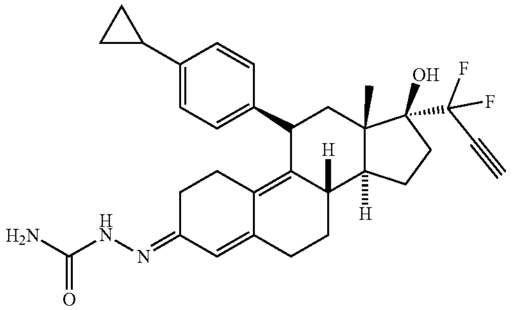

To a stirred solution of (8S,11R,13S,14S, 17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (20 mg, 0.04 mmol, 1.0 equiv) in pyridine (0.4 mL, 0.1M) was added semicarbazide (149) (9.8 mg, 0.13 mmol, 3.0 equiv) followed by p-toluenesulfonic acid mono hydrate (4.1 mg, 0.02 mmol, 0.5 equiv) at ambient temperature. The reaction mixture was stirred at room temperature for 16 h when the reaction was complete by LCMS analysis. The reaction mixture was diluted with 0.2 mL of methanol and purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to afford (E)-2-((8S,11S,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene) hydrazine-1-carboxamide (41) (8.7 mg, 42% yield).

$^1$H NMR (500 MHZ, Chloroform-d3): 7.57 (s, 1H), 7.06 (d, J=8.4 Hz, 2H), 6.96 (d, J=8.4 Hz, 2H), 5.88 (s, 1H), 4.32 (d, J=7.1 Hz, 1H), 2.89 (t, J=5.3, 5.3 Hz, 1H), 2.63 (dt, J=15.0, 5.1, 5.1 Hz, 1H), 2.53-2.47 (m, 3H), 2.46 (s, 1H), 2.43-2.29 (m, 3H), 2.24-2.14 (m, 1H), 2.09 (s, 1H), 2.07-1.97 (m, 2H), 1.90-1.80 (m, 2H), 1.78-1.68 (m, 2H), 1.48-1.35 (m, 2H), 0.93 (dt, J=8.4, 1.7, 1.7 Hz, 2H), 0.70-0.60 (m, 2H), 0.58 (s, 3H). Calculated mass: 519.62, Mass (ESI+) observed: 520.6 [M+H].

Scheme 32 illustrates the preparation of compound 42.

Scheme 32

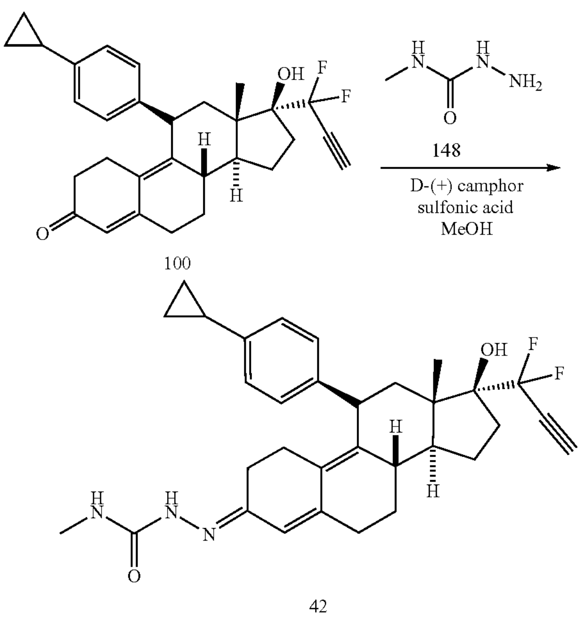

100

42

Example 37: (E)-2-((8S,11S,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)-N-methylhydrazine-1-carboxamide (42)

42

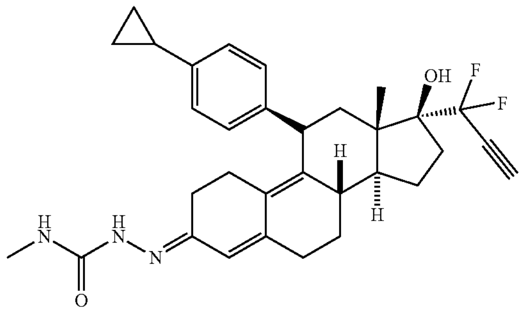

To a stirred solution of (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (0.8 g, 1.73 mmol, 1.0 equiv) in methanol (57 mL, 0.03M) was added the hydrazide (148) 4.86 mmol, 3.0 equiv) followed by D-(+)-camphor-10-sulfonic acid (0.16 g, 6.92 mmol, 0.4 equiv) at ambient temperature. The reaction mixture was stirred at room temperature for 2 h when the reaction was complete by LCMS analysis. The reaction mixture was concentrated and the residue was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B:

5% aqueous acetonitrile to 90% aqueous acetonitrile over 40 min) to afford (E)-2-((8S,11S,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)-N-methylhydrazine-1-carboxamide (42) (633.6 mg, 71% yield).

$^1$H NMR (500 MHZ, Chloroform-d3): δ 7.08-7.02 (m, 2H), 6.95 (d, J=8.4 Hz, 2H), 5.94 (d, J=18.1 Hz, 1H), 4.32 (d, J=6.8 Hz, 1H), 2.89 (t, J=5.4, 5.4 Hz, 1H), 2.68-2.55 (m, 1H), 2.55-2.43 (m, 4H), 2.43-2.30 (m, 3H), 2.26 (d, J=13.2 Hz, 2H), 2.22-2.11 (m, 1H), 2.11-1.97 (m, 3H), 1.84 (ddd, J=13.5, 8.5, 5.1 Hz, 2H), 1.80-1.68 (m, 2H), 1.47-1.33 (m, 2H), 0.97-0.88 (m, 2H), 0.65 (ddd, J=7.0, 5.1, 1.6 Hz, 2H), 0.58 (d, J=5.0 Hz, 3H). Calculated mass: 518.6. Mass (ESI+) observed: 519.4 [M+H].

Scheme 33 illustrates the preparation of compounds 43 and 44.

Scheme 33

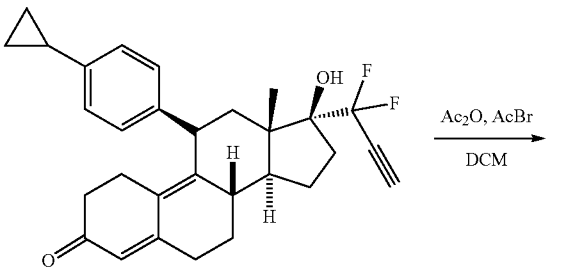

100

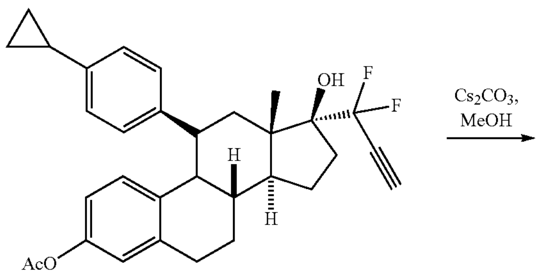

43

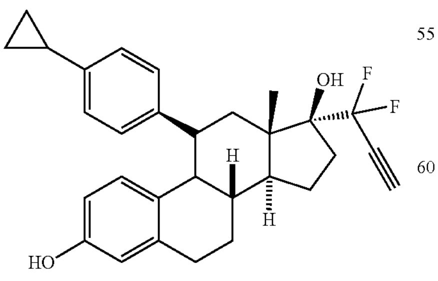

44

Example 38: (8S,11R,13S,14S,17S)-11-(4-cyclopropylphenyl)-17-(1,1-difluoroprop-2-yn-1-yl)-17-hydroxy-13-methyl-7,8,9,11,12,13,14,15,16,17-decahydro-6H-cyclopenta[a]phenanthren-3-yl acetate (43)

43

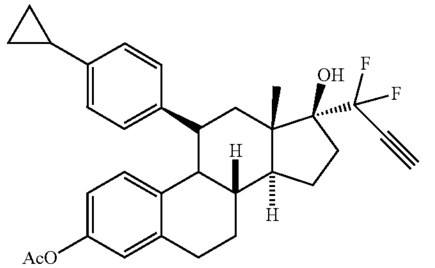

To a stirred solution of (8S,11R,13S,14S,17S)-11-(4-(cyclopropylsulfonyl)phenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (400 mg, 0.76 mmol, 1.0 equiv) in DCM (40 mL) were added acetic anhydride (78 mg, 0.76 mmol, 1.0 equiv) and acetyl bromide (233 mg, 1.90 mmol, 2.5 equiv) at ambient temperature. The reaction mixture was stirred at room temperature for 16 h when the reaction was complete by LCMS analysis. The reaction mixture was poured into a solution of sodium bicarbonate (661 mg, 7.6 mmol, 10 equiv) in water (300 mL) and extracted with ethyl acetate (80 mL×3). The combined organic layers were washed with water (2×150 mL), brine (150 mL), dried over anhydrous sodium sulfate and concentrated under vacuum to give the product (410 mg, 95% yield) as a light-yellow solid. The product (60 mg) was purified by Prep-HPLC with the following conditions: Column: XBridge Prep OBD C18 Column, 30×150 mm, 5 um; Mobile Phase A: Water (10 mmol/L $NH_4HCO_3$), Mobile Phase B: 20 mm NaOH+10% ACN; Flow rate: 60 mL/min; Gradient: 45% B to 75% B in 7 min; Wave Length: 254 nm/220 nm; RT (min): 6.9 to afford (8S,11R,13S,14S,17S)-11-(4-cyclopropylphenyl)-17-(1,1-difluoroprop-2-yn-1-yl)-17-hydroxy-13-methyl-7,8,9,11,12,13,14,15,16,17-decahydro-6H-cyclopenta[a]phenanthren-3-yl acetate (43) (13.5 mg, 22% yield) as a white solid.

$^1$H NMR (400 MHZ, DMSO-$d_6$): δ 7.60 (d, J=8.2 Hz, 2H), 7.31 (d, J=8.1 Hz, 2H), 6.97 (d, J=8.6 Hz, 1H), 6.86 (d, J=2.6 Hz, 1H), 6.67 (dd, J=8.5, 2.6 Hz, 1H), 5.41 (s, 1H), 4.34-4.18 (m, 2H), 3.05 (t, J=14.4 Hz, 1H), 2.96-2.70 (m, 3H), 2.48-2.37 (m, 2H), 2.30-2.07 (m, 5H), 2.06-1.84 (m, 2H), 1.78-1.62 (m, 2H), 1.45-1.29 (m, 2H), 1.12-0.91 (m, 4H), 0.35 (s, 3H). Calculated mass: 568.21, Mass (ESI-) observed: 567.35 [M−H].

Example 39: (8S,11R,13S,14S,17S)-11-(4-cyclopropylphenyl)-17-(1,1-difluoroprop-2-yn-1-yl)-13-methyl-7,8,9,11,12,13,14,15,16,17-decahydro-6H-cyclopenta[a]phenanthrene-3,17-diol (44)

44

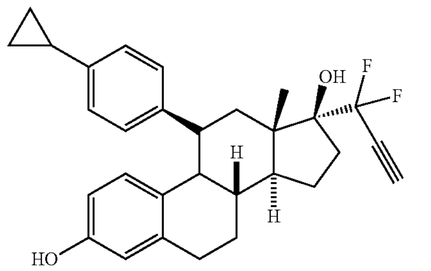

To a stirred solution of (8S,11R,13S,14S,17S)-11-(4-cyclopropylphenyl)-17-(1,1-difluoroprop-2-yn-1-yl)-17-hydroxy-13-methyl-7,8,9,11,12,13,14,15,16,17-decahydro-6H-cyclopenta[a]phenanthren-3-yl acetate (43) (350 mg, 0.62 mmol, 1.0 equiv) (43) in methanol (10 mL) was added cesium carbonate (604 mg, 1.86 mmol, 3.0 equiv) at ambient temperature. The reaction mixture was stirred at room temperature for 2 h when the reaction was complete by LCMS analysis. The reaction mixture was purified by Prep-TLC (ethyl acetate/petroleum ether =2:1) to afford (8S,11R,13S,14S,17S)-11-(4-cyclopropylphenyl)-17-(1,1-difluoroprop-2-yn-1-yl)-13-methyl-7,8,9,11,12,13,14,15,16,17-decahydro-6H-cyclopenta[a]phenanthrene-3,17-diol (44) (280 mg, 86% yield) as a light-yellow solid. Calculated mass: 526.20, Mass (ESI-) observed: 525.25 [M−H].

Scheme 34 illustrates the preparation of compound 45.

Scheme 34

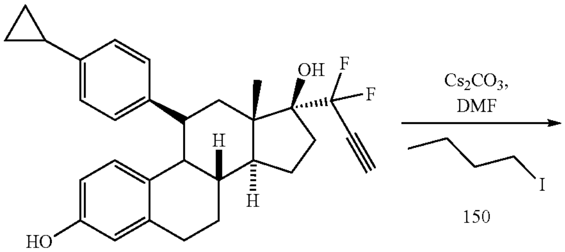

44

150

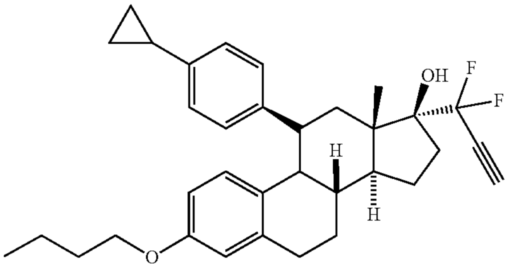

45

Example 40: (8S,11R,13S,14S,17S)-3-butoxy-11-(4-cyclopropylphenyl)-17-(1,1-difluoroprop-2-yn-1-yl)-13-methyl-7,8,9,11,12,13,14,15,16,17-decahydro-6H-cyclopenta[a]phenanthren-17-ol (45)

45

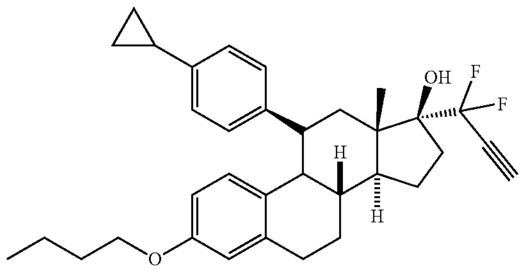

To a stirred solution of (8S,11R,13S,14S,17S)-11-(4-cyclopropylphenyl)-17-(1,1-difluoroprop-2-yn-1-yl)-13-methyl-7,8,9,11,12,13,14,15,16,17-decahydro-6H-cyclopenta[a]phenanthrene-3,17-diol (50 mg, 0.095 mmol, 1.0 equiv) (44) in DMF (2.5 mL) were added cesium carbonate (93 mg, 0.285 mmol, 3.0 equiv) and 1-iodobutane (150) (26 mg, 0.143 mmol, 1.5 equiv) at ambient temperature. The reaction mixture was stirred at room temperature for 16 h when the reaction was complete by LCMS analysis. The reaction mixture was quenched with water (15 mL) and extracted with ethyl acetate (20 mL×3). The combined organic layers were washed with water (20 mL×2) and brine (20 mL), dried over anhydrous sodium sulfate, filtered and concentrated under vacuum. The residue was purified by Prep-HPLC with the following conditions: Column: XBridge Prep OBD C18 Column, 30×150 mm, 5 um; Mobile Phase A: Water (10 mmol/L $NH_4HCO_3$), Mobile Phase B: 20 mm NaOH+10% ACN; Flow rate: 60 mL/min; Gradient: 60% B to 90% B in 7 min; Wave Length: 254 nm/220 nm; RT (min): 7.0 to afford (8S,11R,13S,14S,17S)-3-butoxy-11-(4-cyclopropylphenyl)-17-(1,1-difluoroprop-2-yn-1-yl)-13-methyl-7,8,9,11,12,13,14,15,16,17-decahydro-6H-cyclopenta[a]phenanthren-17-ol (45) (19.8 mg, 35% yield) as a white solid.

$^1H$ NMR (400 MHZ, DMSO-$d_6$): δ 7.59 (d, J=8.1 Hz, 2H), 7.32 (d, J=8.0 Hz, 2H), 6.83 (d, J=8.6 Hz, 1H), 6.65 (d, J=2.7 Hz, 1H), 6.48 (dd, J=8.6, 2.7 Hz, 1H), 5.41 (s, 1H), 4.29 (t, J=5.3 Hz, 1H), 4.19 (t, J=5.9 Hz, 1H), 3.85 (t, J=6.5 Hz, 2H), 3.08-2.94 (m, 1H), 2.89-2.71 (m, 3H), 2.48-2.34 (m, 2H), 2.23-2.05 (m, 2H), 2.04-1.84 (m, 2H), 1.75-1.56 (m, 4H), 1.45-1.26 (m, 4H), 1.09-0.94 (m, 4H), 0.90 (t, J=7.4 Hz, 3H), 0.34 (s, 3H). Calculated mass: 582.26, Mass (ESI−) observed: 581.45 [M−H].

Scheme 35 illustrates the preparation of compound 46.

Scheme 35

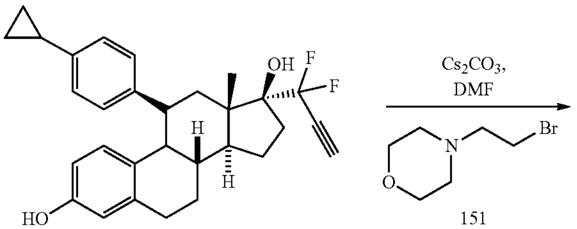

44

151

-continued

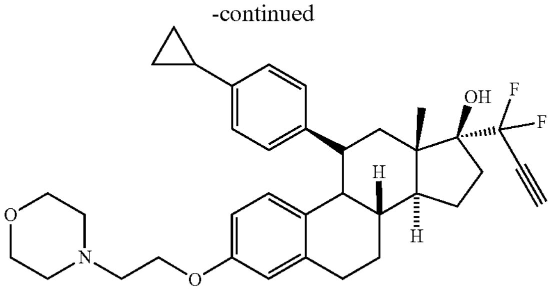

46

Example 41: (8S,11R,13S,14S,17S)-11-(4-cyclopropylphenyl)-17-(1,1-difluoroprop-2-yn-1-yl)-13-methyl-3-(2-morpholinoethoxy)-7,8,9,11,12,13,14,15,16,17-decahydro-6H-cyclopenta[a]phenanthren-17-ol (46)

46

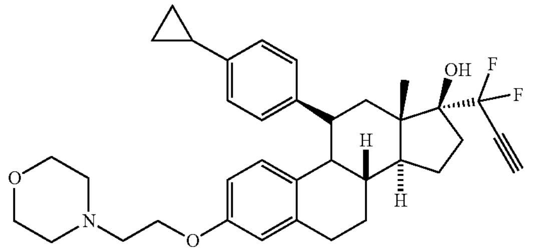

To a stirred solution of (8S,11R,13S,14S, 17S)-11-(4-cyclopropylphenyl)-17-(1,1-difluoroprop-2-yn-1-yl)-13-methyl-7,8,9,11,12,13,14,15,16,17-decahydro-6H-cyclopenta[a]phenanthrene-3,17-diol (44) (50 mg, 0.095 mmol, 1.0 equiv) in DMF (2.5 mL) were added cesium carbonate (93 mg, 0.285 mmol, 3.0 equiv) and 4-(2-bromoethyl) morpholine hydrobromide (151) (39 mg, 0.143 mmol, 1.5 equiv) at ambient temperature. The reaction mixture was stirred at room temperature for 16 h when the reaction was complete by LCMS analysis. The reaction mixture was quenched with water (15 mL) and extracted with ethyl acetate (20 mL×3). The combined organic layers were washed with water (20 mL×2), brine (20 mL), dried over anhydrous sodium sulfate, filtered and concentrated under vacuum. The residue was purified by Prep-HPLC with the following conditions: Column: XSelect CSH C18 Column, 30×150 mm, 5 μm; Mobile Phase A: Water (0.1% FA), Mobile Phase B: 20 mm NaOH +10% ACN; Flow rate: 60 mL/min; Gradient: 42% B to 72% B in 7 min; Wave Length: 254 nm; RT (min): 6.55 to afford (8S,11R,13S,14S,17S)-11-(4-cyclopropylphenyl)-17-(1,1-difluoroprop-2-yn-1-yl)-13-methyl-3-(2-morpholinoethoxy)-7,8,9,11,12,13,14,15,16,17-decahydro-6H-cyclopenta[a]phenanthren-17-ol (46) (25.1 mg, 40% yield) as a white solid.

$^1$H NMR (400 MHZ, DMSO-d6): δ 7.60 (d, J=8.1 Hz, 2H), 7.32 (d, J=8.0 Hz, 2H), 6.84 (d, J=8.7 Hz, 1H), 6.69 (d, J=2.7 Hz, 1H), 6.50 (dd, J=8.6, 2.7 Hz, 1H), 5.41 (s, 1H), 4.29 (t, J=5.4 Hz, 1H), 4.21 (t, J=6.5 Hz, 1H), 3.98 (t, J=5.8 Hz, 2H), 3.56 (t, J=4.6 Hz, 4H), 3.02 (t, J=14.4 Hz, 1H), 2.91-2.71 (m, 3H), 2.63 (t, J=5.8 Hz, 2H), 2.49-2.35 (m, 6H), 2.24-2.07 (m, 2H), 2.05-1.86 (m, 2H), 1.77-1.62 (m, 2H), 1.44-1.27 (m, 2H), 1.10-0.94 (m, 4H), 0.35 (s, 3H). Calculated mass: 639.28, Mass (ESI+) observed: 640.45 [M+H].

Scheme 36 illustrates the preparation of compound 47.

Scheme 36

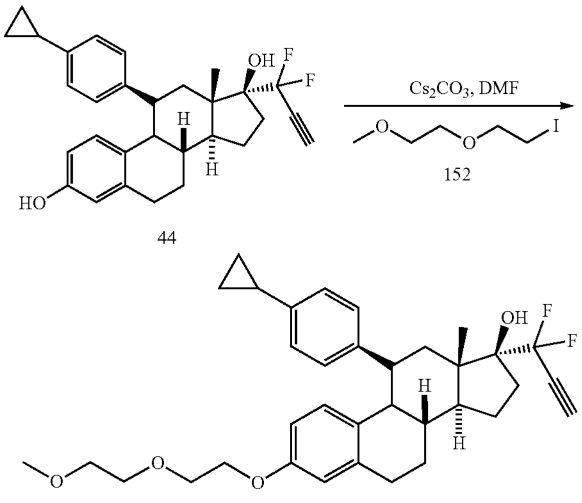

44

152

47

Example 42: 8S,11R,13S,14S,17S)-11-(4-cyclopropylphenyl)-17-(1,1-difluoroprop-2-yn-1-yl)-3-(2-(2-methoxyethoxy)ethoxy)-13-methyl-7,8,9,11,12,13,14,15,16,17-decahydro-6H-cyclopenta[a]phenanthren-17-ol (47)

47

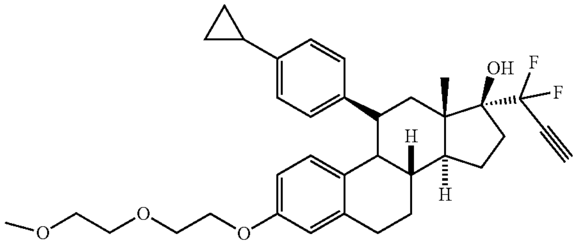

To a stirred solution of (8S,11R,13S,14S, 17S)-11-(4-cyclopropylphenyl)-17-(1,1-difluoroprop-2-yn-1-yl)-13-methyl-7,8,9,11,12,13,14,15,16,17-decahydro-6H-cyclopenta[a]phenanthrene-3,17-diol (44) (50 mg, 0.095 mmol, 1.0 equiv) in DMF (2.5 mL) were added cesium carbonate (93 mg, 0.285 mmol, 3.0 equiv) and 1-iodo-2-(2-methoxyethoxy)ethane (152) (33 mg, 0.143 mmol, 1.5 equiv) at ambient temperature. The reaction mixture was stirred at room temperature for 16 h when the reaction was complete by LCMS analysis. The reaction mixture was quenched with water (15 mL) and extracted with ethyl acetate (20 mL×3). The combined organic layers were washed with water (20 mL×2) and brine (20 mL), dried over anhydrous sodium sulfate, filtered and concentrated under vacuum. The residue was purified by Prep-HPLC with the following conditions: Column: XBridge Prep OBD C18 Column, 30×150 mm, 5 um; Mobile Phase A: Water (10 mmol/L NH4HCO3+0.05%

NH3H2O), Mobile Phase B: 20 mm NaOH+10% ACN; Flow rate: 60 mL/min; Gradient: 3% B to 10% B in 8 min; Wave Length: 254 nm/220 nm; RT (min): 7.3 to afford 8S, 11R,13S,14S,17S)-11-(4-cyclopropylphenyl)-17-(1,1-difluoroprop-2-yn-1-yl)-3-(2-(2-methoxyethoxy)ethoxy)-13-methyl-7,8,9,11,12,13,14,15,16,17-decahydro-6H-cyclopenta[a]phenanthren-17-ol (47) (22.6 mg, 37% yield) as a white solid.

$^1$H NMR (400 MHz, DMSO-d6): δ 7.60 (d, J=8.1 Hz, 2H), 7.32 (d, J=8.1 Hz, 2H), 6.84 (d, J=8.7 Hz, 1H), 6.68 (d, J=2.7 Hz, 1H), 6.50 (dd, J=8.6, 2.7 Hz, 1H), 5.40 (s, 1H), 4.28 (t, J=5.4 Hz, 1H), 4.19 (t, J=5.8 Hz, 1H), 4.03-3.92 (m, 2H), 3.73-3.62 (m, 2H), 3.58-3.52 (m, 2H), 3.47-3.40 (m, 2H), 3.22 (s, 3H), 3.09-2.95 (m, 1H), 2.90-2.72 (m, 3H), 2.49-2.34 (m, 2H), 2.24-2.06 (m, 2H), 2.04-1.84 (m, 2H), 1.77-1.62 (m, 2H), 1.44-1.26 (m, 2H), 1.12-0.92 (m, 4H), 0.34 (s, 3H). Calculated mass: 628.27, Mass (ESI-) observed: 627.40 [M−H].

Scheme 37 illustrates the preparation of compounds 48 and 49.

Scheme 37

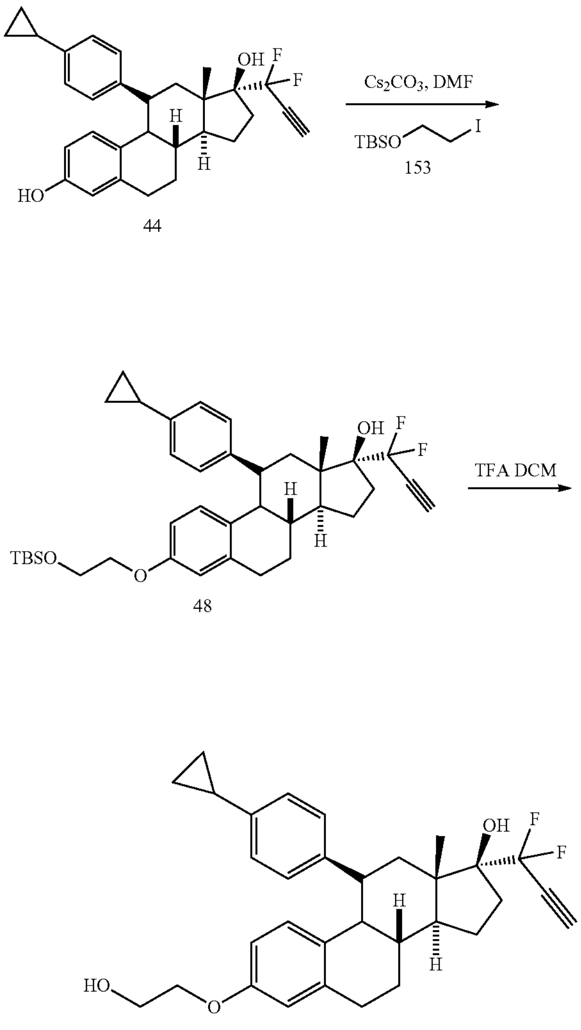

44

48

49

Example 43: (8S,11R,13S,14S,17S)-3-(2-((tert-butyldimethylsilyl)oxy)ethoxy)-11-(4-cyclopropylphenyl)-17-(1,1-difluoroprop-2-yn-1-yl)-13-methyl-7,8,9,11,12,13,14,15,16,17-decahydro-6H-cyclopenta[a]phenanthren-17-ol (48)

48

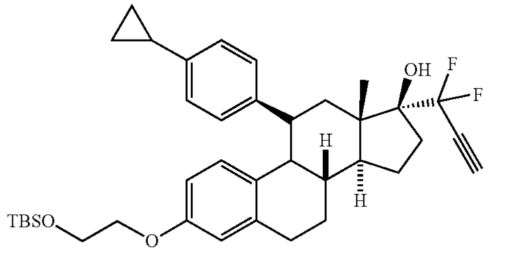

To a stirred solution of (8S,11R,13S,14S,17S)-11-(4-cyclopropylphenyl)-17-(1,1-difluoroprop-2-yn-1-yl)-13-methyl-7,8,9,11,12,13,14,15,16,17-decahydro-6H-cyclopenta[a]phenanthrene-3,17-diol (44) (80 mg, 0.152 mmol, 1.0 equiv) in DMF (4 mL) was added cesium carbonate (148 mg, 0.456 mmol, 3.0 equiv) and tert-butyl (2-iodoethoxy)dimethylsilane (153) (65 mg, 0.228 mmol, 1.5 equiv) at ambient temperature. The reaction mixture was stirred at room temperature for 16 h when the reaction was complete by LCMS analysis. The reaction mixture was quenched with water (30 mL) and extracted with ethyl acetate (30 mL×3). The combined organic layers were washed with water (30 mL×2) and brine (30 mL), dried over anhydrous sodium sulfate, filtered and concentrated under vacuum. The residue was purified by Prep-TLC (ethyl acetate/petroleum ether=−1:1) to afford (8S,11R,13S,14S,17S)-3-(2-((tert-butyldimethylsilyl)oxy)ethoxy)-11-(4-cyclopropylphenyl)-17-(1,1-difluoroprop-2-yn-1-yl)-13-methyl-7,8,9,11,12,13,14,15,16,17-decahydro-6H-cyclopenta[a]phenanthren-17-ol (48) (70 mg, 67% yield) as a light-yellow solid. Calculated mass: 684.31, Mass (ESI-) observed: 683.45 [M−H].

Example 44: (8S,11R,13S,14S,17S)-11-(4-cyclopropylphenyl)-17-(1,1-difluoroprop-2-yn-1-yl)-3-(2-hydroxyethoxy)-13-methyl-7,8,9,11,12,13,14,15,16,17-decahydro-6H-cyclopenta[a]phenanthren-17-ol (49)

49

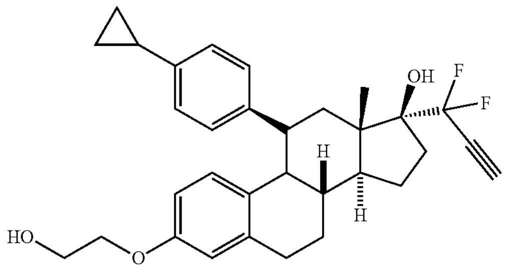

To a solution of (8S,11R,13S, 14S,17S)-3-(2-((tert-butyldimethylsilyl)oxy)ethoxy)-11-(4-cyclopropylphenyl)-17-(1,1-difluoroprop-2-yn-1-yl)-13-methyl-7,8,9,11,12,13,14,15,16,17-decahydro-6H-cyclopenta[a]phenanthren-17-ol

(48) (60 mg, 0.088 mmol, 1.0 equiv) in DCM (5 mL) was added TFA (0.5 mL). The reaction mixture was stirred at room temperature for 1 h when the reaction was complete by LCMS analysis. The reaction mixture was concentrated and the residue was purified by Prep-HPLC under the following conditions: Column: XBridge Prep OBD C18 Column, 30×150 mm, 5 um; Mobile Phase A: Water (10 mmol/L $NH_4HCO_3$), Mobile Phase B: 20 mm NaOH+10% ACN; Flow rate: 60 mL/min; Gradient: 34% B to 64% B in 7 min; Wave Length: 254 nm/220 nm; RT (min): 6.9 to afford (8S,11R,13S,14S,17S)-11-(4-cyclopropylphenyl)-17-(1,1-difluoroprop-2-yn-1-yl)-3-(2-hydroxyethoxy)-13-methyl-7,8,9,11,12,13,14,15,16,17-decahydro-6H-cyclopenta[a]phenanthren-17-ol (49) (24.7 mg, 49% yield) as a white solid.

$^1$H NMR (400 MHZ, DMSO-$d_6$): δ 7.60 (d, J=8.2 Hz, 2H), 7.32 (d, J=8.1 Hz, 2H), 6.84 (d, J=8.6 Hz, 1H), 6.67 (d, J=2.7 Hz, 1H), 6.49 (dd, J=8.6, 2.7 Hz, 1H), 5.40 (s, 1H), 4.78 (t, J=5.5 Hz, 1H), 4.28 (t, J=5.4 Hz, 1H), 4.19 (t, J=6.0 Hz, 1H), 3.87 (t, J=5.0 Hz, 2H), 3.65 (q, J=5.2 Hz, 2H), 3.02 (t, J=15.9 Hz, 1H), 2.90-2.72 (m, 3H), 2.48-2.34 (m, 2H), 2.24-2.06 (m, 2H), 2.05-1.84 (m, 2H), 1.76-1.62 (m, 2H), 1.44-1.26 (m, 2H), 1.11-0.91 (m, 4H), 0.34 (s, 3H). Calculated mass: 570.23, Mass (ESI-) observed: 569.35 [M–H].

Scheme 38 illustrated the preparation of compound 50.

Scheme 38

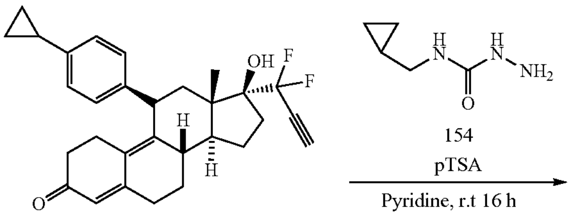

100

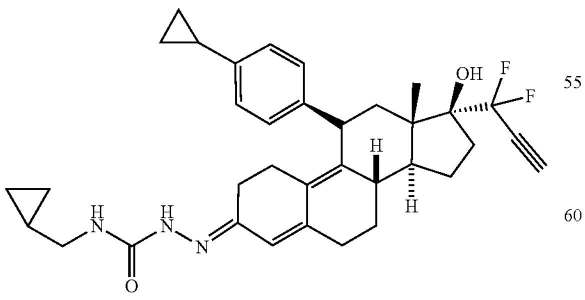

50

Example 45: (E)-N-(cyclopropylmethyl)-2-((8S,11S,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)hydrazine-1-carboxamide (50)

50

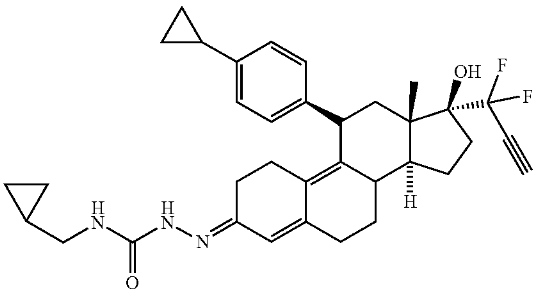

To a stirred solution of (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (37 mg, 0.08 mmol, 1.0 equiv) in pyridine (0.8 mL, 0.1M) was added N-(cyclopropylmethyl)hydrazinecarboxamide (154) (31.0 mg, 0.24 mmol, 3.0 equiv) followed by p-toluenesulfonic acid monohydrate (7.6 mg, 0.04 mmol, 0.5 equiv) at ambient temperature. The reaction mixture was stirred at room temperature for 16 h when the reaction was complete by LCMS analysis. The reaction mixture was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to afford (E)-N-(cyclopropylmethyl)-2-((8S,11S,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)hydrazine-1-carboxamide (50) (18.5 mg, 40% yield).

$^1$H NMR (500 MHZ, DMSO-d6): δ 9.11 (s, 1H), 7.04 (d, J=8.2 Hz, 2H), 6.96 (d, J=8.5 Hz, 2H), 6.69 (t, J=6.1, 6.1 Hz, 1H), 5.85 (s, 1H), 5.41 (s, 1H), 4.31 (d, J=6.8 Hz, 1H), 4.24 (t, J=5.2, 5.2 Hz, 1H), 2.97 (t, J=6.5, 6.5 Hz, 2H), 2.41 (d, J=13.4 Hz, 2H), 2.13 (ddt, J=27.1, 15.5, 8.2, 8.2 Hz, 3H), 1.98-1.91 (m, 1H), 1.83 (ddd, J=13.4, 8.4, 5.0 Hz, 1H), 1.80-1.57 (m, 4H), 1.39-1.20 (m, 2H), 0.97-0.86 (m, 3H), 0.63-0.57 (m, 2H), 0.45 (s, 3H), 0.39-0.34 (m, 2H), 0.19-0.13 (m, 2H). Calculated mass: 573.3, Mass (ESI+) observed: 574.6 [M+H].

Scheme 39 illustrates the preparation of compound 51.

Scheme 39

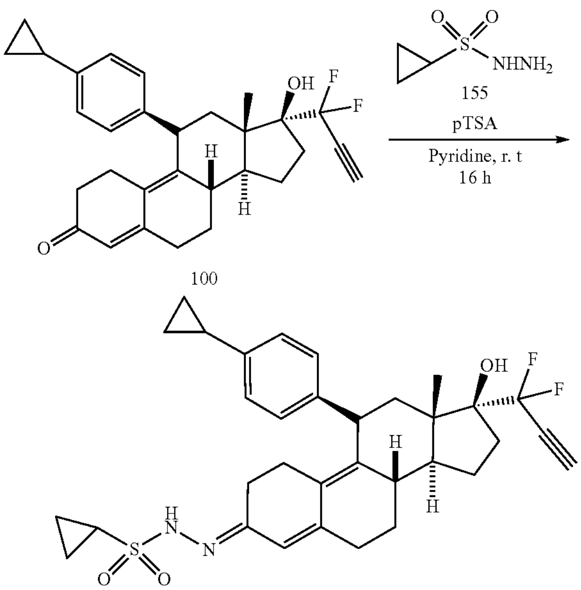

100

51

Example 46: N'-((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)cyclopropanesulfonohydrazide (51)

51

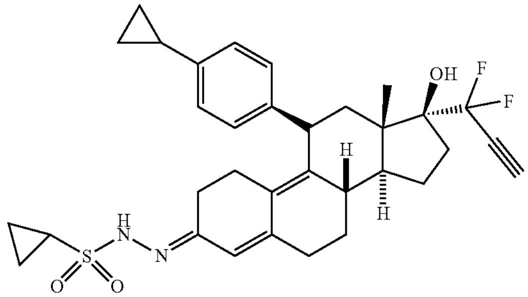

To a stirred solution of (8S,11R,13S,14S, 17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (0.6 g, 1.29 mmol, 1.0 equiv) in pyridine (0.7 mL, 0.1M) was added cyclopropanesulfonohydrazide (155) (0.53 g, 3.89 mmol, 3.0 equiv) followed by p-toluenesulfonic acid monohydrate (0.111 g, 0.65 mmol, 0.5 equiv) at ambient temperature. The reaction mixture was stirred at room temperature for 16 h when the reaction was complete by LCMS analysis. The reaction mixture was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to afford N'-((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene) cyclopropanesulfonohydrazide (51) (0.202 g, 27% yield). $^1$H NMR (500 MHZ, Chloroform-d3): 9.91 (s, 1H), 7.03 (d, J=8.4 Hz, 2H), 6.95 (d, J=8.4 Hz, 2H), 6.23 (s, 1H), 5.42 (s, 1H), 4.31 (d, J=7.0 Hz, 1H), 4.24 (t, J=5.4, 5.4 Hz, 1H), 2.64-2.54 (m, 3H), 2.42 (dd, J=20.2, 12.8 Hz, 3H), 2.30 (ddd, J=14.6, 11.2, 5.2 Hz, 1H), 2.23-2.14 (m, 2H), 2.14-2.05 (m, 1H), 1.95 (dq, J=12.9, 4.5, 4.3, 4.3 Hz, 1H), 1.90-1.79 (m, 2H), 1.79-1.56 (m, 3H), 1.40-1.27 (m, 1H), 1.27-1.20 (m, 1H), 0.97 (dt, J=5.2, 3.0, 3.0 Hz, 2H), 0.95-0.86 (m, 4H), 0.63-0.56 (m, 2H), 0.46 (s, 3H). Calculated mass: 580.2, Mass (ESI+) observed: 581.5 [M+H].

Scheme 40 illustrates the preparation of compound 52.

Scheme 40

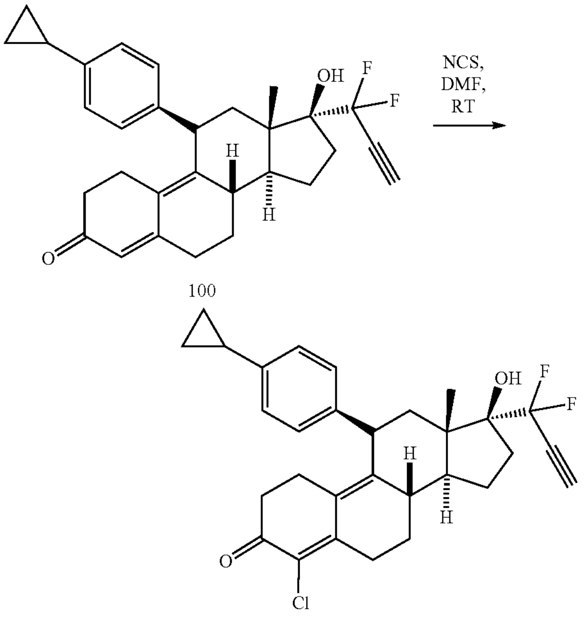

100

52

Example 47: (8S,11S,13S,14S,17S)-4-chloro-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (52)

52

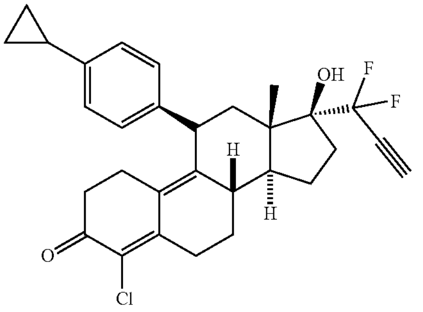

To a stirred solution of (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (50 mg, 0.10 mmol) in DMF (2 mL) was added NCS (17 mg, 0.13 mmol). The reaction mixture was stirred at room temperature for 18 h, quenched with water (20 mL) and extracted with ethyl acetate (20 mL×3). The combined organic extracts were washed with water (20 mL), brine (20 mL), dried over anhydrous sodium sulfate and concentrated under vacuum. The residue was purified by Prep-HPLC with the following conditions: Column: XBridge Prep Phenyl Column, 30×150 mm, 5 u m; Mobile Phase A: Water (10 mmol/L $NH_4HCO_3$+0.05% $NH_3H_2O$), Mobile Phase B: ACN; Flow rate: 60 mL/min; Gradient: 50% B to 80% B in 8 min; Wave Length: 254 nm/220 nm; RT (min): 7.96 to give (8S,11S,13S,14S,17S)-4-chloro-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (52) (13.4 mg, 25%) as a white solid.

$^1$H NMR (400 MHZ, DMSO-$d_6$): δ 7.06-6.96 (m, 4H), 5.48 (s, 1H), 4.45 (d, J=6.8 Hz, 1H), 4.27 (t, J=8.0 Hz, 1H), 3.06-3.00 (m, 1H), 2.77-2.71 (m, 1H), 2.63-2.54 (m, 2H), 2.47-2.40 (m, 2H), 2.34-2.23 (m, 2H), 2.17-1.99 (m, 3H), 1.88-1.63 (m, 4H), 1.43-1.24 (m, 2H), 0.95-0.84 (m, 2H), 0.63-0.59 (m, 2H), 0.50 (s, 3H). ESI-MS $[M+H]^+$calcd for (C30H31ClF2O2) 497.20, 499.20, found: 497.30, 499.30.

Scheme 41 illustrates the preparation of compounds 54 and 55.

Scheme 41

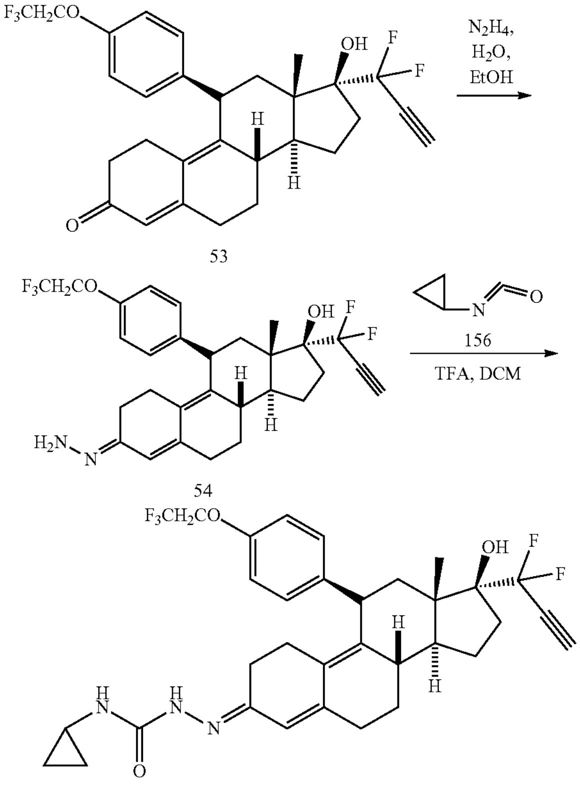

53

54

55

Example 48: (8S,11S,13S,14S,17S,E)-17-(1,1-difluoroprop-2-yn-1-yl)-3-hydrazineylidene-13-methyl-11-(4-(2,2,2-trifluoroethoxy)phenyl)-2,3,6,7,8,11,12,13,14,15,16,17-dodecahydro-1H-cyclopenta[a]phenanthren-17-ol (54)

54

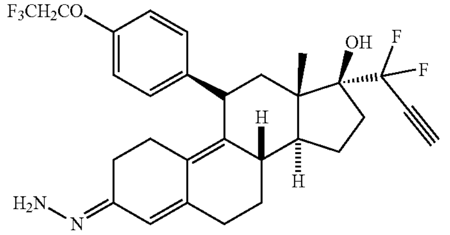

To a stirred solution of (8S,11R,13S,14S,17S)-17-(1,1-difluoroprop-2-yn-1-yl)-17-hydroxy-13-methyl-11-(4-(2,2,2-trifluoroethoxy)phenyl)-1,2,6,7,8,11,12,13,14,15,16,17-dodecahydro-3H-cyclopenta[a]phenanthren-3-one (53) (180 mg, 0.35 mmol) in ethanol (5 mL) was added hydrazine hydrate (51 mg, 1.04 mmol). The reaction mixture was stirred at room temperature for 1 day, concentrated under vacuum, washed with petroleum ether (30 ml×5) and dried under reduced pressure to give (8S,11S,13S,14S,17S,E)-17-(1,1-difluoroprop-2-yn-1-yl)-3-hydrazineylidene-13-methyl-11-(4-(2,2,2-trifluoroethoxy)phenyl)-2,3,6,7,8,11,12,13,14,15,16,17-dodecahydro-1H-cyclopenta[a]phenanthren-17-ol (200 mg, crude) (54) as a white solid. ESI-MS $[M+H]^+$calcd for ($C_{29}H_{31}F_5N_2O2$) 535.23, found: 535.30.

Example 49: (E)-N-cyclopropyl-2-((8S,11S,13S,14S,17S)-17-(1,1-difluoroprop-2-yn-1-yl)-17-hydroxy-13-methyl-11-(4-(2,2,2-trifluoroethoxy)phenyl)-1,2,6,7,8,11,12,13,14,15,16,17-dodecahydro-3H-cyclopenta[a]phenanthren-3-ylidene)hydrazine-1-carboxamide (55)

55

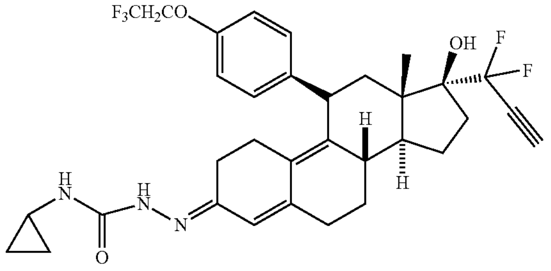

To a stirred solution of (8S,11S,13S,14S,17S,E)-17-(1,1-difluoroprop-2-yn-1-yl)-3-hydrazineylidene-13-methyl-11-(4-(2,2,2-trifluoroethoxy)phenyl)-2,3,6,7,8,11,12,13,14,15,16,17-dodecahydro-1H-cyclopenta[a]phenanthren-17-ol (54) (55 mg, 0.10 mmol) and triethylamine (31 mg, 0.30 mmol) in DCM (3 mL) under nitrogen was added isocyanatocyclopropane (155) (15 mg, 0.18 mmol) at 0° C. The reaction mixture was stirred at room temperature for 4 h, quenched with water (20 mL) and extracted with ethyl acetate (20 mL×3). The combined organic layers was washed with water (30 mL), brine (30 mL×2), dried over anhydrous sodium sulfate and concentrated under vacuum. The residue was purified by Prep-HPLC with the following conditions: Column: XBridge Prep OBD $C_{18}$ Column, 30×150 mm, 5 μm; Mobile Phase A: Water (10 mmol/L $NH_4HCO_3$), Mobile Phase B: ACN; Flow rate: 60 mL/min; Gradient: 50% B to 80% B in 7 min; Wave Length: 254 nm/220 nm; RT (min): 5.7, 6.2 to give (E)-N-cyclopropyl-2-((8S,11S,13S,14S,17S)-17-(1,1-difluoroprop-2-yn-1-yl)-17-hydroxy-13-methyl-11-(4-(2,2,2-trifluoroethoxy)phenyl)-1,2,6,7,8,11,12,13,14,15,16,17-dodecahydro-3H-cyclopenta[a]phenanthren-3-ylidene)hydrazine-1-carboxamide (14.8 mg, 23%) as a white solid.

$^1H$ NMR (400 MHZ, DMSO-$d_6$): δ 9.48-9.17 (m, 1H), 7.13 (d, J=8.0 Hz, 2H), 6.95 (d, J=8.0 Hz, 2H), 6.65-6.47 (m, 1H), 5.84 (s, 1H), 5.44 (s, 1H), 4.70 (q, J=8.8 Hz, 2H), 4.35-4.25 (m, 2H), 2.59-2.53 (m, 3H), 2.43-2.39 (m, 4H), 2.27-2.06 (m, 3H), 2.01-1.93 (m, 1H), 1.85-1.62 (m, 4H), 1.46-1.26 (m, 2H), 0.60-0.44 (m, 7H). ESI-MS $[M+H]^+$ calcd for ($C_{33}H_{36}F_5N_3O_3$) 618.27, found: 618.50.

Scheme 42 illustrates the preparation of compound 57.

Scheme 42

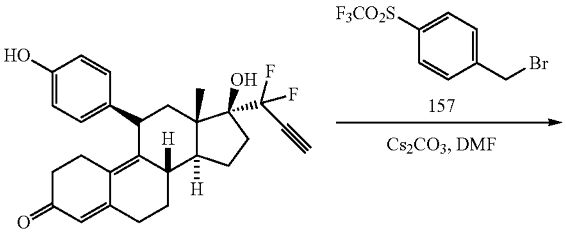

56

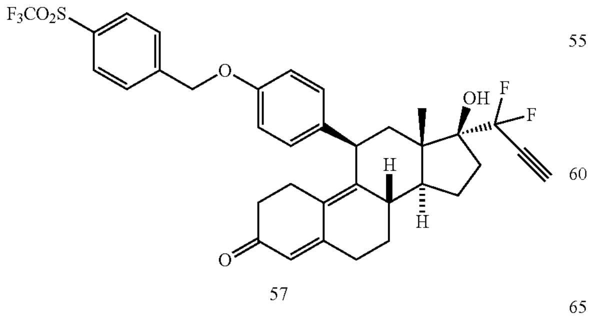

57

Example 50: (8S,11S,13S,14S,17S)-17-(1,1-difluoroprop-2-yn-1-yl)-17-hydroxy-13-methyl-11-(4-((4-((trifluoromethyl)sulfonyl)benzyl)oxy)phenyl)-1,2,6,7,8,11,12,13,14,15,16,17-dodecahydro-3H-cyclopenta[a]phenanthren-3-one (57)

57

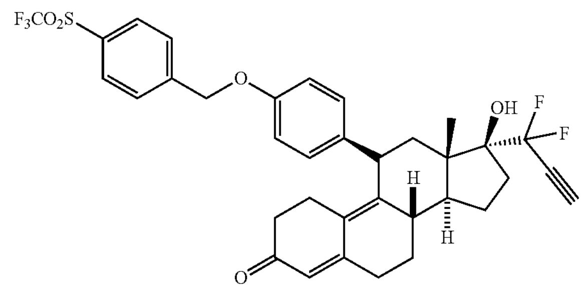

To a solution of (8S,11S,13S,14S, 17S)-17-(1,1-difluoroprop-2-yn-1-yl)-17-hydroxy-11-(4-hydroxyphenyl)-13-methyl-1,2,6,7,8,11,12,13,14,15,16,17-dodecahydro-3H-cyclopenta[a]phenanthren-3-one (50 mg, 0.114 mmol) (56) in DMF (4 mL) were added 1-(bromomethyl)-4-((trifluoromethyl)sulfonyl)benzene (157) (69 mg, 0.228 mmol) and $Cs_2CO_3$ (148 mg, 0.456 mmol). The reaction mixture was stirred at room temperature for 3 h, quenched with water (30 mL) and extracted with ethyl acetate (3×30 mL). The combined organic layers was washed with brine (50 mL), dried over $Na_2SO_4$ and concentrated under vacuum. The residue was purified by Prep-HPLC with the following conditions: Column: XBridge Prep OBD C18 Column, 30×150 mm, 5 μm; Mobile Phase A: Water (10 mmol/L $NH_4HCO_3$), Mobile Phase B: ACN; Flow rate: 60 mL/min; Gradient: 31% B to 61% B in 7 min; Wave Length: 254 nm/220 nm; RT (min): 6.2 to afford (8S,11S,13S,14S,17S)-17-(1,1-difluoroprop-2-yn-1-yl)-17-hydroxy-13-methyl-11-(4-((4-((trifluoromethyl)sulfonyl)benzyl)oxy)phenyl)-1,2,6,7,8,11,12,13,14,15,16,17-dodecahydro-3H-cyclopenta[a]phenanthren-3-one (57) (37.5 mg, 50%) as a white solid.

$^1H$ NMR (400 MHZ, DMSO-$d_6$): δ 8.15 (d, J=8.8 Hz, 2H), 7.87 (d, J=8.4 Hz, 2H), 7.11 (d, J=8.4 Hz, 2H), 6.94 (d, J=8.8 Hz, 2H), 5.64 (s, 1H), 5.45 (s, 1H), 5.28 (s, 2H), 4.40 (d, J=6.8 Hz, 1H), 4.25 (t, J=5.6 Hz, 1H), 2.80-2.67 (m, 1H), 2.67-2.55 (m, 1H), 2.54-2.50 (m, 1H), 2.47-2.45 (m, 1H), 2.44-2.37 (m, 1H), 2.36-2.25 (m, 1H), 2.25-2.00 (m, 4H), 2.00-1.90 (m, 1H), 1.85-1.56 (m, 3H), 1.41-1.18 (m, 2H), 0.50 (s, 3H). ESI-MS $[M+H]^+$ calcd for ($C_{35}H_{33}F_5O_5S$) 661.20 found: 661.45.

Scheme 43 illustrates the preparation of compounds 58 and 59.

Scheme 43

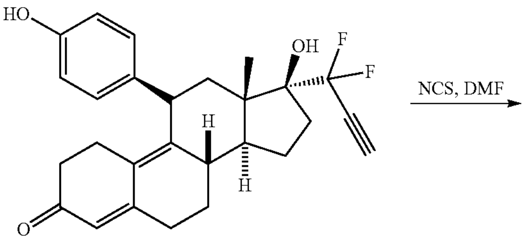

56

-continued

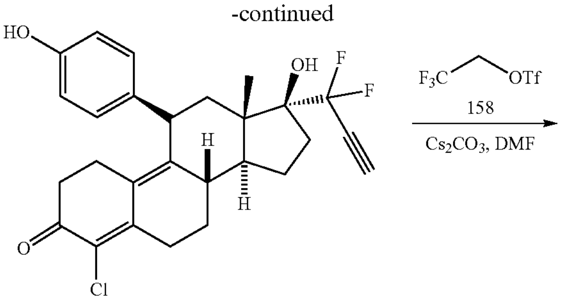

58

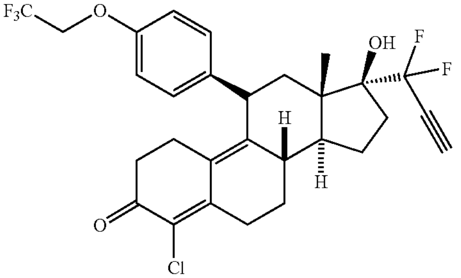

59

Example 51: (8S,11S,13S,14S,17S)-4-chloro-17-(1,1-difluoroprop-2-yn-1-yl)-17-hydroxy-11-(4-hydroxyphenyl)-13-methyl-1,2,6,7,8,11,12,13,14,15,16,17-dodecahydro-3H-cyclopenta[a]phenanthren-3-one (58)

58

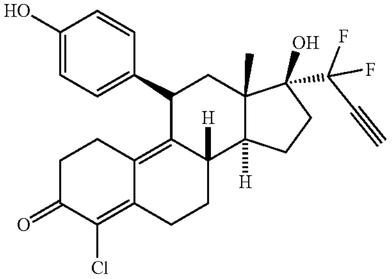

To a stirred solution of (8S,11S,13S,14S, 17S)-17-(1,1-difluoroprop-2-yn-1-yl)-17-hydroxy-11-(4-hydroxyphenyl)-13-methyl-1,2,6,7,8,11,12,13,14,15,16,17-dodecahydro-3H-cyclopenta[a]phenanthren-3-one (56) (50 mg, 0.11 mmol) in DMF (2 mL) was added NCS (17 mg, 0.13 mmol). The reaction mixture was stirred at room temperature for 18 h, quenched with water (10 mL) and extracted with ethyl acetate (10 mL×3). The combined organic layers were washed with water (30 mL) and brine (20 mL×2), dried over anhydrous sodium sulfate and concentrated under reduced pressure. The residue was purified by Prep-TLC (ethyl acetate/petroleum ether=1:2) to afford (8S,11S,13S,14S,17S)-4-chloro-17-(1,1-difluoroprop-2-yn-1-yl)-17-hydroxy-11-(4-hydroxyphenyl)-13-methyl-1,2,6,7,8,11,12,13,14,15,16,17-dodecahydro-3H-cyclopenta[a]phenanthren-3-one (58) (50 mg, 92%) as a white solid. ESI-MS $[M+H]^+$ calcd for $(C_{27}H_{27}ClF_2O_3)$ 473.16, 475.16 found: 473.20, 475.20.

Example 52: (8S,11S,13S,14S,17S)-4-chloro-17-(1,1-difluoroprop-2-yn-1-yl)-17-hydroxy-13-methyl-11-(4-(2,2,2-trifluoroethoxy)phenyl)-1,2,6,7,8,11,12,13,14,15,16,17-dodecahydro-3H-cyclopenta[a]phenanthren-3-one (59)

59

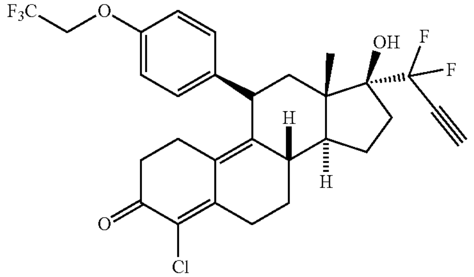

To a stirred solution of (8S,11S,13S,14S,17S)-4-chloro-17-(1,1-difluoroprop-2-yn-1-yl)-17-hydroxy-11-(4-hydroxyphenyl)-13-methyl-1,2,6,7,8,11,12,13,14,15,16,17-dodecahydro-3H-cyclopenta[a]phenanthren-3-one (58) (50 mg, 0.10 mmol) in DMF (2 mL) were added cesium carbonate (69 mg, 0.21 mmol) and 2,2,2-trifluoroethyl trifluoromethanesulfonate (158) (37 mg, 0.16 mmol). The reaction mixture was stirred at room temperature for 4 h, quenched with water (10 mL) and extracted with ethyl acetate (10 mL×3). The combined organic layers was washed with water (20 mL), brine (20 mL×2), dried over anhydrous sodium sulfate and concentrated under vacuum. The residue was purified by Prep-HPLC with the following conditions: Column: XBridge Prep OBD C18 Column, 30×150 mm, 5 um; Mobile Phase A: Water (10 mmol/L $NH_4HCO_3$+0.05% $NH_3H_2O$), Mobile Phase B: ACN; Flow rate: 60 mL/min; Gradient: 35% B to 65% B in 8 min; Wave Length: 254 nm/220 nm; RT (min): 6.98 to afford (8S,11S, 13S,14S, 17S)-4-chloro-17-(1,1-difluoroprop-2-yn-1-yl)-17-hydroxy-13-methyl-11-(4-(2,2,2-trifluoroethoxy)phenyl)-1,2,6,7,8,11,12,13,14,15,16,17-dodecahydro-3H-cyclopenta[a]phenanthren-3-one (59) (1.7 mg, 2.8%) as a white solid.

$^1H$ NMR (400 MHZ, DMSO-$d_6$) δ 7.14 (d, J=8.4 Hz, 2H), 6.96 (d, J=8.8 Hz, 2H), 5.50 (s, 1H), 4.71 (q, J=8.8 Hz, 2H), 4.47 (d, J=6.0 Hz, 1H), 4.28 (t, J=5.4 Hz, 1H) 3.05-3.00 (m, 1H), 2.78-2.72 (m, 1H), 2.65-2.54 (m, 2H), 2.47-2.38 (m, 2H), 2.33-2.24 (m, 2H), 2.18-2.09 (m, 2H), 2.04-2.00 (m, 1H), 1.81-1.64 (m, 3H), 1.44-1.24 (m, 2H), 0.51 (s, 3H). ESI-MS $[M+H]^+$calcd for $(C_{29}H_{28}ClF_5O_3)$ 555.16, 557.16, found: 555.40, 557.40.

Scheme 44 illustrates the preparation of compound 60.

Scheme 44

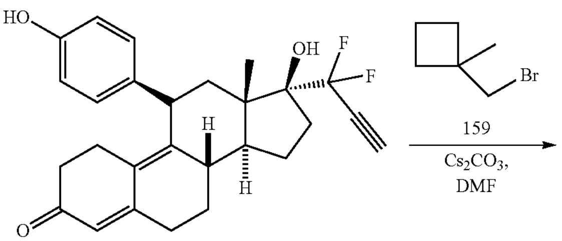

56

-continued

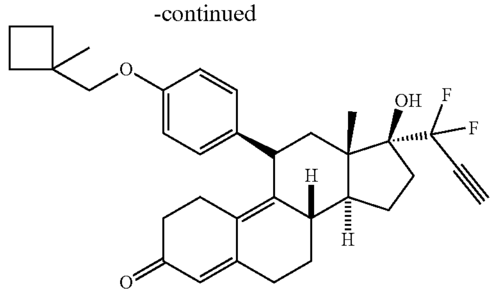

60

Example 53: (8S,11S,13S,14S,17S)-17-(1,1-difluoroprop-2-yn-1-yl)-17-hydroxy-13-methyl-11-(4-((1-methylcyclobutyl)methoxy)phenyl)-1,2,6,7,8,11,12,13,14,15,16,17-dodecahydro-3H-cyclopenta[a]phenanthren-3-one (60)

60

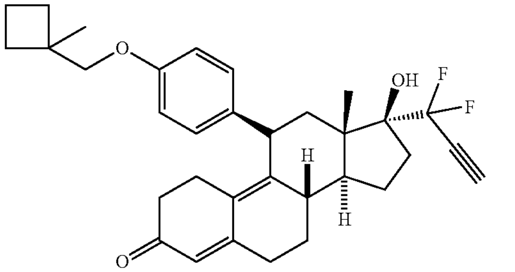

To a stirred solution of (8S,11S,13S,14S,17S)-17-(1,1-difluoroprop-2-yn-1-yl)-17-hydroxy-11-(4-hydroxyphenyl)-13-methyl-1,2,6,7,8,11,12,13,14,15,16,17-dodecahydro-3H-cyclopenta[a]phenanthren-3-one (56) (50 mg, 0.12 mmol) in DMF (4 mL) was added Cs2$CO_3$ (112 mg, 0.34 mmol) and 1-(bromomethyl)-1-methylcyclobutane (159) (37 mg, 0.23 mmol). The reaction mixture was stirred at room temperature for one day, quenched with water (20 mL) and extracted with ethyl acetate (3×30 mL). The combined organic layers was washed with water (50 mL) and brine (2×50 mL), dried over $Na_2SO_4$ and concentrated under vacuum to provide a crude residue which was purified by prep-HPLC under the following conditions: Column: XBridge Prep OBD C18 Column, 30×150 mm, 5 μm; Mobile Phase A: Water (10 mmol/L $NH_4HCO_3$), Mobile Phase B: ACN; Flow rate: 60 mL/min; Gradient: 31% B to 61% B in 7 min; Wave Length: 254 nm/220 nm; RT (min): 6.9 to afford (8S,11S,13S,14S,17S)-17-(1,1-difluoroprop-2-yn-1-yl)-17-hydroxy-13-methyl-11-(4-((1-methylcyclobutyl)methoxy)phenyl)-1,2,6,7,8,11,12,13,14,15,16,17-dodecahydro-3H-cyclopenta[a]phenanthren-3-one (60) (15.3 mg, 25%) as a white solid.

$^1$H NMR (400 MHz, DMSO-$d_6$): δ 7.07 (d, J=8.4 Hz, 2H), 6.86 (d, J=8.6 Hz, 2H), 5.66 (s, 1H), 5.47 (s, 1H), 4.40 (d, J=6.8 Hz, 1H), 4.27 (t, J=5.4 Hz, 1H), 3.76 (s, 2H), 2.78-2.52 (m, 3H), 2.48-2.02 (m, 7H), 2.02-1.58 (m, 10H), 1.45-1.23 (m, 2H), 1.19 (s, 3H), 0.51 (s, 3H). ESI-MS [M+H] calcd for ($C_{33}H_{38}F_2O_3$) 521.28 found: 521.20.

Scheme 45 illustrates the preparation of compounds 61 and 62.

Scheme 45

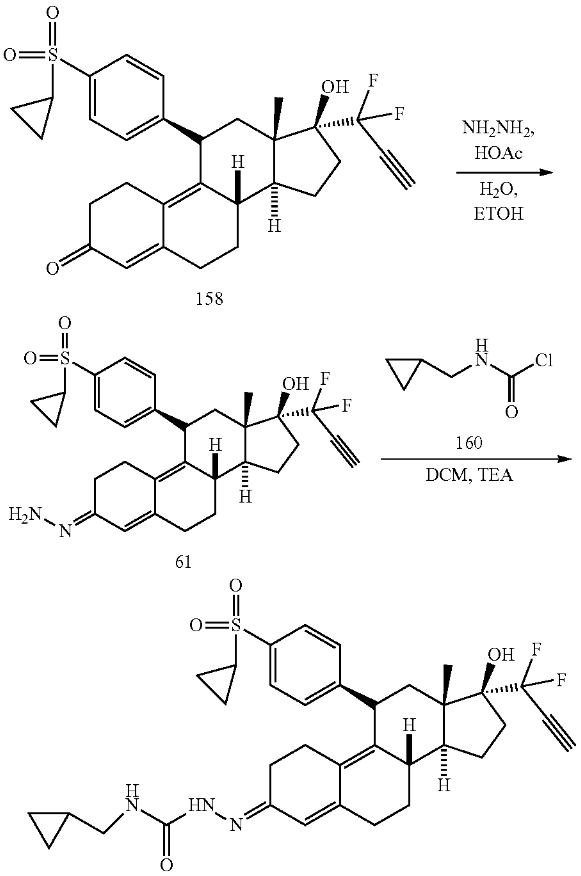

158

61

62

Example 54: (8S,11S,13S,14S,17S,E)-11-(4-(cyclopropylsulfonyl)phenyl)-17-(1,1-difluoroprop-2-yn-1-yl)-3-hydrazineylidene-13-methyl-2,3,6,7,8,11,12,13,14,15,16,17-dodecahydro-1H-cyclopenta[a]phenanthren-17-ol (61)

61

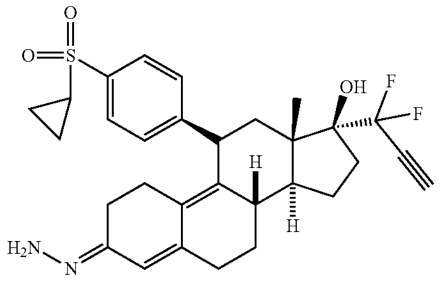

To a stirred solution of (8S,11R,13S,14S,17S)-11-(4-(cyclopropylsulfonyl)phenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (158) (300 mg, 0.57 mmol) in ethanol (8 mL) were added hydrazine hydrate (0.06 mL, 1.14 mmol) and acetic acid (6.53 μL, 0.11 mmol). The reaction mixture was stirred at room temperature for 16 h and concentrated under vacuum to give (8S,11S,13S,14S,17S,E)-11-(4-(cyclopropylsulfonyl)phenyl)-17-(1,1-difluoroprop-2-yn-1-yl)-3-hydrazineylidene-13-methyl-2,3,6,7,8,11,12,13,14,15,16,17-dodecahydro-1H-cyclopenta[a]phenanthren-17-ol (61) (350 mg, crude) as a light-yellow solid. ESI-MS $[M+H]^+$ calcd for $(C_{30}H_{34}F_2N_2O_3S)$ 541.23 found: 541.30.

Preparation of Compound 160

160

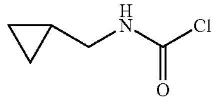

To a stirred solution of 1-cyclopropylmethanamine (50 mg, 0.70 mmol) in dichloromethane (4 mL) were added triphosgene (104 mg, 0.35 mmol) and sodium bicarbonate (177 mg, 2.11 mmol). The reaction mixture was stirred at room temperature for 2 h, filtered and concentrated under vacuum to provide crude 160.

Example 55: (E)-N-(cyclopropylmethyl)-2-((8S,11S,13S,14S,17S)-11-(4-(cyclopropylsulfonyl)phenyl)-17-(1,1-difluoroprop-2-yn-1-yl)-17-hydroxy-13-methyl-1,2,6,7,8,11,12,13,14,15,16,17-dodecahydro 3H-cyclopenta[a]phenanthren-3-ylidene)hydrazine-1-carboxamide (62)

62

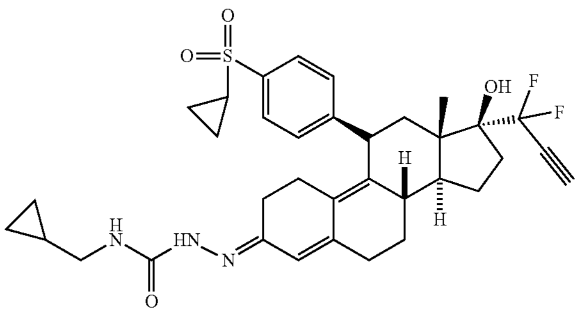

Crude compound 160 was dissolved in dichloromethane (3 mL) and added dropwise to a solution of (8S,11S,13S,14S,17S,E)-11-(4-(cyclopropylsulfonyl)phenyl)-17-(1,1-difluoroprop-2-yn-1-yl)-3-hydrazineylidene-13-methyl-2,3,6,7,8,11,12,13,14,15,16,17-dodecahydro-1H-cyclopenta[a]phenanthren-17-ol (61) (50 mg, 0.09 mmol) and triethylamine (15 mg, 0.15 mmol) in dichloromethane (4 mL). The reaction mixture was stirred at room temperature for 16 h and concentrated under vacuum to provide a residue which was purified by prep-HPLC under the following conditions: Column: XBridge Prep OBD C18 Column, 30×150 mm, 5 um; Mobile Phase A: Water (10 mmol/L $NH_4HCO_3$), Mobile Phase B: ACN; Flow rate: 45 mL/min; Gradient: 34% B to 66% B in 7 min; Wave Length: 254 nm/220 nm; RT (min): 6.4 to afford (E)-N-(cyclopropylmethyl)-2-((8S,11S,13S,14S,17S)-11-(4-(cyclopropylsulfonyl)phenyl)-17-(1,1-difluoroprop-2-yn-1-yl)-17-hydroxy-13-methyl-1,2,6,7,8,11,12,13,14,15,16,17-dodecahydro 3H-cyclopenta[a]phenanthren-3-ylidene)hydrazine-1-carboxamide (62) (7.4 mg, 12%) as a white solid.

$^1H$ NMR (400 MHZ, DMSO-$d_6$): δ 9.16 (s, 1H), 7.79 (d, J=8.4 Hz, 2H), 7.47 (d, J=8.4 Hz, 2H), 6.72 (t, J=6.0 Hz, 1H), 5.89 (s, 1H), 5.48 (s, 1H), 4.54 (d, J=7.0 Hz, 1H), 4.29 (t, J=5.4 Hz, 1H), 2.97 (t, J=6.4 Hz, 2H), 2.87-2.76 (m, 1H), 2.69-2.54 (m, 3H), 2.49-2.41 (m, 3H), 2.35-2.21 (m, 1H), 2.19-2.04 (m, 2H), 2.03-1.93 (m, 1H), 1.84-1.59 (m, 4H), 1.45-1.21 (m, 2H), 1.14-1.06 (m, 2H), 1.05-0.99 (m, 2H), 0.99-0.91 (m, 1H), 0.43 (s, 3H), 0.41-0.34 (m, 2H), 0.21-0.14 (m, 2H). ESI-MS $[M+H]^+$ calcd for $(C_{35}H_{41}F_2N_3O_4S)$ 638.28 found: 638.50.

Scheme 46 illustrates the preparation of compound 63.

Scheme 46

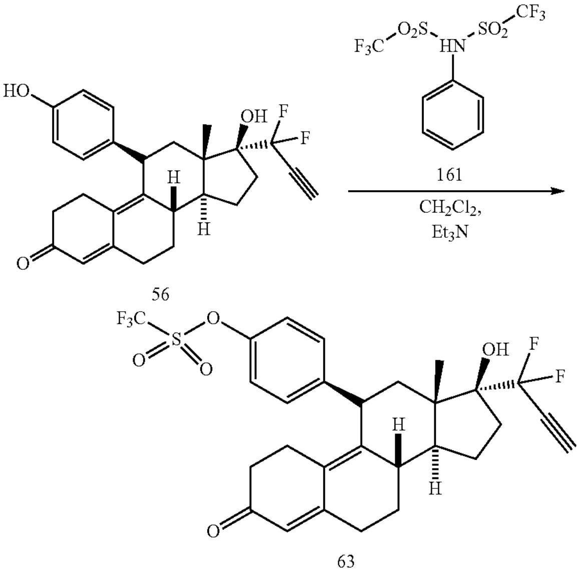

Example 56:4-((8S,11S,13S,14S,17S)-17-(1,1-difluoroprop-2-yn-1-yl)-17-hydroxy-13-methyl-3-oxo-2,3,6,7,8,11,12,13,14,15,16,17-dodecahydro-1H-cyclopenta[a]phenanthren-11-yl)phenyl trifluoromethanesulfonate (63)

63

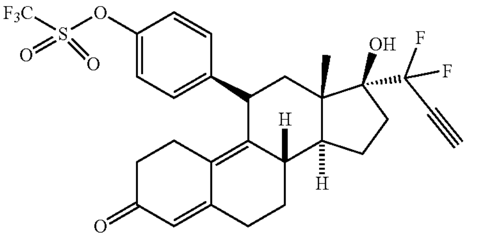

To a mixture of (8S,11S,13S,14S,17S)-17-(1,1-difluoroprop-2-yn-1-yl)-17-hydroxy-11-(4-hydroxyphenyl)-13-methyl-1,2,6,7,8,11,12,13,14,15,16,17-dodecahydro-3H-cyclopenta[a]phenanthren-3-one (56) (50 mg, 0.114 mmol) and 1,1,1-trifluoro-N-phenyl-N-((trifluoromethyl)sulfonyl)methanesulfonamide (161) (49 mg, 0.137 mmol) in dichloromethane (4 mL) was added triethylamine (23 mg, 0.228 mmol). The reaction mixture was stirred at room temperature for 1 day, concentrated under vacuum and the residue was purified by Prep-HPLC under the following conditions: Column: XBridge Prep OBD $C_{18}$ Column, 30×150 mm, 5 μm; Mobile Phase A: Water (10 mmol/L $NH_4HCO_3$), Mobile Phase B: ACN; Flow rate: 60 mL/min; Gradient: 50% B to 80% B in 7 min; Wave Length: 254 nm/220 nm; RT (min): 6.1 to afford 4-((8S,11S,13S,14S,17S)-17-(1,1-difluoroprop-2-yn-1-yl)-17-hydroxy-13-methyl-3-oxo-2,3,6,7,8,11,12,13,14,15,16,17-dodecahydro-1H-cyclopenta[a]phenanthren-11-yl) phenyl trifluoromethanesulfonate (63) (11.3 mg, 17%) as a white solid.

$^1$H NMR (400 MHZ, DMSO-$d_6$) δ 7.46-7.30 (m, 4H), 5.68 (s, 1H), 5.51 (s, 1H), 4.57 (d, J=7.2 Hz, 1H), 4.28 (t, J=5.6 Hz, 1H), 2.84-2.61 (m, 2H), 2.59-2.53 (m, 1H), 2.49-2.23 (m, 4H), 2.23-1.93 (m, 4H), 1.88-1.58 (m, 3H), 1.46-1.18 (m, 2H), 0.45 (s, 3H). ESI-MS [M+H]$^+$ calcd for ($C_{28}H_{27}F_5O_5S$) 571.15 found: 571.35.

Scheme 47 illustrates the preparation of compound 64.

Scheme 47

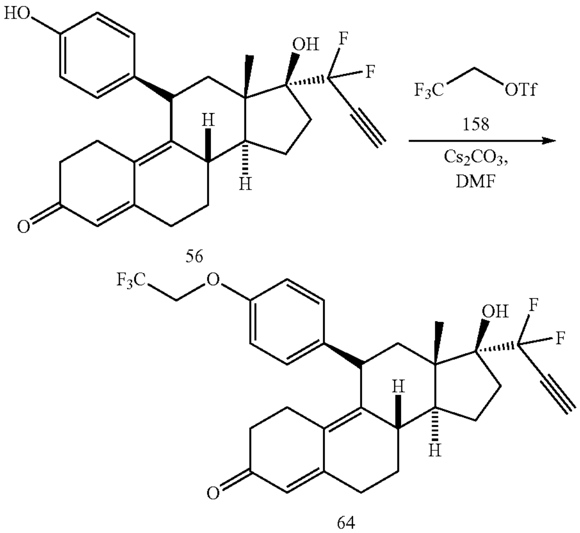

56

64

Example 57: (8S,11S,13S,14S,17S)-17-(1,1-difluoroprop-2-yn-1-yl)-17-hydroxy-13-methyl-11-(4-(2,2,2-trifluoroethoxy)phenyl)-1,2,6,7,8,11,12,13,14,15,16,17-dodecahydro-3H-cyclopenta[a]phenanthren-3-one (64)

64

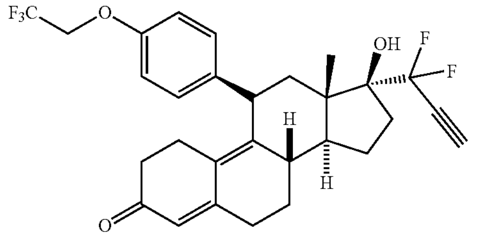

To a stirred solution of (8S,11S,13S,14S, 17S)-17-(1,1-difluoroprop-2-yn-1-yl)-17-hydroxy-11-(4-hydroxyphenyl)-13-methyl-1,2,6,7,8,11,12,13,14,15,16,17-dodecahydro-3H-cyclopenta[a]phenanthren-3-one (56) (40 mg, 0.09 mmol) in DMF (4 mL) were added $Cs_2CO_3$ (60 mg, 0.18 mmol) and 2,2,2-trifluoroethyl trifluoromethanesulfonate (155) (32 mg, 0.14 mmol). The reaction mixture was stirred at room temperature for 4 h, quenched with water (20 mL) and extracted with ethyl acetate (3×30 mL). The combined organic layers were washed with water (50 mL), brine (2×50 mL), dried over $Na_2SO_4$ and concentrated under vacuum to provide a residue which was purified by prep-HPLC under the following conditions: Column: YMC-Actus Triart C 18ExRS, 30×150 mm, 5 um; Mobile Phase A: Water (10 mmol/L $NH_4HCO_3$), Mobile Phase B: ACN; Flow rate: 60 mL/min; Gradient: 41% B to 71% B in 8 min; Wave Length: 254 nm/220 nm; RT (min): 7.0 to afford (8S,11S,13S,14S,17S)-17-(1,1-difluoroprop-2-yn-1-yl)-17-hydroxy-13-methyl-11-(4-(2,2,2-trifluoroethoxy)phenyl)-1,2,6,7,8,11,12,13,14,15,16,17-dodecahydro-3H-cyclopenta[a]phenanthren-3-one (64) (40.5 mg, 85%) as a white solid.

$^1$H NMR (400 MHZ, DMSO-$d_6$): δ 7.14 (d, J=8.8 Hz, 2H), 6.96 (d, J=8.8 Hz, 2H), 5.66 (s, 1H), 5.49 (s, 1H), 4.70 (q, J=8.8 Hz, 2H), 4.43 (d, J=6.8 Hz, 1H), 4.27 (t, J=5.4 Hz, 1H), 2.79-2.69 (m, 1H), 2.68-2.57 (m, 1H), 2.56-2.52 (m, 1H), 2.50-2.46 (m, 1H), 2.45-2.39 (m, 1H), 2.38-2.29 (m, 1H), 2.28-1.94 (m, 5H), 1.87-1.60 (m, 3H), 1.43-1.21 (m, 2H), 0.50 (s, 3H). ESI-MS [M+H]$^+$ calcd for ($C_{29}H_{29}F_5O_3$) 521.20 found: 521.35.

Scheme 48 illustrates the preparation of compounds 65 and 66.

Scheme 48

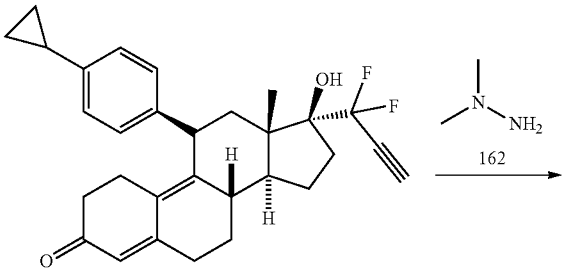

100

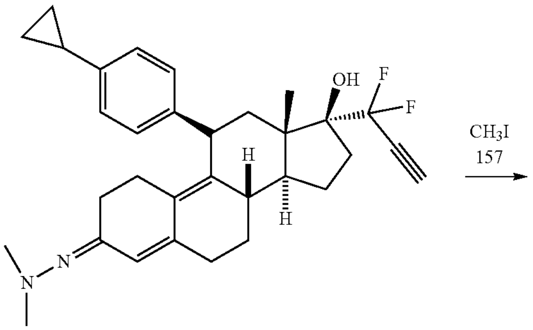

65

-continued

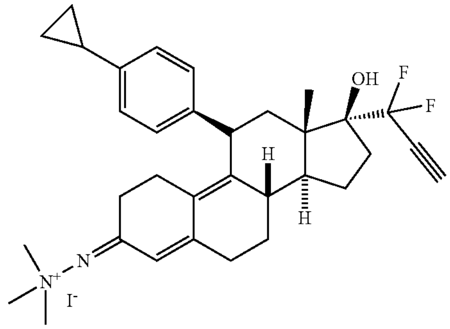

66

Example 58: (8S,11S,13S,14S,17S)-11-(4-cyclopropylphenyl)-17-(1,1-difluoroprop-2-yn-1-yl)-3-(2,2-dimethylhydrazineylidene)-13-methyl-2,3,6,7,8,11,12,13,14,15,16,17-dodecahydro-1H-cyclopenta[a]phenanthren-17-ol (65)

65

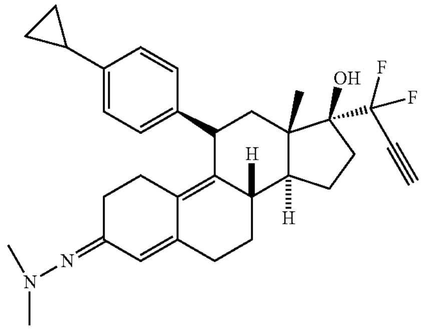

To a stirred solution of (8S,11R,13S,14S, 17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (150 mg, 0.32 mmol, 1.0 equiv) in pyridine (3.2 mL, 0.1M) was added 1,1-dimethylhydrazine: HCl (162) (94.0 mg, 0.97 mmol, 3.0 equiv) followed by p-toluenesulfonic acid monohydrate (31.0 mg, 0.16 mmol, 0.5 equiv) at ambient temperature. The reaction mixture was stirred at room temperature for 18h until the reaction was determined to be complete by LCMS analysis. The reaction mixture was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to afford (8S,11S,13S,14S,17S)-11-(4-cyclopropylphenyl)-17-(1,1-difluoroprop-2-yn-1-yl)-3-(2,2-dimethylhydrazineylidene)-13-methyl-2,3,6,7,8,11,12,13,14,15,16,17-dodecahydro-1H-cyclopenta[a]phenanthren-17-ol (65) (125 mg, 76% yield).

Example 59:2-((8S,11S,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)-1,1,1-trimethylhydrazin-1-ium (66)

66

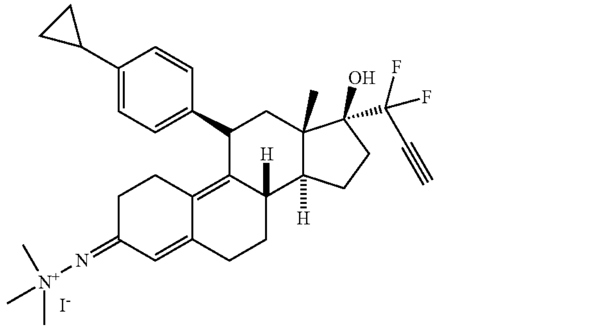

To (8S,11S,13S,14S,17S)-11-(4-cyclopropylphenyl)-17-(1,1-difluoroprop-2-yn-1-yl)-3-(2,2-dimethylhydrazineylidene)-13-methyl-2,3,6,7,8,11,12,13,14,15,16,17-dodecahydro-1H-cyclopenta[a]phenanthren-17-ol (65) (10 mg, 0.02 mmol) in dichloromethane (0.2 mL) was added methyl iodide (0.2 mL) at room temperature. The reaction mixture was stirred room temperature for 18 h until the reaction was determined to be complete by LCMS analysis. The reaction mixture was concentrated to afford (2-((8S,11S,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)-1,1,1-trimethylhydrazin-1-ium (66) (8.4 mg, 82%).

$^1$H NMR (500 MHZ, Chloroform-d) δ 7.03-6.91 (m, 4H), 4.33 (dd, J=23.4, 6.5 Hz, 1H), 3.75 (s, 2H), 3.72-3.66 (m, 1H), 3.64 (s, 1H), 3.19 (q, J=7.6, 7.5, 7.5 Hz, 1H), 3.15-2.84 (m, 2H), 2.84-2.65 (m, 3H), 2.64-2.50 (m, 2H), 2.49-2.27 (m, 4H), 2.26-1.87 (m, 3H), 1.84 (t, J=7.4, 7.4 Hz, 2H), 1.77 (h, J=5.4, 5.4, 5.0, 5.0, 5.0 Hz, 2H), 1.54-1.36 (m, 2H), 0.98-0.89 (m, 2H), 0.70-0.56 (m, 5H). Calculated mass: 519.6, Mass (ESI+) observed: 519.4 [M+H].

Scheme 49 illustrates the preparation of compounds 67 and 68.

Scheme 49

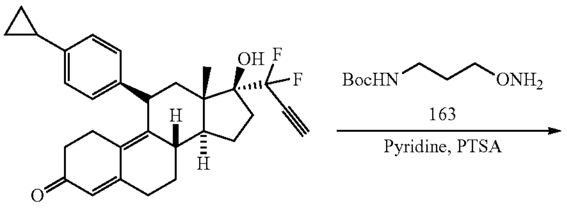

100

-continued

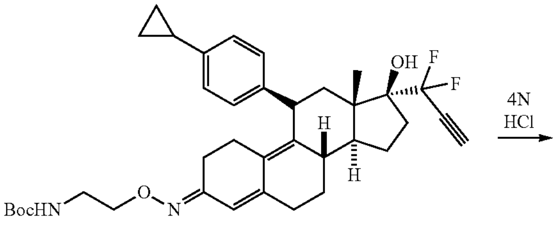

67

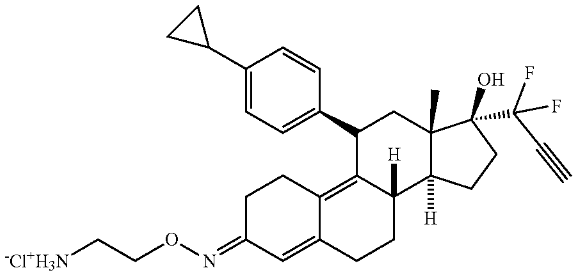

68

Example 60: tert-butyl (2-((((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)amino)oxy)ethyl)carbamate (67)

67

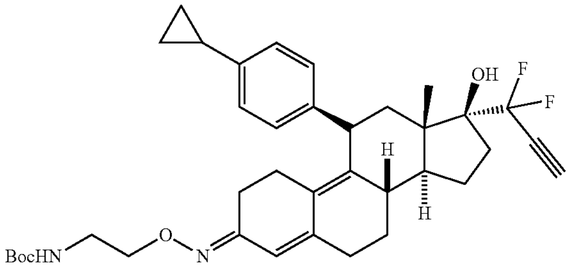

To a stirred solution of (8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (100) (150 mg, 0.32 mmol, 1.0 equiv) in pyridine (3.2 mL, 0.1M) was added tert-butyl (2-(aminooxy)ethyl)carbamate (163) (114.0 mg, 0.65 mmol, 2.0 equiv) followed by p-toluenesulfonic acid monohydrate (31.0 mg, 0.16 mmol, 0.5 equiv) at ambient temperature. The reaction mixture was stirred at room temperature for 3 h at which time the reaction was determined to be complete by LCMS analysis. The reaction mixture was purified by reverse phase HPLC (CLIPEUS C-18 10 um (Higgins Analytical Inc) 20×250 mm; ELSD and 254 UV detection; mobile phase A: 10 mmol ammonium bicarbonate in water; mobile phase B: 5% aqueous acetonitrile to 90% aqueous acetonitrile over 40 min) to afford (67) (156 mg, 77% yield).

Example 61:2-((((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)amino)oxy)ethan-1-aminium chloride (68)

68

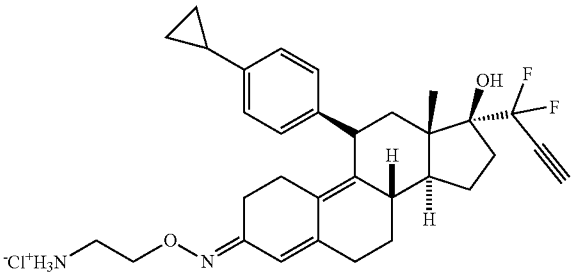

To tert-butyl (2-((((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)amino)oxy)ethyl)carbamate (67) (25 mg, 0.04 mmol) was added 4M HCl (in dioxane) (0.4 mL) at room temperature. The reaction mixture was stirred room temperature for 2 h at which time the reaction was determined to be complete by LCMS analysis. The reaction mixture was concentrated to afford (2-((((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)amino)oxy)ethan-1-aminium chloride (68) (19.1 mg, 74%).

$^{1}H$ NMR (500 MHZ, DMSO-d6): δ 7.86 (d, J=16.8 Hz, 3H), 7.02 (dd, J=8.4, 4.6 Hz, 2H), 6.97-6.92 (m, 2H), 6.41 (s, 1H), 5.42 (s, 1H), 4.31 (d, J=7.9 Hz, 1H), 4.24 (t, J=5.3, 5.3 Hz, 1H), 4.10 (dt, J=12.6, 5.2, 5.2 Hz, 2H), 3.72-3.62 (m, 1H), 3.55 (s, 2H), 3.46 (dd, J=15.0, 4.8 Hz, 1H), 3.03 (dq, J=10.0, 5.5, 5.5, 5.5 Hz, 2H), 2.62-2.50 (m, 2H), 2.40 (dd, J=12.9, 7.1 Hz, 2H), 2.29-2.03 (m, 4H), 1.97-1.90 (m, 1H), 1.83 (ddd, J=13.5, 8.4, 5.1 Hz, 2H), 1.76-1.57 (m, 3H), 1.28 (dt, J=44.9, 7.9, 7.9 Hz, 2H), 0.94-0.81 (m, 2H), 0.59 (qd, J=5.1, 4.3, 4.3, 2.9 Hz, 2H), 0.45 (d, J=3.8 Hz, 3H). Calculated mass: 520.2, Mass (ESI+) observed: 521.5 [M+H].

Scheme 50 illustrates the preparation of compounds 69 and 70.

Scheme 50

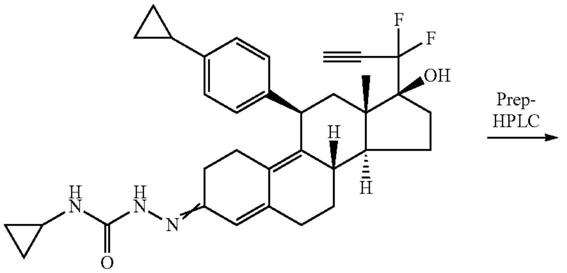

32

-continued

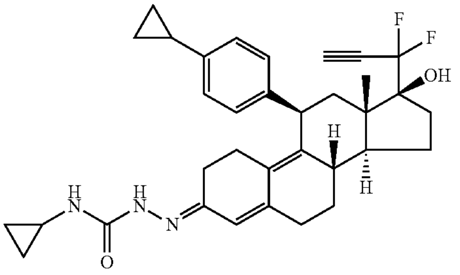

69

+

-continued

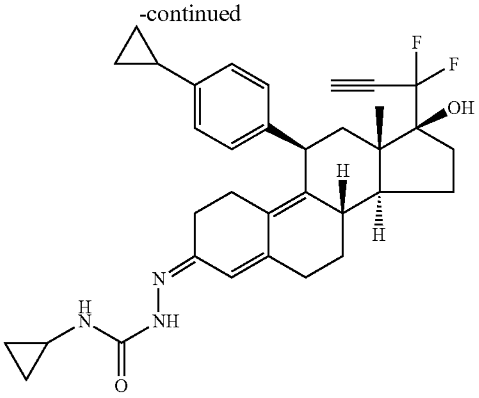

70

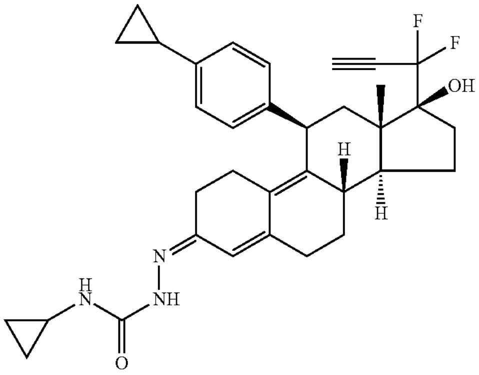

70

Example 62: (E)-N-cyclopropyl-2-((8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)hydrazine-1-carboxamide (69) and (Z)—N-cyclopropyl-2-((8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)hydrazine-1-carboxamide (70)

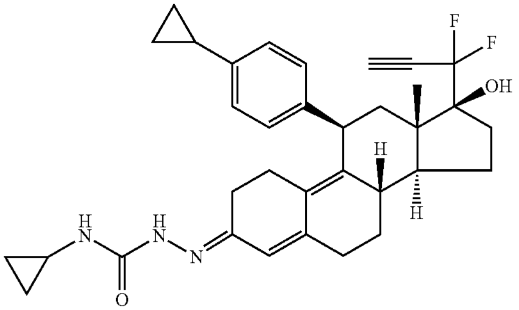

69

+

N'-((8S,11S,13S,14S,17S,E)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene) methanesulfonohydrazide (33) (75 mg) was separated by Prep-HPLC with the following conditions: Column: XBridge Prep OBD C18 Column, 30×150 mm, 5 um; Mobile Phase A: Water (10 mmol/L $NH_4HCO_3$), Mobile Phase B: Acetonitrile; Flow rate: 60 mL/min; Gradient: 26% B to 56% B in 8.0 min; Wave Length: 254 nm/220 nm; RT1 (min): 7.15 to afford (Z)—N-cyclopropyl-2-((8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)hydrazine-1-carboxamide (70) (20.6 mg, 27%) as a white solid; and RT2 (min): 7.3 to afford (E)-N-cyclopropyl-2-((8S,11R,13S,14S,17S)-11-(4-cyclopropylphenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-ylidene)hydrazine-1-carboxamide (69) (26.4 mg, 35%) as a white solid.

Compound 69: $^1H$ NMR (400 MHZ, DMSO-$d_6$): δ 9.17 (s, 1H), 7.04 (d, J=8.0 Hz, 2H), 6.96 (d, J=8.0 Hz, 2H), 6.64 (d, J=2.4 Hz, 1H), 5.83 (s, 1H), 5.42 (s, 1H), 4.31 (d, J=6.4 Hz, 1H), 4.25 (t, J=5.2 Hz, 1H), 2.69-2.52 (m, 3H), 2.49-2.35 (m, 4H), 2.24-2.02 (m, 3H), 2.00-1.89 (m, 1H), 1.88-1.55 (m, 5H), 1.42-1.18 (m, 2H), 0.96-0.84 (m, 2H), 0.68-0.54 (m, 4H), 0.46 (s, 5H). ESI-MS $[M+H]^+$ calcd for ($C_{34}H_{39}F_2N_3O_2$) 560.30 found: 560.45.

Compound 70: $^1H$ NMR (400 MHZ, DMSO-$d_6$): δ 9.48 (s, 1H), 7.04 (d, J=8.0 Hz, 2H), 6.96 (d, J=8.0 Hz, 2H), 6.57 (d, J=2.8 Hz, 1H), 6.46 (s, 1H), 5.43 (s, 1H), 4.30 (d, J=6.4 Hz, 1H), 4.26 (t, J=5.3 Hz, 1H), 2.61-2.51 (m, 3H), 2.47-2.35 (m, 3H), 2.34-2.04 (m, 4H), 2.00-1.91 (m, 1H), 1.90-1.79 (m, 2H), 1.78-1.57 (m, 3H), 1.41-1.18 (m, 2H), 0.97-0.82 (m, 2H), 0.67-0.52 (m, 4H), 0.46 (s, 5H). ESI-MS $[M+H]^+$ calcd for ($C_{34}H_{39}F_2N_3O_2$) 560.30 found: 560.45.

Scheme 51 illustrates the preparation of compound 71.

Scheme 51

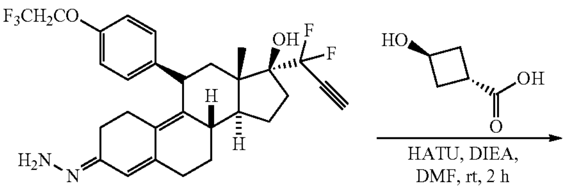

54

-continued

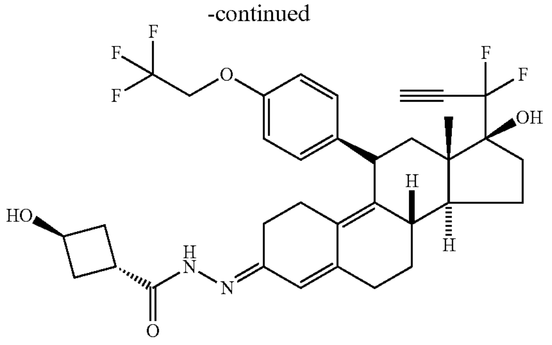

71

Example 63: trans-N'-((8S,11R,13S,14S,17S)-17-(1,1-difluoroprop-2-yn-1-yl)-17-hydroxy-13-methyl-11-(4-(2,2,2-trifluoroethoxy)phenyl)-1,2,6,7,8,11,12,13,14,15,16,17-dodecahydro-3H-cyclopenta[a]phenanthren-3-ylidene)-3-hydroxycyclobutane-1-carbohydrazide (71)

71

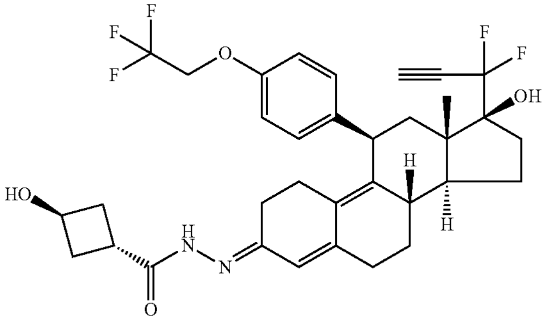

To a mixture of (8S,11R,13S,14S,17S)-17-(1,1-difluoroprop-2-yn-1-yl)-3-hydrazineylidene-13-methyl-11-(4-(2,2,2-trifluoroethoxy)phenyl)-2,3,6,7,8,11,12,13,14,15,16,17-dodecahydro-1H-cyclopenta[a]phenanthren-17-ol (54) (60 mg, 0.11 mmol, 1 equiv) and trans-3-hydroxycyclobutanecarboxylic acid (16 mg, 0.13 mmol, 1.2 equiv) in DMF (2.5 mL) was added HATU (64 mg, 0.17 mmol, 1.5 equiv) and DIEA (44 mg, 0.34 mmol, 3 equiv). The reaction was stirred at room temperature for 2 h. The reaction mixture was quenched with water (20 mL) and extracted with ethyl acetate (50 mL×3). The combined organic layers was washed with water (100 mL) and brine (100 mL), dried over anhydrous sodium sulfate and concentrated under vacuum. The residue was purified by Pre-HPLC with the following conditions: Column: XBridge Prep OBD C18 Column, 30×150 mm, 5 μm; Mobile Phase A: Water (10 mmol/L $NH_4HCO_3$), Mobile Phase B: ACN; Flow rate: 60 mL/min; Gradient: 32% B to 62% B in 7 min; Wave Length: 254 nm/220 nm; RT (min): 6.9 to give trans-N'-((8S,11R,13S,14S,17S)-17-(1,1-difluoroprop-2-yn-1-yl)-17-hydroxy-13-methyl-11-(4-(2,2,2-trifluoroethoxy)phenyl)-1,2,6,7,8,11,12,13,14,15,16,17-dodecahydro-3H-cyclopenta[a]phenanthren-3-ylidene)-3-hydroxycyclobutane-1-carbohydrazide (71) (16.7 mg, 23%) as a white solid.

$^1H$ NMR (400 MHZ, DMSO-$d_6$) δ 10.40-9.83 (m, 1H), 7.16-7.09 (m, 2H), 6.99-6.91 (m, 2H), 6.55-5.78 (m, 1H), 5.55-5.37 (m, 1H), 5.09-4.97 (m, 1H), 4.70 (q, J=8.9 Hz, 2H), 4.43-4.10 (m, 3H), 3.61-3.49 (m, 0.5H), 3.11-2.95 (m, 0.5H), 2.69-2.53 (m, 3H), 2.44-2.36 (m, 2H), 2.36-2.23 (m, 3H), 2.21-2.06 (m, 3H), 2.05-1.89 (m, 3H), 1.86-1.55 (m, 4H), 1.42-1.20 (m, 2H), 0.47 (d, J=5.4 Hz, 3H). Calculated mass: 632.27, Mass (ESI+) observed: 633.55 [M+H].

Scheme 52 illustrates the preparation of compound 72.

Scheme 52

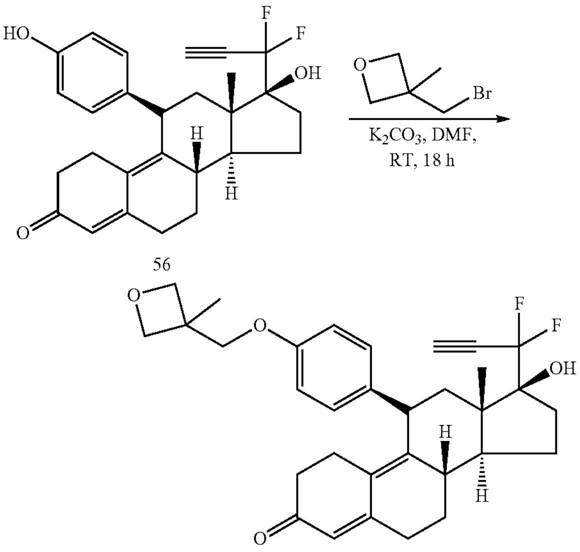

56

72

Example 64: (8S,11R,13S,14S,17S)-17-(1,1-difluoroprop-2-yn-1-yl)-17-hydroxy-13-methyl-11-(4-((3-methyloxetan-3-yl)methoxy)phenyl)-1,2,6,7,8,11,12,13,14,15,16,17-dodecahydro-3H-cyclopenta[a]phenanthren-3-one (72)

72

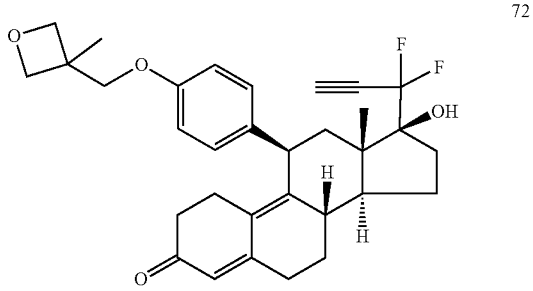

To a solution of (8S,11R,13S,14S, 17S)-17-(1,1-difluoroprop-2-yn-1-yl)-17-hydroxy-11-(4-hydroxyphenyl)-13-methyl-1,2,6,7,8,11,12,13,14,15,16,17-dodecahydro-3H-cyclopenta[a]phenanthren-3-one (54) (50 mg, 0.12 mmol, 1 equiv) in DMF (2 mL) was added 3-(bromomethyl)-3-methyloxetane (57 mg, 0.34 mmol, 3 equiv) and $K_2CO_3$ (95 mg, 0.68 mmol, 6 equiv). The reaction mixture was stirred at room temperature for 18 h. The reaction mixture was quenched with water (15 mL) and extracted with ethyl acetate (3×20 mL). The combined organic layers was washed with water (50 mL) and brine (50 mL), dried over sodium sulfate and concentrated under vacuum. The residue was purified by pre-HPLC with the following conditions: Column: XBridge Prep OBD C18 Column, 30×150 mm, 5 μm; Mobile Phase A: Water (10 mmol/L $NH_4HCO_3$+0.05% $NH_3H_2O$), Mobile Phase B: ACN; Flow rate: 60 mL/min; Gradient: 39% B to 69% B in 8 min; Wave Length: 254 nm/220 nm; RT (min): 7.5 to give (8S,11R,13S,14S, 17S)-17-(1,1-difluoroprop-2-yn-1-yl)-17-hydroxy-13-methyl-11-(4-((3-methyloxetan-3-yl)methoxy)phenyl)-1,2,6,7,8,11,12,13,14,15,16,17-dodecahydro-3H-cyclopenta[a]phenanthren-3-one (72) (33.3 mg, 55%) as a white solid.

$^1$H NMR (400 MHZ, DMSO-$d_6$) δ 7.10 (d, J=8.4 Hz, 2H), 6.89 (d, J=8.4 Hz, 2H), 5.66 (s, 1H), 5.48 (s, 1H), 4.47 (d, J=5.7 Hz, 2H), 4.41 (d, J=7.0 Hz, 1H), 4.34-4.23 (m, 3H), 4.00 (s, 2H), 2.80-2.69 (m, 1H), 2.68-2.57 (m, 1H), 2.57-2.51 (m, 1H), 2.45-2.39 (m, 1H), 2.38-2.05 (m, 6H), 2.04-1.93 (m, 1H), 1.86-1.58 (m, 3H), 1.45-1.22 (m, 5H), 0.51 (s, 3H). Calculated mass: 522.26, Mass (ESI+) observed: 523.40 [M+H].

Scheme 53 illustrates the preparation of compounds 73, 74, 75 and 76.

Scheme 53

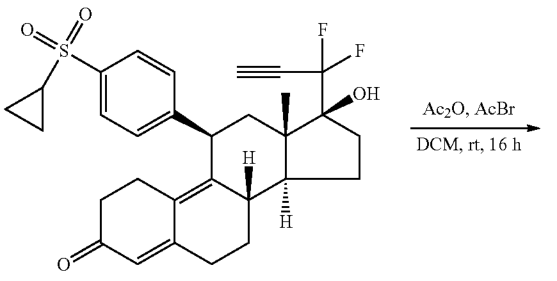

63

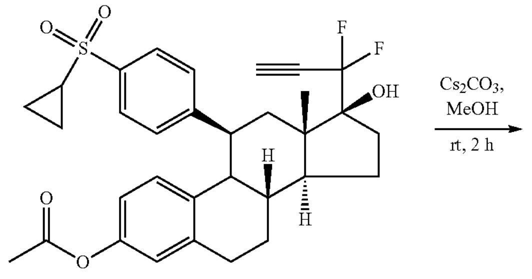

73

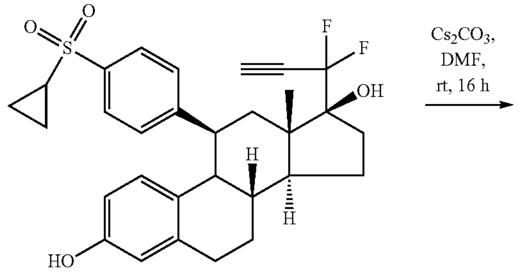

74

-continued

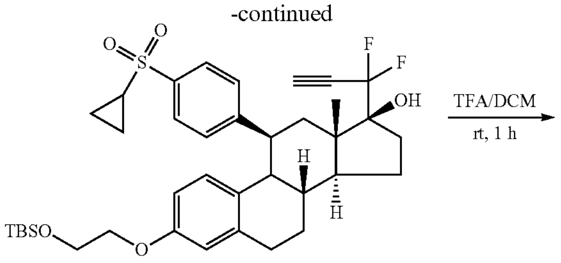

75

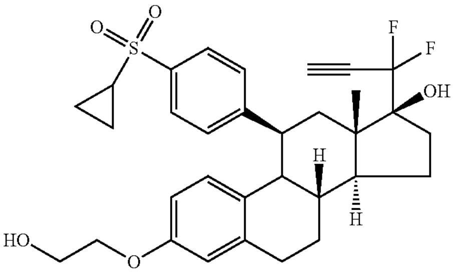

76

Example 65: (8S,11S,13S,14S,17S)-11-(4-(cyclopropylsulfonyl)phenyl)-17-(1,1-difluoroprop-2-yn-1-yl)-17-hydroxy-13-methyl-7,8,9,11,12,13,14,15,16,17-decahydro-6H-cyclopenta[a]phenanthren-3-yl acetate (73)

73

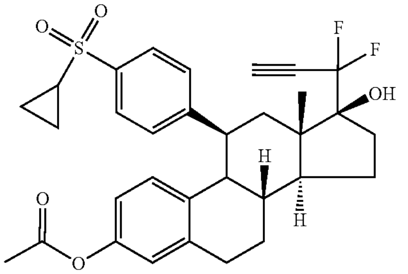

To a stirred solution of (8S,11R,13S,14S,17S)-11-(4-(cyclopropylsulfonyl)phenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (63) (400 mg, 0.76 mmol, 1.0 equiv) in DCM (40 mL) were added acetic anhydride (78 mg, 0.76 mmol, 1.0 equiv) and acetyl bromide (233 mg, 1.90 mmol, 2.5 equiv) at ambient temperature. The reaction mixture was stirred at room temperature for 16 h at which time the reaction was determined to be complete by LCMS analysis. The reaction mixture was poured into a solution of sodium bicarbonate (661 mg, 7.6 mmol, 10 equiv) in water (300 mL) and extracted with ethyl acetate (80 mL×3). The combined organic layers was washed with water (2×150 mL) and brine (150 mL), dried over anhydrous sodium sulfate and concentrated under vacuum to give the product (410 mg, 95% yield) as a light-yellow solid. The product (60 mg) was purified by Prep-HPLC with the following conditions: Column: XBridge Prep OBD C18 Column, 30×150 mm, 5 μm; Mobile Phase A: Water (10 mmol/L $NH_4HCO_3$), Mobile Phase B: 20 mm NaOH+10% ACN; Flow rate: 60 mL/min; Gradient: 45% B to 75% B in 7 min; Wave Length: 254 nm/220 nm; RT (min): 6.9 to afford (8S,11S,13S,14S,17S)-11-(4-(cyclopropylsulfonyl)phenyl)-17-(1,1-difluoroprop-2-yn-1-yl)-17-hydroxy-13-methyl-7,8,9,11,12,13,14,15,16,17-decahydro-6H-cyclopenta[a]phenanthren-3-yl acetate (73) (13.5 mg, 22% yield) as a white solid.

$^1$H NMR (400 MHZ, DMSO-$d_6$) δ 7.60 (d, J=8.2 Hz, 2H), 7.31 (d, J=8.1 Hz, 2H), 6.97 (d, J=8.6 Hz, 1H), 6.86 (d, J=2.6 Hz, 1H), 6.67 (dd, J=8.5, 2.6 Hz, 1H), 5.41 (s, 1H), 4.34-4.18 (m, 2H), 3.05 (t, J=14.4 Hz, 1H), 2.96-2.70 (m, 3H), 2.48-2.37 (m, 2H), 2.30-2.07 (m, 5H), 2.06-1.84 (m, 2H), 1.78-1.62 (m, 2H), 1.45-1.29 (m, 2H), 1.12-0.91 (m, 4H), 0.35 (s, 3H). Calculated mass: 568.21, Mass (ESI−) observed: 567.35 [M−H].

Example 66: 8S,11S,13S,14S,17S)-11-(4-(cyclopropylsulfonyl)phenyl)-17-(1,1-difluoroprop-2-yn-1-yl)-13-methyl-7,8,9,11,12,13,14,15,16,17-decahydro-6H-cyclopenta[a]phenanthrene-3,17-diol (74)

74

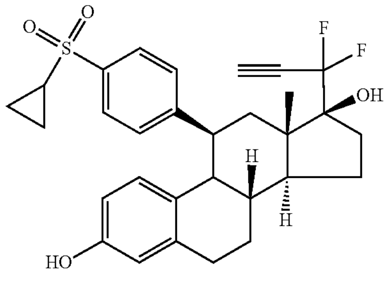

To a stirred solution of (8S,11S,13S,14S,17S)-11-(4-(cyclopropylsulfonyl)phenyl)-17-(1,1-difluoroprop-2-yn-1-yl)-17-hydroxy-13-methyl-7,8,9,11,12,13,14,15,16,17-decahydro-6H-cyclopenta[a]phenanthren-3-yl acetate (74) (350 mg, 0.62 mmol, 1.0 equiv) in methanol (10 mL) was added cesium carbonate (604 mg, 1.86 mmol, 3.0 equiv) at ambient temperature. The reaction mixture was stirred at room temperature for 2 h at which time the reaction was determined to be complete by LCMS analysis. The reaction mixture was purified by Prep-TLC (ethyl acetate/petroleum ether=2:1) to afford (8S,11S,13S,14S,17S)-11-(4-(cyclopropylsulfonyl)phenyl)-17-(1,1-difluoroprop-2-yn-1-yl)-13-methyl-7,8,9,11,12,13,14,15,16,17-decahydro-6H-cyclopenta[a]phenanthrene-3,17-diol (74) (280 mg, 86% yield) as a light-yellow solid. Calculated mass: 526.20, Mass (ESI-) observed: 525.25 [M−H].

Example 67: (8S,11S,13S,14S,17S)-3-(2-((tert-butyldimethylsilyl)oxy)ethoxy)-11-(4-(cyclopropylsulfonyl)phenyl)-17-(1,1-difluoroprop-2-yn-1-yl)-13-methyl-7,8,9,11,12,13,14,15,16,17-decahydro-6H-cyclopenta[a]phenanthren-17-ol (75)

75

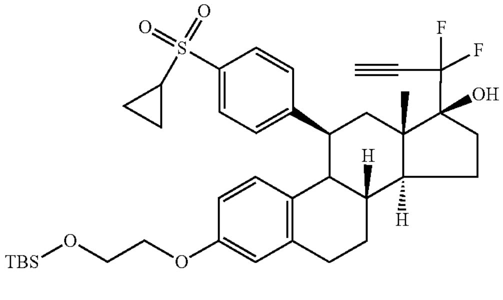

To a stirred solution of (8S,11S,13S,14S, 17S)-11-(4-(cyclopropylsulfonyl)phenyl)-17-(1,1-difluoroprop-2-yn-1-yl)-13-methyl-7,8,9,11,12,13,14,15,16,17-decahydro-6H-cyclopenta[a]phenanthrene-3,17-diol (74) (80 mg, 0.152 mmol, 1.0 equiv) in DMF (4 mL) were added cesium carbonate (148 mg, 0.456 mmol, 3.0 equiv) and tert-butyl (2-iodoethoxy) dimethylsilane (65 mg, 0.228 mmol, 1.5 equiv) at ambient temperature. The reaction mixture was stirred at room temperature for 16 h at which time the reaction was determined to be complete by LCMS analysis. The reaction mixture was quenched with water (30 mL) and extracted with ethyl acetate (30 mL×3). The combined organic layers were washed with water (30 mL×2) and brine (30 mL), dried over anhydrous sodium sulfate, filtered and concentrated under vacuum. The residue was purified by Prep-TLC (ethyl acetate/petroleum ether=−1:1) to afford (8S,11S,13S,14S,17S)-3-(2-((tert-butyldimethylsilyl)oxy) ethoxy)-11-(4-(cyclopropylsulfonyl)phenyl)-17-(1,1-difluoroprop-2-yn-1-yl)-13-methyl-7,8,9,11,12,13,14,15,16,17-decahydro-6H-cyclopenta[a]phenanthren-17-ol (75) (70 mg, 67% yield) as a light-yellow solid. Calculated mass: 684.31, Mass (ESI−) observed: 683.45 [M−H].

Example 68: (8S,11S,13S,14S,17S)-11-(4-(cyclopropylsulfonyl)phenyl)-17-(1,1-difluoroprop-2-yn-1-yl)-3-(2-hydroxyethoxy)-13-methyl-7,8,9,11,12,13,14,15,16,17-decahydro-6H-cyclopenta[a]phenanthren-17-ol (76)

76

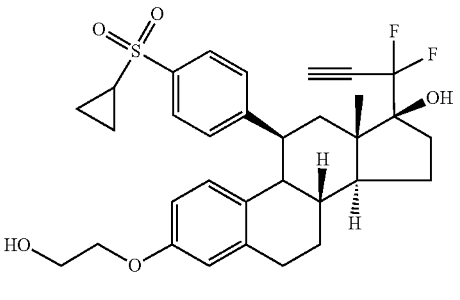

To a solution of (8S,11S,13S,14S,17S)-3-(2-((tert-butyldimethylsilyl)oxy)ethoxy)-11-(4-(cyclopropylsulfonyl)phenyl)-17-(1,1-difluoroprop-2-yn-1-yl)-13-methyl-7, 8,9,11,12,13,14,15,16,17-decahydro-6H-cyclopenta[a]phenanthren-17-ol (75) (60 mg, 0.088 mmol, 1.0 equiv) in DCM (5 mL) was added TFA (0.5 mL). The reaction mixture was stirred at room temperature for 1 h at which time the reaction was determined to be complete by LCMS analysis. The reaction mixture was concentrated under vacuum. The residue was purified by Prep-HPLC with the following conditions: Column: XBridge Prep OBD $C_{18}$ Column, 30×150 mm, 5 μm; Mobile Phase A: Water (10 mmol/L $NH_4HCO_3$), Mobile Phase B: 20 mm NaOH+10% ACN; Flow rate: 60 mL/min; Gradient: 34% B to 64% B in 7 min; Wave Length: 254 nm/220 nm; RT (min): 6.9 to afford (8S,11S,13S,14S,17S)-11-(4-(cyclopropylsulfonyl)phenyl)-17-(1,1-difluoroprop-2-yn-1-yl)-3-(2-hydroxyethoxy)-13-methyl-7,8,9,11,12,13,14,15,16,17-decahydro-6H-cyclopenta[a]phenanthren-17-ol (76) (24.7 mg, 49% yield) as a white solid.

$^1$H NMR (400 MHZ, DMSO-$d_6$) δ 7.60 (d, J=8.2 Hz, 2H), 7.32 (d, J=8.1 Hz, 2H), 6.84 (d, J=8.6 Hz, 1H), 6.67 (d, J=2.7 Hz, 1H), 6.49 (dd, J=8.6, 2.7 Hz, 1H), 5.40 (s, 1H), 4.78 (t, J=5.5 Hz, 1H), 4.28 (t, J=5.4 Hz, 1H), 4.19 (t, J=6.0 Hz, 1H), 3.87 (t, J=5.0 Hz, 2H), 3.65 (q, J=5.2 Hz, 2H), 3.02 (t, J=15.9 Hz, 1H), 2.90-2.72 (m, 3H), 2.48-2.34 (m, 2H), 2.24-2.06 (m, 2H), 2.05-1.84 (m, 2H), 1.76-1.62 (m, 2H), 1.44-1.26 (m, 2H), 1.11-0.91 (m, 4H), 0.34 (s, 3H). Calculated mass: 570.23, Mass (ESI−) observed: 569.35 [M−H].

Scheme 54 illustrates the preparation of compound 77.

Scheme 54

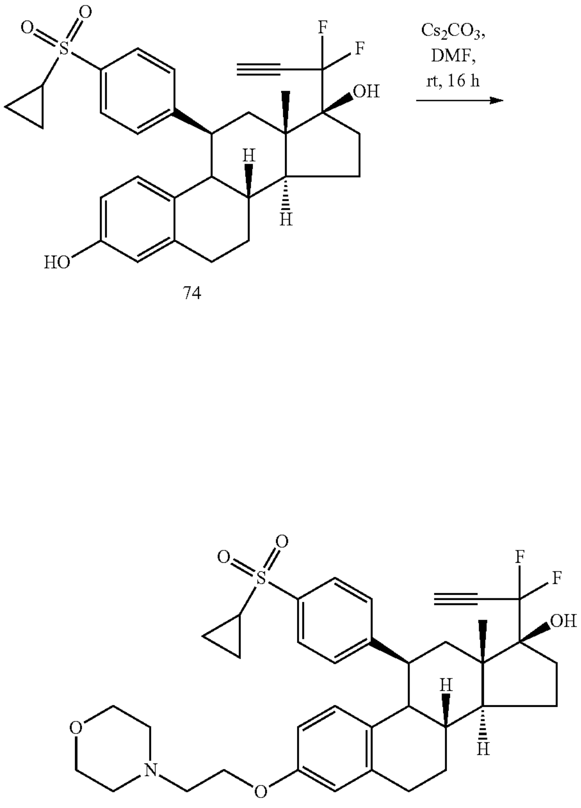

74

77

Example 69: (8S,11S,13S,14S,17S)-11-(4-(cyclopropylsulfonyl)phenyl)-17-(1,1-difluoroprop-2-yn-1-yl)-13-methyl-3-(2-morpholinoethoxy)-7,8,9,11,12,13,14,15,16,17-decahydro-6H-cyclopenta[a]phenanthren-17-ol (77)

77

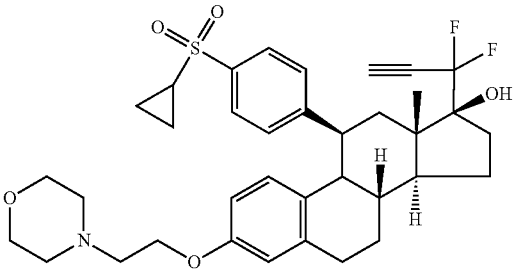

To a stirred solution of (8S,11S,13S, 14S,17S)-11-(4-(cyclopropylsulfonyl)phenyl)-17-(1,1-difluoroprop-2-yn-1-yl)-13-methyl-7,8,9,11,12,13,14,15,16,17-decahydro-6H-cyclopenta[a]phenanthrene-3,17-diol (74) (50 mg, 0.095 mmol, 1.0 equiv) in DMF (2.5 mL) were added cesium carbonate (93 mg, 0.285 mmol, 3.0 equiv) and 4-(2-bromoethyl) morpholine hydrobromide (39 mg, 0.143 mmol, 1.5 equiv) at ambient temperature. The reaction mixture was stirred at room temperature for 16 h at which time the reaction was determined to be complete by LCMS analysis. The reaction mixture was quenched with water (15 mL) and extracted with ethyl acetate (20 mL×3). The combined organic layers were washed with water (20 mL×2) and brine (20 mL), dried over anhydrous sodium sulfate, filtered and concentrated under vacuum. The residue was purified by Prep-HPLC with the following conditions: Column: XSelect CSH $C_{18}$ Column, 30 x150 mm, 5 um; Mobile Phase A: Water (0.1% FA), Mobile Phase B: 20 mm NaOH+10% ACN; Flow rate: 60 mL/min; Gradient: 42% B to 72% B in 7 min; Wave Length: 254 nm; RT (min): 6.55 to afford (8S,11S,13S,14S,17S)-11-(4-(cyclopropylsulfonyl)phenyl)-17-(1,1-difluoroprop-2-yn-1-yl)-13-methyl-3-(2-morpholinoethoxy)-7,8,9,11,12,13,14,15,16,17-decahydro-6H-cyclopenta[a]phenanthren-17-ol (77) (25.1 mg, 40% yield) as a white solid.

$^1$H NMR (400 MHZ, DMSO-$d_6$) δ 7.60 (d, J=8.1 Hz, 2H), 7.32 (d, J=8.0 Hz, 2H), 6.84 (d, J=8.7 Hz, 1H), 6.69 (d, J=2.7 Hz, 1H), 6.50 (dd, J=8.6, 2.7 Hz, 1H), 5.41 (s, 1H), 4.29 (t, J=5.4 Hz, 1H), 4.21 (t, J=6.5 Hz, 1H), 3.98 (t, J=5.8 Hz, 2H), 3.56 (t, J=4.6 Hz, 4H), 3.02 (t, J=14.4 Hz, 1H), 2.91-2.71 (m, 3H), 2.63 (t, J=5.8 Hz, 2H), 2.49-2.35 (m, 6H), 2.24-2.07 (m, 2H), 2.05-1.86 (m, 2H), 1.77-1.62 (m, 2H), 1.44-1.27 (m, 2H), 1.10-0.94 (m, 4H), 0.35 (s, 3H). Calculated mass: 639.28, Mass (ESI+) observed: 640.45 [M+H].

Scheme 55 illustrates the preparation of compound 78.

Scheme 55

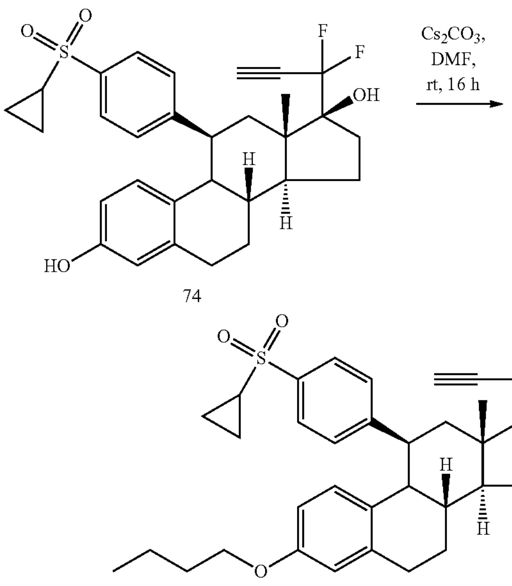

74

78

Example 70: (8S,11S,13S,14S,17S)-3-butoxy-11-(4-(cyclopropylsulfonyl)phenyl)-17-(1,1-difluoroprop-2-yn-1-yl)-13-methyl-7,8,9,11,12,13,14,15,16,17-decahydro-6H-cyclopenta[a]phenanthren-17-ol (78)

78

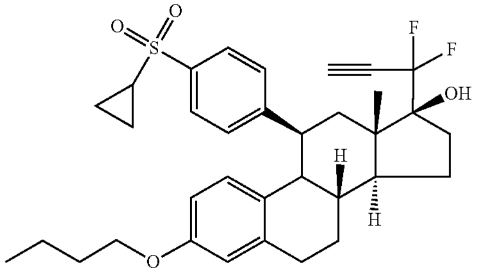

To a stirred solution of (8S,11S,13S,14S,17S)-11-(4-(cyclopropylsulfonyl)phenyl)-17-(1,1-difluoroprop-2-yn-1-yl)-13-methyl-7,8,9,11,12,13,14,15,16,17-decahydro-6H-cyclopenta[a]phenanthrene-3,17-diol (50 mg, 0.095 mmol, 1.0 equiv) in DMF (2.5 mL) were added cesium carbonate (93 mg, 0.285 mmol, 3.0 equiv) and 1-iodobutane (26 mg, 0.143 mmol, 1.5 equiv) at ambient temperature. The reaction mixture was stirred at room temperature for 16 h at which time the reaction was determined to be complete by LCMS analysis. The reaction mixture was quenched with water (15 mL) and extracted with ethyl acetate (20 mL×3). The combined organic layers were washed with water (20 mL×2) and brine (20 mL), dried over anhydrous sodium sulfate, filtered and concentrated under vacuum. The residue was purified by Prep-HPLC with the following conditions: Column: XBridge Prep OBD C18 Column, 30×150 mm, 5 μm; Mobile Phase A: Water (10 mmol/L $NH_4HCO_3$), Mobile Phase B: 20 mm NaOH+10% ACN; Flow rate: 60 mL/min; Gradient: 60% B to 90% B in 7 min; Wave Length: 254 nm/220 nm; RT (min): 7.0 to afford (8S,11S,13S,14S,17S)-3-butoxy-11-(4-(cyclopropylsulfonyl)phenyl)-17-(1,1-difluoroprop-2-yn-1-yl)-13-methyl-7,8,9,11,12,13,14,15,16,17-decahydro-6H-cyclopenta[a]phenanthren-17-ol (78) (19.8 mg, 35% yield) as a white solid.

$^1$H NMR (400 MHZ, DMSO-$d_6$) δ 7.59 (d, J=8.1 Hz, 2H), 7.32 (d, J=8.0 Hz, 2H), 6.83 (d, J=8.6 Hz, 1H), 6.65 (d, J=2.7 Hz, 1H), 6.48 (dd, J=8.6, 2.7 Hz, 1H), 5.41 (s, 1H), 4.29 (t, J=5.3 Hz, 1H), 4.19 (t, J=5.9 Hz, 1H), 3.85 (t, J=6.5 Hz, 2H), 3.08-2.94 (m, 1H), 2.89-2.71 (m, 3H), 2.48-2.34 (m, 2H), 2.23-2.05 (m, 2H), 2.04-1.84 (m, 2H), 1.75-1.56 (m, 4H), 1.45-1.26 (m, 4H), 1.09-0.94 (m, 4H), 0.90 (t, J=7.4 Hz, 3H), 0.34 (s, 3H). Calculated mass: 582.26, Mass (ESI−) observed: 581.45 [M−H].

Scheme 56 illustrates the preparation of compound 79.

Scheme 56

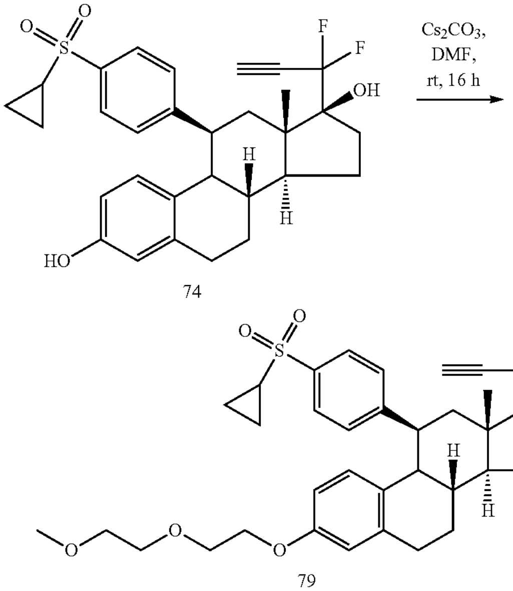

74

79

Example 71: 8S,11S,13S,14S,17S)-11-(4-(cyclopropylsulfonyl)phenyl)-17-(1,1-difluoroprop-2-yn-1-yl)-3-(2-(2-methoxyethoxy)ethoxy)-13-methyl-7,8,9,11,12,13,14,15,16,17-decahydro-6H-cyclopenta[a]phenanthren-17-ol (79)

79

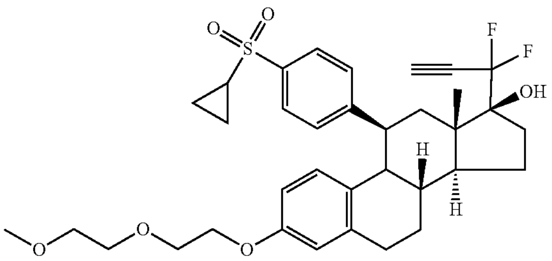

To a stirred solution of (8S,11S,13S,14S,17S)-11-(4-(cyclopropylsulfonyl)phenyl)-17-(1,1-difluoroprop-2-yn-1-yl)-13-methyl-7,8,9,11,12,13,14,15,16,17-decahydro-6H-cyclopenta[a]phenanthrene-3,17-diol 974) (50 mg, 0.095 mmol, 1.0 equiv) in DMF (2.5 mL) were added cesium carbonate (93 mg, 0.285 mmol, 3.0 equiv) and 1-iodo-2-(2-methoxyethoxy)ethane (33 mg, 0.143 mmol, 1.5 equiv) at ambient temperature. The reaction mixture was stirred at room temperature for 16 h at which time the reaction was determined to be complete by LCMS analysis. The reaction mixture was quenched with water (15 mL) and extracted with ethyl acetate (20 mL×3). The combined organic layers were washed with water (20 mL×2) and brine (20 mL), dried over anhydrous sodium sulfate, filtered and concentrated under vacuum. The residue was purified by Prep-HPLC with the following conditions: Column: XBridge Prep OBD $C_{18}$ Column, 30×150 mm, 5 um; Mobile Phase A: Water (10 mmol/L $NH_4HCO_3$+0.05% $NH_3H_2O$), Mobile Phase B: 20 mm NaOH+10% ACN; Flow rate: 60 mL/min; Gradient: 3% B to 10% B in 8 min; Wave Length: 254 nm/220 nm; RT (min): 7.3 to afford (8S,11S,13S,14S,17S)-11-(4-(cyclopropylsulfonyl)phenyl)-17-(1,1-difluoroprop-2-yn-1-yl)-3-(2-(2-methoxyethoxy)ethoxy)-13-methyl-7,8,9,11,12,13,14,15,16,17-decahydro-6H-cyclopenta[a]phenanthren-17-ol (79) (22.6 mg, 37% yield) as a white solid.

$^1$H NMR (400 MHZ, DMSO-$d_6$) δ 7.60 (d, J=8.1 Hz, 2H), 7.32 (d, J=8.1 Hz, 2H), 6.84 (d, J=8.7 Hz, 1H), 6.68 (d, J=2.7 Hz, 1H), 6.50 (dd, J=8.6, 2.7 Hz, 1H), 5.40 (s, 1H), 4.28 (t, J=5.4 Hz, 1H), 4.19 (t, J=5.8 Hz, 1H), 4.03-3.92 (m, 2H), 3.73-3.62 (m, 2H), 3.58-3.52 (m, 2H), 3.47-3.40 (m, 2H), 3.22 (s, 3H), 3.09-2.95 (m, 1H), 2.90-2.72 (m, 3H), 2.49-2.34 (m, 2H), 2.24-2.06 (m, 2H), 2.04-1.84 (m, 2H), 1.77-1.62 (m, 2H), 1.44-1.26 (m, 2H), 1.12-0.92 (m, 4H), 0.34 (s, 3H). Calculated mass: 628.27, Mass (ESI−) observed: 627.40 [M−H].

Scheme 57 illustrates the preparation of compound 80.

Scheme 57

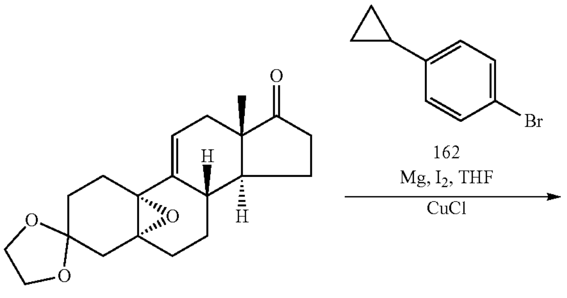

161

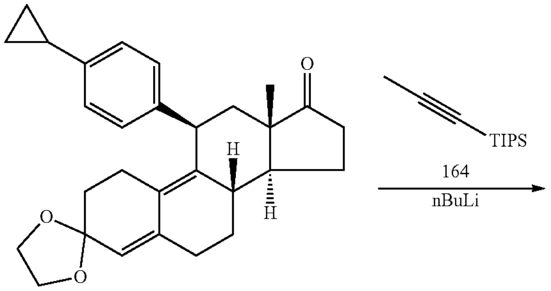

163

-continued

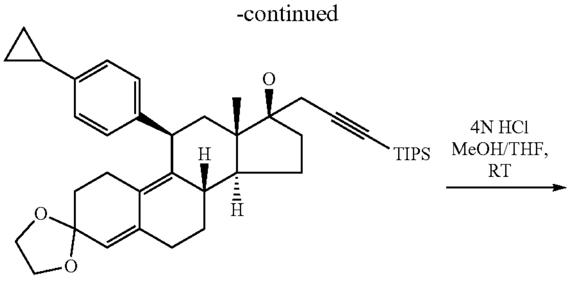

165

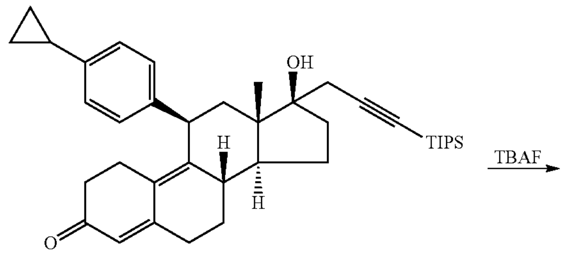

166

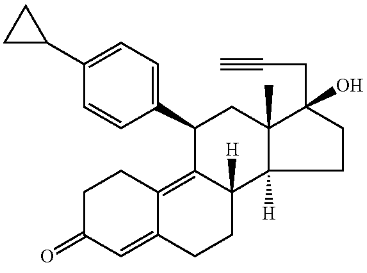

80

Preparation of Compound 163

163

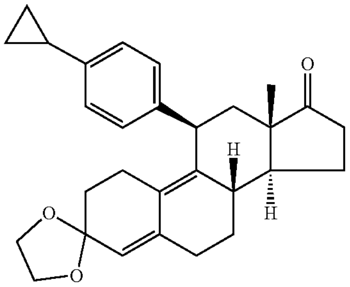

To a mixture of magnesium turnings (112 mg, 4.65 mmol) and an iodine crystal in a flask under nitrogen was added THF (5 mL). To the stirred mixture was added 1,2-dibromoethane (0.16 mL) dropwise and the flask was warmed gently with a heat gun. When a persistent exotherm was observed (in the absence of heating), a solution of bromide 162 was added dropwise (887 mg. 3 eq) in 8 mL of THF. The resultant mixture was heated to 60° C. for 30 min, after which the Mg solid was consumed. The mixture was cooled to 0° C. and CuCl (134 mg, 0.9 eq) was added. The mixture was stirred for 30 min, then a solution of starting material 161 (495 mg, 1.5 mmol, 1 eq) in 5 mL of THF was added dropwise. The mixture was stirred at room temperature for 1 hr, after which TLC showed complete conversion of compound 161. The mixture was cooled to 0° C. and a saturated solution of $NH_4Cl$ (15 mL) was added to quench the reaction. The resultant mixture was extracted with EtOAc (3×50 mL) and the combined extracts were washed with water (50 mL) and brine (50 mL). The EtOAc solution was dried over sodium sulfate, filtered, and concentrated to provide a yellow oil (1 g crude). The crude was carried into the next step without further purification. Exact mass: 430.25

Preparation of Compound 163

165

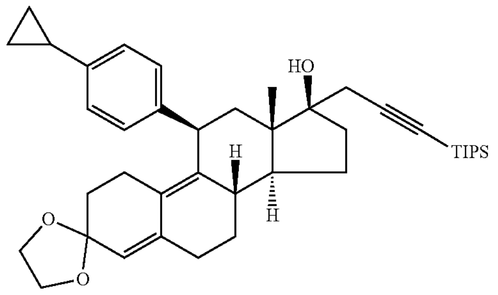

A solution of alkyne 164 (164 mg, 0.837 mmol) in THF (0.7 mL) was cooled to −78° C. and a solution of 2.5 M n-BuLi in hexane (0.33 mL) was added dropwise. The resultant mixture was stirred for 10 min at −78° C., then allowed to warm to room temperature. The mixture was stirred at ambient temperature for 40 min, then re-cooled to −78° C. A solution of 163 (300 mg, 0.7 mmol) in 0.7 mL THF was added dropwise and the resultant mixture was stirred at −78° C. for 1.5 hr. The cooling bath was removed and the reaction mixture quenched by the addition of saturated ammonium chloride (1.5 mL). The mixture was diluted by the addition of EtOAc (100 mL), washed with water (50 mL) and brine (50 mL). After drying the organic phase over sodium sulfate the solution was filtered and concentrated in vacuo. The residue was purified by flash chromatography on silica (EtOAc/hexane gradient) to provide compound 165 (54 mg, 12%) and recovered 163 (170 mg, 57%). Exact mass: 626.42.

Preparation of Compound 166

166

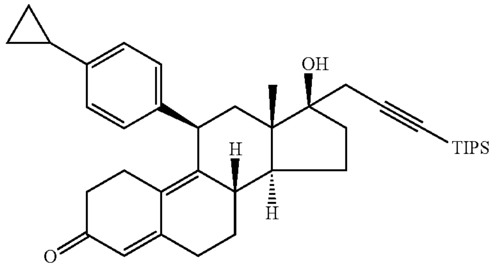

To a solution of 165 (54 mg, 0.087 mmol) in a mixture of THF (0.9 mL) and MeOH (0.9 mL) was added 4N HCl (65 μL, 0.26 mmol, 3 eq) and the resultant mixture was stirred at room temperature for 7 hr. TLC analysis at this point showed complete conversion to a more polar product. The reaction mixture was diluted with EtOAc (100 mL) and the resultant mixture was washed with water (50 mL) and brine (50 mL). The combined extracts were dried over sodium sulfate, filtered, and concentrated under reduced pressure. Crude compound 166 (47.9 mg, 95%) was obtained that was carried into the next step. Exact mass: 582.30

Example 72: Preparation of Compound 80

80

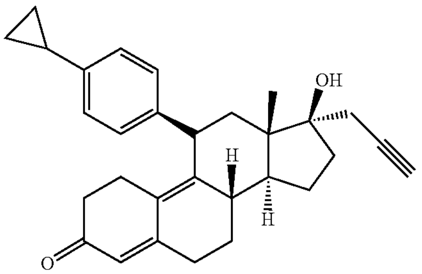

To a solution of compound 166 (47.9 mg,) in 0.9 mL THF was added 0.165 mL of 1M TBAF in THF and the mixture was stirred at room temperature for 1 hr. The resultant mixture was evaporated under a nitrogen stream and redissolved in EtOAc (100 mL), washed with water (50 mL), brine (50 mL) and the combined extracts dried over sodium sulfate. The solution was filtered and concentrated in vacuo to provide a thick brown oil (44.6 mg). This material was dissolved in DMF (ca. 1 mL) and the solution purified by preparative HPLC on $C_{18}$ reverse phase. The pure fractions were combined and lyophilized to give an off-while solid of compound 80 (7.3 mg).

$^1$H NMR (500 MHZ, DMSO-d6) δ 7.04 (d, J=8.2 Hz, 2H), 6.98-6.92 (m, 2H), 5.64 (s, 1H), 4.35 (d, J=6.8 Hz, 2H), 2.72-2.61 (m, 2H), 2.57 (d, J=13.1 Hz, 1H), 2.42 (s, 1H), 2.33-2.24 (m, 3H), 2.19-2.02 (m, 2H), 2.00-1.90 (m, 2H), 1.83 (tp, J=8.4, 8.4, 3.0, 3.0, 2.7, 2.7 Hz, 2H), 1.63, 1.46 (m, 2H), 1.35-1.20 (m, 1H), 0.97 (d, J=6.3 Hz, 8H), 0.94-0.84 (m, 3H), 0.63-0.57 (m, 2H), 0.40 (s, 3H). Exact mass: 426.26.

Scheme 58 illustrates the preparation of compound 56.

Scheme 58

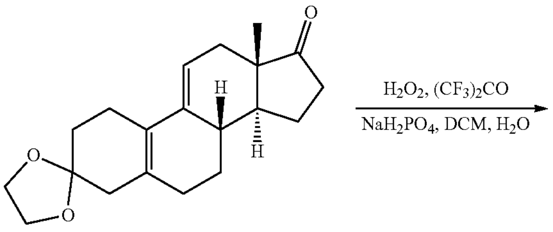

167

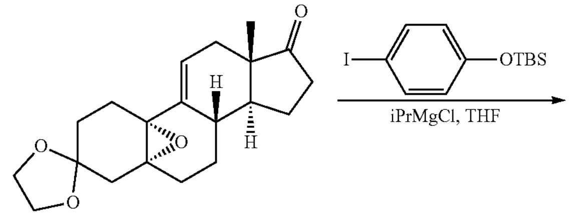

168

-continued

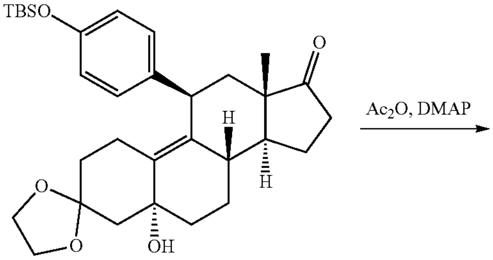

169

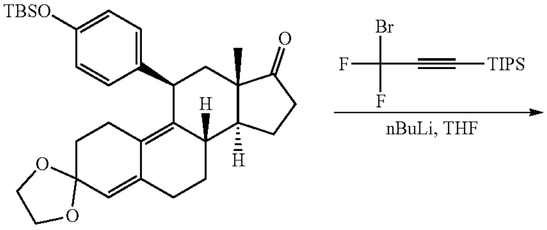

170

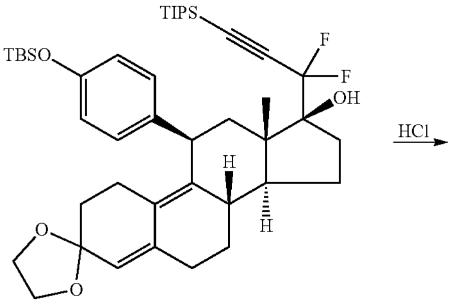

171

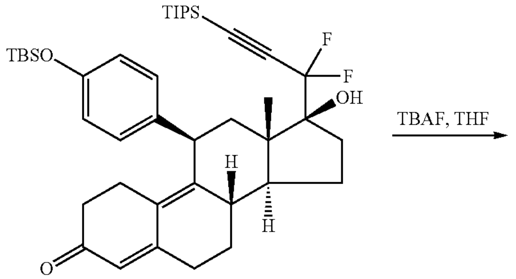

172

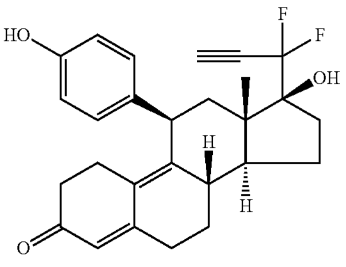

56

Preparation of (1'R,5'S,9'S,10'S,13'R)-5'-methyl-18'-oxaspiro[1,3-dioxolane-2,15'-pentacyclo [11.4.1.0^{1,13}0.0^{2,10}0.0^{5,9}] octadecan]-2'-en-6'-one (168)

168

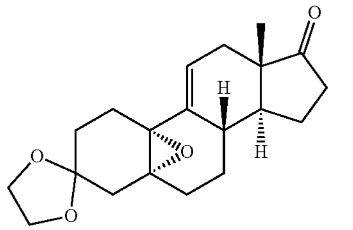

To a stirred solution of $Na_2HPO_4$ (361 g, 2.54 mol, 2.00 equiv) in DCM (2 L) was added hexafluoroacetone trihydrate (352 mL, 1.60 mol, 1.26 equiv) and $H_2O_2$ (632 mL, 2.00 equiv, 30%) at 0° C. The mixture was stirred for 1 h at 0° C. Then (3aS,3bS,11aS)-11a-methyl-2,3,3a,3b,4,5,6,8,9,11-decahydrospiro[cyclopenta[a]phenanthrene-7,2'-[1,3]dioxolan]-1-one (167) (400 g, 1.27 mol, 1 equiv) in 700 mL DCM was added into the mixture at 0° C. The resulting solution was stirred for 18 h at 0° C. To the mixture was added 10% $Na_2SO_3$ solution (1L) which was stirred for 15 min. The organic fraction was extracted with $H_2O$ (3x1L), the organic layers was dried over anhydrous sodium sulfate and concentrated under reduced pressure. The residue was purified by trituration with (diisopropyl ether: Ethyl acetate (5:1)), the solid was filtered and dried to afford (1'R,5'S, 9'S,10'S, 13'R)-5'-methyl-18'-oxaspiro[1,3-dioxolane-2, 15'-pentacyclo[11.4.1.0^{1,13}0.0^{2,10}0.0^{5,9}] octadecan]-2'-en-6'-one (168) (280 g, 66%) as a white solid. Calculated mass: 330.18, Mass (ESI+) observed: 331.15 [M+H].

Preparation of (3aS,3bS,5aR,10R,11aS)-10-{4-[(tert-butyldimethylsilyl)oxy]phenyl}-5a-hydroxy-11a-methyl-3,3a,3b,4,5,6,8,9,10,11-decahydro-2H-spiro[cyclopenta[a]phenanthrene-7,2'-[1,3]dioxolan]-1-one (169)

169

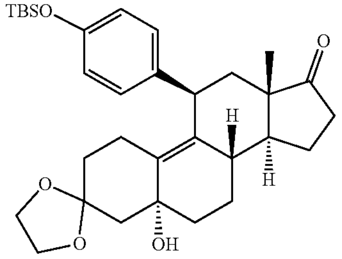

To a solution of tert-butyl(4-iodophenoxy)dimethylsilane (182 g, 544 mmol, 1.50 equiv) in THF (2.5 L) was added isopropylmagnesium chloride (2 M, 363 mL, 726 mmol, 2.00 equiv) dropwise at −10° C. under $N_2$. The resulting solution was stirred for 30 min at −10° C. Then copper (I) chloride (21.5 g, 217 mmol, 0.60 equiv) was added and the solution was stirred for 30 min at 0° C. After 30 min, (1'R,5'S,9'S,10'S,13'R)-5'-methyl-18'-oxaspiro[1,3-dioxolane-2,15'-pentacyclo[11.4.1.0^{1,13}0.0^{2,10}0.0^{5,9}] octadecan]-2'-en-6'-one (168) (120 g, 363 mmol, 1.00 equiv) (in 500 mL THF) dropwise at 0° C. and stirred for 15 min. Then the resulting solution was allowed to warm to RT and stirred for 16 h at RT. The reaction was cooled and quenched by the addition of sat. $NH_4Cl$ (aq.) (1.5 L) at 0° C. and extracted with ethyl acetate (3×2 L), the organic layers were washed with brine, dried over $Na_2SO_4$ and concentrated under reduced pressure. The crude product was purified by silica gel column, eluting with petroleum ether/ethyl acetate (1:1) to afford (3aS,3bS,5aR,10R,11aS)-10-{4-[(tert-butyldimethylsilyl)oxy]phenyl}-5a-hydroxy-11a-methyl-3,3a,3b,4,5,6,8,9,10,11-decahydro-2H-spiro[cyclopenta[a]phenanthrene-7,2'-[1,3]dioxolan]-1-one (169) (90 g, 41%) as a white solid. Calculated mass: 538.31, Mass (ESI+) observed: 539.10 [M+H].

Preparation of (3aS,3bS,10R,11aS)-10-{4-[(tert-butyldimethylsilyl)oxy]phenyl}-11a-methyl-2,3,3a,3b,4,5,8,9,10,11-decahydrospiro[cyclopenta[a]phenanthrene-7,2'-[1,3]dioxolan]-1-one (170)

170

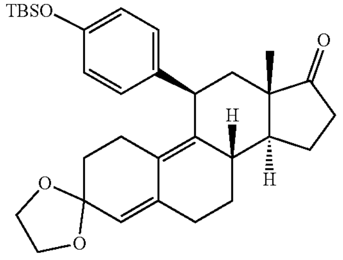

A mixture of (3aS,3bS,5aR,10R,11aS)-10-{4-[(tert-butyldimethylsilyl)oxy]phenyl}-5a-hydroxy-11a-methyl-3,3a,3b,4,5,6,8,9,10,11-decahydro-2H-spiro[cyclopenta[a]phenanthrene-7,2'-[1,3]dioxolan]-1-one (169) (80.0 g, 148 mmol, 1.00 equiv), acetyl acetate (75.8 g, 742 mmol, 5.00 equiv) and N,N-dimethylpyridin-4-amine (1.81 g, 14.8 mmol, 0.10 equiv) in pyridine (1 L) was stirred for 36 h at 65° C. The resulting solution was partially concentrated under reduced pressure. The residue was purified by reverse flash column (column, C18 silica gel, 300 g, 20-35 immobile phase, water with 0.1% FA and ACN (10% to 100% gradient in 50 min); detector UV 254/220 nm) to afford (3aS,3bS,10R,11aS)-10-{4-[(tert-butyldimethylsilyl)oxy]phenyl}-11a-methyl-2,3,3a,3b,4,5,8,9,10,11-decahydrospiro[cyclopenta[a]phenanthrene-7,2'-[1,3]dioxolan]-1-one (170) (55 g, 64%) as a yellow oil. The reaction was repeated 2 times to afford 110 g product. Calculated mass: 520.30, Mass (ESI+) observed: 521.25 [M+H].

Preparation of (1S,3aS,3bS,10R,11aS)-10-{4-[(tert-butyldimethylsilyl)oxy]phenyl}-1-[1,1-difluoro-3-(triisopropylsilyl)prop-2-yn-1-yl]-11a-methyl-2,3,3a,3b,4,5,8,9,10,11-decahydrospiro[cyclopenta[a]phenanthrene-7,2'-[1,3]dioxolan]-1-ol (171)

171

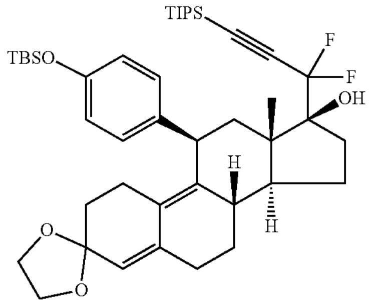

(3aS,3bS,10R,11aS)-10-{4-[(tert-butyldimethylsilyl)oxy]phenyl}-11a-methyl-2,3,3a,3b,4,5,8,9,10,11-decahydrospiro[cyclopenta[a]phenanthrene-7,2'-[1,3]dioxolan]-1-one (170) (20.0 g, 38.4 mmol, 1.00 equiv) and (3-bromo-3,3-difluoroprop-1-yn-1-yl) triisopropylsilane (35.8 g, 115 mmol, 3.00 equiv) were dissolved in THF (1.4 L) and cooled to −78° C. Then butyllithium (46.1 mL, 115 mmol, 3.00 equiv, 2.50 M) was added dropwise and the resulting solution was stirred for 1 h at −78° C. The reaction was quenched by adding sat solution of $NH_4Cl$ (1 L) and extracted with EA (3×1 L). The organic layers were washed with brine, dried over $Na_2SO_4$ and concentrated under reduced pressure to afford (1S,3aS,3bS,10R,11aS)-10-{4-[(tert-butyldimethylsilyl)oxy]phenyl}-1-[1,1-difluoro-3-(triisopropylsilyl) prop-2-yn-1-yl]-11a-methyl-2,3,3a,3b,4,5,8,9,10,11-decahydrospiro[cyclopenta[a]phenanthrene-7,2'-[1,3]dioxolan]-1-ol (21 g, 58.08%) as a colorless oil. The reaction was repeated 6 times to afford 126 g (crude) product. Calculated mass: 752.45, Mass (ESI+) observed: 753.20 [M+H].

Preparation of (1S,3aS,3bS,10R,11aS)-10-{4-[(tert-butyldimethylsilyl)oxy]phenyl}-1-[1,1-difluoro-3-(triisopropylsilyl) prop-2-yn-1-yl]-1-hydroxy-11a-methyl-2H,3H,3aH,3bH,4H,5H,8H,9H,10H,11H-cyclopenta[a]phenanthren-7-one (172)

172

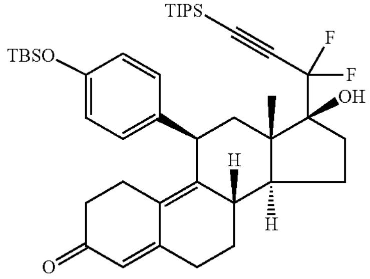

To a solution of (1S,3aS,3bS,10R,11aS)-10-{4-[(tert-butyldimethylsilyl)oxy]phenyl}-1-[1,1-difluoro-3-(triisopropylsilyl) prop-2-yn-1-yl]-11a-methyl-2,3,3a,3b,4,5,8,9,10,11-decahydrospiro[cyclopenta[a]phenanthrene-7,2'-[1,3]

dioxolan]-1-ol (171) (21.0 g, 27.8 mmol, 1.00 equiv) in THF (570 mL) and methanol (570 mL) was added 4 N solution of HCl (20.9 mL, 83.6 mmol, 3.00 equiv) dropwise at 0° C. The resulting solution was stirred for 1 h at 0° C. during which time TLC showed complete conversion of the starting material to the product. The reaction was quenched and acidified to pH 8 by addition of sat solution of $NaHCO_3$. The mixture was extracted with ethyl acetate (3×1 L) and the combined organic layers were washed with brine, dried over $Na_2SO_4$ and concentrated under reduced pressure. The residue was purified by silica gel column chromatography, eluted with petroleum ether/ethyl acetate (3:1) to afford (1S,3aS,3bS,10R,11aS)-10-{4-[(tert-butyldimethylsilyl)oxy]phenyl}-1-[1,1-difluoro-3-(triisopropylsilyl) prop-2-yn-1-yl]-1-hydroxy-11a-methyl-2H,3H,3aH,3bH,4H,5H,8H,9H,10H,11H-cyclopenta[a]phenanthren-7-one (172) (11 g, 50%) as a yellow oil. The reaction was repeated 6 times to afford 66 g product. Calculated mass: 708.42, Mass (ESI+) observed: 709.40 [M+H].

Example 73: Preparation of (1S,3aS,3bS,10R,11aS)-1-(1,1-difluoroprop-2-yn-1-yl)-1-hydroxy-10-(4-hydroxyphenyl)-11a-methyl-2H,3H,3aH,3bH,4H,5H,8H,9H,10H,11H-cyclopenta[a]phenanthren-7-one (56)

56

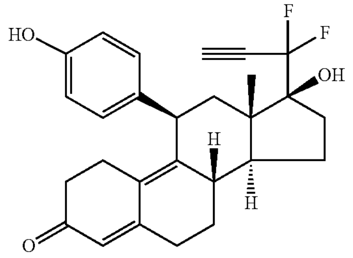

To a solution of (1S,3aS,3bS,10R,11aS)-10-{4-[(tert-butyldimethylsilyl)oxy]phenyl}-1-[1,1-difluoro-3-(triisopropylsilyl) prop-2-yn-1-yl]-1-hydroxy-11a-methyl-2H,3H,3aH,3bH,4H,5H,8H,9H,10H,11H-cyclopenta[a]phenanthren-7-one (50.0 g, 70.5 mmol, 1.00 equiv) (172) in THF (4 L) was added TBAF (1 M, 140 mL) at 0° C. The resulting mixture was stirred for 20 min at RT. The reaction was quenched by the addition of water (5 L). The resulting mixture was extracted with EA (3×5 L). The combined organic layers were washed with brine (1 L), dried over anhydrous sodium sulfate. After filtration, the filtrate was concentrated under reduced pressure. The residue was purified by silica gel column chromatography, eluted with n-hexane/EA (1:1) to afford (1S,3aS,3bS,10R,11aS)-1-(1,1-difluoroprop-2-yn-1-yl)-1-hydroxy-10-(4-hydroxyphenyl)-11a-methyl-2H,3H,3aH,3bH,4H,5H,8H,9H,10H,11H-cyclopenta[a]phenanthren-7-one (56) (23.5303 g, 74%) as a yellow solid.

$^1$H NMR (300 MHz, DMSO-$d_6$) δ 9.17 (s, 1H), 6.96 (d, J=8.3 Hz, 2H), 6.67 (d, J=8.5 Hz, 2H), 5.65 (s, 1H), 5.48 (s, 1H), 4.35 (d, J=6.7 Hz, 1H), 4.27 (t, J=5.4 Hz, 1H), 2.80-2.69 (m, 1H), 2.60 (dd, J=26.5, 13.2 Hz, 2H), 2.47-2.26 (m, 3H), 2.24-2.05 (m, 4H), 1.98-1.95 (m, 1H), 1.86-1.56 (m, 3H), 1.38-1.27 (m, 2H), 0.51 (s, 3H). Calculated mass: 438.20, Mass (ESI+) observed: 439.20 [M+H].

Scheme 59 illustrates the preparation of intermediate 158.

Scheme 59

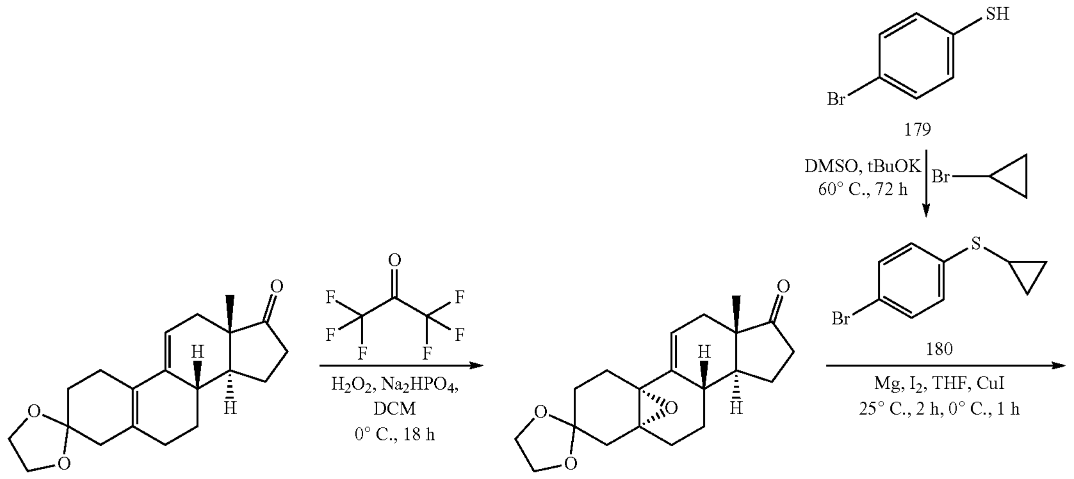

179

180

173

174

-continued

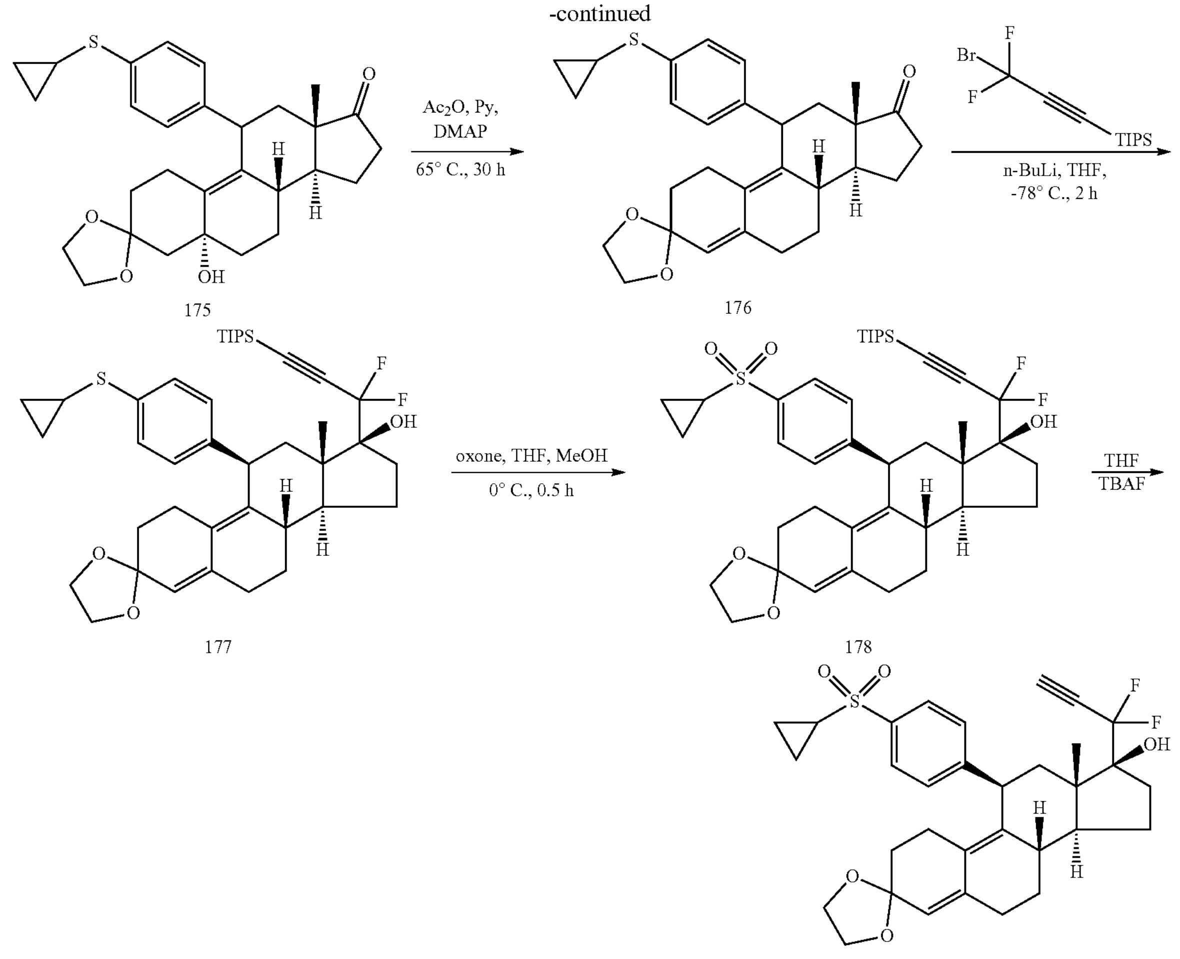

175 176 177 178 158

(4-bromophenyl)(cyclopropyl)sulfane (180)

180

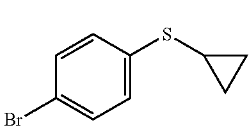

The reaction was run in two batches. Into two 2 L flask was placed 4-bromobenzenethiol (179) (400 g, 2115.6 mmol, 1.0 equiv), DMSO (2 L) at 25° C. Then t-BuOK (308.6 g, 2750.3 mmol, 1.3 equiv) was added by portions at 0° C. and the resulting mixture was stirred for 15 min at 25° C. Then bromocyclopropane (766 g, 6383.3 mmol, 3.0 equiv) was added and the resulting mixture was stirred for 72 h at 60° C., cooled to 25° C. and poured into 2 L of ice/water, extracted with ethyl acetate (2 L×2). The combined organic layers were washed with brine (3 L×3), dried over anhydrous $Na_2SO_4$ and concentrated under reduced pressure. The residue was purified by silica gel column chromatography, eluted with ethyl acetate:petroleum ether (2:98) to afford (4-bromophenyl) (cyclopropyl) sulfane (180) (334 g, 63.4%) as a yellow liquid.

$^1$H-NMR ($CDCl_3$, 400 MHZ) δ (ppm): 7.41 (d, J=8.4 Hz, 2H), 7.25 (d, J=8.8 Hz, 2H), 2.15-2.21 (m, 1H), 1.07-1.12 (m, 2H), 0.69-0.73 (m, 2H). Calculated mass: 227.96, Mass (ESI+) observed: 229.26 [M+H].

Preparation of (5'R,8'S,10'R,13'S,14'S)-13'-methyl-1',2',6',7',8',12',13',14',15',16'-decahydro-4'H,17'H-spiro[1,3]dioxolane-2,3'-[5,10]epoxycyclopenta[a]phenanthren]-17'-one (174)

174

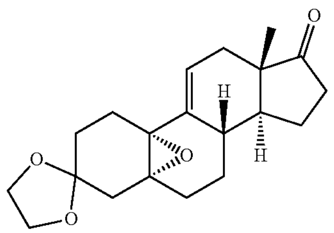

Into a 5 L 3-necked flask was placed $Na_2HPO_4$ (99.3 g, 699.7 mmol, 1.1 equiv), DCM (2 L). Then hexafluoroacetone (180 mL) and $H_2O_2$ (30%, 320 mL) was added at 0° C. and stirred for 1 h. Then (8S,13S,14S)-13-methyl-1,4,6,7,8,12,13,14,15,16-decahydrospiro[cyclopenta[a]phenanthrene-3,2'-[1,3]dioxolan]-17 (2H)-one (173) (200 g, 636.1 mmol, 1.0 equiv) was added at 0° C. and the solution was stirred for 18 h at-5 ~0° C. The reaction was quenched by the addition of 10% $Na_2SO_3$ (aq., 1 L). The resulting mixture was extracted with DCM (1 L×2). The combined organic layers were washed with 10% Na2SO3 (2 L×2), dried over anhydrous $Na_2SO_4$ and concentrated under reduced pressure. The residue was dissolved in 1 L (ethyl acetate: 2-isopropoxypropane: =1:3, containing 0.1% pyridine) and stirred for 15 h at 25° C. The resulting mixture was filtered, the filter cake was washed with (ethyl acetate: 2-isopropoxypropane: =1:3, containing 0.1% pyridine) (400 mL×1) which provided (5'R,8'S,10'R,13'S, 14'S)-13'-methyl-1',2',6',7',8',12',13',14',15',16'-decahydro-4'H,17'H-spiro[[1,3]dioxolane-2,3'-[5, 10]epoxycyclopenta[a]phenanthren]-17'-one (174) (120 g, 51.4%) as a white solid.

$^1$H-NMR ($CDCl_3$, 400 MHZ) δ (ppm): 6.03-6.06 (m, 1H), 3.85-3.96 (m, 4H), 2.47-2.50 (m, 2H), 2.01-2.18 (m, 6H), 1.84-1.98 (m, 3H), 1.65-1.80 (m, 2H), 1.46-1.58 (m, 4H), 1.17-1.30 (m, 1H), 0.87 (s, 3H). Calculated mass: 330.18, Mass (ESI+) observed: 331.35 [M+H].

(5R,8S,13S,14S)-11-(4-(cyclopropylthio)phenyl)-5-hydroxy-13-methyl-1,4,5,6,7,8,11,12,13,14,15,16-dodecahydrospiro[cyclopenta[a]phenanthrene-3,2'-[1,3]dioxolan]-17 (2H)-one

175

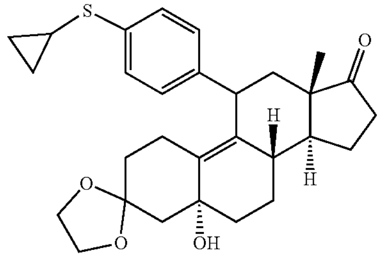

Into a 1 L 3-necked flask was placed Mg (6.6 g, 272.4 mmol, 6 equiv), I2 (0.12 g, 0.45 mmol, 0.01 equiv), THF (125 mL). Then (4-bromophenyl) (cyclopropyl) sulfane (180) (31.2 g, 136.2 mmol, 3.0 equiv) in THF (125 mL) was added dropwise under $N_2$ atmosphere at 60~70° C. (1/4 of the material was added to initiate the reaction, after a few minutes the other 3/4 material was added and the bath was carefully maintained between 60~70° C.). After the addition was complete, the temperature was cooled to 25° C. over 30 minutes) to provide solution A. Into another 1 L 3-necked flask was placed (5'R,8'S,10'R,13'S,14'S)-13'-methyl-1',2',6', 7',8', 12', 13',14',15', 16'-decahydro-4'H, 17'H-spiro[1,3]dioxolane-2,3'-[5,10]epoxycyclopenta[a]phenanthren]-17'-one (174) (15 g, 45.4 mmol, 1 equiv), THF (190 mL), CuI (17.3 g, 90.8 mmol, 2.0 equiv), then solution A was added dropwise at 0° C. under $N_2$ atmosphere. The resulting mixture was stirred for 1 h at 0° C. under $N_2$ atmosphere. The reaction was quenched with $NH_4Cl$ (aq. 400 mL), extracted with ethyl acetate (500 mL×1). The organic layer was washed with $NH_4Cl$ (aq. 500 mL×2), brine (500 mL×1), dried over anhydrous $Na_2SO_4$ and concentrated under reduced pressure. The residue was purified by silica gel column chromatography eluted with ethyl acetate:petroleum ether (1:1) to afford (5R,8S,13S, 14S)-11-(4-(cyclopropylthio)phenyl)-5-hydroxy-13-methyl-1,4,5,6,7,8,11,12,13,14,15,16-dodecahydrospiro[cyclopenta[a]phenanthrene-3,2'-[1,3]dioxolan]-17 (2H)-one (175) (23 g, 93%) as an off-white solid.

$^1$H-NMR ($CDCl_3$, 400 MHZ) δ (ppm): 7.26 (d, J=8.4 Hz, 2H), 7.15 (d, J=8.4 Hz, 2H), 4.39 (s, 1H), 4.29 (d, J=6.8 Hz, 1H), 3.91-4.06 (m, 4H), 2.29-2.50 (m, 5H), 2.00-2.20 (m, 5H), 1.75-1.91 (m, 3H), 1.50-1.70 (m, 5H), 1.23-1.34 (m, 1H), 1.02-1.09 (m, 2H), 0.66-0.73 (m, 2H), 0.51 (s, 3H). Calculated mass: 480.23, Mass (ESI+) observed: 480.35 [M+H].

Preparation of (8S,13S,14S)-11-(4-(cyclopropylthio)phenyl)-13-methyl-1,6,7,8,11,12,13,14,15,16-decahydrospiro[cyclopenta[a]phenanthrene-3,2'-[1,3]dioxolan]-17 (2H)-one (176)

176

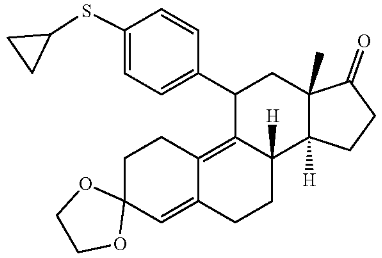

The reaction was run in two batches. Into two 2 L flask was placed (5R,8S,13S,14S)-11-(4-(cyclopropylthio)phenyl)-5-hydroxy-13-methyl-1,4,5,6,7,8,11,12,13,14,15,16-dodecahydrospiro[cyclopenta[a]phenanthrene-3,2'-[1,3]dioxolan]-17 (2H)-one (175) (140 g, 291.3 mmol, 1 equiv), pyridine (1400 mL), Ac2O (148.7 g, 1456.3 mmol, 5.0 equiv), DMAP (3.56 g, 29.1 mmol, 0.1 equiv). The solution was stirred for 30 h at 65° C. The mixture was allowed to cool down to 25° C. and then concentrated under reduced pressure. The residue was diluted with $H_2O$ (1 L). The resulting mixture was extracted with ethyl acetate (1 L×2). The combined organic layers were washed with brine (2 L×2), dried over anhydrous $Na_2SO_4$. After filtration, the filtrate was concentrated under reduced pressure. This resulted in (8S,13S,14S)-11-(4-(cyclopropylthio)phenyl)-13-methyl-1,6,7,8,11,12,13,14,15,16-decahydrospiro[cyclopenta[a]phenanthrene-3,2'-[1,3]dioxolan]-17 (2H)-one (176) (134 g, 89.5%) as a brown solid.

$^1$H-NMR ($CDCl_3$, 400 MHZ) δ (ppm): 7.26 (d, J=8.4 Hz, 2H), 7.15 (d, J=8.4 Hz, 2H), 5.41 (s, 1H), 4.26-4.33 (m, 1H), 3.85-4.05 (m, 4H), 2.40-2.58 (m, 5H), 2.01-2.19 (m, 6H), 1.71-1.91 (m, 3H), 1.44-1.60 (m, 3H), 1.03-1.08 (m, 2H), 0.65-0.72 (m, 2H), 0.54 (s, 3H). Calculated mass: 462.22, Mass (ESI+) observed: 462.31 [M+H].

Preparation of (8S,11R,13S,14S,17S)-11-(4-(cyclopropylthio)phenyl)-17-(1,1-difluoro-3-(triisopropylsilyl) prop-2-yn-1-yl)-13-methyl-1,2,6,7,8,11,12,13,14,15,16,17-dodecahydrospiro[cyclopenta[a]phenanthrene-3,2'-[1,3]dioxolan]-17-ol and (8S,11R,13S,14S,17S)-11-(4-(cyclopropylthio)phenyl)-17-(1,1-difluoro-3-(triisopropylsilyl) prop-2-yn-1-yl)-17-hydroxy-13-methyl-1,2,6,7,8,11,12,13,14,15,16,17-dodecahydro-3H-cyclopenta[a]phenanthren-3-one (177)

177

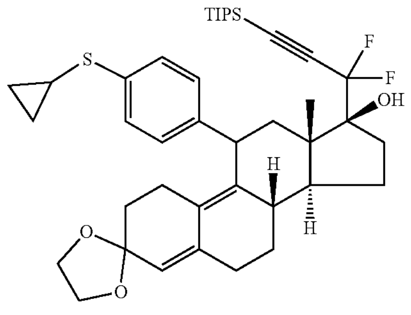

Into a 2 L 3-necked flask was placed (8S,13S,14S)-11-(4-(cyclopropylthio)phenyl)-13-methyl-1,6,7,8,11,12,13,14,15,16-decahydrospiro[cyclopenta[a]phenanthrene-3,2'-[1,3]dioxolan]-17 (2H)-one (176 ((40 g, 86.5 mmol, 1 equiv), THF (1 L), and (3-bromo-3,3-difluoroprop-1-yn-1-yl) triisopropylsilane (107.6 g, 345.8 mmol, 4.0 equiv). Then n-BuLi (173 mL, 5.0 equiv) was added dropwise at −78° C. under $N_2$ atmosphere. The solution was stirred for 2 h at −78° C. under $N_2$ atmosphere. The reaction was quenched with $NH_4Cl$ (aq., 700 mL) at-78° C. The resulting mixture was extracted with ethyl acetate (700 mL×2). The combined organic layers were washed with brine (1 L×2), dried over anhydrous $Na_2SO_4$ and concentrated under reduced pressure. The residue was purified by silica gel column chromatography eluted with EA: PE (1:9) to afford (8S,11R,13S,14S, 17S)-11-(4-(cyclopropylthio)phenyl)-17-(1,1-difluoro-3-(triisopropylsilyl) prop-2-yn-1-yl)-13-methyl-1,2,6,7,8,11,12,13,14,15,16,17-dodecahydrospiro[cyclopenta[a]phenanthrene-3,2'-[1,3]dioxolan]-17-ol (177) (15 g, 22.5%) as a yellow solid.

$^1$H-NMR ($CDCl_3$, 400 MHZ) δ (ppm): 7.23 (d, J=8.4 Hz, 2H), 7.11 (d, J=8.4 Hz, 2H), 5.35 (s, 1H), 4.27-4.30 (m, 1H), 3.85-4.01 (m, 4H), 3.73 (s, 1H), 2.30-2.49 (m, 8H), 2.06-2.18 (m, 3H), 1.88-1.94 (m, 1H), 1.67-1.81 (m, 5H), 1.01-1.13 (m, 23H), 0.65-0.70 (m, 2H), 0.58 (s, 3H). Calculated mass: 694.37, Mass (ESI+) observed: 694.33 [M+H].

Preparation of (8S,11R,13S,14S,17S)-11-(4-(cyclopropylsulfonyl)phenyl)-17-(1,1-difluoro-3-(triisopropylsilyl) prop-2-yn-1-yl)-17-hydroxy-13-methyl-1,2,6,7,8,11,12,13,14,15,16,17-dodecahydro-3H-cyclopenta[a]phenanthren-3-one (178)

178

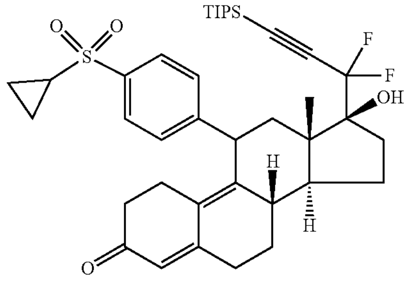

Into a 1 L 3-necked flask was placed (8S,11R,13S,14S,17S)-11-(4-(cyclopropylthio)phenyl)-17-(1,1-difluoro-3-(triisopropylsilyl) prop-2-yn-1-yl)-13-methyl-1,2,6,7,8,11,12,13,14,15,16,17-dodecahydrospiro[cyclopenta[a]phenanthrene-3,2'-[1,3]dioxolan]-17-ol (177) (15 g, 21.6 mmol, 1 equiv), THF (200 mL), MeOH (200 mL), and oxone (22.4 g, 64.7 mmol, 3.0 equiv) in $H_2O$ (130 mL) was added dropwise at 0° C. and the solution was stirred for 0.5 h at 0° C. LCMS showed 70% product at 254 nm.

Into a another 1 L 3-necked flask was placed (8S,11R,13S,14S,17S)-11-(4-(cyclopropylthio)phenyl)-17-(1,1-difluoro-3-(triisopropylsilyl)prop-2-yn-1-yl)-17-hydroxy-13-methyl-1,2,6,7,8,11,12,13,14,15,16,17-dodecahydro-3H-cyclopenta[a]phenanthren-3-one (11 g, 16.9 mmol, 1.0 equiv), THF (125 mL), MeOH (125 mL), and oxone (15.9 g, 45.9 mmol, 3.0 equiv) in $H_2O$ (80 mL) was added dropwise at 0° C. and the solution was stirred for 0.5 h at 0° C. LCMS showed 71% product at 254 nm.

The two batches was combined and filtered. The filtrate was concentrated under reduced pressure and the resulting mixture was diluted with 500 mL of $H_2O$ and extracted with ethyl acetate (500 mL×2). The combined organic layers were dried over anhydrous $Na_2SO_4$ and concentrated under reduced pressure. The residue was purified by silica gel column chromatography, eluted with EA: PE (35:65) to afford (8S,11R,13S,14S,17S)-11-(4-(cyclopropylsulfonyl) phenyl)-17-(1,1-difluoro-3-(triisopropylsilyl)prop-2-yn-1-yl)-17-hydroxy-13-methyl-1,2,6,7,8,11,12,13,14,15,16,17-dodecahydro-3H-cyclopenta[a]phenanthren-3-one (178) (15 g, 57%) as a yellow solid.

$^1$H-NMR ($CDCl_3$, 400 MHZ) δ (ppm): 7.80 (d, J=8.4 Hz, 2H), 7.37 (d, J=8.4 Hz, 2H), 5.80 (s, 1H), 4.48 (d, J=6.4 Hz, 1H), 2.66-2.74 (m, 1H), 2.50-2.65 (m, 5H), 2.32-2.49 (m, 5H), 2.20-2.29 (m, 1H), 2.05-2.18 (m, 2H), 1.72-1.86 (m, 2H), 1.40-1.52 (m, 2H), 1.30-1.37 (m, 2H), 1.07-1.15 (m, 21H), 1.00-1.05 (m, 2H), 0.55 (s, 3H). Calculated mass: 682.33, Mass (ESI+) observed: 683.21 [M+H].

Preparation of (8S,11R,13S,14S,17S)-11-(4-(cyclopropylsulfonyl)phenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (158)

158

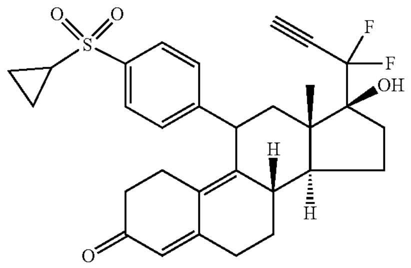

The reaction was run with five batches (10 g×5 batches). Into five 2 L 3-necked flask was placed (8S,11R,13S,14S,17S)-11-(4-(cyclopropylsulfonyl)phenyl)-17-(1,1-difluoro-3-(triisopropylsilyl) prop-2-yn-1-yl)-17-hydroxy-13-methyl-1,2,6,7,8,11,12,13,14,15,16,17-dodecahydro-3H-cyclopenta[a]phenanthren-3-one (178) (50 g, 73.2 mmol, 1 equiv) THF (4 L), the TBAF (14.6 mL, 14.6 mmol, 0.2 equiv) was added dropwise at 0° C. and the mixture was stirred for 5 min at 0° C. TLC showed the reaction was complete. The reaction was quenched by the addition of $H_2O$ (4 L) at 0° C. and the resulting mixture was extracted with ethyl acetate (4 L×1). The organic layer was dried over anhydrous $Na_2SO_4$. After filtration, the filtrate was concentrated under reduced pressure. The residue was purified by silica gel column chromatography eluted with ethyl acetate: petroleum ether (1:1) to afford (8S,11R,13S,14S,17S)-11-(4-(cyclopropylsulfonyl)phenyl)-17-(1,1-difluoroprop-2-yn-1-yl)-17-hydroxy-13-methyl-1,2,6,7,8,11,12,13,14,15,16,17-dodecahydro-3H-cyclopenta[a]phenanthren-3-one (158) (25.1 g, 61.7%) as an off-white solid.

$^1$H-NMR (DMSO-$d_6$, 400 MHZ) δ (ppm): 7.80 (d, J=8.4 Hz, 2H), 7.48 (d, J=8.0 Hz, 2H), 5.69 (s, 1H), 5.52 (s, 1H), 4.62 (d, J=7.2 Hz, 1H), 4.27-4.30 (m, 1H), 2.73-2.87 (m, 2H), 2.60-2.72 (m, 1H), 2.50-2.57 (m, 3H), 2.27-2.40 (m, 2H), 1.95-2.22 (m, 4H), 1.60-1.87 (m, 3H), 1.24-1.44 (m, 2H), 1.07-1.12 (m, 2H), 0.97-1.05 (m, 2H), 0.46 (s, 3H). Calculated mass: 526.20, Mass (ESI+) observed: 527.18 [M+H].

Example 74: Senescence Assay Procedure and Results

Cells were maintained in DMEM media (high glucose, 4 mM L-glutamine, no sodium pyruvate) supplemented with 10% fetal bovine serum in a humidified incubator at 37° C. with 5% carbon dioxide. Senescence was induced via treatment with a sublethal concentration of chemotherapy (bleomycin, gemcitabine, doxorubicin, 5-fluorouridine), followed by a rest period without chemotherapy similarly to what is reported by others in the field (e.g., Aoshiba et al., 2003 Eur Respir J 22:436-443). Senescence was qualified by low EdU (5-ethynyl-2'-deoxyuridine) incorporation and high SA-β-Gal (senescence-associated beta-galactosidase) staining compared to proliferating untreated cells. Senescent cells were plated into 96-well plates at a density of 5-15,000 cells/well. The next day, compounds were added in duplicate across ten different concentrations spanning roughly four Log10 units. Cells were incubated with the compounds for 24-72 hours, at which point viability was quantified using CellTiter-Glo (Promega) or XTT (R&D Systems). The viability for treated cells was determined relative to untreated control cells. The log of the compound concentration vs. normalized mean viability was fit to a four parameters Hill function with variable slope. The bottom was constrained to be greater than zero. The X mean value for Y=50 was interpolated to determine the absolute $IC_{50}$. The results in Table 2 indicate that many of the compounds are active in cells and can induce a dose dependent decrease in the viability of senescent HEPG2 and A549 cells.

The results are presented in Table 2 below.

TABLE 2

| | Absolute IC50 average | |
|---|---|---|
| Compound # | HEPG2_SEN IC50 | A549_SEN IC50 |
| 66 | n.t. | ** |
| 24 | **** | *** |
| 26 | **** | **** |
| 28 | *** | n.t. |
| 31 | *** | n.t. |
| 30 | **** | n.t. |
| 50 | **** | n.t. |
| 32 | **** | **** |
| 33 | **** | **** |
| 51 | **** | n.t. |
| 35 | **** | n.t. |
| 36 | **** | n.t. |
| 37 | **** | n.t. |
| 38 | **** | **** |
| 39 | **** | *** |
| 40 | **** | n.t. |
| 41 | **** | n.t. |
| 42 | **** | *** |
| 27 | *** | n.t. |
| 2 | *** | n.t. |
| 6 | **** | n.t. |
| 7 | n.t. | *** |
| 8 | *** | ** |
| 68 | n.t. | *** |
| 9 | **** | *** |
| 3 | *** | n.t. |
| 11 | **** | n.t. |
| 14 | **** | n.t. |
| 16 | *** | ** |
| 17 | * | n.t. |
| 18 | **** | *** |
| 5 | *** | n.t. |
| 20 | **** | n.t. |
| 12 | **** | n.t. |
| 15 | *** | n.t. |
| 21 | **** | n.t. |
| 52 | n.t. | *** |
| 59 | n.t. | *** |
| 62 | n.t. | *** |
| 55 | n.t. | *** |
| 53 | n.t. | *** |
| 63 | n.t. | *** |
| 57 | n.t. | *** |
| 60 | n.t. | **** |
| 80 | * | * |
| 72 | n.t. | *** |
| 77 | n.t. | * |
| 71 | n.t. | *** |

* 1E-06 M or greater,  1E-07 to 1E-06 M, * 1E-08 to 1E-07 M, **** 1E-10 to 1E-08M, n.t. not tested.

Example 75: Inhibition of Glutathione Peroxidase 4 (GPX4)

Enzymatic activity of (GPX4) was analyzed using for example the glutathione peroxidase 4 inhibitor screening assay (Item No. 701880, Cayman Chemical, Michigan USA), which is designed to identify inhibitors of the GPX4. GPX4 activity can be assessed by using cumene hydroperoxide as the substrate (Lawrence and Bur, Biochem Biophys Res Commun 1976 71 (4): 952). The GPX4 enzyme employs reduced glutathione (GSH) as electron donor. Glutathione disulfide (GSSH) which is formed is recycled back to the reduced state by glutathione reductase (EC no. 1.8.1.7) and NADPH. The oxidation of NADPH to NADP+ is accompanied by a decrease in absorbance at 340 nm measured by a UV/vis spectrometer which allows for an indirect assessment of GPX4 activity. In brief, compounds were preincubated with recombinant human GPX4 enzyme for 1.5 hours at room temperature or 37° C. followed by the addition of glutathione reductase, GSH, cumene hydroperoxide and NADPH. Kinetic changes in absorbance were measured. Uninhibited activity was set to 100% activity, and a condition without the addition of GPX4 enzyme was used to estimate complete inhibition of GPX4 activity. ML162, a prototype GPX4 inhibitor (Moosmayer et al., Acta Crystallogr D Struct Biol 2021 77 (Pt 2): 237-248; Shin et al., Free Rad Biol Med 2018 129:454-462) was used as a reference compound titrated from top concentration of 25 μM. All compounds were tested from 25 μm as the top concentration in duplicates with the inhibitory activity of selected compounds results in the GPX4 inhibitor screening assay shown in Table 3.

TABLE 3

Example 76: Compound 21 affects the electrophoretic gel mobility of cellular GPX4 in human cells and mice

| Compound | % Inhibition at 25.00 μM | % Inhibition at 2.50 μM | % Inhibition at 0.25 μM |
|---|---|---|---|
| ML162 | 96 | 88 | 15 |
| 17 | 102 | 99 | 30 |
| 26 | 74 | 67 | 16 |
| 51 | 41 | 45 | 12 |

Modifications of GPX4 in cellular assays can be detected by electrophoretic gel mobility shifts based on the expected nature of covalent binding. To this end, the A549 cancer cell line (ATCC) was exposed to 2 μM of compound 21 for 5 hours. Following cell treatment with the indicated compound, cells were collected and lysed by IGEPAL CA-630 and sodium dodecyl sulfate (SDS) in the presence of a protease inhibitor cocktail (4693132001, Roche). The soluble protein fraction was isolated and heat-denatured in the presence of dithiothreitol (DTT). Proteins were electrophoretically separated using a Bis-Tris protein gel with 12% polyacrylamide concentration. Following the transfer of proteins to a PVDF membrane, the membrane was probed with an anti-GPX4 monoclonal antibody (ab125066, Abcam) followed by an anti-rabbit IgG HRP conjugated antibody (31460, ThermoFisher). Chemiluminescent following HRP substrate addition (34580, ThermoFisher) was detected by the ChemiDoc XRS+System (BioRad). Treatment of cells with compound 21 results in a reduction of electrophoretic mobility of GPX4 by a molecular weight estimated to be ~1 kDa, which correlates with the molecular weight of compound 21 and is illustrated in FIG. 1.

Example 77: Electrophoretic Gel Mobility Shift of GPX4 Protein in Response to Treatment of Cultured Cells with Compound 32

Figure 2:
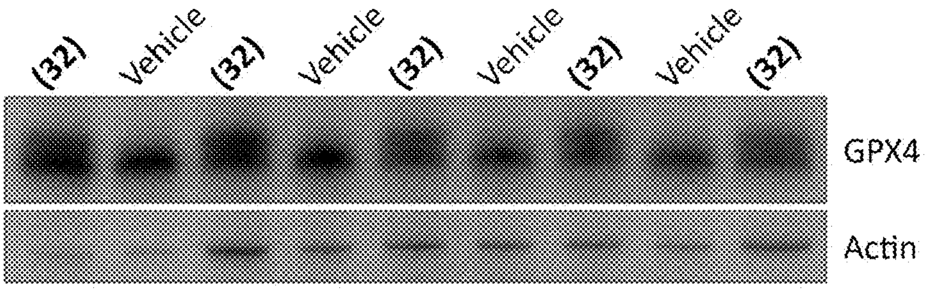
FIG. 2 illustrates the electrophoretic gel mobility shift of GPX4 protein isolated from mouse skin treated with compound 32.

An electrophoretic gel mobility shift assay of GPX4 was applied to determine the level of target engagement of compound 32 as a direct biomarker in tissues. For example, target engagement of compound 32 was assessed in the skin of mice exposed to mitomycin C, a potent inducer of cellular senescence. Following 24 hr treatment with compound 32, the skin of treated BALB/c mice (Charles River Laboratories) was collected and lysed by IGEPAL CA-630 and sodium dodecyl sulfate (SDS) in the presence of a protease inhibitor cocktail (4693132001, Roche) and benzonase (E1014, Sigma-Aldrich). The soluble protein fraction was isolated and heat-denatured in the presence of dithiothreitol (DTT). Proteins were electrophoretically separated using a Bis-Tris protein gel with 12% polyacrylamide concentration. Following the transfer of proteins to a PVDF membrane, the membrane was probed with an anti-GPX4 monoclonal antibody (ab125066, Abcam) and anti-beta-Actin (4970, Cell Signaling Technology), followed by an anti-rabbit IgG HRP conjugated antibody (31460, ThermoFisher). Chemiluminescent following HRP substrate addition (34580, ThermoFisher) was detected by the ChemiDoc XRS+System (BioRad). A slower migrating band for GPX4 was observed in the compound 32 treated mice, which is consistent with the band shift expected for covalent binding of compound 32 to GPX4, which is illustrated in FIG. 2.

Example 78: Compounds 32 and 69 Covalently Bind GPX4 Protein in Human Cells

Figure 3:
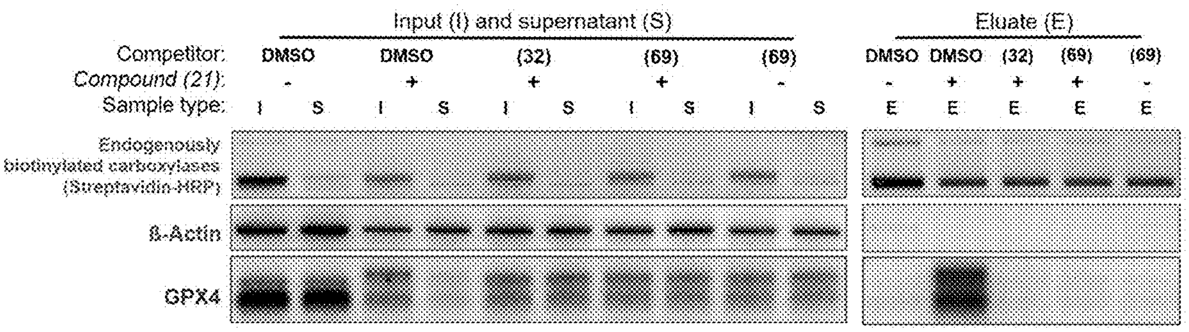
FIG. 3 illustrates use of compounds 32 and 69 and their biotinylated analogs allow for the identification of competitive binding to GPX4 protein in cultured human cells.

Binding of compounds 32 and 69 to the target protein GPX4 in cultured cells can be assessed by the use of biotinylated analogs such as compound 21 that retain their cellular activities. Cells or tissue simultaneously or sequentially exposed to compounds 32 and 69 and biotinylated analog 21 can be analyzed for exogenous biotinylated proteins and thereby enables the identification of cellular targets of compounds 32 and 69. The A549 cancer cell line (ATCC) was exposed to 2 μM of compounds 32 and 69 for 2 hours followed by the addition of 2 μM of compound 21 for 5 hours. Cells were collected and lysed by IGEPAL CA-630 and sodium dodecyl sulfate (SDS) in the presence of a protease inhibitor cocktail (4693132001, Roche). The soluble protein fraction was isolated and incubated with Streptavidin Mag Sepharose (28-9857-38, Cytiva) at 4° C. for 16 hours. The streptavidin-unbound fraction was collected allowing for the quantification of the proportion of GPX4 depleted by the biotinylated compound 21 relative to samples not treated with Streptavidin Mag Sepharose. Furthermore, biotinylated proteins were eluted from Streptavidin Mag Sepharose by head-denaturation in the presence of excess biotin (5 mM). Streptavidin Mag Sepharose untreated samples (also referred to as “Input”), streptavidin-unbound fractions (also referred to as “Supernatant”) and streptavidin-bound fractions (also referred to as “Eluate’) were heat-denatured in the presence of dithiothreitol (DTT). Proteins were electrophoretically separated using a Bis-Tris protein gel with 12% polyacrylamide concentration. Following the transfer of proteins to a PVDF membrane, the membrane was probed with an anti-GPX4 monoclonal antibody (ab125066, Abcam), anti-beta-Actin (4970, Cell Signaling Technology), anti-rabbit IgG HRP conjugated antibody (31460, ThermoFisher) and Streptavidin-HRP (N504, ThermoFisher). Chemiluminescent following HRP substrate addition (34580, ThermoFisher) was detected by the ChemiDoc XRS+ System (Bio-Rad). Depicted in FIG. 3 is the treatment of A549 cells with 2 μM of the biotinylated analog compound 21 for 5 hours, which results in an estimated depletion of more than 50% of GPX4 protein in the streptavidin-unbound fraction relative its input sample. Pre-treatment of cells with 2 μM of compounds 32 and 69 reduces the compound 21 dependent depletion of GPX4 protein in the streptavidin-unbound fraction, and the enrichment in the streptavidin-bound fraction. Such assay results support that compounds 32 and 69 compete with compound 21 for the same binding site of GPX4.

Example 79: Compound 32 Induces Lipid Peroxidation in Human Cells

Figure 4:
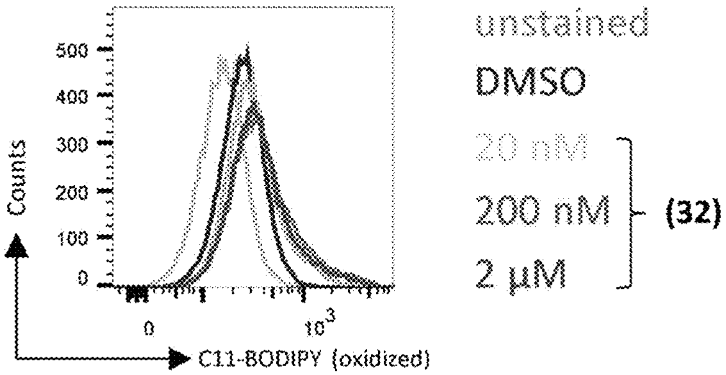
FIG. 4 shows that compound 32 provided herein induced markers of cellular lipid peroxidation.

Inhibition of the cellular activity of GPX4 can be estimated by changes in lipid peroxidation levels that can be detected by the oxidation of BODIPY 581/591 C11, a ratiometric fluorescent indicator reacting with free radicals produced during membrane peroxidation (Drummen et al., Free Radic Biol Med 2002 33 (4): 473-90; and Martinez et al., Methods Mol Biol 2020 2018:125-130). For a lipid peroxidation assay by flow cytometry, A549 cells were seeded at 333,000 cells per well in 12-well plates. On the following day, culture media was replaced with 1 mL media containing either DMSO or compound 32 (0.02, 0.2 and 2 μm), and cultures were incubated at 37° C. for 18.5 hours. Thirty minutes before the end of the incubation period, 2 μm BODIPY 581/591 C11 (D3861, Invitrogen) was added to cells. Following cell collection by trypsinization, cells were subjected to flow cytometry analysis (BD FACSAria), and gated for the live cell population, which was analyzed for fluorescence signal associated with the oxidized state of BODIPY 581/591 C11. The results are illustrated in FIG. 4.

Figure 5:
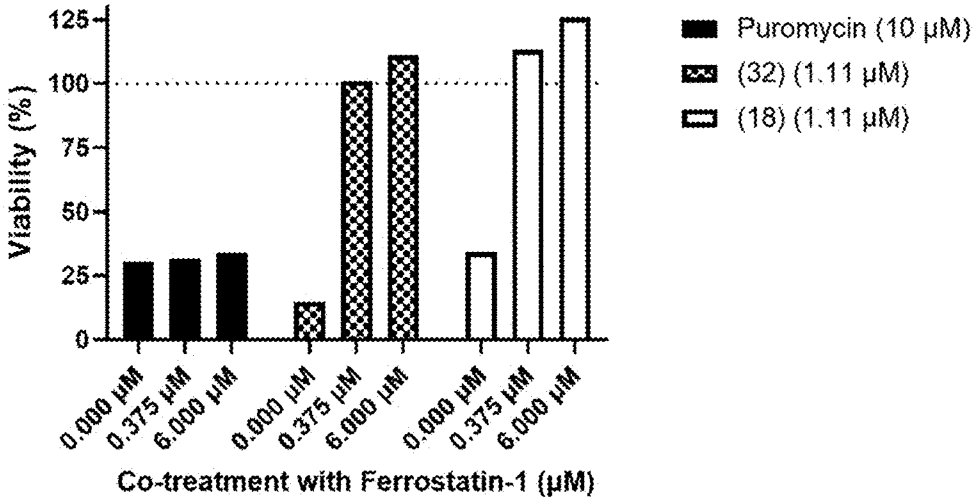
FIG. 5 shows that cell death-inducing activities of compounds 18 and 32 provided herein can be inhibited by an anti-ferroptotic agent.

Example 80: Cell Death Induced by Compounds 18 and 32 is Inhibited by Radical Trapping Agents Cell death induced by ferroptosis-inducing agents can be characterized by rescuing the cellular response with radical trapping agents that prevent the accumulation of phospholipid hydroperoxides (Stockwell et al., Cell Chem Biol 2020 27 (4): 365-375). As such, ferrostatin-1 was identified as a potent inhibitor of ferroptosis for which a free radical trapping mechanism had been reported (Skouta et al., J Am Chem Soc 2014 136 (12): 4551-6; Zika et al., ACS Cent Sci. 2017 3 (3): 232-243; and Miotto et al., Redox Biol. 2020; 101328). To determine whether compounds 18 and 32 induce ferroptosis in senescent cells, normal human dermal fibroblasts were induced to undergo senescence by treatment with a sublethal concentration of chemotherapy (bleomycin sulfate), followed by a rest period without chemotherapy similarly to previous reports (Aoshiba et al., 2003 3:436-43). Cells were maintained in DMEM media (high glucose, 4 mM L-glutamine, no sodium pyruvate) supplemented with 10% heat-inactivated fetal bovine serum in a humidified incubator at 37° C. with 5% carbon dioxide and 5% oxygen. Cellular senescence was qualified by reduced EdU (5-ethynyl-2'-deoxyuridine) incorporation and increased SA-β-Gal (senescence-associated beta-galactosidase) staining compared to proliferating untreated cells. Senescent fibroblasts were plated into 96-well plates at a density of 10,000 cells per well. The next day, ferrostatin-1 was diluted in cell medium to reach a final concentration of 0.375 and 6 μM and was added to cells. Approximately 30 minutes after the addition of ferrostatin-1, compounds 18 and 32 at 1.11 μM, or the peptidyl transfer inhibitor puromycin at 10 μM were added to cells. Cells were incubated with the compounds for 24 hours, at which point viability was quantified using the CellTiter-Glo assay (Promega). The viability for treated cells was determined relative to untreated control cells. As depicted in FIG. 5, ferrostatin-1 at tested concentrations potently inhibits cell death induced by compounds 18 and 32, which supports the engagement of ferroptosis as the mechanism of cell death.

What is claimed is:

1. A compound having the structure:

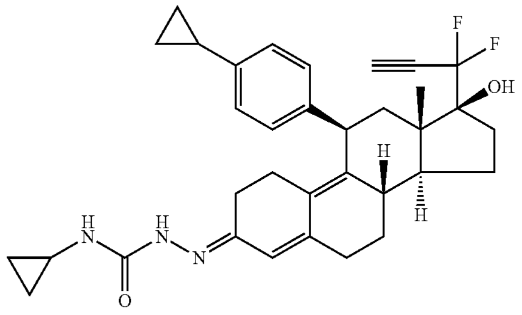

or pharmaceutically acceptable salts, hydrates or solvates thereof.

2. A pharmaceutical composition comprising the compound of claim 1 and a pharmaceutically acceptable vehicle.

3. A compound having the structure:

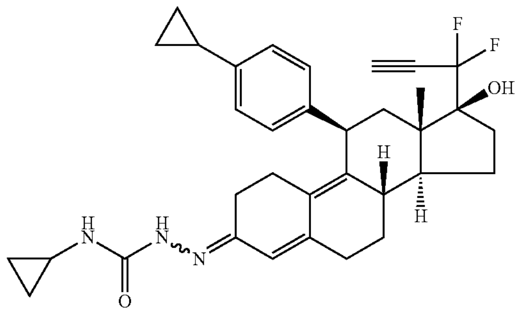

or pharmaceutically acceptable salts, hydrates or solvates thereof.

4. A pharmaceutical composition comprising the compound of claim 3 and a pharmaceutically acceptable vehicle.

5. A compound having the structure:

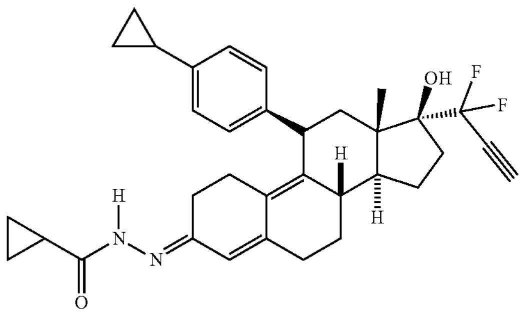

or pharmaceutically acceptable salts, hydrates or solvates thereof.

6. A pharmaceutical composition comprising the compound of claim 5 and a pharmaceutically acceptable vehicle.

7. A compound having the structure:

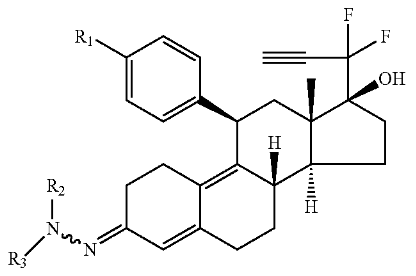

or pharmaceutically acceptable salts, hydrates or solvates thereof wherein:

$R_1$ is cycloalkyl; $R_2$ is —H, alkyl, cycloalkyl or —C(O) $CH_3$; $R_3$ is $R_4CO$— or $R_5R_6NCO$—; $R_4$ is cycloalkyl; $R_5$ is hydrogen or alkyl; and $R_6$ is cycloalkyl.

8. The compound of claim 7 having the structure:

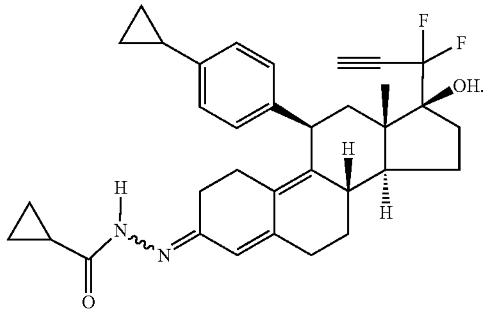

9. A pharmaceutical composition comprising the compound of claim 7 and a pharmaceutically acceptable vehicle.

10. A pharmaceutical composition comprising the compound of claim 8 and a pharmaceutically acceptable vehicle.

* * * * *